US012661654B2

(12) United States Patent
Hill et al.

(10) Patent No.: US 12,661,654 B2
(45) Date of Patent: Jun. 23, 2026

(54) METHODS OF USING MICROFLUIDIC POSITIONAL ENCODING DEVICES

(71) Applicant: ELEGEN CORPORATION, Los Altos, CA (US)

(72) Inventors: Matthew Hill, Decatur, GA (US); Marc Unger, San Mateo, CA (US); Alex Sugarbaker, Atherton, CA (US)

(73) Assignee: Elegen Corporation, Menlo Park, CA (US)

( * ) Notice: Subject to any disclaimer, the term of this patent is extended or adjusted under 35 U.S.C. 154(b) by 1366 days.

(21) Appl. No.: 17/420,988

(22) PCT Filed: Jan. 7, 2020

(86) PCT No.: PCT/US2020/012627
§ 371 (c)(1),
(2) Date: Jul. 6, 2021

(87) PCT Pub. No.: WO2020/146425
PCT Pub. Date: Jul. 16, 2020

(65) Prior Publication Data
US 2022/0126298 A1 Apr. 28, 2022

Related U.S. Application Data

(60) Provisional application No. 62/863,712, filed on Jun. 19, 2019, provisional application No. 62/811,506, (Continued)

(51) Int. Cl.
*C12Q 1/686* (2018.01)
*B01L 3/00* (2006.01)
*B01L 7/00* (2006.01)

(52) U.S. Cl.
CPC ........... *B01L 7/52* (2013.01); *B01L 3/502715* (2013.01); *B01L 3/502784* (2013.01); (Continued)

(58) Field of Classification Search
CPC ......... B01J 19/0046; B01J 2219/00722; B01L 3/502715
See application file for complete search history.

(56) References Cited

U.S. PATENT DOCUMENTS 5,730,850 A 3/1998 Kambara et al.
5,833,827 A 11/1998 Anazawa et al.
(Continued)

FOREIGN PATENT DOCUMENTS

EA 2015-90285 A1 10/2015
EP 2602608 9/2016
(Continued)

OTHER PUBLICATIONS

Lee et al., "A microfluidic oligonucleotide synthesizer," Nucleic Acids Research, February, vol. 38, No. 8, pp. 2514-2521. (Year: 2010).*
(Continued)

*Primary Examiner* — Young J Kim
(74) *Attorney, Agent, or Firm* — McDermott Will & Schulte LLP

(57) ABSTRACT

The invention relates to methods and compositions useful for routing and tracking multiple mobile units within a microfluidic device. Mobile units may be routed through a plurality of chemical environments, and the mobile units may be tracked to determine the path and/or environments that the mobile units have routed through. Mobile units may be routed in accordance with a predetermined algorithm. Mobile units may be routed through microfluidic devices in ordered flow. Mobile units routed through the microfluidic device can be used to perform various chemical reactions uniquely associated to the units, including without limitation peptide synthesis, enzymatic gene synthesis and gene assembly.

22 Claims, 44 Drawing Sheets

Related U.S. Application Data filed on Feb. 27, 2019, provisional application No. 62/810,196, filed on Feb. 25, 2019, provisional application No. 62/789,505, filed on Jan. 7, 2019, provisional application No. 62/789,506, filed on Jan. 7, 2019.

(52) U.S. Cl.
CPC ... *B01L 2200/0673* (2013.01); *B01L 2200/16* (2013.01); *B01L 2300/0864* (2013.01); *C12Q 1/686* (2013.01)

(56) References Cited

U.S. PATENT DOCUMENTS

| | | | |
|---|---|---|---|
| 6,017,765 | A | 1/2000 | Yamada et al. |
| 6,408,878 | B2 | 6/2002 | Unger et al. |
| 6,899,137 | B2 | 5/2005 | Unger et al. |
| 7,340,957 | B2 | 3/2008 | Kaduchak et al. |
| 8,162,149 | B1 | 4/2012 | Perroud et al. |
| 8,528,589 | B2 | 9/2013 | Miller et al. |
| 8,658,430 | B2 | 2/2014 | Miller et al. |
| 9,347,595 | B2 | 5/2016 | Toner et al. |
| 9,364,803 | B2 | 6/2016 | Yurkovetsky et al. |
| 10,435,676 | B2 | 10/2019 | Champion et al. |
| 10,712,255 | B2 | 7/2020 | Simpson et al. |
| 10,752,887 | B2 | 8/2020 | Champion et al. |
| 10,837,040 | B2 | 11/2020 | Ybert et al. |
| 10,913,964 | B2 | 2/2021 | Ybert et al. |
| 11,059,849 | B2 | 7/2021 | Ybert et al. |
| 2002/0127736 | A1 | 9/2002 | Chou et al. |
| 2002/0187501 | A1 | 12/2002 | Huang et al. |
| 2003/0039957 | A1 | 2/2003 | McCarthy et al. |
| 2004/0209354 | A1 | 10/2004 | Mathies et al. |
| 2005/0072946 | A1 | 4/2005 | Studer et al. |
| 2006/0040226 | A1 | 2/2006 | Ahonen |
| 2008/0003142 | A1 | 1/2008 | Link et al. |
| 2008/0223721 | A1 | 9/2008 | Cohen et al. |
| 2008/0286751 | A1 | 11/2008 | Renaud et al. |
| 2010/0304429 | A1 | 12/2010 | Butler et al. |
| 2011/0124049 | A1 | 5/2011 | Li et al. |
| 2011/0190146 | A1 | 8/2011 | Boehm et al. |
| 2011/0201057 | A1 | 8/2011 | Carr |
| 2011/0269119 | A1 | 11/2011 | Hutchison et al. |
| 2012/0220497 | A1 | 8/2012 | Jacobson et al. |
| 2012/0231444 | A1 | 9/2012 | Quake et al. |
| 2012/0277902 | A1 | 11/2012 | Sharpe et al. |
| 2012/0292233 | A1 | 11/2012 | Toner et al. |
| 2013/0313113 | A1 | 11/2013 | Koser |
| 2013/0313170 | A1 | 11/2013 | Bohm et al. |
| 2014/0273179 | A1 | 9/2014 | Sharpe et al. |
| 2014/0363852 | A1 * | 12/2014 | Efcavitch .............. C12Q 1/6806 435/91.5 |
| 2015/0093743 | A1 | 4/2015 | Sadri et al. |
| 2015/0268244 | A1 | 9/2015 | Cho |
| 2016/0040226 | A1 | 2/2016 | Mehta et al. |
| 2016/0068901 | A1 | 3/2016 | Eckhardt et al. |
| 2016/0108382 | A1 | 4/2016 | Efcavitch et al. |
| 2016/0257993 | A1 | 9/2016 | Fu et al. |
| 2018/0080020 | A1 | 3/2018 | Link et al. |
| 2019/0300923 | A1 | 10/2019 | Ybert et al. |
| 2020/0002690 | A1 | 1/2020 | Ybert et al. |
| 2020/0023362 | A1 | 1/2020 | Yu et al. |
| 2020/0370027 | A1 | 11/2020 | Ybert et al. |
| 2021/0009994 | A1 | 1/2021 | Godron et al. |
| 2021/0130863 | A1 | 5/2021 | Ybert et al. |
| 2021/0214382 | A1 | 7/2021 | Sarac et al. |

FOREIGN PATENT DOCUMENTS

| | | |
|---|---|---|
| GB | 2561587 | 10/2018 |
| JP | 2005-538727 A | 12/2005 |
| JP | 2008-516251 A | 5/2008 |
| JP | 2010-506136 A | 2/2010 |
| WO | WO 2003/009940 A2 | 2/2003 |
| WO | 2006/044956 A1 | 4/2006 |
| WO | 2011/056872 A2 | 5/2011 |
| WO | WO 2014/001781 A1 | 1/2014 |
| WO | WO 2017/123311 A2 | 7/2017 |
| WO | WO 2017/156085 A1 | 9/2017 |
| WO | WO 2018/102748 A1 | 6/2018 |
| WO | 2019/033062 A2 | 2/2019 |
| WO | WO-2019040599 A1 * | 2/2019 ........ G01N 15/1459 |
| WO | 2020/176548 A1 | 9/2020 |

OTHER PUBLICATIONS

Li et al., "Combinatorial Peptide Microarray Synthesis Based on Microfluidic Impact Printing," ACS Comb. Sci., December, vol. 21, pp. 6-10. (Year: 2018).*

Jensen et al., "Template-Independent Enzymatic Oligonucleotide Synthesis (TiEOS): Its History, Prospects, and Challenges," Biochemistry, March, vol. 57, pp. 1821-1832. (Year: 2018).*

Sarac et al., "Terminal Deoxynucleotidyl Transferase in the Synthesis and Modification of Nucleic Acids," ChemBioChem, vol. 20, pp. 860-871. (Year: 2018).*

Albert et al., "Light-directed 5'Δ3' synthesis of complex oligonucleotide microarrays," Nucleic Acids Research, Apr. 1, 2003, vol. 31, No. 7 e35, DOI: 10.1093/nar/gng035.

Nuwaysir et al., "Gene Expression Analysis Using Oligonucleotide Arrays Produced by Maskless Photolithography," Genome Res. 2002. 12:1749-1755, doi: 10.1101/gr.362402.

Hölz, K., et al. High-Efficiency Reverse (5'→3') Synthesis of Complex DNA Microarrays. Sci Rep 8, 15099 (2018). https://doi.org/10.1038/s41598-018-33311-3.

Li, Sixing et al., "An on-chip, multichannel droplet sorter using standing surface acoustic waves (SSAW)," Anal Chem. Jun. 4, 2013; 85(11): 5468-5474. doi:10.1021/ac400548d.

Ding, Xiaoyun et al. "Standing surface acoustic wave (SSAW) based multichannel cell sorting," Lab Chip. Nov. 7, 2012; 12(21): 4228-4231. doi:10.1039/c21c40751e.

Choi, Ghoon et al., "Microfluidic deformability-activated sorting of single particles," Microfluidic deformability-activated sorting of single particles, (2020)6 :11 Microsystems & Nanoengineering.

Chen, Yuncong, et al., Microfluidic droplet sorting using integrated bilayer micro-valves,: Appl. Phys. Lett. 109, 143510 (2016), https://doi.org/10.1063/1.4964644.

Caen, Quriel, et al., "High-throughput multiplexed fluorescence-activated droplet sorting," Microsystems & Nanoengineering (2018) 4:33, doi 10.1038/s41378-018-0033-2.

Aus der Wiesche, et al., "Dynamics in Microfluidic Systems with Microheaters," Dept. of Measurement, Control and Microtechnology MRM, University of Ulm, Germany (1999).

Chen, C., et al., "Micromachined bubble-jet cell sorter with multiple operation modes," Science Direct, Sensors and Actuators B. 2006; 117: 523-529.

Vercruysse, D., et al., "A High-Speed Miniaturized Cell Sorter with Lens-Free Imaging and Thermal Bubble Based Jet Flow Sorting," 18th International Conference on Miniaturized Systems for Chemistry and Life Sciences, Oct. 2014: 382-384.

Singh-Gasson, et al., "Maskless fabrication of light-directed oligonucleotide microarrays using a digital micromirror array," Nat. Biotechnol. 17, 974-978 (1999). https://doi.org/10.1038/13664.

Abbosh, C. et al., "Phylogenetic ctDNA analysis depicts early-stage lung cancer evolution," Nature, vol. 545, Apr. 26, 2017, pp. 446-451.

Applied Biosystems, "Technical Bulletin: Cleavage, Deprotection, and Isolation of Peptides after Fmoc Synthesis," May 1998, pp. 1-12.

Ashraf, M.W. et al., "Micro Electromechanical Systems (MEMS) based microfluidic devices for biomedical applications," International Journal of Molecular Sciences, vol. 12, Jun. 7, 2011, pp. 3648-3704.

Baker, C.A. et al., "Recent advances in microfluidic detection systems," Bioanalysis, Aug. 2009, vol. 1, No. 5, pp. 967-975.

Bell, C.J. et al., "Carrier Testing for Severe Childhood Recessive Diseases by Next-Generation Sequencing," Science Translational Medicine, vol. 3, Iss 65 65ra4, Jan. 12, 2011, pp. 1-14.

(56) References Cited

OTHER PUBLICATIONS

Bradshaw, R. A. et al. "The Chemical Synthesis of DNA and RNA Oligonucleotides for Drug Development and Synthetic Biology Applications." Encyclopedia of Cell Biology, vol. 1, Aug. 2015, p. 50.

Businesswire, "Twist Bioscience to Provide One Billion Base Pairs of Synthetic DNA to Ginkgo Bioworks to Support Expansion into New Industries," Oct. 3, 2017, five pages, [Online] [Retrieved on Aug. 9, 2021] <URL: https://www.businesswire.com/news/home/20171003005632/en/Twist-Bioscience-to-Provide-One-Billion-Base-Pairs-of-Synthetic-DNA-to-Ginkgo-Bioworks-to-Support-Expansion-into-New-Industries>.

European Patent Office, Extended European Search Report and Opinion, EP Patent Application No. 18848022.2, Apr. 20, 2021, seven pages.

Finkel, N.H. et al., "Barcoding the microworld," Analytical Chemistry, Oct. 1, 2004, pp. 353-359.

Froehler, B.C. et al., "Synthesis of DNA via deoxynucleoside H-phosphonate intermediates," Nucl. Acids Res., 1986, vol. 14, No. 13, pp. 5399-5407.

Gao, M. et al., Electroosmotic Flow Pump. in Advances in Microfluidics—New Applications in Biology, Energy, and Materials Sciences (ed. Yu, X.-Y.), IntechOpen, Nov. 23, 2016, pp. 237-253.

Gilham, P.T. et al., "Studies on Polynucleotides. I. A New and General Method for the Chemical Synthesis of the C5'-C3' Internucleotidic Linkage. Syntheses of Deoxyribo-dinucleotides," J. Amer. Chem. Soc., 1958, vol. 80, No. 23, pp. 6212-6222.

Gong, Y. et al., "Microfluidic Flow Rate Detection With a Large Dynamic Range by Optical Manipulation," IEEE Photonics Letters, Dec. 1, 2015, vol. 27, No. 23, pp. 2508-2511.

Heo, Y.J. et al., "Real-time Image Processing for Microscopy-based Label-free Imaging Flow Cytometry in a Microfluidic Chip," Scientific Reports, 2017, pp. 1-9.

Holmes, D. et al., "Optical and impedance detection of DNA hybridisation using barcoded micro-particles in a microfluidic device," NSTI-Nanotech, 2006, vol. 2, pp. 666-669.

Hossan, M. R. et al., "Review: Electric field driven pumping in microfluidic device," Electrophoresis 39, Nov. 11, 2017, pp. 702-731.

Hu, D. et al., "Effective optimization of antibody affinity by phage display integrated with high-throughput DNA synthesis and sequencing technologies," PLoS One 10, e0129125, Jun. 5, 2015, pp. 1-17.

Iliescu, C. et al., "A practical guide for the fabrication of microfluidic devices using glass and silicon," Biomicrofluidics, 2012, vol. 6, No. 1, pp. 016505-1-016505-16.

Iverson, B.D. et al., "Recent advances in microscale pumping technologies: a review and evaluation," Microfluidics and Nanofluidics, 2008, vol. 5, No. 2, pp. 145-174.

Jensen, M.A. et al., "Template-Independent Enzymatic Oligonucleotide Synthesis (TiEOS): Its History, Prospects, and Challenges," Biochemistry 57(12), Mar. 27, 2018, pp. 1821-1832.

Kaczmarek, J. C. et al., "Advances in the delivery of RNA therapeutics: From concept to clinical reality," Genome Medicine, vol. 9, Jun. 27, 2017, pp. 1-16.

Kalra, P. et al., "Simple Methods and Rational Design for Enhancing Aptamer Sensitivity and Specificity," Frontiers in Molecular Biosciences, vol. 5, May 14, 2018, pp. 1-16.

Kirkizlar, E. et al., "Detection of Clonal and Subclonal Copy-Number Variants in Cell-Free DNA from Patients with Breast Cancer Using a Massively Multiplexed PCR Methodology," Translational Oncology, vol. 8, Iss. 5, Oct. 2015, pp. 407-416.

Kohara, Y. et al., "DNA hybridization using "Bead-Array": Probe-attached beads arrayed in a capillary in a predetermined order," Nucleic Acids Symposium Series, Nov. 1, 2001, vol. 1, No. 1, pp. 83-84.

Kohara. Y. et al., "DNA probes on beads arrayed in a capillary, 'Bead-array', exhibited high hybridization performance," Nucleic Acids Research, Aug. 1, 2002, vol. 30, No. 16, pp. 1-7.

Kosuri, S. et al., "Large-scale de novo DNA synthesis: technologies and applications," Nature Methods, May 2014, vol. 11, No. 5, pp. 499-507.

Lee, H.H. et al., "Enzymatic DNA synthesis for digital information storage," Nature Communications, Jun. 16, 2018, pp. 1-31.

Letsinger, R.L. et al., "Nucleotide chemistry. XIII. Synthesis of oligothymidylates via phosphotriester intermediates," J. Amer. Chem. Soc., 1969, vol. 91, No. 12, pp. 3350-3355.

Lu, H. et al., "High throughput single cell counting in droplet-based microfluidics," Scientific Reports, 2017, vol. 7, No. 1, pp. 1-9.

Meijering, E. et al., "Methods for cell and particle tracking," Methods in Enzymology, 2012, vol. 504, pp. 183-200.

Miralles, V. et al., "A review of heating and temperature control in microfluidic systems: techniques and applications," Diagnostics, 2013, vol. 3, No. 1, DD. 33-67.

Noda, H. et al., "A bead-alignment device with a bead-sized microchamber on a rotating cylinder for fabrication of a miniaturized probe array," Journal of Bioscience and Bioengineering, 2003, vol. 96, No. 1, pp. 86-88.

Noda, H. et al., "Automated Bead Alignment Apparatus Using a Single Bead Capturing Technique for Fabrication of a Miniaturized Bead-Based DNA Probe Array," Anal. Chem. 2003, vol. 75, No. 13, pp. 3250-3255.

Palluk, S. et al. "De novo DNA synthesis using polymerase-nucleotide conjugates," Nature Biotechnology, vol. 36, Iss. 7, Jun. 18, 2018, pp. 645-650.

PCT International Search Report & Written Opinion, International Application No. PCT/US2018/047485, dated Dec. 7, 2018, 24 pages.

PCT International Search Report and Written Opinion, PCT Application No. PCT/US20/12627, May 28, 2020, 23 pages.

Pengpumkiat, S. et al., "Rapid Synthesis of a Long Double-Stranded Oligonucleuotide from a Single-Stranded Nucleotide Using Magnetic Beads and an Oligo Library," PLoS One, Mar. 1, 2016, vol. 11, No. 3, pp. 1-10.

Porteus, M., "Genome Editing: A New Approach to Human Therapeutics," Annual Review Pharmacology and Toxicology, vol. 56, Nov. 9, 2015, pp. 163-190.

Qvortrup, K. et al., "A Photolabile Linker for the Solid-Phase Synthesis of Peptide Hydrazides and Heterocycles," Organic Letters, Aug. 28, 2014, pp. 4782-4785.

Reese, C.B., "The chemical synthesis of oligo- and poly-nucleotides by the phosphotriester approach," Tetrahedron, 1978, vol. 34, No. 12, pp. 3143-3179.

Rodiger, S. et al., "Nucleic acid detection based on the use of microbeads: a review," Microchimica Acta, Apr. 11, 2014, No. 181, pp. 1151-1168.

Roy, E. et al., "Overview of Material for Microfluidic Applications," Advances in Microfluidics—New Applications in Biology, Energy, and Materials Science, Nov. 23, 2016, pp. 335-355.

Rutgers, "The Next Step in DNA Synthesis," Nov. 2014, pp. 1-4, [Online] [Retrieved on Aug. 9, 2021] Retrieved from the Internet <URL: http://2014.igem.org/Team:Rutgers>.

Ryan, A. et al., "Validation of an Enhanced Version of a Single-Nucleotide Polymorphism-Based Noninvasive Prenatal Test for Detection of Fetal Aneuploidies," Fetal Diagnosis and Therapy, vol. 40, No., 3, Mar. 31, 2016, pp. 219-223.

Sajeesh, P. et al., "Particle separation and sorting in microfluidic devices: a review," Microfluidics and Nanofluidics, 2014, vol. 17, No. 1, pp. 1-52.

Shevkoplyas, S.S. et al., "The force acting on a superparamagnetic bead due to an applied magnetic field," Lab Chip, vol. 7, Jul. 25, 2007, pp. 1294-1302.

Shields, C.W et al., "Microfluidic Cell Sorting: A Review of the Advances in the Separation of Cells from Debulking to Rare Cell Isolation," Lab Chip, Feb. 16, 2015, vol. 15, No. 5, pp. 1230-1249.

Simon, M.G. et al., "Microfluidic Droplet Manipulations and Their Applications," Microdroplet Technology, 2012, pp. 23-50.

Tangen, U. et al., "On demand nanoliter-scale microfluidic droplet generation, injection, and mixing using a passive microfluidic device," Biomicrofluidics, 2015, vol. 9, No. 1, pp. 014119-1-014119-17.

(56)          References Cited

OTHER PUBLICATIONS

Vorobyeva, M.A. et al., "Key Aspects of Nucleic Acid Library Design for in Vitro Selection," International Journal of Molecular Sciences, vol. 19, Feb. 5, 2018, pp. 1-21.

Wang, X. et al., "Electroosmotic pumps and their applications in microfluidic systems," Microfluid Nanofluidics, vol. 6, Feb. 2009, pp. 145-162.

Wapner, R.J. et al., "Expanding the scope of noninvasive prenatal testing: Detection of fetal microdeletion syndromes," American Journal of Obstetrics and Gynecology, vol. 212, Iss. 3, Mar. 2015, pp. 332.e1-332.e9.

Yao, S. et al., "Porous glass electroosmotic pumps: Design and experiments," Journal of Colloid and Interface Science, vol. 268, Dec. 2003, pp. 143-153.

Zuo, X. et al., "A novel sandwich assay with molecular beacon as report probe for nucleic acids detection on one-dimensional microfluidic beads array," Analytica Chimica Acta, Mar. 21, 2007, vol. 587, No. 1, pp. 9-13.

European Patent Office, Extended European Search Report, Application No. 20763822.2, Apr. 18, 2023, 8 pages.

International Preliminary Report on Patentability, PCT Application No. PCT/US2020/019761, Aug. 25, 2021, 18 pages.

Office Action, Chinese Application No. 202080030248, Dec. 14, 2022, 12 pages.

PCT International Search Report and Written Opinion, PCT Application No. PCT/US2020/019761, Jul. 20, 2020, 21 pages.

PCT International Search Report and Written Opinion, PCT Application No. PCT/US2022/075957, Jan. 2, 2023, 11 pages.

Yasmin, Rubina et al., "A modifiable microarray-based universal sensor: providing sample-to-results automcation," vol. 2, No. 10, Oct. 1, 2026, p. e00179.

Bradshawn et al "Encyclopedia of Cell Biology". vol. 1 Molecular Cell Biology Netherlands: Elsevier Science. Chapter "the Chemical Synthesis of DNA and RNA Oligonucleotides for Drug Development and Synthetic Biology Applications" p. 50 (Year: 2016).

Carr, et al., "Genome Engineering," Nature Biotechnology, vol. 27, No. 12, Dec. 1, 2009, pp. 1151-1162.

Cheng-Chung et al., "A Microfluidic Oligonucleotide Synthesizer," Nucleic Acids Research, vol. 38, No. 8, Feb. 21, 2010, pp. 2514-2521.

European Patent Office, Extended European Search Report, EP Application No. 20739043.6, Jan. 5, 2023, 10 pages.

Examination Report No. 1, Australian Application No. 20183221141, Sep. 27, 2022, 7 pages.

Japan Patent Office, Office Action, JP Patent Application No. 2020-532853, Jul. 4, 2022, 6 pages.

Nawaz et al."Acoustofluidic Fluorescence Activated Cell Sorter" Analytical Chemistry (Year: 2015).

Notice of Preliminary Rejection, Korean Application No. 10-2020-7008309; Jan. 2, 2023 (with English translation), 8 pages.

Rospatent, Office Action, RU Patent Application No. 2020111806, Jun. 24, 2022, 20 pages.

Wang et al "Microfluidic Platform with Multiplexed Electronic Detection for Spatial Tracking of Particles". Jove Journal (Year: 2017).

PCT International Search Report and Written Opinion, International Application No. PCT/US2020/012627, dated May 28, 2020, 23 Pages.

Plamann, Michael D., et al., "Complete nucleotide sequence of the *E. coli* glyA gene," vol. 11, No. 7, 1983 Nucleic Acids Research.

* cited by examiner

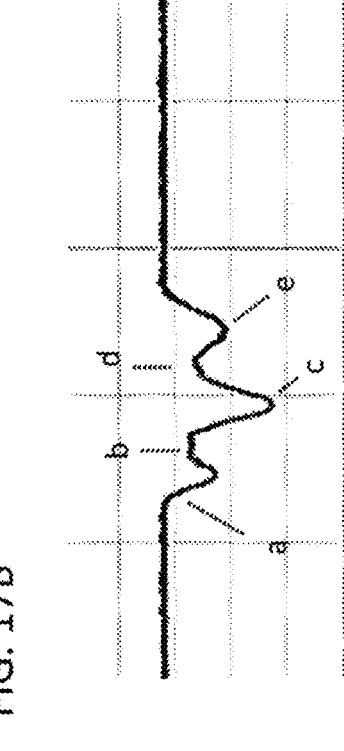
FIG. 17A
FIG. 17B
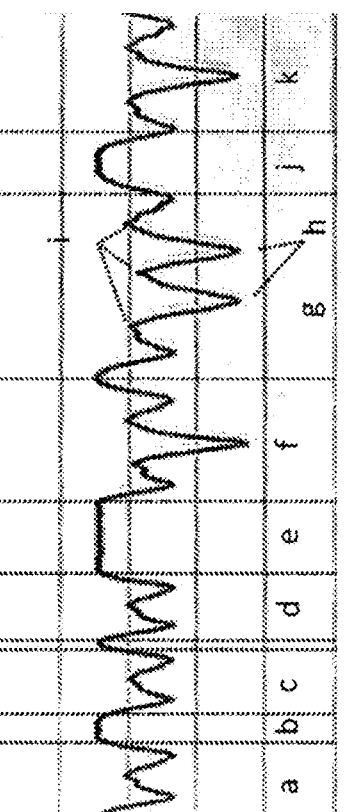
FIG. 17C

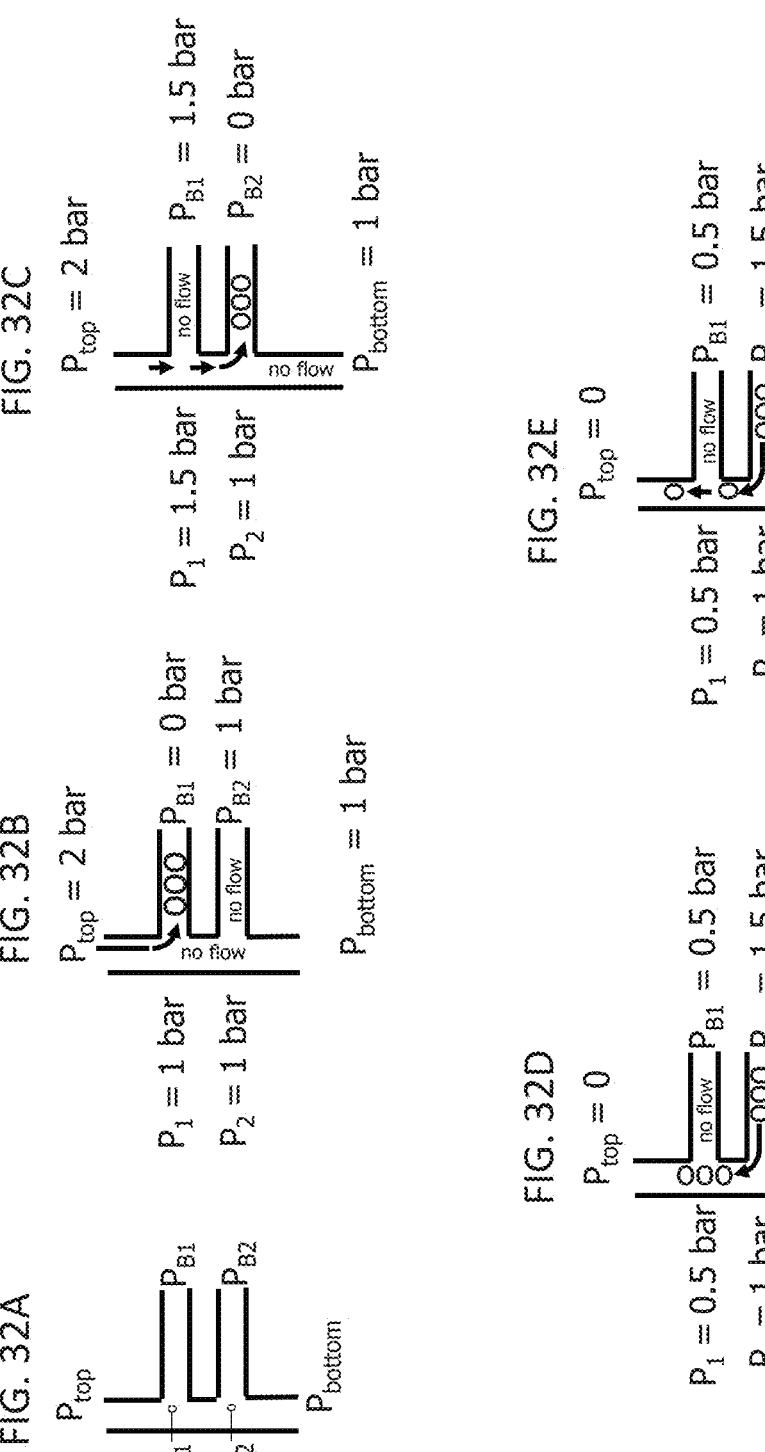

SPACE/RE-STACK DEMONSTRATED WITH > 5000 BEADS

DEMONSTRATES IMPORTANT BEAD MANIPULATIONS, EXCLUDING SORTING. >5000 BEADS AND >500 CYCLES WITHOUT PERMANENT JAMS

ACTUAL DEVICE

DEVICE SCHEMATIC

PARTIAL RE-STACK SHOWN. BEADS FULLY STACK AT SUBSEQUENT BEAD STOP.

STEERING - SINGLE BRANCH

- BEADS WERE SPACED PRIOR TO SORTING WITH AN "INLINE" SPACER, THEN FLUID PRESSURE WAS APPLIED TO CHANNEL ONE OR CHANNEL TWO, TO SORT BEADS BETWEEN TWO OUTPUT LEGS OF BIFURCATION.

CHANNEL 1 (PUSH DOWN)

10μm SLIT

CHANNEL 2 (PUSH UP)

Y-JUNCTION

BEAD STACK

BEAD STOP

INLINE SPACER

SORTER

METHODS OF USING MICROFLUIDIC POSITIONAL ENCODING DEVICES

CROSS-REFERENCE TO RELATED APPLICATIONS

This application is the National Stage of International Application No. PCT/US2020/012627, filed Jan. 7, 2020, which claims the benefit of and priority to U.S. Provisional Application Nos. 62/789,505, filed Jan. 7, 2019, 62/789,506 filed on Jan. 7, 2019, 62/810,196 filed on Feb. 25, 2019, 62/811,506 filed on Feb. 27, 2019, and 62/863,712 filed on Jun. 19, 2019, all of which are incorporated by reference in their entirety.

BACKGROUND OF THE INVENTION

In biology, chemistry, and other areas it is often desirable to both create large collections of chemical compounds or products and to evaluate the characteristics, properties, performance, or utility of these products. Historically, individual products were manufactured and characterized in separate vessels. Batch type procedures have been developed and disclosed that enable production of multiple products at a time. However, due to the cost, space requirements, and physical manipulations required, there has been a long-standing desire to develop alternative methods that can produce or evaluate very large libraries of products. Approaches such as split synthesis require encoding, randomness, redundancy, and underrepresentation problems in libraries. It can be time consuming, costly, or laborious to discover the identity of the product of interest associated with a unit. Further, encoding approaches have challenges relating to cost effectiveness, scalability, speed, and accuracy.

Since the advent of PCR in 1983, the uses of customized synthetic DNA have exploded to include a rich array of applications that impact the health of millions. Among these are noninvasive prenatal tests for fetal trisomies, tests for carriers of inherited diseases, and tests that allow the selection of the cancer treatments. Synthetic DNA is also a critical input into the development of therapeutic RNAs, aptamers, and antibodies, as well as gene editing. However, orders of large numbers of DNA fragments from existing DNA suppliers result in wait-times of days and sometimes many weeks. This latency results in enormous hidden financial and opportunity costs, and fundamentally slows the pace of development of new diagnostics and therapeutics.

Therefore, there is a need for a novel microfluidic technology to enable the rapid, massively parallel, cost-efficient synthesis of nucleic acids that is able to produce thousands of high-quality nucleic acid fragments in hours. Giving scientists access to one to thousands of nucleic acid fragments, nearly on demand, stands to dramatically accelerate the pace development of new diagnostics and therapeutics, lower cost by increasing overall productivity, and open up new research paradigms based on rapid design iteration that were not previously feasible.

SUMMARY OF THE INVENTION

Disclosed herein are methods and compositions relating to tracking of mobile units within a microfluidic device. In various embodiments, the tracking of mobile units is achieved by controlling or recording the position, e.g. the relative position, of the mobile units, for example as the mobile units are moving through various compartments of the microfluidic device. The tracked mobile units may be split into the channels of a microfluidic device, for example by employing a router, such as a distributor, and recombined. The order of the mobile units upon recombination may be indicative of the path each mobile unit took through the microfluidic device. Individual channels of the microfluidic device may be used to perform reactions, such as synthesis reactions. Such reactions may be performed in parallel. Reagents for each reaction may be delivered to the individual channels, for example via separate reagent delivery channels. Suitable reaction conditions, such as temperature, pressure, and flow rate may be set in the individual channels.

In a first aspect, the methods and compositions described herein relate to tracking of mobile units within a microfluidic device. The tracking may comprise moving k mobile units through a first channel of a microfluidic device in a first order; splitting the k mobile units into z branch channels; and moving the k mobile units into a second channel in a second order.

Each of the k mobile units may be mappable to one of the z branch channels based on the second order. The k mobile units may further be moved from the second channel to the first channel. The second channel may be in fluidic communication with the first channel. The steps of moving k mobile units through a first channel of a microfluidic device in a first order, splitting the k mobile units into z branch channels, and moving the k mobile units into a second channel in a second order may be repeated n times. In some embodiments, n is or is at least 2, 3, 4, 5, 6, 7, 8, 9, 10, 15, 20, 30, 40, 50, 60, 75, 100, 150, 200, 300, 400, 500, 750, 1000, or more. In some embodiments, n is 2. In some embodiments, n is 3, 4, 5, 6, 7, 8, 9, 10, 15, 20, 30, 40, 50, 60, 75, 100, 150, 200, 300, 400, 500, 750, 1000, or more. The mobile units may be beads, droplets, cells, bubbles, slugs or immiscible volumes. The beads may comprise glass or silica beads, metal beads, hydrogel or polymer beads, or chemically resistant polymer beads. The microfluidic device may comprise at least i channels having a largest cross-section no greater than x times the mean cross-section of the mobile units. In some embodiments, x is or is less than 2, 1.9, 1.8, 1.7, 1.6, 1.5, 1.4, 1.3, 1.2, 1.1, 1.05, 1.02, 1.01, or 1. In some embodiments, i is or is greater than 2, 3, 4, 5, 10, 20, 50, 100, 1000, 5000, or 10000. The microfluidic device may comprise at least j channels having a largest cross-section no greater than 500, 400, 300, 250, 200, 150, 100, 90, 75, 70, 65, 60, 55, 50, 45, 40, 35, 30, 25, 20, 15, or 10 micrometers. In some embodiments, j is or is greater than 2, 3, 4, 5, 10, 20, 50, 100, 1000, 5000, or 10000. In some embodiments, the cross-section coefficient of variation for the k mobile units is or is less than 20%, 19%, 18%, 17%, 16%, 15%, 14%, 13%, 12%, 11%, 10%, 9%, 8%, 7%, 6%5, 5% 4%, 3%, 2%, 1%, or less. In some embodiments, a different set of reagents is delivered to each of a subset or all of the z branch channels. The one or more sets of reagents may comprise a 2'-deoxynucleoside phosphoramidite. The first order or the second order may be predetermined. In some embodiments, z is or is more than 2, 3, 4, 5, 6, 7, 8, 9, 10, 20, 30, 50, or more. Each of a subset or all of the z branch channels may comprise valves at one or both ends. One or more reagent channels may be configured to deliver reagents to each of a subset or all of the z branch channels. The delivery of reagents from at least one of the one or more reagent channels may be controlled by a valve. In some embodiments, k is or is greater than 2, 3, 4, 5, 6, 7, 8, 9, 10, 20, 30, 50, 100, 500, 1000, 10000, 50000, 100000, 500000, or 1000000. In some embodiments, k is or is less than 5000000, 1000000, 500000, 100000, 50000, 10000, 1000, 500, 100, 50, 30, 20, or less. In some embodiments, k is between 2 and 500.

In a second aspect, the methods and compositions described herein relate to a microfluidic device and uses thereof. The microfluidic device may comprise a first channel in fluidic communication with a set of z branch channels, wherein the set of z branch channels may be configured to accept mobile units from the first channel in a first order; and a second channel in fluidic communication with the set of z branch channels, wherein the second channel may be configured to accept mobile units from the set of z branch channels in a second order. The first or the second order may be controllable. The second order may be determinative of the particular channel of the set of z branch channels that is configured to deliver a mobile unit in the second order. The microfluidic device may comprise k mobile units. The microfluidic device may comprise a router, e.g. a distributor, between the first channel and the set of z branch channels. In some embodiments, z is or is greater than 2, 3, 4, 5, 6, 7, 8, 9, 10, 20, 30, 50, or more. In some embodiments, k is or is greater than 2, 3, 4, 5, 6, 7, 8, 9, 10, 20, 30, 50, 100, 500, 1000, 10000, 50000, 100000, 500000, 1000000, or more. In some embodiments, k is or is less than 5000000, 1000000, 500000, 100000, 50000, 10000, 1000, 500, 100, 50, 30, 20, or less. In some embodiments, k is between 2 and 500.

In a third aspect, the methods and compositions described herein relate to a microfluidic device comprising k mobile units, wherein a different compound is associated with each of the k mobile units and wherein the synthesis history of each of the different compounds associated with the k mobile units is determinable based on the configuration of the k mobile units in the microfluidic device. The microfluidic device may further comprise i fiducial marks. The configuration of the k mobile units may depend on the relative position of j mobile units with respect to the i fiducial marks. In some embodiments, i is or is greater than 1, 2, 3, 4, 5, 6, 7, 8, 9, 10, or more. In some embodiments, j is or is greater than 1, 2, 3, 4, 5, 6, 7, 8, 9, 10, or more. In some embodiments, k is or is greater than 2, 3, 4, 5, 6, 7, 8, 9, 10, 20, 30, 50, 100, 500, 1000, 10000, 50000, 100000, 500000, 1000000, or more.

A fourth aspect of the methods and compositions described herein relates to a system comprising computer comprising a computer-readable medium; and a microfluidic device comprising k mobile units, wherein a different compound is associated with each of the k mobile units and wherein the synthesis history of each of the different compounds associated with the k mobile units is determinable based on the configuration of the k mobile units in the microfluidic device; wherein the computer is configured to record data associated with the position of the k mobile units in the computer-readable medium repeatedly.

A fifth aspect of the methods and compositions described herein relates to a system comprising a computer comprising a computer-readable medium and a microfluidic device. The microfluidic device may comprise a first channel in fluidic communication with a set of z branch channels, wherein the set of z branch channels is configured to accept mobile units from the first channel in a first order; and a second channel in fluidic communication with the set of z branch channels, wherein the second channel is configured to accept mobile units from the set of z branch channels in a second order. The second order may be determinative or predictive of the particular channel of the set of z branch channels that is configured to deliver a mobile unit in the second order. The computer may be configured to record data associated with the position of the mobile units in the computer-readable medium repeatedly.

In a sixth aspect, the methods and compositions described herein relate to routing of mobile units within a microfluidic device. The method may comprise a) routing k mobile units through a first channel of a microfluidic device in a first order; b) distributing the k mobile units into z branch channels; and c) routing the k mobile units into a second channel in a second order. The routing in step a may be performed in accordance with a predetermined unit routing algorithm through the microfluidic device for at least a subset of the k mobile units. The unit routing algorithm may comprise a routing selection at at least one branch point of the microfluidic device. At least a subset or all of the k mobile units may be mappable to a path comprising a specific one of the z branch channels. At least a subset or all of the k mobile units may be mappable to a path comprising a specific one of the z branch channels based on unit tracking information from at least one detector configured to track the movement of mobile units inside the microfluidic device. At least a subset or all of the k mobile units may be mappable to a path comprising a specific one of the z branch channels based on the second order. At least a subset of the k mobile units in step c may comprise all of the k mobile units. The first channel and the second channel may be the same. Between steps b and c, the flow direction of at least a subset of the k mobile units may be reversed. In step b, at least one unit may be routed into a first branch channel through a first branch channel end and in step c, the at least one unit may be routed out of the first branch channel through the first branch channel end. In step b, at least one unit may be routed into a first branch channel through a first branch channel end and, in step c, the at least one unit may be routed out of the first branch channel through a second branch channel end that is different than the first branch channel end. The method may further comprise routing the k mobile units from the second channel to the first channel. The second channel may be in fluidic communication with the first channel. The method may further comprise repeating steps a-c n times. n may be 2. n may be 2 to 10. n may be 10 to 100. n may be 100 to 1000. n may be 3, 4, 5, 6, 7, 8, 9, 10, 15, 20, 30, 40, 50, 60, 75, 100, 150, 200, 300, 400, 500, 750, 1000, or more. n may be at least or at least about 2, 3, 4, 5, 6, 7, 8, 9, 10, 15, 20, 30, 40, 50, 60, 75, 100, 150, 200, 300, 400, 500, 750, 1000, or more. Units may be beads. The mobile units may be selected from the group consisting of beads, droplets, cells, bubbles, slugs and immiscible volumes. The beads comprise glass beads or polymer beads. The microfluidic device may comprise i channels having a largest cross-section x times the mean cross-section of the k mobile units. i may be 2-10000. x may be 1.05-2.0. i may be 2-100. i may be 100-1000. The microfluidic device may comprise at least i channels having a largest cross-section no greater than x times the mean cross-section of the k mobile units. The mobile units may be beads. x may be or may be less than 2, 1.9, 1.8, 1.7, 1.6, 1.5, 1.4, 1.3, 1.2, 1.1, 1.05, or less. X may be or may be more than 1.05, 1.1, 1.2, 1.3, 1.4, 1.5, 1.6, 1.7, 1.8, 1.9, 2, or more. i may be or may be more than 2, 3, 4, 5, 10, 20, 50, 100, 1000, 5000, 10000, or more. The microfluidic device may comprise at least j channels having a largest cross-section no greater than 200 micrometers. j may be 2 to 10000. The largest cross-section of the at least j channels may be no greater than 10 micrometers. The microfluidic device may comprise at least j channels having a largest cross-section no greater than 200 micrometers. j may be 2, 3, 4, 5, 10, 20, 50, 100, 500, 1000, 5000, 10000, or more. The cross-section coefficient of variation for the k mobile units may be 1% to 20%. The cross-section coefficient of variation for the k mobile units may be 2% to 5%. The cross-section coefficient of variation for the k mobile units may be less than 20%, 19%, 18%, 17%, 16%, 15%, 14%, 13%, 12%, 11%, 10%, 9%, 8%, 7%, 6%, 5%, 4%, 3%, 2%, 1%, or less. The method may further comprise delivering different reagents to each of the z branch channels. The reagents may comprise a 2'-deoxynucleoside phosphoramidite. The method may further comprise directing at least one mobile units into a side channel. The method may further comprising directing the at least one mobile units in the side channel to the second channel. The first order may be predetermined. The second order may be predetermined. z may be 2-10 z may be 10-100. z may be 100-1000. z may be at least 1, 2, 3, 4, 5, 6, 7, 8, 9, 10, 20, 30, 50, 100, or more. z may be less than 100, 50, 30, 20, 10, 9, 8, 7, 6, 5, 4, 3, 2, or less. Each of the z branch channels may be capped by valves or unit stops on one or two ends. One or more reagent channels may be configured to deliver reagents to each of the z branch channels. Delivery of reagents from at least one of the one or more reagent channels may be controlled by a valve. Delivery of reagents from at least one of the one or more reagent channels may be controlled by application of differential pressures to selected points in the z branch channels and the reagent channels. k may be between 2 and 1000000. k may be 2-5000000. k may be 20-100. k may be 100-1000. k may be 10000-100000. k may be 100000-1000000. k may be between 2 and 500. K may be at least 2, 3, 4, 5, 6, 7, 8, 9, 10, 20, 30, 50, 100, 500, 1000, 10000, 50000, 100000, 500000, 1000000, or more. k may be less than 5000000, 1000000, 500000, 100000, 50000, 10000, 1000, 500, 100, 50, 30, or 20. At least one mobile unit may comprise a label. The position of the at least one mobile unit in the second order may be verified using the at least one unit's label. At least one mobile unit may comprise a label. The position of the at least one mobile unit in the first order may be verified using the at least one unit's label. The at least one mobile unit may comprise at least two mobile units. The labels of the at least two mobile units may be not unique.

In a seventh aspect, the methods and compositions described herein relate to a microfluidic device comprising: a) a first channel in fluidic communication with a set of z branch channels, wherein the set of z branch channels is configured to accept mobile units from the first channel in a first order; and b) a second channel in fluidic communication with the set of z branch channels, wherein the second channel is configured to accept mobile units from the set of z branch channels in a second order; wherein the second order is determinative of the particular branch channel of the set of z branch channels that is configured to deliver a mobile unit in the second order. The first order or the second order may be controllable. The device may further comprise k mobile units. The device may further comprise a distributor between the first channel and the set of z branch channels. z may be between 2 and 50. z may be at least 2, 3, 4, 5, 6, 7, 8, 9, 10, 20, 30, 50, or more. z may be less than 50, 30, 20, 10, 9, 8, 7, 6, 5, 4, 3, 2, or less. k may be between 2 and 500. k may be between 2 and 5000000. k may be at least 2, 3, 4, 5, 6, 7, 8, 9, 10, 20, 30, 50, 100, 500, 1000, 10000, 50000, 100000, 500000, 1000000, 5000000, or more. k may be less than 5000000, 1000000, 500000, 100000, 50000, 10000, 1000, 500, 100, 50, 30, 20, 10, 9, 8, 7, 6, 5, 4, 3, 2, or less.

In an eight aspect, the methods and compositions described herein relate to a microfluidic device comprising k mobile units, wherein a different compound is associated with each of the k mobile units and wherein a synthesis history of each of the different compounds associated with the k mobile units is determinable based on the configuration of the k mobile units in the microfluidic device.

In a ninth aspect, the methods and compositions described herein relate to a microfluidic device comprising k mobile units, wherein a different compound is associated with each of the k mobile units and wherein a treatment history for each of the k mobile units is determinable based on the configuration of the k mobile units in the microfluidic device. The treatment history may comprise a light treatment history, a heat treatment history, an enzymatic treatment history, a cleavage treatment history, an isomerization history, an acetylation history, a synthesis history, an amplification history, or a reaction history. The microfluidic device may further comprise i fiducial marks. The configuration of the k mobile units may depend on the relative position of j mobile units with respect to the i fiducial marks. i may be 1, 2, 3, 4, 5, 6, 7, 8, 9, 10, or more. i may be less than 10, 9, 8, 7, 6, 5, 4, 3, 2, or less. j may be 1, 2, 3, 4, 5, 6, 7, 8, 9, 10, or more. j may be less than 10, 9, 8, 7, 6, 5, 4, 3, 2, or less.

In a tenth aspect, the methods and compositions described herein relate to a system comprising a) a computer comprising a computer-readable medium; and b) a microfluidic device comprising k mobile units, wherein a different compound is associated with each of the k mobile units and wherein a treatment history of each of the different compounds associated with the k mobile units is determinable based on the configuration of the k mobile units in the microfluidic device; wherein the computer is configured to record data associated with the position of the k mobile units in the computer-readable medium repeatedly. The treatment history may comprise a light treatment history, a heat treatment history, an enzymatic treatment history, a cleavage treatment history, an isomerization history, an acetylation history, a synthesis history, an amplification history, or a reaction history.

In an eleventh aspect, the methods and compositions described herein relate to a system comprising: a) a computer comprising a computer-readable medium; and b) a microfluidic device comprising i) a first channel in fluidic communication with a set of z branch channels, wherein the set of z branch channels is configured to accept mobile units from the first channel in a first order; ii) a second channel in fluidic communication with the set of z branch channels, wherein the second channel is configured to accept mobile units from the set of z branch channels in a second order; wherein the second order is determinative of the particular channel of the set of z branch channels that is configured to deliver a mobile unit in the second order; and wherein the computer is configured to record data associated with the position of the mobile units in the computer-readable medium repeatedly.

In a twelfth aspect, the methods and compositions described herein relate to a method of tracking, the method comprising: a) moving k mobile units through a first channel of a microfluidic device in a first order; b) routing at least a subset of the k mobile units within the microfluidic device, thereby creating a second order; c) performing a comparison of the second order to a predesignated post-routing order; and d) separating j mobile units into a correction area based on the comparison of step c by separating the j mobile units from a remainder of the at least a subset of the k mobile units; wherein each of the remainder of the at least a subset of the k mobile units is mappable to a routing path. The routing path may comprise the location of a mapped mobile unit after the routing step in step b. The routing path may comprise the location of a mapped mobile unit before the routing step in step b. The location of a mobile unit may comprise the unit's relative positional order with respect to m mapping mobile units. M may be at least 1, 2, 3, 4, 5, 6, 7, 8, 9, 10, 20, 30, 40, 50, 100, or more. m may be less than 100, 90, 80, 70, 60, 50, 40, 30, 20, 10, 9, 8, 7, 6, 5, 4, 3, 2, or less. The m mapping mobile units may comprise the m closest mobile units to the mapped mobile unit along a fluidically connected path originating from the mapped mobile unit. Routing may comprise distributing into at least one branch channel of the microfluidic device. Routing may comprise merging from a plurality of branch channels of the microfluidic device. The correction area may comprise a channel of the microfluidic device. The method may further comprise merging at least one of the j mobile units with at least a subset of the remainder of the at least a subset of the k mobile units. k may be between 2 and 500. k may be between 2 and 100000. k may be at least 2, 3, 4, 5, 6, 7, 8, 9, 10, 20, 30, 50, 100, 500, 1000, 10000, 50000, 100000, 500000, 1000000, or more. k may be less than 5000000, 1000000, 500000, 100000, 50000, 10000, 1000, 500, 100, 50, 30, 20, 10, 9, 8, 7, 6, 5, 4, 3, 2, or less. At least one mobile unit may comprise a label. The position of the at least one mobile unit in the second order may be verified using the at least one unit's label. At least one mobile unit of the k mobile units may comprise a label. The position of the at least one mobile unit in the first order may be verified using the at least one unit's label. The at least one mobile unit may comprise at least two mobile units. The labels of the at least two mobile units may be not unique. j may be between 1 and 1000000. j may be at least 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 10000, 100000, 1000000, or more. j may be less than 1000000, 100000, 10000, 1000, 900, 800, 700, 600, 500, 400, 300, 200, 100, 90, 80, 7, 60, 50, 40, 30, 20, 19, 18, 17, 16, 15, 14, 13, 12, 11, 10, 9, 8, 7, 6, 5, 4, 3, 2, or less. The method may further comprise repeating steps a-c n times. n may be 2. n may be 3, 4, 5, 6, 7, 8, 9, 10, 15, 20, 30, 40, 50, 60, 75, 100, 150, 200, 300, 400, 500, 750, 1000, or more. n may be at least 2, 3, 4, 5, 6, 7, 8, 9, 10, 15, 20, 30, 40, 50, 60, 75, 100, 150, 200, 300, 400, 500, 750, 1000, or more. n may be less than 100, 750, 500, 400, 300, 200, 150, 100, 75, 60, 50, 40, 30, 20, 15, 10, 9, 8, 7, 6, 5, 4, 3, 2, or less. The mobile units may be selected from the group consisting of beads, droplets, cells, bubbles, slugs and immiscible volumes. Beads may comprise glass beads or polymer beads. The comparison in step c may comprise verifying by at least one detector the position of at least one unit in the first order. The comparison in step c may comprise verifying by at least one detector the position of at least one unit in the second order. The comparison in step c may comprise counting units by at least one detector after the routing in step b is performed on one or more units, thereby generating a list of unit counts, and comparing the list of unit counts to an expected list of unit counts based on the predesignated post-routing order. The comparison in step c may comprise detecting one or more labels on one or more units by at least one detector after the routing in step b is performed on one or more units, thereby generating a list of detected unit labels, and comparing the list of detected unit labels to an expected list of unit labels based on the predesignated post-routing order.

In a thirteenth aspect, the methods and compositions described herein relate to a system comprising a) a microfluidic channel configured to carry beads in a carrier fluid; b)

a detector configured to detect signals from a detection path through the microfluidic channel; and c) computer operably connected to the detector; wherein the system is calibrated to identify the signal of an isolated single bead in the microfluidic channel passing through the detection path. The system may be further calibrated to identify the signal of n adjacent beads in the microfluidic channel passing through the detection path. n may be 2 to 100. n may be at least 2, 3, 4, 5, 6, 7, 8, 9, 10, 11, 12, 13, 14, 15, 16, 17, 18, 19, 20, 30, 40, 50, 60, 70, 80, 90, 100, or more. n may be less than 100, 90 80, 70, 60, 50, 40, 30, 20, 19, 18, 17, 16, 15, 14, 13, 12, 11, 10, 9, 8, 7, 6, 5, 4, 3, 2, or less. The system may be further calibrated to identify the signal of a gas bubble or a dust particle in the microfluidic channel passing through the detection path. The system may further comprise a router configured to route one or more beads from the microfluidic channel. The system may be configured to send a desired routing signal to the router to effectuate routing upon identification of an isolated single bead, a plurality of adjacent beads, a gas bubble or dust particle passing through the detection path. The router may comprise a distributor. The system may further comprise a bead spacer. The bead spacer may be configured to space beads flowing adjacently within the microfluidic channel. The system may further comprise a second microfluidic channel. The router may be configured to route beads into the second microfluidic channel. The router may comprise a merger.

In a fourteenth aspect, the methods and compositions described herein relate to a microfluidic device comprising: a) a primary channel; b) a branch point; c) a first branch channel, wherein the first branch channel is fluidically connected to the primary channel through the branch point; and d) a first router configured to route units flowing in the primary channel into the first branch channel. The first router may be configured to route units from the primary channel into the first branch channel by causing a pressure differential between one or more locations within the primary channel and a location within the first branch channel. The device may further comprise a second branch channel, wherein the second branch channel is fluidically connected to the primary channel through the branch point. The first router may be configured to route units from the primary channel into the first branch channel by causing a pressure differential between one or more locations within the primary channel, a location within the first branch channel, and a location within the second branch channel. The first router may be configured to route units from the primary channel into the second branch channel by causing a pressure differential between one or more locations within the primary channel, a location within the first branch channel, and a location within the second branch channel. The device may further comprise z branch channels. The first router may be configured to route units from the primary channel into the first branch channel by causing a pressure differential between one or more locations within the primary channel and a location within the first branch channel, and pressure differentials between one or more locations within the primary channel and a location within each of the z branch channels. The router may comprise a network of fluidic outlets configured to connect to pressure controllers, such that the router is capable to regulate the fluidic pressure within channels that are connected through the branch point. The branch channels may connect to the primary channel at separate positions of the primary channel. The device may further comprise a second router configured to route units from at least one of the branch channels to the primary channel. The first router may comprise the second router. The second router may comprise a merger.

In a fifteenth aspect, the methods and compositions described herein relate to a microfluidic device comprising a microfluidic channel holding k mobile units wherein the microfluidic device is configured to maintain the relative positional order of the k mobile units and wherein the microfluidic channel is configured to flow the k mobile units in a carrier fluid. There may be a distance greater than a minimum distance between each pair of the k mobile units measured along a path of fluidic connection. The minimum distance may be at least 1.5 times the mean diameter of the pair of the k mobile units. The minimum distance may be 2 to 10000 times the mean diameter of the pair of the k mobile units. The minimum distance may be at least 2, 3, 4, 5, 6, 7, 8, 9, 10, 15, 20, 100, 1000, 5000, 10000, or more times the mean diameter of the pair of the k mobile units. The minimum distance may be less than 10000, 5000, 1000, 100, 20, 15, 10, 9, 8, 7, 6, 5, 4, 3, 2, times the mean diameter of the pair of the k mobile units, or less. The width of the microfluidic channel may be at least 2 times the average diameter of the k mobile units. The width of the microfluidic channel may be at least 2.5, 3, 4, 5, 6, 7, 8, 9, 10, 20, 30, 40, 50, 60, 70, 80, 90, 100, 1000, 10000 times the average diameter of the k mobile units or more. The width of the microfluidic channel may be less than 50000, 10000, 1000, 100, 90, 80, 70, 60, 50, 50, 30, 20, 10, 9, 8, 7, 6, 5, 4, 3, 2.5, 2 times the average diameter of the k mobile units or less.

In a sixteenth aspect, the methods and compositions described herein relate to a method of separating beads in a microfluidic device, the method comprising: a) providing a microfluidic device comprising a first microfluidic channel and a second channel, wherein the first microfluidic channel and the second channel are connected by a bead spacer; b) moving a plurality of beads through the first microfluidic channel toward the bead spacer; c) passing a first bead and a second bead serially through the bead spacer into the second channel; and d) moving a carrier fluid through the second channel such that a desired length of carrier fluid is spaced between the first bead and the second bead in the second channel. Steps a-d may be repeated at least n times. n may comprise 2 to 1000000. n may be at least 2, 3, 4, 5, 6, 7, 8, 9, 10, 20, 30, 40, 50, 100, 500, 1000, 5000, 10000, 100000, 1000000, or more. n may be at most 10000000, 1000000, 100000, 10000, 5000, 1000, 500, 100, 50, 40, 30, 20, 10, 9, 8, 7, 6, 5, 4, 3, 2, or less. The plurality of beads may comprise 2 to 1000000 beads. The plurality of beads may comprise at least 2, 3, 4, 5, 6, 7, 8, 9, 10, 20, 30, 40, 50, 100, 500, 1000, 5000, 10000, 100000, 1000000, or more beads. The plurality of beads may comprise at most 1000000, 100000, 10000, 5000, 1000, 500, 100, 50, 40, 30, 21, 10, 9, 8, 7, 6, 5, 4, 3, 2, or fewer beads. The desired length of carrier fluid may be 1 to 1000 times the average size of the plurality of beads. The desired length of carrier fluid may be at least 1, 2, 3, 4, 5, 6, 7, 8, 9, 10, 20, 25, 30, 40, 50, 100, 200, 300, 400, 500, 600, 700, 800, 900, or 1000 times the average size of the plurality of beads, or greater. The desired length of carrier fluid may be at most 10000, 1000, 900, 800, 700, 600, 500, 400, 300, 200, 100, 50, 40, 30, 25, 20, 10, 9, 8, 7, 6, 5, 4, 3, 2, or 1 times the average size of the plurality of beads, or less. The plurality of beads may comprise 2 to 1000000 beads. The plurality of beads may comprise at least 2, 3, 4, 5, 6, 7, 8, 9, 10, 20, 30, 40, 50, 100, 500, 1000, 10000, 50000, 100000, 500000, 1000000, or more beads. The plurality of beads may comprise at most 10000000, 1000000, 500000, 100000, 50000, 10000, 1000, 500, 100, 50, 40, 30, 20, 10, 9, 8, 7, 6, 5, 4, 3, 2, or fewer beads. The first channel width may be 1 to 2 times the average diameter of the beads. The first channel width may be less than 2, 1.9, 1.8, 1.7, 1.6, 1.5, 1.4, 1.3, 1.2, 1.1, 1.05, or 1.01 times the average diameter of the beads, or less. The first channel width may be more than 1.01, 1.05, 1.1, 1.2, 1.3, 1.4, 1.5, 1.6, 1.7, 1.8, 1.9, 2 times the average diameter of the beads, or more. The second channel width may be 1.01 and 100 times the average diameter of the beads. The second channel width may be at least 1.01, 1.05, 1.1, 1.2, 1.3, 1.4, 1.5, 1.6, 1.7, 1.8, 1.9, 2, 2.5, 3, 4, 5, 6, 7, 8, 9, 10, 20, 30, 40, 50, 60, 70, 80, 90, or 100 times the average diameter of the beads, or greater. The second channel width may be at most 1000, 100, 90, 80, 70, 60, 50, 40, 30, 20, 10, 9, 8, 7, 6, 5, 4, 3, 2, 1.9, 1.8, 1.7, 1.6, 1.5, 1.4, 1.3, 1.2, 1.1, 1.05, or 1.01 times the average diameter of the beads, or smaller. The carrier fluid speed may be less than 50 meters/ sec, 10 meters/sec, 1 meters/sec, 100 millimeters/sec, 10 millimeters/sec, 11 millimeters/sec, 0.1 millimeters/sec, or 0.01 millimeters/sec, or less. The carrier fluid speed may be at least 0.01, 0.1, 1, 10, 100 millimeters/sec, 1, 10, or 50 meters/sec, or more. The first and the second bead may be passed through the bead spacer within less than 10 sec, 1 sec, 0.1 sec, 0.01 sec, 1 msec, 0.1 msec, or 0.01 msec, or faster.

In a seventeenth aspect, the methods and compositions described herein relate to a microfluidic device comprising a microfluidic channel holding k mobile units wherein the microfluidic device is configured to maintain the relative positional order of the k mobile units and wherein the microfluidic channel is configured to flow the k mobile units in a carrier fluid. The width of the microfluidic channel may be 0.05 to 2 times the average diameter of the k mobile units measured outside of the microfluidic channel. The width of the microfluidic channel may be less than 2, 1.9, 1.8, 1.7, 1.6, 1.5, 1.4, 1.3, 1.2, 1.1, 1.05, 1.01, 1, 0.95, 0.9, 0.8, 0.7, 0.6, 0.5, 0.4, 0.4, 0.3, 0.2, 0.1, or 0.05 times the average diameter of the k mobile units measured outside of the microfluidic channel, or smaller. The width of the microfluidic channel is more than 0.05, 0.1, 0.2, 0.3, 0.4, 0.5, 0.6, 0.7, 0.8, 0.9, 0.95, 1, 1.01, 1.1, 1.2, 1.3, 1.4, 1.5, 1.6, 1.7, 1.8, 1.9, or 1.95 times the average diameter of the k mobile units measured outside of the microfluidic channel, or greater. The device may be configured to move the k mobile units within the microfluidic channel along a moving direction of the microfluidic channel. There may be a center to center distance between adjacent pairs of k mobile units within the microfluidic channel along the moving direction of the microfluidic channel of less than 2 times the average diameter of the k mobile units. The center to center distance may be 0.01 to 1.9 times the average diameter of the k mobile units. The center to center distance may be less than 1.9, 1.8, 1.7, 1.6, 1.5, 1.4, 1.3, 1.2, 1.1, 1, 0.9, 0.8, 0.7, 0.65. 0.6, 0.55, 0.5, 0.4, 0.3, 0.2, 0.1, 0.05, or 0.01 times the average diameter of the k mobile units, or less. The center to center distance may be greater than 0.01, 0.05, 0.1, 0.2, 0.3, 0.4, 0.5, 0.55, 0.6, 0.65, 0.7, 0.8, 0.9, 1, 1.1, 1.2, 1.3, 1.4, 1.5, 1.6, 1.7, 1.8, 1.9, or 2 times the average diameter of the k mobile units, or greater. The device may be configured to move the k mobile units within the microfluidic channel along a moving direction of the microfluidic channel. The shortest distance between adjacent pairs of k mobile units within the microfluidic channel along the moving direction of the microfluidic channel may be less than 2, 1.9, 1.8, 1.7, 1.6, 1.5, 1.4, 1.3, 1.2, 1.1, 1, 0.9, 0.8, 0.7, 0.65. 0.6, 0.55, 0.5, 0.4, 0.3, 0.2, 0.1, 0.05, or 0.01 times the average diameter of the k mobile units as measured outside of the microfluidic channel, or smaller. The shortest distance between adjacent pairs of k mobile units within the microfluidic channel along the moving direction of the microfluidic channel may be greater than 0.01, 0.05, 0.1, 0.2, 0.3, 0.4, 0.5, 0.55, 0.6, 0.65, 0.7, 0.8, 0.9, 1, 1.1, 1.2, 1.3, 1.4, 1.5, 1.6, 1.7, 1.8, 1.9, or 2 times the average diameter of the k mobile units as measured outside of the microfluidic channel, or greater. The maximum deviation from the average width of the microfluidic channel may be less than 20%, 15%, 10%, 5%, 4%, 3%, 2%, 1%, 0.10%, or less. The maximum deviation from the average width of the microfluidic channel may be more than 0.1%, 1%, 2%, 3%, 4%, 5%, 10%, 15%, 20%, or more. The coefficient of variance in the diameter of the k mobile units may be less than 10%, 9%, 8%, 7%, 6%, 5%, 4%, 3%, 2%, 1%, or less. The coefficient of variance in the diameter of the k mobile units is more than 1%, 2%, 3%, 4%, 5%, 6%, 7%, 8%, 9%, or 10%.

In an eighteenth aspect, the methods and compositions described herein relate to a microfluidic device comprising k mobile units, wherein the coefficient of variance in the diameter of the k mobile units is less than 10%, 9%, 8%, 7%, 6%, 5%, 4%, 3%, 2%, 1%, or less. The coefficient of variance in the diameter of the k mobile units may be more than 1%, 2%, 3%, 4%, 5%, 6%, 7%, 8%, 9%, 10%, or more.

In a nineteenth aspect, the methods and compositions described herein relate to a method of sorting, the method comprising: a) providing k mobile units; b) introducing the k mobile units into a unit size sorter; c) separating a subset of k mobile units having sizes falling outside of a predetermined range of unit size from the remainder of the k mobile units; and d) introducing at least a subset of the remainder of the k mobile units into a microfluidic device. The upper limit of the predetermined range of unit size may be less than 1.3, 1.25, 1.2, 1.15, 1.14, 1.13, 1.12, 1.11, 1.1, 1.09, 1.08, 1.07, 1.06, 1.05, 1.03, or 1.02 times the lower limit of the predetermined range, or less. The upper limit of the predetermined range of unit size may be more than 1.02, 1.03, 1.05, 1.06, 1.07, 1.08, 1.09, 1.1, 1.11, 1.12, 1.13, 1.14, 1.15, 1.2, 1.25, or 1.3 times the lower limit of the predetermined range, or more.

In a twentieth aspect, the methods and compositions described herein relate to a method of separating units in a microfluidic device, the method comprising: a) providing a microfluidic device comprising a first microfluidic channel and a second channel, wherein the first microfluidic channel and the second channel are connected by a unit spacer; b) moving a plurality of units through the first microfluidic channel toward the unit spacer; c) passing a first unit and a second unit serially through the unit spacer into the second channel; and d) moving a carrier fluid through the second channel such that a desired length of carrier fluid is spaced between the first unit and the second unit in the second channel. The steps a-d may be repeated at least n times. n may be 2 to 1000000. n may be at least 2, 3, 4, 5, 6, 7, 8, 9, 10, 20, 30, 40, 50, 100, 500, 1000, 5000, 10000, 100000, 1000000, or more. n may be at most 10000000, 1000000, 100000, 10000, 5000, 1000, 500, 100, 50, 40, 30, 20, 10, 9, 8, 7, 6, 5, 4, 3, 2, or less. The plurality of units may comprise 2 to 1000000 units. The plurality of units may comprise at least 2, 3, 4, 5, 6, 7, 8, 9, 10, 20, 30, 40, 50, 100, 500, 1000, 5000, 10000, 100000, 1000000 or more units. The plurality of units may comprise at most 1000000, 100000, 100000, 5000, 1000, 500, 100, 50, 40, 30, 20, 10, 9, 8, 7, 6, 5, 4, 3, 2, or fewer units. The desired length of carrier fluid may be 1 to 1000 times the average size of the plurality of units. The desired length of carrier fluid may be at least 1, 2, 3, 4, 5, 6, 7, 8, 9, 10, 20, 25, 30, 40, 50, 100, 200, 300, 400, 500, 600, 700, 800, 900, or 1000 times the average size of the plurality of units, or greater. The desired length of carrier fluid may be at most 10000, 1000, 900, 800, 700, 600, 500, 400, 300, 200, 100, 50, 40, 30, 25, 20, 10, 9, 8, 7, 6, 5, 4, 3, 2, or 1 times the average size of the plurality of units, or smaller. The first channel width may be 1.1 to 2 times the average diameter of the units. The first channel width may be less than 2, 1.9, 1.8, 1.7, 1.6, 1.5, 1.4, 1.3, 1.2, or 1.1 times the average diameter of the units, or smaller. The first channel width may be more than 1.05, 1.1, 1.2, 1.3, 1.4, 1.5, 1.6, 1.7, 1.8, 1.9, 2 times the average diameter of the units, or greater. The second channel width may be 1.05 to 100 times the average diameter of the units. The second channel width may be at least 1.05, 1.1, 1.2, 1.3, 1.4, 1.5, 1.6, 1.7, 1.8, 1.9, 2, 2.5, 3, 4, 5, 6, 7, 8, 9, 10, 20, 30, 40, 50, 60, 70, 80, 90, or 100 times the average diameter of the units, or greater. The second channel width may be at most 1000, 100, 90, 80, 70, 60, 50, 40, 30, 20, 10, 9, 8, 7, 6, 5, 4, 3, 2, 1.9, 1.8, 1.7, 1.6, 1.5, 1.4, 1.3, 1.2, 1.1, or 1.05 times the average diameter of the units, or smaller. The carrier fluid speed may be at least 0.01, 0.1, 1, 10, 100 millimeters/sec, 1, 10, or 50 meters/sec, or faster. The carrier fluid speed may be less than 50 meters/sec, 10 meters/sec, 1 meters/sec, 100 millimeters/sec, 10 millimeters/sec, 11 millimeters/sec, 0.1 millimeters/sec, or 0.01 millimeters/sec, or slower. The first and the second unit may be passed through the unit spacer within 0.01 msec to 10 sec. The first and the second unit may be passed through the unit spacer within less than 10 sec, 1 sec, 0.1 sec, 0.01 sec, 1 msec, 0.1 msec, 0.01 msec, or faster. The microfluidic device may be configured to maintain the relative positional order of the plurality of units. The plurality of units may be selected from the group consisting of beads, droplets, cells, bubbles, slugs and immiscible volumes. Beads may comprise glass beads or polymer beads.

In a twenty first aspect, the methods and compositions described herein relate to a system comprising: a) a computer comprising a computer-readable medium; and b) a microfluidic device comprising r routers and c microfluidic channels in fluidic connectivity, wherein the r routers are configured to route k mobile units through at least a subset of the c microfluidic channels; and c) d detectors operably connected to the computer, wherein the detectors are configured to detect signals from detection paths through the at least c microfluidic channels or the at least r routers; wherein the computer is configured to record data associated with detected signals from the at least d detectors in the computer-readable medium repeatedly and to generate routing paths for at least a subset of the k mobile units. c may be 2 to 1000. c may be at least 2, 3, 4, 5, 6, 7, 8, 9, 10, 11, 12, 13, 14, 15, 16, 17, 18, 19, 20, 30, 32, 40, 48, 50, 60, 64, 70, 72, 80, 90, 96, 100, 200, 300, 400, 500, 600, 700, 800, 900, 1000, or more. c may be at most 10000, 1000, 900, 800, 700, 600, 500, 400, 300, 200, 100, 96, 90, 80, 72, 70, 64, 60, 50, 48, 40, 32, 30, 20, 19, 18, 17, 16, 15, 14, 13, 12, 11, 10, 9, 8, 7, 6, 5, 4, 3, 2 or less. d may be 2 to 1000. d may be at least 2, 3, 4, 5, 6, 7, 8, 9, 10, 11, 12, 13, 14, 15, 16, 17, 18, 19, 20, 30, 32, 40, 48, 50, 60, 64, 70, 72, 80, 90, 96, 100, 200, 300, 400, 500, 600, 700, 800, 900, 1000, or more. d may be at most 10000, 1000, 900, 800, 700, 600, 500, 400, 300, 200, 100, 96, 90, 80, 72, 70, 64, 60, 50, 48, 40, 32, 30, 20, 19, 18, 17, 16, 15, 14, 13, 12, 11, 10, 9, 8, 7, 6, 5, 4, 3, 2, or less. r may be 2 to 1000. r may be at least 2, 3, 4, 5, 6, 7, 8, 9, 10, 11, 12, 13, 14, 15, 16, 17, 18, 19, 20, 30, 32, 40, 48, 50, 60, 64, 70, 72, 80, 90, 96, 100, 200, 300, 400, 500, 600, 700, 800, 900, 1000, or more. r may be at most 10000, 1000, 900, 800, 700, 600, 500, 400, 300, 200, 100, 96, 90, 80, 72, 70, 64, 60, 50, 48, 40, 32, 30, 20, 19, 18, 17, 16, 15, 14, 13, 12, 11, 10, 9, 8, 7, 6, 5, 4, 3, 2, or less. k may be 2 to 1000000. k may be at least at least 2, 3, 4, 5, 6, 7, 8, 9, 10, 20, 30, 50, 100, 500, 1000, 10000, 50000, 100000, 500000, 1000000, or more. k may be at most 5000000, 1000000, 500000, 100000, 50000, 10000, 1000, 500, 100, 50, 30, 20, or less. The system may be further configured to route at least j units of the k mobile units to a first channel of the c microfluidic channels n times. n may be 2 to 1000. n may be at least 2, 3, 4, 5, 6, 7, 8, 9, 10, 11, 12, 13, 14, 15, 16, 17, 18, 19, 20, 30, 32, 40, 48, 50, 60, 64, 70, 72, 80, 90, 96, 100, 200, 300, 400, 500, 600, 700, 800, 900, 1000, or more. n may be at most 10000, 1000, 900, 800, 700, 600, 500, 400, 300, 200, 100, 96, 90, 80, 72, 70, 64, 60, 50, 48, 40, 32, 30, 20, 19, 18, 17, 16, 15, 14, 13, 12, 11, 10, 9, 8, 7, 6, 5, 4, 3, 2, or less. j may be 2 to 5000000. j may be at least 2, 3, 4, 5, 6, 7, 8, 9, 10, 20, 30, 50, 100, 500, 1000, 10000, 50000, 100000, 500000, 1000000, 5000000, or more. j may be at most 5000000, 1000000, 500000, 100000, 50000, 10000, 1000, 500, 100, 50, 30, 20, or less. The k mobile units may be selected from the group consisting of beads, droplets, cells, bubbles, slugs and immiscible volumes. The c routers may comprise one or more distributors, mergers, or spacers. The routing path may comprise the location of a mapped mobile unit downstream of a router. The routing path may comprise the location of a mapped mobile unit upstream of a router. The location of a mobile unit may comprise the unit's relative positional order with respect to m mapping mobile units. m may be 1 to 100. m may be at least 1, 2, 3, 4, 5, 6, 7, 8, 9, 10, 20, 30, 40, 50, 100, or more. m may be at most 100, 50, 40, 30, 20, 10, 9, 8, 7, 6, 5, 4, 3, 2, or less. The m mapping mobile units may comprise the m closest mobile units to the mapped mobile unit along a fluidically connected path originating from the mapped mobile unit. The r routers may be configured to route mobile units in accordance with a predetermined unit routing algorithm through the microfluidic device. The computer may be configured to perform a comparison between a first post-routing order for the at least a subset of the k mobile units after a routing event by at least one of the r routers and a predesignated post-routing order. The computer may be configured to generate routing paths for i of the at least a subset of the k mobile units based on the comparison. The r routers may be configured to route i mobile units in accordance with the routing paths for the i mobile units. i may be 2 to 1000000. i may be at least 2, 3, 4, 5, 6, 7, 8, 9, 10, 20, 30, 50, 100, 500, 1000, 10000, 50000, 100000, 500000, 1000000, or more. i may be at most 5000000, 1000000, 500000, 100000, 50000, 10000, 1000, 500, 100, 50, 30, 20, or less. The r routers may be configured to separate j mobile units from a remainder of the at least a subset of the k mobile units into a correction area based on the comparison. The r routers may be configured to route mobile through the microfluidic device randomly.

In a twenty second aspect, the methods and compositions described herein relate to a method of tracking, the method comprising: a) providing a microfluidic device comprising a first microfluidic channel and a second microfluidic channel in fluidic connection with the first microfluidic channel; and b) routing k mobile units through the first microfluidic channel into the second microfluidic channel in ordered flow. The first microfluidic channel and the second microfluidic channel may be the same. The first microfluidic channel and the second microfluidic channel may be connected by a union, unit spacer, distributor, or merger. The microfluidic device may further comprise a third microfluidic channel. The method may further comprise routing the plurality of mobile units through the second microfluidic channel into the third microfluidic channel in ordered flow. The second microfluidic channel and the third microfluidic channel may be the same. The first microfluidic channel and the third microfluidic channel may be the same. The second microfluidic channel and the third microfluidic channel may be connected by a union, unit spacer, distributor, or merger. The width of the first microfluidic channel may be 0.01 to 2 times the average diameter of the k mobile units as measured outside of the microfluidic channel. The width of the first microfluidic channel may be less than 2, 1.9, 1.8, 1.7, 1.6, 1.5, 1.4, 1.3, 1.2, 1.1, 1, 0.9, 0.8, 0.7, 0.65, 0.6, 0.55, 0.5, 0.4, 0.3, 0.2, 0.1, 0.05, 0.01 times the average diameter of the k mobile units as measured outside of the microfluidic channel, or smaller. The width of the first microfluidic channel may be greater than 0.01, 0.05, 0.1, 0.2, 0.3, 0.4, 0.5, 0.55, 0.6, 0.65, 0.7, 0.8, 0.9, 1, 1.1, 1.2, 1.3, 1.4, 1.5, 1.6, 1.7, 1.8, 1.9, 2 times the average diameter of the k mobile units as measured outside of the microfluidic channel, or greater. The width of the second microfluidic channel may be 1.05 to 100 times the average diameter of the units. The width of the second microfluidic channel may be greater than 1.05, 1.1, 1.2, 1.3, 1.4, 1.5, 1.6, 1.7, 1.8, 1.9, 2, 2.5, 3, 4, 5, 6, 7, 8, 9, 10, 20, 30, 40, 50, 60, 70, 80, 90, 100 times the average diameter of the units, or greater. The width of the second microfluidic channel may be less than 1000, 100, 90, 80, 70, 60, 50, 40, 30, 20, 10, 9, 8, 7, 6, 5, 4, 3, 2, 1.9, 1.8, 1.7, 1.6, 1.5, 1.4, 1.3, 1.2, 1.1, 1.05 times the average diameter of the units, or smaller. The width of the third microfluidic channel may be 0.01 to 2 times the average diameter of the k mobile units as measured outside of the microfluidic channel. The width of the third microfluidic channel may be less than 2, 1.9, 1.8, 1.7, 1.6, 1.5, 1.4, 1.3, 1.2, 1.1, 1, 0.9, 0.8, 0.7, 0.65, 0.6, 0.55, 0.5, 0.4, 0.3, 0.2, 0.1, 0.05, 0.01 times the average diameter of the k mobile units as measured outside of the microfluidic channel, or smaller. The width of the third microfluidic channel may be greater than 0.01, 0.05, 0.1, 0.2, 0.3, 0.4, 0.5, 0.55, 0.6, 0.65, 0.7, 0.8, 0.9, 1, 1.1, 1.2, 1.3, 1.4, 1.5, 1.6, 1.7, 1.8, 1.9, 2 times the average diameter of the k mobile units as measured outside of the microfluidic channel, or greater. The width of the first microfluidic channel may be 1.05 to 100 times the average diameter of the units. The width of the first microfluidic channel may be greater than 1.05, 1.1, 1.2, 1.3, 1.4, 1.5, 1.6, 1.7, 1.8, 1.9, 2, 2.5, 3, 4, 5, 6, 7, 8, 9, 10, 20, 30, 40, 50, 60, 70, 80, 90, 100 times the average diameter of the units, or greater. The width of the first microfluidic channel may be less than 1000, 100, 90, 80, 70, 60, 50, 40, 30, 20, 10, 9, 8, 7, 6, 5, 4, 3, 2, 1.9, 1.8, 1.7, 1.6, 1.5, 1.4, 1.3, 1.2, 1.1, 1.05 times the average diameter of the units, or smaller. The width of the second microfluidic channel may be 0.01 to 2 times the average diameter of the k mobile units as measured outside of the microfluidic channel. The width of the second microfluidic channel may be less than 2, 1.9, 1.8, 1.7, 1.6, 1.5, 1.4, 1.3, 1.2, 1.1, 1, 0.9, 0.8, 0.7, 0.65, 0.6, 0.55, 0.5, 0.4, 0.3, 0.2, 0.1, 0.05, 0.01 times the average diameter of the k mobile units as measured outside of the microfluidic channel, or smaller. The width of the second microfluidic channel may be greater than 0.01, 0.05, 0.1, 0.2, 0.3, 0.4, 0.5, 0.55, 0.6, 0.65, 0.7, 0.8, 0.9, 1, 1.1, 1.2, 1.3, 1.4, 1.5, 1.6, 1.7, 1.8, 1.9, 2 times the average diameter of the k mobile units as measured outside of the microfluidic channel, or greater. The width of the third microfluidic channel may be 1.05 to 100 times the average diameter of the units. The width of the third microfluidic channel may be greater than 1.05, 1.1, 1.2, 1.3, 1.4, 1.5, 1.6, 1.7, 1.8, 1.9, 2, 2.5, 3, 4, 5, 6, 7, 8, 9, 10, 20, 30, 40, 50, 60, 70, 80, 90, 100 times the average diameter of the units, or greater. The width of the third microfluidic channel may be less than 1000, 100, 90, 80, 70, 60, 50, 40, 30, 20, 10, 9, 8, 7, 6, 5, 4, 3, 2, 1.9, 1.8, 1.7, 1.6, 1.5, 1.4, 1.3, 1.2, 1.1, 1.05 times the average diameter of the units, or smaller.

In a twenty third aspect, the methods and compositions described herein relate to a method of synthesizing oligomers associated with mobile units, the method comprising: a) routing k mobile units through a first channel of a microfluidic device in a first order; b) distributing at least a subset of the k mobile units into at least z branch channels; and c) routing the at least a subset of the k mobile units into a second channel in a second order; wherein at least a subset of the k mobile units are functionalized with a group suitable to synthesize an oligomer; wherein at least a subset of the k mobile units are mappable to a path comprising a specific one of the z branch channels; wherein at least a subset of the k mobile units are subjected to reaction conditions comprising conditions for a step of a synthesis reaction inside the z branch channels; and wherein steps a-c are repeated for n cycles. In some embodiments, the synthesis reaction comprises a nucleic acid synthesis reaction or a peptide synthesis reaction. In some embodiments, the reaction conditions comprise an enzyme. In some embodiments, the enzyme is selected from a terminal deoxynucleotidyl transferase, a thermostable DNA polymerase, a DNA polymerase theta, a Poly(A) polymerase, and a DNA polymerase encoded by a variant of the 9°N DNA Polymerase gene from *Thermococcus* species 9°N-7. In some embodiments, the variant of the 9°N DNA Polymerase gene comprises the 9°N (D141A/E143A/A485L) DNA Polymerase gene or the 9°N (E143D) DNA Polymerase gene. In some embodiments, the enzyme is conjugated to a nucleotide or a nucleotide analog. In some embodiments, the reaction conditions comprise a nucleotide or a nucleotide analog. In some embodiments, at least a subset of the k mobile units are functionalized with an initiator nucleic acid or a nascent oligonucleotide. In some embodiments, the nucleic acid synthesis reaction is a template independent nucleic acid synthesis reaction. In some embodiments, the method further comprises performing a coupling reaction by catalyzing the formation of a covalent bond between the terminal nucleotide of initiator nucleic acids or nascent oligonucleotides associated with at least a subset of the k mobile units and a new nucleotide or nucleotide analog in the presence of a transferase enzyme. In some embodiments, the new nucleotide or nucleotide analog comprises a blocking moiety. In some embodiments, the method further comprises performing a deblocking reaction thereby removing the blocking moiety from the newly incorporated nucleotide or nucleotide analog. In some embodiments, the method further comprises one or more steps selected from the group consisting of a washing step, a modification step, a cleaving step, and a capping step. In some embodiments, two or more of the steps selected from the group consisting of the coupling reaction, the deblocking reaction, the washing step, the modification step, the cleaving step, and the capping step are performed in different cycles. In some embodiments, the oligomers are oligonucleotides and wherein the method further comprises assembling the oligonucleotides into genes. In some embodiments, assembling of the oligonucleotides into genes is performed using one or more method selected from the group consisting of polymerase-cycling assembly, enzymatic gene assembly, annealing and ligation reaction, shotgun ligation, shotgun ligation and co-ligation, gene synthesis via one strand, template directed ligation, ligase chain reaction, microarray-mediated gene synthesis, Blue Heron technology, Sloning building block technology, Golden Gate assembly, Dual-Asymmetric (DA) PCR, Overlap Extension (OE) Asymmetric PCR, Thermodynamically-Balanced Inside Out (TBIO), Two-Step (DA+OE), Polymerase Assembly Multiplexing (PAM), One-Step Simplified Gene Synthesis, Single Molecule PCR, TopDown Real-Time Gene Synthesis, Two-step Ligation and PCR, Brick-based assembly, Sequence- and Ligation-Independent Cloning (SLIC), Transformation-associated Recombination, Biobrick assembly, PCR-based two-step DNA synthesis (PTDS), successive PCR method. In some embodiments, the reaction conditions comprise one or more of reagents selected from the group consisting of an amino acid, a dipeptide, a polypeptide, and a carbodiimide. In some embodiments, the method further comprises performing a coupling reaction by catalyzing the formation of a covalent bond between the terminal end of nascent peptides associated with at least a subset of the k mobile units and a new amino acid, dipeptide or polypeptide. In some embodiments, the method further comprises performing one or more step selected from the group consisting of a capping step, a washing step, and a deprotecting step. In some embodiments, two or more of the steps selected from the group consisting of the coupling reaction, capping step, washing step and the deprotecting step are performed in different cycles. In some embodiments, the same z branch channels are used in at least two of the n cycles. In some embodiments, n is 2. In some embodiments, n is 2 to 10. In some embodiments, n is 10 to 100. In some embodiments, n is 100 to 200. In some embodiments, n is at least 3, 4, 5, 6, 7, 8, 9, 10, 15, 20, 30, 40, 50, 60, 75, 100, 150, 200, 300, 400, 500, 750, or 1000. In some embodiments, n is at most 1000, 750, 500, 400, 300, 200, 150, 100, 75, 60, 50, 40, 30, 20, 15, 10, 9, 8, 7, 6, 5, 4, 3, 2, or less. n may fall within a range bounded by any of the foregoing values, e.g. 100-200, 200-300, 300-400, 400-500, 500-1000. In some embodiments, z is 2-100. In some embodiments, z is at least 1, 2, 3, 4, 5, 6, 7, 8, 9, 10, 20, 30, 50, 100, or more. In some embodiments, z is at most 100, 50, 30, 20, 10, 9, 8, 7, 6, 5, 4, 3, or 2. z may fall within a range that is bounded by any of the foregoing values, e.g. 2-100, 2-16, 4-20, 2-24, etc. In some embodiments, k is at most 1000000000000, 100000000000, 10000000000, 1000000000, 100000000, 10000000, 1000000, 100000, 10000, 1000, 500, 100, or less. In some embodiments, k is between 20-500. In some embodiments, k is at least 2, 3, 4, 5, 6, 7, 8, 9, 10, 20, 30, 50, 100, 500, 1000, 10000, 50000, 100000, 500000, 1000000, or more. k may fall within a range that is bounded by any of the foregoing values, e.g. 2-50000, 10-50, 20-500 etc. In some embodiments, the mobile units are selected from the group consisting of beads, droplets, cells, bubbles, slugs, immiscible volumes, glass beads, polymer beads, cross-linked beads, cross-linked polymer beads, divinylbenzene cross-linked polymer beads, and divinylbenzene cross-linked polystyrene beads. In some embodiments, the first order is different in at least two of the n cycles. In some embodiments, the second order is different in at least two of the n cycles. In some embodiments, the first channel is the same as the second channel.

In a twenty fourth aspect of the methods and compositions described herein relate to a composition comprising n cross-linked beads wherein the coefficient of variation for bead diameter is less than 20%. In some embodiments, the coefficient of variation for bead diameter is less than 15%, 10%, 9%, 8%, 7%, 6%, 5%, 4%, 3%, 2%, 1% or less. In some embodiments, the mean diameter of the beads is between 0.1-500 µm. In some embodiments, the mean diameter of the beads is between 10-50 µm. In some embodiments, the mean diameter of the beads is between 20-150 µm. In some embodiments, the mean diameter of the beads is at least 0.1 µm, 1 µm, 10 µm, 20 µm, 30 µm, 35 µm, 40 µm, 45 µm, 50 µm, 60 µm, 70 µm, 75 µm, 80 µm, 90 µm, 100 µm, 150 µm 200 µm, 300 µm, 400 µm, 500 µm, or greater. In some embodiments, the mean diameter of the beads is at most 500 µm, 400 µm, 300 µm, 200 µm, 150 µm, 100 µm, 90 µm, 80 µm, 75 µm, 70 µm, 60 µm, 50 µm, 40 m, 30 µm, 20 µm, or smaller. The mean diameter of the beads may fall within a range bounded by any of the foregoing values, e.g. 30-40 µm, 40-50 µm, 50-60 µm, 60-70 µm, 70-80 µm, 20-50 µm, 80-90 µm, 90-100 µm, 0.1-400 µm, etc. In some embodiments, the beads are functionalized with a group suitable for oligomer synthesis. In some embodiments, the beads are functionalized with one or more groups selected from the group consisting of amine, hydroxyl, chloromethyl, aminomethyl, benzhydrodrylamino, silane, alkylsilane, and carboxyl groups. In some embodiments, the beads are cross-linked at a molar cross-linker ratio of at least 15%, 20%, 25%, 30%, 35%, 40%, 45%, 50%, 55%, 60%, 65%, 70%, 75%, 80%, or more. In some embodiments, the beads are cross-linked at a molar cross-linker ratio of at most 85%, 80%, 75%, 70%, 65%, 60%, 55%, 50%, 45%, 40%, 35%, 30%, 25%, 20%, 15%, or less. The beads may be cross-linked at a molar cross-linker ratio that falls within any range bounded by the foregoing values, e.g. 20-40%, 15-50%, 25-45% etc. In some embodiments, the beads are cross-linked using one or more cross-linkers selected from the group consisting of divinylbenzene, glutaraldehyde, formaldehyde, an epoxy compound, dialdehyde, and dichloroethane. In some embodiments, the beads are cross-linked using radiation or oxidation. In some embodiments, the variation in bead diameter suspended in organic solvent versus aqueous solvent is less than 80%, 30%, 15%, 10%, 9%, 8%, 7%, 6%, 5%, 4%, 3%, 2%, 1%, 0.5% or less. In some embodiments, the variation in bead diameter suspended in organic solvent versus aqueous solvent is greater than 0.1%, 0.2%, 0.3%, 0.4%, 0.5%, 1%, 2%, 3%, 4%, 5%, 6%, 7%, 8%, 9%, 10%, 15%, 30%, 50%, or more. Variation in bead diameter suspended in organic solvent versus aqueous solvent may fall within a range bounded by any of the foregoing values, e.g. 0.5-2%, 1-5%, 2-10%, 1-50% etc. In some embodiments, the organic solvent is selected from the group consisting of toluene, acetonitrile, toluene, dichloromethane, tetrahydrofuran (THF), pyridine, N-methyl pyrrolidinone (NMP), 2,6-lutidine, carbon disulfide, 1,2-dichloroethane, 1,1-dichloroethane, chloroform, dimethylformamide, dimethylacetamide, dimethylsulfoxide (DMSO), ethylene carbonate, 1,4-dioxane, DME (1,2-dimethoxyethane), nitromethane, methyl tert-butyl ether, methyl ethyl ketone (butanone), and dichloromethane. In some embodiments, n is at least 500, 1000, 10000, 100000, 1000000, 5000000, 10000000, 100000000, 1000000000, 10000000000, 100000000000, 1000000000000 or more. In some embodiments, n is at most 1000000000000, 100000000000, 10000000000, 1000000000, 100000000, 10000000, 1000000, 100000, 10000, 1000, or less. n may fall within a range bounded by any of the foregoing values, e.g., 500-10000, 1000-10000000000, 10000-1000000000000 etc. In various embodiments, bead compositions described herein are contained in a microfluidic device.

In a twenty fifth aspect the methods and compositions described herein relate to a system comprising: a) a microfluidic device comprising i delivery channels each in fluidic communication with a different set of z branch channels, wherein each of the sets of z branch channels is configured to accept a plurality of mobile units in a first order from one of the i delivery channels through a branch point; b) one or more routers configured to route mobile units into one of the z branch points at the first branch point; and c) a controller configured to control the one or more routers to route mobile units into one of the z branch points at the first branch point; wherein the first order is determinative of the particular branch channel of the set of z branch channels into which the controller is configured to control the one or more routers to route a specific mobile unit. The system may further comprise j outlet channels in fluidic communication with some or all of the set of z branch channels, wherein the outlet channels are configured to accept mobile units from the branch channels in a second order. In some embodiments, the second order is determinative of the particular branch channel of the set of z branch channels that is configured to deliver a specific mobile unit into one of the outlet channels. In some embodiments, the delivery channels and the outlet channels are the same. In some embodiments, at least a subset of the one or more routers comprise one or more microfluidic structures configured to generate a vortex. In some embodiments, the microfluidic structures configured to generate a vortex are positioned a distance from the branch point that is at least 100 µm, 150 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 1000 m, 1.1 mm, 1.2 mm, 1.3 mm, 1.4 mm, 1.5 mm, 1.6 mm, 1.7 mm, 1.8 mm, 1.9 mm 2.0 mm, 2.1 mm, 2.2 mm, 2.3 mm, 2.4 mm, 2.5 mm, 3 mm, 4 mm, 5 mm, 6 mm, 7 mm, 8 mm, 9 mm, 10 mm, or greater. In some embodiments, the microfluidic structures configured to generate a vortex are positioned a distance from the branch point that is at most 10 mm, 9 mm, 8 mm, 7 mm, 6 mm, 5 mm, 4 mm, 3 mm, 2 mm, 1 mm, 900 µm, 800 µm, 700 µm, 600 µm, 500 µm, 400 µm, 300 µm, 200 µm, 100 µm, or smaller. The microfluidic structures configured to generate a vortex may be positioned a distance from the branch point that falls within a range bounded by any of the foregoing values, e.g. 100 µm-2.3 mm, 200 µm-450 µm, 150 µm-750 µm, etc. In some embodiments, at least a subset of the one or more routers comprise a thermal bubble forming apparatus. In some embodiments, z is at least 1, 2, 3, 4, 5, 6, 7, 8, 9, 10, 20, 30, 50, 100, or more. In some embodiments, z is at most 100, 50, 30, 20, 10, 9, 8, 7, 6, 5, 4, 3, or 2. z may fall within a range bounded by any of the foregoing values, e.g. 2-50, 4-20, 3-10, etc. In some embodiments, i is at least 1, 2, 3, 4, 5, 6, 7, 8, 9, 10, 20, 30, 50, 100, 500, 1000 or more. In some embodiments, i is at most 1000, 500, 100, 50, 30, 20, 10, 9, 8, 7, 6, 5, 4, 3, 2, or 1. i may fall within a range bounded by any of the foregoing values, e.g. 2-30, 3-20, 10-500, etc In some embodiments, j is at least 1, 2, 3, 4, 5, 6, 7, 8, 9, 10, 20, 30, 50, 100, 500, 1000 or more. In some embodiments, j is at most 1000, 500, 100, 50, 30, 20, 10, 9, 8, 7, 6, 5, 4, 3, 2, or 1. j may fall within a range bounded by any of the foregoing values, e.g. 1-10, 5-20, 10-100, etc In some embodiments, i equals j.

In a twenty sixth aspect, the methods and compositions described herein relate to a method of DNA assembly, comprising: disposing a solid phase support column in a chamber of a microfluidics circuit; performing an enzymatic reaction in a channel of the microfluidics circuit to produce a reaction mixture, the channel fluidly coupled to the chamber; and flowing the reaction mixture over the solid phase support column in the chamber to capture assembled oligos. In some embodiments, the method further comprises flowing a wash mixture over the solid phase support column to remove remaining portions of the reaction mixture. In some embodiments, the method further comprises flowing an elution fluid over the solid phase support column to elute the assembled plurality of oligonucleotides.

BRIEF DESCRIPTION OF THE DRAWINGS

These and other aspects and features of the present invention will become apparent to those ordinarily skilled in the art upon review of the following description of specific embodiments of the invention in conjunction with the accompanying figures, wherein:

FIG. 17A-C provide examples of the signal generated by unit singlets (17A), unit doublets (17B), and unit singlets, doublets and multiples (17C) as they pass through the optical detection system of FIG. 16B configured in accordance with the schematics shown in FIG. 16A.

FIG. 32A-E provides diagrams of differential pressure for distributing units in a double T junction.

FIG. 35A illustrates an exemplary 3D printed unit trap: A disk shaped element with slit in channel is configured to allow fluid flow while preventing units from passing. FIG. 35B illustrates an exemplary unit spacer that is configured to introduce spaces between stacked units. FIG. 35C illustrates an exemplary laser unit detector: 40 μm units, such as beads may be detected by laser as they move left to right in channel.

FIG. 37A is a plan view of the example device; FIG. 37B is an elevation view of a schematic of the example device; FIG. 37C is a snapshot of a video of a region of view about a first spacer in the example device; FIG. 37D is an image of a detector region of the example device; FIG. 37E is an image of signals produced as beads pass the detector; and FIG. 37F is a snapshot of a video of a region of view about a second spacer in the example device, which when operated in reverse removes or reduces excess fluid between beads and returns them to a more packed configuration.

DETAILED DESCRIPTION OF THE PREFERRED EMBODIMENTS

Figure 1:
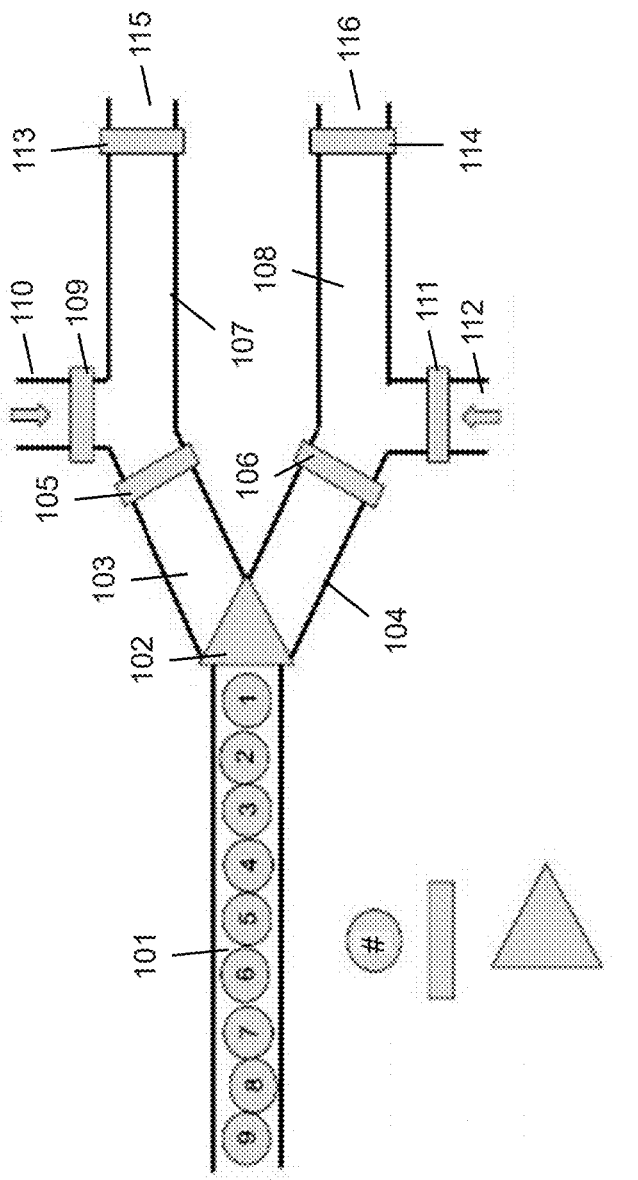
FIG. 1 provides an illustrative example of a microfluidic device comprising a first primary channel having a plurality of ordered mobile units, such as beads. A router, e.g. a distributor, (triangle) at the connection of the first channels with two branch channels can serve to direct each of the mobile units into one of the two branch channels. Valves in the two branch channels may be configured to control entry and exit of the mobile units. Reagents may be delivered to the two branch channels via reagent delivery channels. Delivery of reagents may be controlled with a valve. This configuration can be representative of one of many iterative steps a plurality of beads may undergo through the microfluidic device. The circles with numbers depict units with unit ID numbers; the rectangles depict valves; and the triangles depict routers, e.g. distributors.

Briefly, and as described in more detail below, described herein are methods and compositions relating to tracking of mobile units within microfluidic devices. Mobile units may be tracked by controlling or recording the relative positioning of the mobile units within the microfluidic device. The tracked mobile units may be distributed into the channels of a microfluidic device, for example by employing a router, such as a distributor, and recombined. The order in which mobile units move through the microfluidic device as they are split into and are recombined from various compartments of the microfluidic device may be controlled and/or recorded. The order or relative position of the mobile units upon recombination may be used to determine the path each mobile unit took through the microfluidic device. Individual channels of the microfluidic device may be used to perform reactions, such as synthesis reactions, e.g. nucleic acid synthesis reactions. Such reactions may be performed in parallel. Reagents for each reaction may be delivered to the individual channels, for example via separate reagent delivery channels. Suitable reaction conditions, such as temperature, pressure, and flow rate may be set in the individual channels. The mobile units may comprise beads such as glass beads, polymer beads, or chemically resistant polymer beads. Synthesis reactions may be performed on a nascent chain on the beads. The mobile units may or may not carry labels or barcodes. The terms 'label' and 'barcode' shall be used interchangeably herein.

Provided herein are methods of positionally tracking and moving units within a microfluidic device. The units may be loaded into a microfluidic device. In relation to jamming, clogging, aggregating, and/or keystoning of beads (or other units) at a capillary opening into the microfluidic device, embodiments of the system(s) and method(s) described can implement structures that facilitate loading of beads (or other units) into a capillary in a desired manner.

In a first embodiment, a first end of a capillary is inserted into a reservoir containing the beads (or other units) in solution, and applying positive pressure to the reservoir to drive beads (or other units), with the solution, into the capillary in a desired manner. Positive pressure can be applied by way of a pump coupled to the reservoir, where the applied pressure can be configured in a manner that controls the rate at which fluid and beads (or other units) are driven into the end of the capillary interfacing with the reservoir.

Additionally or alternatively, in a second embodiment, a first end of a capillary is inserted into a reservoir containing the beads (or other units) in solution, and a negative pressure (e.g., vacuum) is applied to another region of the capillary (e.g., a second end) to deliver beads (or other units), with the solution, into the capillary in a desired manner. Negative pressure can be applied in a manner that controls the rate at which fluid and beads (or other units) are driven into the end of the capillary interfacing with the reservoir.

In any of the embodiments of loading described herein, loading beads (or other units) into a capillary can be supplemented with agitation of the vessel or the solution containing the beads (or other units) or by adjusting concentration of the units in solution to modulate bead/unit throughput, and/or to minimize simultaneous bead arrival at the capillary opening(s). For instance, the vessel containing the beads may be affixed to a device that provides any motion including vibration, rocking, shaking, rotation, randomly or periodically. Such motion may be achieved through use of a piezoelectric device, an ultrasound device, or a mechanical mechanism. Additionally or alternatively, fluid containing the beads may be circulated or agitated inside an otherwise stationary vessel using ultrasound, stirrers, stir-bars, paddles, propellers, or additional fluid connections delivering jets of fluids. Additionally or alternatively, a dilution reagent that affects concentration and/or viscosity of the solution can be used to flow beads or units through the device or capillary.

Additionally or alternatively, in any of the embodiments of loading described herein, the capillary and/or channels fluidly coupled to the capillary upstream of the capillary can be configured with various geometries that reduce the likelihood that multiple beads arrive at the capillary opening simultaneously or in another undesired manner. Such geometries can include changes (e.g., step changes, gradual changes) channel width or diameter, or in wall width or diameter along a downstream-to-upstream direction, which can yield a configuration where the beads or other units are transmitted from the reservoir into the capillary one-by-one. Beads or other units may then be rapidly accelerated into the capillary due to increasing flow rates with smaller cross-sectional area along the flow path into the capillary.

Additionally or alternatively, in any of the embodiments of loading described above, the system(s) and/or method(s) described herein can be configured to apply and/or take advantage of forces exerted upon the beads or other units opposite to the unit loading direction, thereby controlling unit loading into the capillary. For instance, in embodiments, one or more of: gravitational forces, magnetic forces, electrophoretic forces, dielectrophoretic forces, fluid forces (e.g., using ultrasound, vibration, agitation, or a sheathing stream surrounding a core stream of fluid), and other forces are used alone or in combination with any of the above-described embodiments. Such applications may be used to mitigate or eliminate jamming or a likelihood of simultaneous bead/unit arrival at an opening of the capillary.

In another such embodiment of a configuration of bead loading using opposing forces, a loading capillary is oriented downward (e.g., parallel to gravitational forces), such that the beads or other units have a natural propensity to flow downward into the capillary due to gravitational forces. Gravity can thus carry the beads or other units, with solution, into the capillary, while an opposing force (e.g., applied negative pressure in an "upward" direction) counters the tendency for units to form aggregates at the opening into the capillary.

In another such embodiment of a configuration of bead loading using opposing forces, a loading capillary is oriented upward (e.g., parallel to gravitational forces), such that the movement of beads into the capillary is countered by gravitational forces. Suction of units, with solution, into the capillary, while gravity serves as an opposing force counters the tendency for units to form aggregates at the opening into the capillary.

In various embodiments the opposing forces already described can be applied intermittently, so as to counter or disrupt aggregates that may have formed at the opening into the capilliary. In the case of gravity, which cannot be intermittently applied, the suction (e.g. negative pressure applied to the fluid in the capillary causing beads and fluid to be drawn into the capillary) or positive pressure (e.g. positive pressure inside the vessel that causes beads and fluid to move into the opening of the capillary) may be intermittently reduced or stopped, so counter or disrupt aggregates that may have formed at the opening of the capillary.

In various embodiments, channels or other fluidic structures fluidly coupled to the capillary can include grooves or similar structures that facilitate formation of rows of units prior to entering the opening of the capillary mitigating likelihood of aggregation at the opening. In variations, however, the capillary may not be oriented upward or downward (e.g., parallel to gravitational forces) and can alternatively be oriented at any angle between vertically upward or vertically downward.

In various embodiments, the systems described herein comprise elements that apply opposing magnetic forces (e.g., for magnetic units) and/or opposing electric forces (e.g., for charged units) or other suitable types of forces described herein or known in the art. Such forces can be used to control flow of beads or other units into a loading channel, e.g. a loading capillary. For instance, adjustment of a net force applied to each unit (e.g. bead) as it enters a capillary, such as through opposing electromagnets or permanent magnets that are placed at an adequate distance relative to the capillary, can be used to control position, velocity, and/or acceleration of unit(s) (e.g. beads) into and within the capillary in a manner that prevents jamming or other undesired transmission.

Additionally or alternatively, in another such embodiment, a Bernoulli force applied across a second end of the capillary away from a first end of the capillary can be used to generate a pressure reduction that promotes transmission of the bead(s) or other units into the capillary in a desired manner. The system can apply a Bernoulli force through structures providing crossflow of fluid across the second end of the capillary.

In various embodiments, unit loading channels are oriented directly parallel or directly opposite forces applied to units in solution prior to loading, or at any other suitable angle. Forces applied to units in pre-loading solution may be adjusted such that the component of the force along the direction of the flow has a suitable absolute or relative value (e.g. relative to the pressure differential for flow into the loading channel) that can mitigate or eliminate aggregation at the entrance of the loading channel.

Provided herein are also methods of spacing or ejecting units within a microfluidic device. Provided herein are methods of steering or distributing units within a microfluidic device. Provided herein are methods of trapping or holding units within a microfluidic device. Provided herein are methods of tracking units within a microfluidic device. Provided herein are methods of dispensing units within a microfluidic device.

Provided further herein are methods to prototype fluidic components and networks including micromachining, soft lithography with polydimethylsiloxane (PDMS), 3D printing, and photolithography. In various embodiments, such methods are used to perform fundamental operations for microfluidic devices and systems described herein (e.g. a desktop synthesizer), including without limitation operations such as moving, stacking, spacing, steering, and counting units, e.g. beads. In various embodiments, stacking of units is achieved by tightly packing units in the microfluidic devices described herein. In some embodiments, stacking is used to allow for efficient application of reaction conditions or treatments (e.g. those aimed to achieve desired chemical reactions) in small reagent volumes. In some embodiments, spacing of units during various routing operations is used to enable deterministic deflection of individual units, e.g. beads. In various embodiments, a method for optical detection is used in order to reliably detect and count units at one or multiple points within the device, allowing for accurate tracking of units some or all times, even in the event that a unit is incorrectly steered.

In further embodiments, use of highly spherical and uniformly sized units allows for thousands of such to be driven as a one-dimensional (1D) array through narrow channels, for example by application of fluidic pressures. In some embodiments, such units in a 1D array hundreds of times in succession are driven through the microfluidic devices described herein without jamming, clogging, or fragmenting.

It must be noted that, as used in the specification and the appended claims, the singular forms "a," "an" and "the" include plural referents unless the context clearly dictates otherwise.

Using phosphoramidite DNA synthesis chemistry molecules can be synthesized on the surface of a solid support substrate in a step-by-step reaction proceeding, generally, in the 3' to 5' direction and consisting of (1) a detritylation step to remove a protecting group from the previously added nucleoside (this prevents more than one nucleoside from being added per cycle), (2) a coupling of the next nucleoside to the growing DNA oligomer, (3) oxidation to convert the phosphite triester intermediate into a more stable phosphate triester, (4) irreversibly capping any unreacted 3' hydroxyls groups. Without being bound by theory, capping unreacted 3' hydroxyl groups can help prevent synthesized sequences having a deletion relative to preselected nucleic acid sequences by avoiding continued polymerization from such 3' hydroxyl groups in subsequent cycles. The cycle can be repeated to add the next base. Solid supports may comprise a variety of units, such as beads, including without limitation highly porous polymeric beads; glass or silica beads including, but not limited to fused silica (amorphous pure silica), quartz (crystalline pure silica); or other any other suitable beads described herein or otherwise known in the art, which can be packed into a chamber or column, to which the synthesis reagents are delivered. The methods, devices and compositions described herein can be used to scale nucleic acid synthesis methods using microfluidic approaches.

Microfluidic approaches can be used to for applications of solid phase phosphoramidite chemistry. In some embodiments, mobile solid support units are delivered to one of four chambers in each cycle of an iterative process. In this approach, mobile units to be extended with a particular nucleoside may be delivered and comingled to the same chamber on that particular cycle. After each cycle the units may be redistributed to be delivered again to the appropriate chamber to receive the next base. In some embodiments, units are selected from beads having a diameter and/or size in the range of 10-100 μm. The beads may be monodisperse. Nucleic acids may be synthesized on a plurality of units, including without limitation beads, for example on ten to ten thousand beads or on hundreds of thousands to millions of beads in parallel in a small microfluidic device. Implementation of this approach may comprise one or more of (1) a set-up for encoding hundreds of thousands to millions of units, such as 10-100 μm beads, with of unique barcodes, (2) a set-up for detecting the units while beads are moving at high speeds, (3) a method for directing or distributing beads into the appropriate output chambers on each iteration, and (4) integration of these components in a functional microfluidic system for iterative operation.

In some embodiments, oligonucleotides are synthesized in the 5' to 3' direction. In some embodiments, 5' to 3' synthesis is achieved by performing one or more of (i) functionalizing of units; e.g. silanization, amino functionalization, hydroxyl functionalization; (ii) providing photolabile 5'-phosophoramidites, e.g. 3'-NPPOC-deoxyadenosine (N6-benzoyl)-5'-β-cyanoethylphosphoramidite, 3'-NPPOC-deoxycytidine (N4-acetyl)-5'-β-cyanoethylphosphoramidite, 3'-NPPOC-deoxyguanosine (N2-dimethylformamidine)-5'-β-cyanoethylphosphoramidite and/or 3'-NPPOCdeoxythymidine-5'-β-cyanoethylphosphoramidite; (iii) dosing the units with light of a suitable wavelength, e.g. UV light; and (iv) coupling a photolabile 5' phosphoramidite to the functionalized unit and/or to a nascent oligonucleotide associated with the unit. Oxidation, capping and deprotection steps may be performed similar to 3' to 5' phosphoramidite synthesis. (See e.g. Albert et al., Nucleic Acids Research, 2003, Vol. 31, No. 7 e35, DOI: 10.1093/nar/gng035; Nuwaysir et al., Genome Res. 2002. 12:1749-1755, doi:10.1101/gr.362402; and Singh-Gasson et al., Nature Biotechnology volume 17, pages 974-78 (1999)).

In some embodiments, 5' to 3' synthesis is achieved by performing one or more of (i) functionalizing of units; (ii) providing phosphoramidites with the benzoyl-2-(2-nitrophenyl)-propoxycarbonyl (BzNPPOC) photolabile protecting group on the 3'-hydroxyl group (reverse BzNPPOC phosphoramidites); (iii) performing a coupling reaction with the reverse BzNPPOC DNA phosphoramidites, e.g. by irradiating the units with light of appropriate wavelength, e.g. UV light; (iv) performing a capping step; and (v) performing an oxidizing step. Deprotection steps may be performed prior to the addition of new reverse BzNPPOC phosphoramidites. (See e.g. Holz et al., Scientific Reports (2018) 8:15099, DOI:10.1038/s41598-018-33311-3.)

Forward and reverse phosphoramidites (i.e., phosphoramidites with a protecting group in the 5' or 3' position, respectively) may be purchased from Glen Research, Sterling, Virginia.

Figure 2:
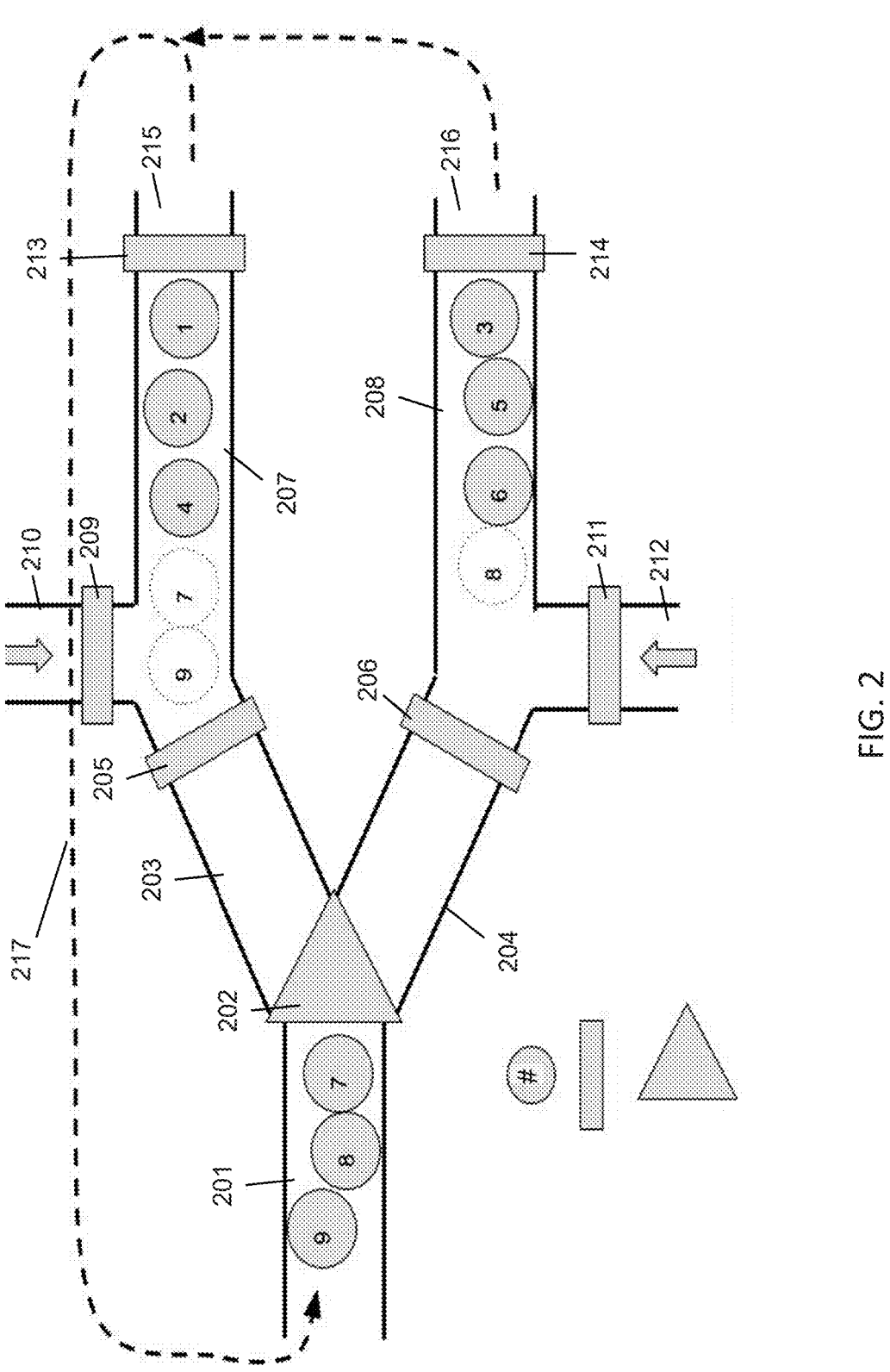
FIG. 2 provides an illustrative example of a microfluidic device. Mobile units 1-6 from a first channel are being directed deterministically into one of two branch channels by using a router, e.g. a distributor. Beads 7-9 are arranged in the first channel, soon to enter the router. The router is programmed to deliver beads 7-9 the positions indicated by the hashed-circles. Once the mobile units are distributed into the branch channels, reagents, such as synthesis reagents may be circulated through the two branch channels that will be holding the mobile units.
Figure 3:
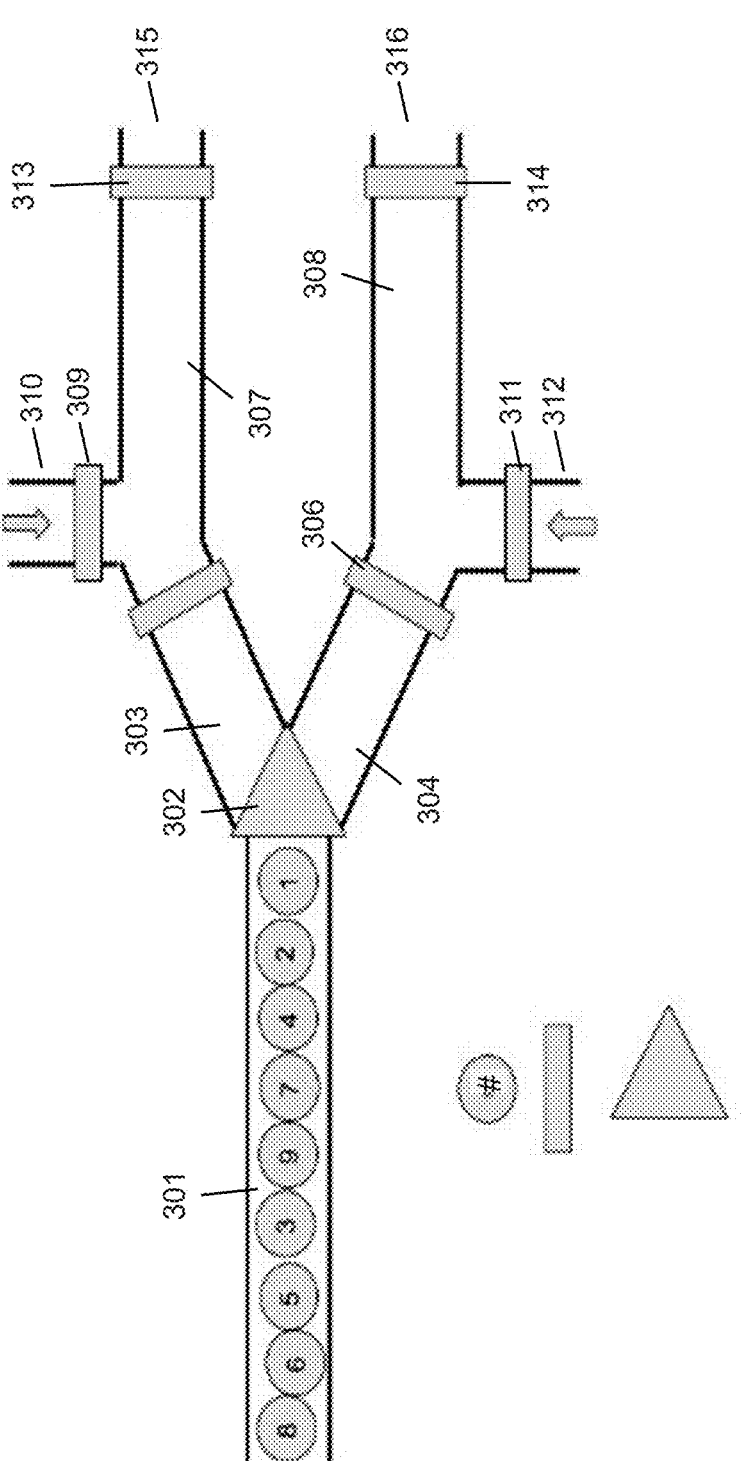
FIG. 3 provides an illustrative example of a snapshot of tracked circulating of mobile units through split channels of a microfluidic device. The order of the mobile units in the channel as the mobile units are about to start a new round is different than the order shown in FIG. 1. The order of the mobile units as they are recirculated back to the first channel may be set in a deterministic manner. The position or relative position of specific mobile units may be known. In this illustrative example, the mobile units are being prepared to be distributed again into the branch channels that may be set to host a pre-assigned sequence of chemistries.

Since microbead barcoding problem had thwarted a number of groups and prevented development of a working device, innovative alternative technology was developed. In various embodiments, methods and compositions described herein comprise a fluidic device in which the beads or other types of units are constrained to narrow fluidic channels, such that they are maintained in a one-dimensional array (FIG. 1-3). This system, in various embodiments, allows the beads or other types units to be identified by their position alone. In some embodiments, beads are loaded into a primary channel. The primary channel may be a capillary or a channel engineered into a suitable substrate. As the beads or other types of units begin the process in a primary channel, they can be pushed, one-by-one, through a distributing mechanism that would direct the beads or other types of units into an appropriate branch channel. Both the primary channel and branch channels may be sized to prevent the beads sliding or squeezing past one another. Once distributed, phosphoramidite chemistry, or other desired chemistry, can take place in the branch channel. After completion of each round of synthesis, the beads or other types of units may be moved in an ordered fashion back into the primary channel for redistributing and a subsequent round of synthesis. In some embodiments, the diameter and/or size of the units and corresponding channels is configured such that units cannot pass each other within a channel or would do so at a rate that is lower than a threshold. For example, units having a diameter and/or size greater than 50% of the width of the channel containing them may be selected.

Figure 4:
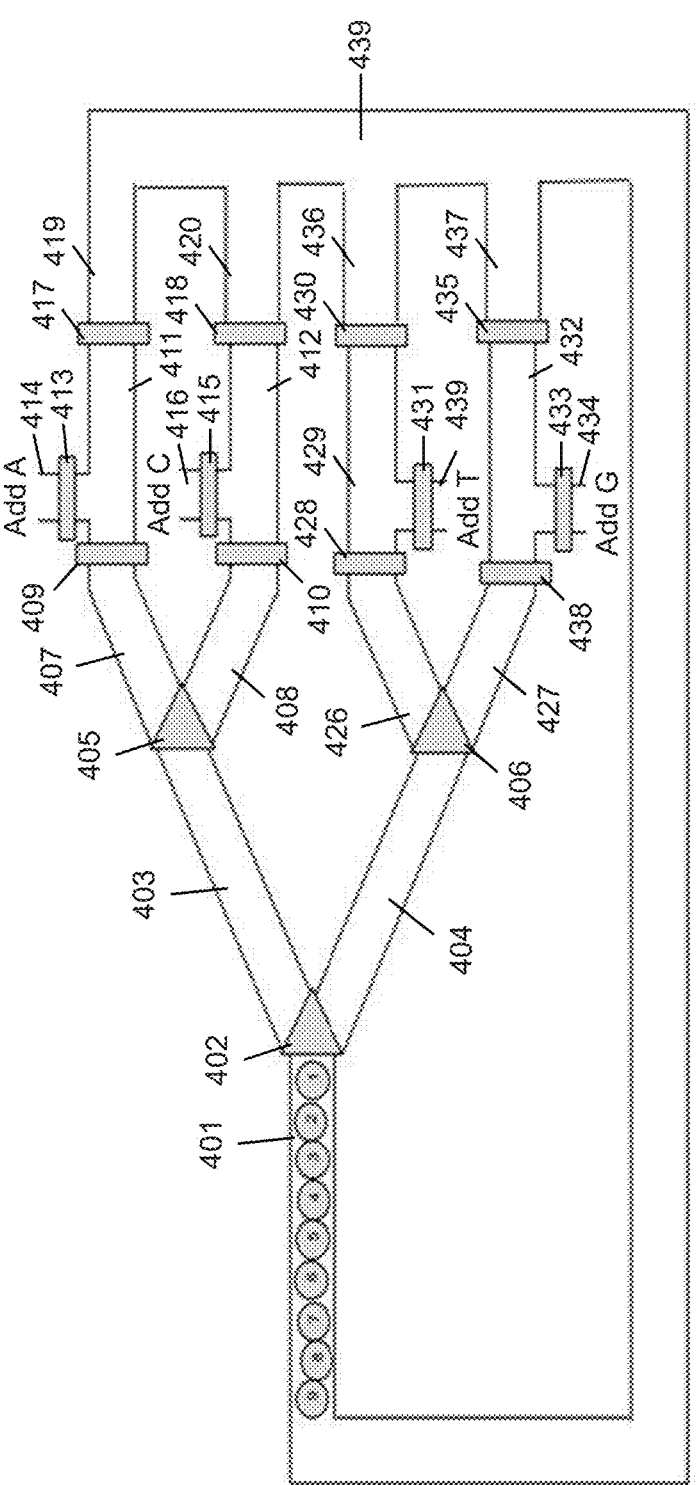
FIG. 4 provides an illustrative example of a microfluidic device wherein mobile units are split into four branch channels passing through two sets of successive routers, e.g. distributors. A device configuration with four branch channels may be used to synthesize nucleic acids in or on the mobile units by successive circulation of the mobile units through the branch channels. Dedicated reagent delivery channels may each provide one of four building blocks for nucleic acid synthesis.

A T-junction or flow focusing method may be configured to eject beads or other types of units from the terminus of the primary array and move them towards a router, e.g. a distributor, for example one at a time. Introducing a gap between units may allow for optical detection and routing, e.g. distribution, before the next unit reaches the router. The router may direct the units into one of the branch channels and/or reaction chambers. One or more of available branch channels or reaction chambers may be configured to allow addition of one of the four DNA bases to a nascent nucleic acid, e.g. DNA chain. The distributing mechanism may potentially comprise a multiway router, or a router with two sequential binary routers enabling multiple branchings (FIG. 4). A set of optical detectors could be positioned at the outlets of one or more routers to verify that each unit was distributed to the intended outlet. Once some or all the units have been distributed, a cycle of the phosphoramidite chemistry may be performed in some or all of the branch channels or reaction chambers and an appropriate nucleoside may be added to nucleic acid molecules in or on some or all the units in some or all of the branch channels or reaction chambers. A subsequent cycle can involve a different chemistry, e.g., addition of modified nucleosides or non-phosphoramidite nucleosides, or treatment e.g., a physical or light based treatment. The methods and devices described herein may be used to apply a different reaction or treatment to some or all branch channels or reaction chambers in some or all cycles. In some embodiments, units are redistributed between cycles of reactions or treatments. The cycles of reactions or treatments may be asynchronous for the units held in different branch channels or reaction chambers. For example, if units are held in two or more branch channels, units held in one branch channel may undergo a first cycle of reaction, and subsequently all of the units held in some or all of the branch channels may undergo a second cycle reaction.

Introduction of the synthesis reagents may be accomplished by using separate reagent ports, e.g. near the beginning of branch channel or reaction chamber outlets. After the completion of a round of synthesis, the units may be recirculated in an ordered fashion back into the primary channel for redistributing and a subsequent round of synthesis. In some embodiments, such recirculation of units comprises reversing the direction of the units backward relative to the direction units entered a branch channel or reaction chamber, thereby causing the units to move into a primary (or main) channel. The process may be repeated as desired, e.g. until the nucleic acid synthesis on all units is complete. In some embodiments, a fluidic device includes an additional output channel to enable synthesis of nucleic acids, e.g. DNA sequences, of different lengths. As modification, e.g. synthesis, on a unit is completed, it may be directed to such an additional output channel and be kept from cycling through the process further. Additional routers, e.g. distributors, and/or sub-channels may be used to handle units that have been incorrectly distributed. Such routers and/or sub-channels may be used to redirect units for redistributing into a correct channel immediately, or directing them into channels where no modifications are made, and then moving these units back into the primary channel before the next cycle so they can be distributed correctly.

This approach can circumvent the need for a barcoding technology entirely. It can also eliminate the need for a complex and potentially expensive optical detection and image processing system. Instead of a costly system, simple optical detectors may be optionally implemented for counting beads. In various embodiments, beads and other types of units may be processed at high speeds. Further, low cost optical checkpoints may be implemented to verify correct distributing.

In various embodiments, the order of the mobile units as they are routed within the microfluidic devices described herein is set in a deterministic manner, for example by distributing and releasing the units into and from reaction chambers in a predetermined manner. The position or relative position of specific mobile units may be known or determinable from the path each mobile unit has taken in a prior round of distributing and recombining. In some embodiments, the order of the units is set by tracking the units by detectors operably connected to detect units as they are routed within the microfluidic devices described herein. The devices and methods described herein allow for positional encoding, such that the order of mobile units within the device at a given time and/or location carries information about the path a unit has followed during routing steps. For example, the order of units may be used to determine, which of a plurality of branch channels a unit has been distributed to and/or merged from. In some embodiments, information that was used to determine the order of the beads, such as tracking information, is itself determinative of elements of the routing path that a unit has been routed through. In some embodiments, the devices and methods described herein are configured to route units through a microfluidic device deterministically. The order of units at a given time and/or location within the microfluidic devices described herein, in combination with such a routing algorithm may be used to determine elements of the routing path that a unit has been routed through.

Elements of a unit's routing path may be determinative of the identity of a compound that was synthesized on a unit as it was routed through the microfluidic devices described herein. More generally, the reaction conditions and/or treatments to which a unit has been subjected to as it was routed through the microfluidic devices described herein, as well as their order, may be determined from the location of the unit. In various embodiments, such location relates to a relative position of a unit within an ordered set of units. Units that have been routed through the microfluidic devices described herein may be mapped to specific routing paths with the use of position information specified relative to other units within the microfluidic device, such as units that are in close vicinity of a particular unit within an ordered set of units.

In various embodiments, chemical products may be associated with mobile units. The chemical compounds may be in or on the mobile units, they may be tethered or attached, or adsorbed by the mobile unit. The units may be identified by their positional relationship either to each other or to the system. The chemical products associated with each unit may be determined by the history modification procedures applied to each unit. In various embodiments, the absolute or relative position of the units is controlled over time. The positional relationship of the mobile units may be controlled by a variety of suitable methods. For example, the positional relationship may be maintained by ordering the units, for example in a one-dimensional array (1d-array; e.g. single row). This array of units can be split into two or more new branch arrays, which may be one dimensional. The direction of the unit flow through the splits may be controlled. The positional information of the units may be updated with each split. The positional information may include both the new branch array assignment and the position within the new branch array. The various branch arrays comprising the units may be subjected to different modification procedures. A modification procedure may be applied to all of the units in a branch array. The modification procedures and the order of application for modification procedures for each unit may be recorded. After performing modification procedures on the branch arrays, the units in the two or more branch arrays may be merged into a single array. The merging of branch arrays can also be controlled such that the order, branch array history, position, and any procedures applied to units in the new array is recorded. This information may be captured and stored in a computer memory using software specifically built for this purpose. The method may consist of any number of splits, modification procedures, and mergers of branch arrays, wherein the position of and the history of the applied procedures for the units are controlled. The units may be moved through splits, branch arrays, and mergers in series, in parallel, in a loop, or a combination thereof. A large number units, e.g. about, more than, or more than about 10, 50, 100, 500, 1000, 5000, 10000, 50000, 100000, 500000, 1000000, 5000000, 10000000 or more units, can be directed in a deterministic fashion, having a large number of independent modification procedures applied to produce large targeted or combinatorial libraries of products on the mobile units. Values for the number of units may range between any of the potential values set forth for the number of unit herein. In some embodiments, units are directed through the channels of a microfluidic device without specifically controlling the path for each unit or randomly. Such units may also be tracked and thereby positionally encoded, for example based on the units' relative positions. Tracking information can be used to determine the chemical steps a unit has gone through, for example in split synthesis applications. The products on each unit may be predicted or determined based on the chemical steps the unit has gone through.

The branch arrays and corresponding modification procedures to be applied to units flowing through may be specifically pre-assigned at every split such that some or all units receive a specific set of modification procedures and are directed appropriately at each splitting event. The series of modifications may be preordained, but assigned to units randomly. In some embodiments, the series of modifications is not preordained. The units may be assigned to a series of modifications deterministically or randomly, e.g. every other unit or an average 50% of units may be directed to a certain path during the splitting event. Regardless of how the assignments are made, the position of units and modification procedures may be recorded.

Suitable designs for the system and units may be selected in order to enable or enhance features of the methods and compositions relating to the invention. For example, ratios between unit size, height, length, width, diameter, and/or cross-section and/or fluidic channel size, height, width, depth, diameter, and/or cross-section may be selected such that the units would not typically be disarranged or mixed under routine operating conditions, thus maintaining the order of the units within a channel, including without limitation in narrow channels physically restricting mixing or as units are moved within channels in maintained order, for example in in laminar or laminar-like flow. The units can be directed from a single channel, into two or more branch channels by any appropriate mechanism, such as pressure differential, flow focusing (e.g., hydrodynamic focusing), lateral movement of the unit in the laminar flow, valves, gates, routers described in further detail herein, e.g. distributors, or switches of various types (e.g. acoustic, electrophoretic, or photonic) and/or other suitable mechanisms known in the art. Flow focusing may include acoustic focusing and inertial focusing, as described in further detail in U.S. Pat. Nos. 7,340,957 and 9,347,595, both of which are herein incorporated by reference in their entirety. The force inducing the movement of the units through the channels may be from fluidic pressure created by a pump, from electroosmotic forces, or any other transport mechanism known in the art. The input channel or the branch channel, or other channels described in further detail elsewhere herein may be associated with a detector. The detector may be configured to count units, confirm that units were directed into the correct channel, or otherwise track the units and/or the units' relationship to each other or to fiducial marks in the microfluidic device. In some embodiments, units are reordered based on detector read-out, for example when units are erroneously distributed. The detector(s) may be coupled to programs, such as computer programs on a computer configured to accept input from the detector(s). Based on the input from the detector(s), for example when the detector detects certain features, the program may execute certain functions. For example, the detector(s) may be coupled to a feedback loop, such as a feedback loop for controlling the pressure of pumps within or coupled to a microfluidic device. The pressure control may be used to control/adjust the speed of the units. The direction or speed of clumped or adhered units may be adjusted. For example, units may be directed into a particular channel so that they can be separated or isolated from the remainder of the units. Detectors of any suitable type may be used in various embodiments of the invention, including without limitation laser or LED detectors, or CCD based devices. Two or more channels, such as branch channels, may converge into one output path. The movement of the units may be controlled and/or positions of the units in the output channel may be updated as the units are combined in the output path. In one embodiment, units from multiple channels may be merged into a single channel by directing units from one channel through a merging branch point first and subsequently directing the units from a second channel through the merging branch point. The absolute or relative positions of some or all of the units may be tracked or determined accordingly.

Channels

Within a microfluidic system designed to hold ordered sets of, for example channels sized to hold i d-arrays of units, the capacity of the channel may be set based on the average diameter, size, or cross-section of the units. The channels may be narrow to physically constrain the units as they move through the channel such that a unit cannot physically pass the unit ahead or behind it. For example, the channel width may be between 1 to 2 times the average or nominal diameter and/or size of the units. In some embodiments, units are constructed of a rigid non-compliant material, such as glass or rigid polymer, e.g. polystyrene cross-linked with divinyl benzene, or other suitable polymer know in the art. In some embodiments, units constructed from rigid non-compliant material are held or flowed in the microfluidic channels described herein. Units constructed from such rigid non-compliant material may be maintained in order by physically preventing them from passing each other inside channels that are narrow enough to constrict them. Channels may be broad enough to allow for the passage of units constructed from rigid non-compliant materials. In some embodiments, the ratio of average or nominal unit diameter and/or size to channel width for all or a portion, such as 90%, 95%, 98%, 99%, 99.5%, 99.9%, 99.99%, 99.999%, 99.9999%, 99.99999% or more, of units flowing through the channel is about, more than, or more than about 0.55, 0.6, 0.65, 0.7, 0.75, 0.8, 0.85, 0.9, 0.95 or more. In some embodiments, the ratio of average or nominal unit diameter and/or size to channel width for all or a portion, such as 90%, 95%, 98%, 99%, 99.5%, 99.9%, 99.99%, 99.999%, 99.9999%, 99.99999% or more, of units flowing through the channel is about, less than, or less than about 0.95, 0.9, 0.85, 0.8, 0.75, 0.7, 0.65, 0.6, 0.55 or less. In some embodiments, the ratio of unit diameter and/or size to channel width for all or a portion, such as 90%, 95%, 98%, 99%, 99.5%, 99.9%, 99.99%, 99.999%, 99.9999%, 99.99999% or more, of units flowing through the channel falls within a range bounded by any of the foregoing values, for example 0.45-0.99, 0.45-0.95, 0.45-0.90, 0.45-0.85, 0.45-0.80, 0.45-0.75, 0.45-0.7, 0.45-0.65, 0.45-0.6, 0.5-0.99, 0.5-0.95, 0.5-0.90, 0.5-0.85, 0.5-0.80, 0.5-0.75, 0.5-0.7, 0.5-0.65, 0.5-0.6, 0.5-0.55, 0.55-0.99, 0.55-0.95, 0.55-0.90, 0.55-0.85, 0.55-0.80, 0.55-0.75, 0.55-0.7, 0.55-0.65, 0.55-0.6, 0.6-0.99, 0.6-0.95, 0.6-0.90, 0.6-0.85, 0.6-0.80, 0.6-0.75, 0.6-0.7, 0.6-0.65, 0.6-0.6, 0.65-0.99, 0.65-0.95, 0.65-0.90, 0.65-0.85, 0.65-0.80, 0.65-0.75, 0.65-0.7, 0.65-0.65, 0.7-0.99, 0.7-0.95, 0.7-0.90, 0.7-0.85, 0.7-0.80, 0.7-0.75, 0.75-0.99, 0.75-0.95, 0.75-0.90, 0.75-0.85, 0.75-0.80, 0.8-0.99, 0.8-0.95, 0.8-0.90, 0.8-0.85, 0.85-0.99, 0.85-0.95, or 0.85-0.90. Values for the channel ratio may range between any of the potential values set forth for the channel ratio herein.

In some embodiments where units are constructed from a compliant material, such as droplets, slugs, immiscible volumes, hydrogels, or compliant polymers, the ratio of average or nominal uncompressed unit diameter and/or size (as measured outside of the channel) to channel width may be substantially larger than 1. In some embodiments, the ratio of average or nominal uncompressed unit diameter and/or size (e.g. as measured outside of the channel) to channel width for all or a portion, such as 90%, 95%, 98%, 99%, 99.5%, 99.9%, 99.99%, 99.999%, 99.9999%, 99.99999% or more, of units flowing through the channel is about, more than, or more than about 0.55, 0.6, 0.65, 0.7, 0.75, 0.8, 0.85, 0.9, 0.95, 1.0, 1.05, 1.1, 1.15, 1.2, 1.25, 1.30, 1.35, 1.4, 1.45, 1.5, 1.55, 1.6, 1.65, 1.70, 1.75, 1.8, 1.85, 1.9, 1.95, 2.0, 2.5, 3.0, 3.5, 4.0 or more. In some embodiments, the ratio of average or nominal uncompressed unit diameter and/or size the ratio of average or nominal uncompressed unit diameter and/or size (as measured outside of the channel) to channel width for all or a portion, such as 90%, 95%, 98%, 99%, 99.5%, 99.9%, 99.99%, 99.999%, 99.9999%, 99.99999% or more, of units flowing through the channel is about, less than, or less than about 4.0, 3.5, 3.0, 2.5, 2.0, 1.95, 1.9, 1.85, 1.8, 1.75, 1.7, 1.65, 1.6, 1.55, 1.5, 1.45, 1.4, 1.35, 1.3, 1.25, 1.2, 1.15, 1.1, 1.05, 1, 0.95, 0.90, 0.85, 0.8, 0.75, 0.7, 0.65, 0.6, 055 or less. In some embodiments, the ratio of unit diameter and/or size to channel width for all or a portion, such as 90%, 95%, 98%, 99%, 99.5%, 99.9%, 99.99%, 99.999%, 99.9999%, 99.99999% or more, of units flowing through the channel falls within a range bounded by any of the foregoing values, for example 0.5-4, 0.5-3.5, 0.5-3, 0.5-2.5, 0.5-2, 0.5-1.95, 0.5-1.85, 0.5-1.8, 0.5-1.75, 0.5-1.7, 0.5-1.65, 0.5-1.6, 0.5-1.55, 0.5-1.5, 0.5-1.45, 0.5-1.4, 0.5-1.35, 0.5-1.3, 0.5-1.25, 0.5-1.2, 0.5-1.15, 0.5-1.1, 0.5-1.05, 0.5-1, 0.5-0.95, 0.5-0.9, 0.5-0.85, 0.5-0.8, 0.5-0.75, 0.5-0.7, 0.5-0.65, 0.5-0.6, 0.5-0.55, 0.55-4, 0.55-3.5, 0.55-3, 0.55-2.5, 0.55-2, 0.55-1.95, 0.55-1.85, 0.55-1.8, 0.55-1.75, 0.55-1.7, 0.55-1.65, 0.55-1.6, 0.55-1.55, 0.55-1.5, 0.55-1.45, 0.55-1.4, 0.55-1.35, 0.55-1.3, 0.55-1.25, 0.55-1.2, 0.55-1.15, 0.55-1.1, 0.55-1.05, 0.55-1, 0.55-0.95, 0.55-0.9, 0.55-0.85, 0.55-0.8, 0.55-0.75, 0.55-0.7, 0.55-0.65, 0.55-0.6, 0.5-0.55, 0.6-4, 0.6-3.5, 0.6-3, 0.6-2.5, 0.6-2, 0.6-1.95, 0.6-1.85, 0.6-1.8, 0.6-1.75, 0.6-1.7, 0.6-1.65, 0.6-1.6, 0.6-1.55, 0.6-1.5, 0.6-1.45, 0.6-1.4, 0.6-1.35, 0.6-1.3, 0.6-1.25, 0.6-1.2, 0.6-1.15, 0.6-1.1, 0.6-1.05, 0.6-1, 0.6-0.95, 0.6-0.9, 0.6-0.85, 0.6-0.8, 0.6-0.75, 0.6-0.7, 0.6-0.65, 0.65-4, 0.65-3.5, 0.65-3, 0.65-2.5, 0.65-2, 0.65-1.95, 0.65-1.85, 0.65-1.8, 0.65-1.75, 0.65-1.7, 0.65-1.65, 0.65-1.6, 0.65-1.55, 0.65-1.5, 0.65-1.45, 0.65-1.4, 0.65-1.35, 0.65-1.3, 0.65-1.25, 0.65-1.2, 0.65-1.15, 0.65-1.1, 0.65-1.05, 0.65-1, 0.65-0.95, 0.65-0.9, 0.65-0.85, 0.65-0.8, 0.65-0.75, 0.65-0.7, 0.7-4, 0.7-3.5, 0.7-3, 0.7-2.5, 0.7-2, 0.7-1.95, 0.7-1.85, 0.7-1.8, 0.7-1.75, 0.7-1.7, 0.7-1.65, 0.7-1.6, 0.7-1.55, 0.7-1.5, 0.7-1.45, 0.7-1.4, 0.7-1.35, 0.7-1.3, 0.7-1.25, 0.7-1.2, 0.7-1.15, 0.7-1.1, 0.7-1.05, 0.7-1, 0.7-0.95, 0.7-0.9, 0.7-0.85, 0.7-0.8, 0.7-0.75, 0.75-4, 0.75-3.5, 0.75-3, 0.75-2.5, 0.75-2, 0.75-1.95, 0.75-1.85, 0.75-1.8, 0.75-1.75, 0.75-1.7, 0.75-1.65, 0.75-1.6, 0.75-1.55, 0.75-1.5, 0.75-1.45, 0.75-1.4, 0.75-1.35, 0.75-1.3, 0.75-1.25, 0.75-1.2, 0.75-1.15, 0.75-1.1, 0.75-1.05, 0.75-1, 0.75-0.95, 0.75-0.9, 0.75-0.85, 0.75-0.8, 0.8-4, 0.8-3.5, 0.8-3, 0.8-2.5, 0.8-2, 0.8-1.95, 0.8-1.85, 0.8-1.8, 0.8-1.75, 0.8-1.7, 0.8-1.65, 0.8-1.6, 0.8-1.55, 0.8-1.5, 0.8-1.45, 0.8-1.4, 0.8-1.35, 0.8-1.3, 0.8-1.25, 0.8-1.2, 0.8-1.15, 0.8-1.1, 0.8-1.05, 0.8-1, 0.8-0.95, 0.8-0.9, 0.8-0.85, 0.85-4, 0.85-3.5, 0.85-3, 0.85-2.5, 0.85-2, 0.85-1.95, 0.85-1.85, 0.85-1.8, 0.85-1.75, 0.85-1.7, 0.85-1.65, 0.85-1.6, 0.85-1.55, 0.85-1.5, 0.85-1.45, 0.85-1.4, 0.85-1.35, 0.85-1.3, 0.85-1.25, 0.85-1.2, 0.85-1.15, 0.85-1.1, 0.85-1.05, 0.85-1, 0.85-0.95, 0.85-0.9, 0.9-4, 0.9-3.5, 0.9-3, 0.9-2.5, 0.9-2, 0.9-1.95, 0.9-1.85, 0.9-1.8, 0.9-1.75, 0.9-1.7, 0.9-1.65, 0.9-1.6, 0.9-1.55, 0.9-1.5, 0.9-1.45, 0.9-1.4, 0.9-1.35, 0.9-1.3, 0.9-1.25, 0.9-1.2, 0.9-1.15, 0.9-1.1, 0.9-1.05, 0.9-1, 0.9-0.95, 0.95-4, 0.95-3.5, 0.95-3, 0.95-2.5, 0.95-2, 0.95-1.95, 0.95-1.85, 0.95-1.8, 0.95-1.75, 0.95-1.7, 0.95-1.65, 0.95-1.6, 0.95-1.55, 0.95-1.5, 0.95-1.45, 0.95-1.4, 0.95-1.35, 0.95-1.3, 0.95-1.25, 0.95-1.2, 0.95-1.15, 0.95-1.1, 0.95-1.05, 0.95-1, 1-4, 1-3.5, 1-3, 1-2.5, 1-2, 1-1.95, 1-1.85, 1-1.8, 1-1.75, 1-1.7, 1-1.65, 1-1.6, 1-1.55, 1-1.5, 1-1.45, 1-1.4, 1-1.35, 1-1.3, 1-1.25, 1-1.2, 1-1.15, 1-1.1, or 1-1.05. Values for the channel width and/or channel ratio may range between any of the potential values set forth for the channel width and/or channel ratio herein.

The units may be flowed from or to areas where positional ordering is maintained by a physical dimensional constraint, as described in further detail elsewhere herein, into, through, or from portions of the device not having constricting dimensions for physically constraining mixing of units. However, ordered flow of units may be maintained under suitable operating conditions, such as by the application of laminar or laminar-like flow. Operating conditions for maintaining positional order may be maintained at all times, or some of the times, during operation of the device. In some embodiments, microfluidic devices described herein have areas of expansions, gradual or abrupt, in the channel width in some or all directions, for example, a narrow channel with a circular cross section transitioning to a channel with a rectangular cross section and a wide aspect ratio. Such expansions may increase one or more dimension of a channel such that mixing of units flowing therein is not constrained by the physical dimensions of the channel. Such areas of expansions may also include corners and/or chambers of various aspect ratios. Without being bound by theory, in laminar or streamline, flow, parallel layers of fluid flow without disruption between the layers. Positional ordering of units may be maintained as the units are moved through an expansion, by moving the units in ordered flow, such as in laminar or laminar-like flow conditions sufficient to maintain ordering of units. Flow in such expansions need not necessarily be laminar, but maintenance of positional ordering may be established by adjusting flow conditions empirically, in accordance with the various embodiments herein. In various embodiments, devices and methods described herein maintain ordered flow of units, including without limitation while moving units in less than perfect laminar flow or while holding beads, for example as limited by the rate of diffusion. In various embodiments, units are flowed from a first area of the device where position is maintained via physical constraints, as described, into a second area, where order can be maintained by the application of suitable fluidic conditions during the operation of the devices described herein. For example, in such a second area, the channel cross-section width at its widest point may be between 2 to 1000 times the average diameter and/or size of the units. The channel cross-section width at its widest point may be about, more than, or more than about 2, 2.2, 2.4, 2.5, 2.8, 3, 3.2, 3.4, 3.5, 3.6, 3.8, 4, 4.2, 4.4, 4.5, 4.6, 4.8, 5, 6, 7, 8, 9, 10, 15, 20, 25, 30, 35, 40, 45, 50, 55, 60, 65, 70, 75, 80, 85, 90, 95, 100, 200, 500, 1000 or more times the average or nominal diameter and/or size of the units. The channel cross-section width in its widest dimension may fall within a range bounded by any of the foregoing values, including for example 2-2.5, 2-4, 2.5-3, 2-5, 3-3.5, 3.5-4, 3.5-5, 4-4.5, 4.5-5. 5-10, 10-25, 25-50, 50-75, or 75-100, 100-200, 200-500, 500-1000 times the nominal or average diameter and/or size of the units. Units may be moved further into a third area of the device having constricting dimensions allowing for maintaining the order of units physically. In various embodiments, units are held in a designated order in channels that expand and/or constrict. For example, units held in a channel having a sufficiently small width to physically constrict unit mixing may be moved into another region of the channel or another channel having greater width in at least one dimension, such as a width that is about, is more than, or is more than about 2, 2.2, 2.4, 2.5, 2.8, 3, 3.2, 3.4, 3.5, 3.6, 3.8, 4, 4.2, 4.4, 4.5, 4.6, 4.8, 5, 6, 7, 8, 9, 10, 15, 20, 25, 30, 35, 40, 45, 50, 55, 60, 65, 70, 75, 80, 85, 90, 95, 100, 200, 500, 1000 or more times the average or nominal diameter and/or size of the units. Units in such an expanded region of a channel may be kept in a designated order, for example by keeping units in laminar flow. Similarly, units kept in designated order within a region of a channel that is too wide for physically constricting mixing may be moved into another region of the channel or another channel having a width that is narrow enough to physically constrict mixing, for example a channel width that is about, is less than, or is less than about 2, 1.9, 1.8, 1.7, 1.6, 1.5, 1.4, 1.3, 1.2, 1.1, 1.05, 1.02, 1.01, or 1 times the average or nominal diameter and/or size of the units therein. Such channel widths may be about, less than, or less than about 0.99, 0.95, 0.9, 0.8, 0.7, 0.6, 0.55, 0.5, 0.4, 0.3, 0.2, 0.1 times the uncompressed (e.g. as measured outside of the channel) average or nominal diameter and/or size of the units therein or less and may still be able to flow compressible or compliant units through. Such channel width transitions may occur in a transition length that is about, is less than, or is less than about 1000 μm, 500 μm, 400 μm, 300 μm, 200 μm, 100 μm, 90 μm, 80 μm, 70 μm, 60 μm, 50 μm, 40 μm, 30 μm, 20 μm, 10 μm, or less. Values for the channel width transitions may range between any of the potential values set forth for the channel width transitions herein.

In some embodiments, the channel width or mean channel width is or is greater than 1 μm, 2 μm, 3 μm, 4 μm, 5 μm, 6 μm, 7 μm, 8 μm, 9 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 125 μm, 150 μm, 175 μm, 200 μm, 300 μm, 400 μm, 500 μm, 1000 μm or greater. In some embodiments, the channel width or mean channel width is or is less than 1000 μm, 500 μm, 400 μm, 300 μm, 200 μm, 175 μm, 150 μm, 125 μm, 100 μm, 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 10 μm, 9 μm, 8 μm, 7 μm, 6 μm, 5 μm, 4 μm, 3 μm, 2 μm, 1 μm, or less. Channels of the devices described herein may have a channel width or mean width within a range bounded by any of the dimensions listed herein, for example 1-5 μm, 3-8 μm, 5-10 μm, 10-20 μm, 20-30 μm, 30-40 μm, 40-50 μm, 50-60 μm, 60-70 μm, 70-80 μm, 80-90 μm, 90-100 μm, 1-100 μm, 100-200 μm, 200-300 μm, 300-400 μm, 400-500 μm, or 100-500 μm, 500-1000 μm. In some embodiments, the height to width aspect ratio of the channel(s) can be 1:100 or greater, e.g. 1:100, 1:90, 1:80, 1:70, 1:60, 1:50, 1:40, 1:30, 1:20, 1:19, 1:18, 1:17, 1:16, 1.15, 1:14, 1:13, 1:12, 1:11, 1:10, 1:9, 1:8, 1:7, 1:6, 1.5, 1:4, 1:3, 1:2, 1:1.5, 1:1.4, 1:1.3, 1:1.2, 1:1.1, 1:1, or greater. The height to width aspect ratio can also be less than 1:1, e.g. less than 1:1, 1:1.5, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 1:30, 1:40, 1:50, 1:60, 1:70, 1:80, 1:90, 1:100 or less. In some embodiments, the height to width aspect ratio of the channel(s) can be 10:1 or less, e.g. 100:1, 90:1, 80:1. 70:1, 60:1, 50:1, 40:1, 30:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1.5:1, 1:1 or less. The height to width aspect ratio can also be greater than 1:1, e.g. greater than 1:1, 1.5:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 30:1, 40:1, 50:1, 60:1, 70:1 80:1, 90:1, or 100:1 or more. The height to width aspect ratio of a channel may fall within a range bounded by any of the values listed above, for example the height width aspect ratio may be between 1:100 and 1:20, 1:20 and 1:1, 1:1.1 and 1.5:1, or 1:3 and 3:1.

The channel(s) length(s) can be about, greater than, or greater than about 0.01 millimeter (mm), 0.1 mm, 0.5 mm, 1 mm, 2 mm, 3 mm, 4 mm, 5 mm, 6 mm, 7 mm, 8 mm, 9 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 90 mm, 100 mm, 15 centimeters (cm), 20 cm, 25 cm, 30 cm, 35 cm, 40 cm, 45 cm, 50 cm, 55 cm, 60 cm, 65 cm, 70 cm, 75 cm, 80 cm, 90 cm, 100 cm, 1.5 meter (m), 2 m, 3 m, 4 m, 5 m, 6 m, 7 m, 8 m, 9 m, 10 m, or more. The channel lengths may fall in a range bounded by any of the dimensions listed herein, e.g. within 1-10 mm, 10-15 mm, 15-20 mm, 20-25 mm, 30-35 mm, 35-45 mm, 45-50 mm, 50-55 mm, 55-60 mm, 60-65 mm, 65-70 mm, 70-75 mm, 75-80 mm, 80-90 mm, 90-100 mm, 10-15 cm, 15-20 cm, 20-25 cm, 30-35 cm, 35-45 cm, 45-50 cm, 50-55 cm, 55-60 cm, 60-65 cm, 65-70 cm, 70-75 cm, 75-80 cm, 80-90 cm, 90-100 cm, 1-2 m, 2-3 m, 3-4 m, 4-5 m, 5-6 m, 6-7 m, 7-8 m, 8-9 m, 9-10 m. The channel(s) length(s) can be about, less than, or is less than about 10 m, 9 m, 8 m, 7 m, 6 m, 5 m, 4 m, 3 m, 2 m, 100 cm, 90 cm, 80 cm, 70 cm, 60 cm, 50 cm, 40 cm, 30 cm, 20 cm, 10 cm, 9 cm, 8 cm, 7 cm, 6 cm, 5 cm, 4 cm, 3 cm, 2 cm, 100 mm, 90 mm, 80 mm, 70 mm, 60 mm, 50 mm, 40 mm, 30 mm, 20 mm, 10 mm, 9 mm, 8 mm, 7 mm, 6 mm, 5 mm, 4 mm, 3 mm, 2 mm, 1 mm, 0.5 mm, 0.1 mm, 0.01 mm, or less. Values for the channel length may range between any of the potential values set forth for the channel length herein.

In some embodiments, the length of one or more channels is selected based on the number of units in the device or the number of units that are designated to fit in the channel. Unit sizes are described in more detail elsewhere herein including without limitation in the Unit section in paragraph 129. The channel length may be selected to fit a number of units in a range bounded by any of the values listed herein, e.g., about 1-1E7 units, 1-10, 10-50, 50-100, 50-1E5, 100-500, 100-5E5, 100-1E7, 500-1E4, 1E4-5E4, 5E4-1E5, 1E5-5E5, 5E5-1E6, 1E6-5E6, or 5E6-1E7 units. The channel length may be selected to fit about, more than, or more than about 1, 10, 50, 100, 500, 1E4, 5E4, 1E5, 5E5, 1E6, 5E6, 1E7, or more units. A channel length may be selected to fit about, less than or less than about 1E7, 5E6, 1E6, 5E5, 1E5, 5E4, 1E4, 500, 100, 50, 40, 30, 20, 10, 5, 4, 3, 2, or 1 units. A branch channel length may be selected to fit a number of units in a range bounded by any of the values listed herein, e.g., 1-1E7 units, 1-10, 10-50, 50-100, 50-1E5, 100-500, 100-5E5, 100-5E7, 500-1E4, 1E4-5E4, 5E4-1E5, 1E5-5E5, 5E5-1E6, 1E6-5E6, or 5E6-1E7 unit lengths. A branch channel length may be selected to fit about, less than, or less than about 1E7, 5E6, 1E6, 5E5, 1E5, 5E4, 1E4, 500, 100, 50, 40, 30, 20, 10, 5, 4, 3, 2, or 1 units. A branch channel length may be selected to fit about, more than, or more than about 1, 5, 10, 20, 30, 40 50, 100, 500, 1E4, 5E4, 1E5, 5E5, 1E6, 5E6, 1E7, or more units. Values for the branch channel length may range between any of the potential values set forth for the branch channel length herein.

The units may be spaced from each other with spacer lengths about, more than, or more than about 1, 2, 3, 4, 5, 6, 7, 8, 9, 10, 20, 25, 30, 40, 50, 100, 200, 300, 400, 500, 600, 700, 800, 900, or 1000 times the nominal or average size and/or diameter of the units or more. The channel(s) may be selected to have sufficient length to accommodate a desired number of units, for example 1-1E7 units with a spacer length of about, more than, or more than about 1, 2, 3, 4, 5, 6, 7, 8, 9, 10, 15, 20, 25, 30, 40, 50, 100, 200, 300, 400, 500, 600, 700, 800, 900, or 1000 times the length of a unit between each unit or more. The channel(s) may be selected to have sufficient length to accommodate 1-1E7 units with a spacer length of about, less than, or less than about 1000, 900, 800, 700, 600, 500, 400, 300, 200, 100, 50, 40, 30, 25, 20, 10, 9, 8, 7, 6, 5, 4, 3, 2, or 1 times the length of a unit between each unit or less. The channel(s) may be selected to have sufficient length to accommodate 1-1E7 units with spacer lengths falling within a range bounded by any of the spacer length values described herein, for example 1-1000, 1-100, 2-25, 3-40, 4-10, 5-100, 6-30, 7-100, 8-100, 9-10, 10-15, 10-20, 20-50, 50-100, 100-200, 200-300, 300-400, 400-500, 500-600, 600-700, 700-800, 800-900, or 900-1000 spacer length between each unit. Values for the spacer length may range between any of the potential values set forth for the spacer length herein.

The channel cross-section shape may be square, rectangle, oval, circular, half-circular, or any other suitable shape. Microfluidic channels can be linear, serpentine, or have another suitable shape or length to enable channels with large unit capacities. Unit capacities of 1E6, 1E7 or higher may be achieved using suitable channel configurations on relatively small fluidic chips.

According to the various embodiments, channels can be used as reaction chambers where modification procedures are used to modify the products, or in some cases the units. Modification procedures may comprise any chemical, physical, optical, or mechanical method. Various embodiments of the invention ensure that modification procedures do not interfere with the arrangement of the units. Chemical reagents may be flowed as liquids or gasses through the fluidic channel(s) containing the units. The characteristics or diameter and/or size of the channel or the units may be selected to enhance the flow of chemical reagents, or the effectiveness or efficiency of chemical procedures. For example, the channels may be constructed from glass, chemically resistant polymers, or non-resistant polymers or coated with the same. In various embodiments, the channels are chemically resistant to the modification procedures applied. Units may be constructed from any suitable material, such as controlled pore glass, plastic, or any suitable polymer. In various embodiments, the size distribution of units may be selected to leave space for fluids to flow over the units while in the channel. In various embodiments, there may be no space for fluid to flow over the units. Treatments and chemical reactions described in further detail elsewhere herein may be performed without requiring space for fluid to flow over the units within the channels of the microfluidic devices described herein. For example, treatments comprising the application of heat or light may be performed without such spaces.

The present invention may include reaction chambers. Various regions within the microfluidic devices described herein, for example branch channels, may be utilized as reaction chambers. Reaction chambers may be enclosed by valves located in or at the end of a channel. Reaction chambers may also be valve-less and the pressure or flow of carrier fluid and/or reagents controlled by pumps with inlets or outlets connecting to the reaction chamber. The units can be flowed from one reaction chamber to another directly or through one or more channel(s). The size of the reaction chamber can vary and may depend on the spacing or size of the valves or pump inlets/outlets defining the reaction chamber(s) and the dimensions, e.g. width, height, diameter, or cross-section of the reaction chamber(s). The size of the reaction chambers can be about, at least, or at least about 10 pl, 20 pl, 30 pl, 40 pl, 50 pl, 60 pl, 70 pl, 80 pl, 90 pl, 100 pl, 200 pl, 300 pl, 400 pl, 500 pl, 600 pl, 700 pl, 800 pl, 900 pl, 1000 pl, 100-200 pl, 200-300 pl, 300-400 pl, 400-500 pl, 500-600 pl, 600-700 pl, 700-800 pl, 800-900 pl, 900-1000 pl, 1 nl, 2 nl, 3 nl, 4 nl, 5 nl, 6 nl, 7 nl, 8 nl, 9 nl, 10 pl nl, 20 nl, 30 nl, 40 nl, 50 nl, 60 nl, 70 nl, 80 nl, 90 nl, 100 nl, 200 nl, 300 nl, 400 nl, 500 nl, 600 nl, 700 nl, 800 nl, 900 nl, 1 µl, 10 µl, 20 µl, 30 µl, 40 µl, 50 µl, 60 µl, 70 µl, 80 µl, 90 µl, 100 µl, 200 µl, 300 µl, 400 µl, 500 µl, or more. The size of the reaction chambers can be less than or less than about 500 µl, 400 µl, 300 µl, 200 µl, 100 µl, 90 µl, 80 µl, 70 µl, 60 µl, 50 µl, 40 µl, 30 µl, 20 µl, 10 µl, 1000 nl, 900 nl, 800 nl, 700 nl, 600 nl, 500 nl, 400 nl, 300 nl, 200 nl, 100 nl, 90 nl, 80 nl, 70 nl, 60 nl, 50 nl, 40 nl, 30 nl, 20 nl, 10 nl, 9 nl, 8 nl, 7 nl, 6 nl, 5 nl, 4 nl, 3 nl, 2 nl, 1 nl, 900 pl, 800 pl, 700 pl, 600 pl, 500 pl, 400 pl, 300 pl, 200 pl, 100 pl, 90 pl, 80 pl, 70 pl, 60 pl, 50 pl, 40 pl, 30 pl, 20 pl, 10 pl, or less. Those of skill in the art will appreciate that the reaction chambers may have a size that falls within any range bound by any of these values, for example 10-50 nl, 10-100 nl, 50-100 nl, 100-200 nl, 200-300 nl, 300-400 nl, 400-500 nl, 500-600 nl, 600-700 nl, 700-800 nl, 800-900 nl, 900-1000 nl, 1 µl, 2 µl, 3 µl, 4 µl, 5 µl, 6 µl, 7 µl, 8 µl, 9 µl, 10 µl, 1-10 µl, 10-100 µl, 100-200 µl, 200-300 µl, 300-400 µl, or 400-500 µl. Values for the reaction chamber may range between any of the potential values set forth for the reaction chamber herein.

Channels in which modification procedures occur may have one or more inlet or outlet ports and/or valves. Reagents may be delivered through valve or port into and out of the channel. These inlet or outlet ports and valves may be configured or suitably occluded so as to prevent units from becoming trapped or disarranged. The units may be held in a channel, for example during a modification procedure, by one or more closed, occlusive, or porous valves, gates, switches, or by magnetic fields. Units having permanent or inducible magnetic properties may be employed to utilize their interaction with magnetic fields. A modification procedure may be operated on some or all of the units in a particular channel. In some cases, the selected modification procedure does not cause a change in the unit or the product associated with the unit. Zero or more modification procedures may be applied to units in given channel. Different channels of a fluidic device may be configured to enable distinct modification procedures that can be applied, either sequentially or simultaneously, to the units in the respective channels. Channels may split more than once before converging, separate modification procedures can be applied to any channel.

In various embodiments, all units intended to receive the application of the same reaction condition(s) are kept in a single channel designated for the application of such reaction condition(s). In some embodiments, units designated to receive the application of the same reaction condition(s) are distributed into a plurality of channels or reaction chambers, including for example branch channels.

The microfluidic device may contain branch points where the channel splits or divides into multiple channels or outlets. The branch points may comprise about, at least, or at least about 2, 3, 4, 5, 6, 7, 8, 9, 10, 20, 30, 40, 50, 60, 70, 80, 90, 100 or more channels or outlets, including without limitation branch channels or reaction chambers. Values for the branch points may range between any of the potential values set forth for the branch points herein. One or more branch points may be arranged sequentially. The branch channels or outlets may have 2-dimensional or 3-dimensional arrangements. For example, a branch point may split a first channel into two or more branch channels in the X, Y plane, resulting in a 2-dimensional planar channel arrangement within the device. Or, a branch point may split a first channel into two or more branch channels in and/or out of the X, Y plane. In such an arrangement, one or more branch channels in a first set may be in one plane A with the portion of the first channel immediately adjacent to the branch point, while the branch-point adjacent portions of one or more branch channels in a second set may be in a different plane than plane A, for example, perpendicular to place A, resulting in a 3-dimensional branch-point channel arrangement within the devices described herein. In some embodiments, one or more channels in the devices described herein are non-linear, for example such devices may have the shape of a spiral, or other curve.

Routing of Units

The microfluidics device described herein can be configured to route units through the device. Routing of units may comprise holding units, moving units, distributing units into channel(s) or branch channel(s) and/or merging units from two or more channels or branch channels to one or more channel(s). The device can also be configured to merge units from two or more channel(s) or branch channel(s) to one or more channel(s). In various embodiments, routing comprises distribution. Units within microfluidic devices described herein may be routed from p locations, e.g. channels, to p+i locations within the microfluidic device, where p, i>0, through a distributor. These p+i locations may be channels generally referred to as branch channels herein. In various embodiments, routing comprises merging. Units within microfluidic devices described herein may be routed from q locations, e.g. channels, into q−j locations, where q, j, q−j>0, through a merger. These q-j locations may be channels generally referred to as merger channels herein. In some embodiments, p is, is at least, or is at least about 1, 2, 3, 4, 5, 6, 7, 8, 9, 10, 15, 120, 30, 40, 50, 60, 70, 80, 90, 100, or more. In some embodiments, p is, is at most, or is at most about 100, 90, 80, 70, 60, 50, 40, 30, 20, 15, 10, 9, 8, 7, 6, 5, 4, 3, 2, or less. In some embodiments, p is between 1-5, 5-10, 10-15, 15-20, 20-25, 25-30, 30-35, 35-40, 40-45, 45-50, 50-55, 55-60, 60-65, 65-70, 70-75, 75-80, 85-90, 90-95, or 95-100. In some embodiments, i is, is at least, or is at least about 1, 2, 3, 4, 5, 6, 7, 8, 9, 10, 15, 120, 30, 40, 50, 60, 70, 80, 90, 100, or more. In some embodiments, i is, is at most, or is at most about 100, 90, 80, 70, 60, 50, 40, 30, 20, 15, 10, 9, 8, 7, 6, 5, 4, 3, 2, or less. In some embodiments, i is between 1-5, 5-10, 10-15, 15-20, 20-25, 25-30, 30-35, 35-40, 40-45, 45-50, 50-55, 55-60, 60-65, 65-70, 70-75, 75-80, 85-90, 90-95, or 95-100. In some embodiments, q is, is at least, or is at least about 1, 2, 3, 4, 5, 6, 7, 8, 9, 10, 15, 120, 30, 40, 50, 60, 70, 80, 90, 100, or more. In some embodiments, q is, is at most, or is at most about 100, 90, 80, 70, 60, 50, 40, 30, 20, 15, 10, 9, 8, 7, 6, 5, 4, 3, 2, or less. In some embodiments, q is between 1-5, 5-10, 10-15, 15-20, 20-25, 25-30, 30-35, 35-40, 40-45, 45-50, 50-55, 55-60, 60-65, 65-70, 70-75, 75-80, 85-90, 90-95, or 95-100. In some embodiments, j is, is at least, or is at least about 1, 2, 3, 4, 5, 6, 7, 8, 9, 10, 15, 120, 30, 40, 50, 60, 70, 80, 90, 100, or more. In some embodiments, j is, is at most, or is at most about 100, 90, 80, 70, 60, 50, 40, 30, 20, 15, 10, 9, 8, 7, 6, 5, 4, 3, 2, or less. In some embodiments, j is between 1-5, 5-10, 10-15, 15-20, 20-25, 25-30, 30-35, 35-40, 40-45, 45-50, 50-55, 55-60, 60-65, 65-70, 70-75, 75-80, 85-90, 90-95, or 95-100. Values for p, q, j, and/or i, may fall within a range bounded by any of the potential values set forth the p, q, j, and/or i, herein. Routing may comprise the movement of units within a channel, or from one location in a fluidic device to another, or from a first channel to a second channel, where the axis of flow of the first channel may be the same as the second, or alternatively the axis of flow of the first may be at any angle, for example, 45° or 90°, to that of the axis of flow of the second. Distribution may comprise the movement of units from a first channel into a branch channel via a branch point, from one or more branch channel(s) or reaction chamber(s) into one or more other channel(s). Merging may comprise the reverse of distribution. Units may be merged by moving units from q locations within a microfluidic device, e.g. q branch channel(s) or reaction chamber(s) via one or more branch point(s) and into q-j locations within the microfluidic device where q>j, for example into a first channel from which the units had been distributed.

The microfluidic device described herein can be configured to steer/route units via any appropriate mechanism known in the art, including but not limited to, mechanisms for generating and modulating fluid flow (e.g., as in electroosmotic mechanisms described below), generating or modulating fluidic pressure, moving mechanical mechanisms, static or non-moving mechanical features, or non-moving force generating mechanism. Routers constructed according to such routing mechanisms or any other suitable mechanism known in the art, may be configured and used to move or route units within a first channel, move or route units from a first channel to a second channel, distribute units from a first channel into two or more branch channels, and/or merge units from two or more branch channels into a first or second channel. The microfluidic device described herein may have one, two, or multiple routing mechanisms.

Fluidic pressure modulation routing mechanisms may include, but are not limited to, mechanisms that increase or decrease the fluidic pressure at one or more locations within a fluidic device. Fluidic pressure modulation mechanisms may comprise any appropriate mechanical device known in the art such as fluidic pumps, gas pressure driven pumps, manual syringes, electronically controlled syringe pumps, electroosmotic pumps, diaphragm pumps, gear pumps, peristaltic pumps, electrohydrodynamic pumps, or any combination thereof. The devices described herein may contain one or more fluidic pressure modulating mechanisms of the same type, or of different types. Fluidic pressure modulating mechanisms may or may not be under specific electronic control, and may have feedback control to ensure appropriate pressure delivery. The fluidic pressure modulating mechanisms may operate independently or be under synchronized control. Not wishing to be bound by theory, units may be moved, flowed, advanced, reversed, held, stopped, directed, and/or redirected in the device by applying increased or decreased relative or absolute pressure to fluids and/or units in the device.

In one embodiment, routing by the microfluidic device is implemented with inclusion of elements for providing pressure-driven crossflows, for example where a pressure-driven crossflow is configured using fluidic pressures, for example externally generated pressures, which may be gated by one or more valves. The valve(s) associated with the pressure-driven crossflow can be integrated with the microfluidic device (e.g., on-chip), or distinct from the microfluidic device (e.g., or off-chip). In an example, the valve(s) include pneumatic values, for example pneumatic valves actuated at 4 bar at over 300 Hz; however, other pressure levels and frequencies of actuation can be implemented by the microfluidic devices described in further detail herein. Furthermore, the medium used to drive the crossflow can be liquid or gas (e.g. air). Routing of units may be performed at rates of, of about, or greater than 10, 20, 30, 40, 50, 60, 70, 80, 90, 100, 125, 150, 175, 200, 250, 300, 350, 400, 450, 500, 550, 600, 650, 700, 750, 800, 850, 900, 950, 1000, 5000, 10000, 15000, 20000, 25000, 30000, 35000, 40000, 45000, 50000 Hz or more.

Moving mechanical routers include, but are not limited to, routers that can be configured to move, control, or alter the movement of units or fluids within a fluidic device. Methods and devices described herein may utilize any suitable moving mechanical routers known in the art, including but not limited to, plugs, pistons, gates, flippers, valves, pins, ratchets, or any combination thereof. Units may be held by a closed mechanical router of a device and/or released upon opening of the mechanical router. Moving mechanical routers may be configured to apply a force either directly to the units, and/or to the fluid in a device described herein such that units may be moved, stopped, held, directed, and/or redirected in the device.

In one embodiment, routing by the microfluidic device is implemented with inclusion of a mechanical actuator includes a cross-channel fluidically connected to two or more chambers, wherein each of the two or more chambers has at least one compliant side (e.g. the roof) which may be deflected to change the volume of the chamber. In a two-chamber embodiment, a first force applied to the compliant side of the chamber displaces fluid towards the flow channel, and a second force applied to the compliant side of the second chamber displaces fluid from the flow channel into the second chamber. Such a configuration can be connected to two sides of a routing junction of a microfluidic device such one chamber can operate in a "pulling mode" and the other chamber can operate in "pushing mode", whereby flow can be configured to be purely across the junction, rather than adding fluid flow along the primary flow direction in a manner that opposes or adds to the primary flow. In variations, the embodiment of the mechanical actuator can include elements for providing forces including one or more of: magnetic forces (e.g., with permanent or electromagnets coupled to the compliant side of the chamber); piezeoelectric-provided forces (e.g., with extending and contracting piezoelectric actuators coupled to the compliant side of a chamber, "buckling"-type actuators); mechanical actuators (e.g., mechanical solenoids coupled to and configured to push and pull the compliant side of a chamber); external pressure sources (e.g., gas pressurizers configured to apply and release pressure by one or more pneumatic valves); and other actuators. In some embodiments, the mechanical actuator includes elements for providing forces using surface acoustic waves, transient surface acoustic waves, electrophoresis, dielectrophoresis, micromechanical valves, optical tweezers, and/or thermal vapor bubbles, for example vapor bubbles created by laser absorption or by electrical heating. Routing of units may be performed at rates of, of about, or greater than 10, 20, 30, 40, 50, 60, 70, 80, 90, 100, 125, 150, 175, 200, 250, 300, 350, 400, 450, 500, 550, 600, 650, 700, 750, 800, 850, 900, 950, 1000, 5000, 10000, 15000, 20000, 25000, 30000, 35000, 40000, 45000, 50000 Hz or more.

In another embodiment, a mechanical component includes a deflector (e.g., flipper valve) that steers flow, beads, or other units toward a desired path or channel. In examples, the deflector(s) can be actuated by one or more of: microelectromechanical systems (MEMS) actuators integrated into a channel network, magnetic actuators providing magnetic fields that actuate magnetic flippers, mechanical actuators/servos, and other actuators for manipulating flippers integrated with the channel network.

Static or non-moving mechanical routers include, but are not limited to, routers that can be configured to move, control, or alter the movement of units or fluids within a fluidic device. Such routers may utilize any appropriate static mechanical mechanism known in the art, including but not limited to pillars, grooves, wedges, walls, scallops, holes, cups, divots, sieves, selective stops (e.g. allow fluids to pass, but units are held back), dams, weirs or other similar mechanism, or any combinations thereof. The microfluidic device described herein may comprise one or multiple static or non-moving mechanical routers. The microfluidic device may comprise a single type of static router, for example one or more selective stop, or two or more types of static routers, for example one or more dam and one or more pillar. Such examples are not meant to be limiting. Static or non-moving mechanical routers may be configured to apply a force either directly to the units, or to the fluid in the device such that units may be moved, stopped, held, directed, and/or redirected in the devices described herein.

Non-moving force generating routers include, but are not limited to, routers that can be configured to move, control, or alter the movement of units or fluids, including without limitation compositions, such as oligomers within such fluids, within a fluidic device (e.g., thermal vapor bubbles). Such routers may use any appropriate static mechanical mechanism known in the art, including but not limited to electrophoresis, dielectrophoretic, acoustophoresis, electroosmosis, magnetophoresis, gravity, or any combination thereof (see e.g., Wyatt Shields C. et al, Lab Chip 2015 15(5):1230-1249, incorporated herein by reference in its entirety). In one embodiment, the units are routed via magnetophoresis. Non-moving force generating routers may be configured to apply a force directly to the units, and/or apply a force to or through the fluid in the device such that units may be moved, stopped, held, directed, and/or redirected in the devices described herein.

In one embodiment, a non-moving force generating router includes one or more magnets (e.g., permanent magnets, electromagnets) configured to route units responsive to magnetic fields or magnetic field gradients (e.g., paramagnetic, superparamagnetic beads may be moved by a magnetic field gradient). Magnetic fields and/or field gradients can be generated by devices integrated within or outside the microfluidic devices described herein. Permanent magnets may be actuated toward and/or away from desired regions of the system to affect fields. Electromagnets may be transitioned between on and off states to affect fields. In embodiments, pointed magnets and/or electromagnet cores are used to produce high-field gradients.

In a related embodiment, microfluidic devices described herein may be configured to implement ferrofluid actuation. A ferrofluid (e.g., a suspension of fine magnetic particles in a liquid medium which is immiscible with the liquid containing beads or other units) is actuated (e.g., by a permanent magnet, by an electromagnet) in response to applied magnetic fields. Such an embodiment can include an operation mode that moves the ferrofluid toward an applied magnetic field in order to displace fluid in a channel, thereby forming a ferrofluid "piston". Such an embodiment can additionally or alternatively include an operation mode where the ferrofluid is configured to become rigid when subjected to a magnetic field. Upon becoming rigid, the ferrofluid may be used to block one or more of the exits of a routing junction, thereby causing the flow and/or units, e.g. beads, to be routed towards an un-blocked channel.

In some embodiments, routers described herein comprise or are implemented in cooperation with one or more electroosmotic pumps. Electroosmotic pumps according to the various embodiments described herein, may be controlled electrically in order to generate a flow across a steering junction. For example, an electroosmotic pump can be coupled to or otherwise interface with multiple sides of a steering junction such that it "pulls" on a first side and "pushes" on another side (e.g., in a closed loop). In such a configuration, flow can be configured to be purely or primarily across the junction, as opposed to requiring added fluid flow along a primary flow direction (which would oppose or add to the primary flow). Furthermore, such a configuration can provide fast response speeds. (e.g., providing responses in less than 1 ms).

In some embodiments, routers described herein comprise or are implemented in cooperation with electrophoretic steering apparatus configured to provide an electric field in solution. For example, units, e.g. coupled to nucleic acid (e.g., DNAs, DNA fragments) can be inherently negatively charged in aqueous solution and manipulated by electrophoretic forces that route such units in a desired manner.

In some embodiments, routers described herein comprise or are implemented in cooperation with dielectrophoretic steering apparatus configured to provide an electric field in solution. For example, a dielectrophoretic apparatus can be configured to manipulate particles that electrically polarize under the influence of an electric field (e.g., high frequency field on the order of kHz). Without being bounded by theory, if the units' polarization is significantly different than that of the surrounding medium, a net dielectric force is exerted on the particles, which can be used for steering the unit (e.g., at a rate of 400 Hz). Dielectric forces may be applied to units in solution directly; additionally or alternatively. In some embodiments, dielectric forces are applied to beads encapsulated in aqueous droplets in an oil. Dielectrophoretic routing of units may be performed at rates of, of about, or greater than 10, 20, 30, 40, 50, 60, 70, 80, 90, 100, 125, 150, 175, 200, 250, 300, 350, 400 Hz or more. In some embodiments, dielectrophoretic routing of units is performed at rates less than 500, 400, 350, 300, 250, 200, 175, 150, 125, 100, 90, 80, 70, 60, 50, 40, 30, 20, 10 Hz or less. Dielectrophoretic routers may be configured to route units within the microfluidic devices described herein at a rate that falls within a range bounded by any of the foregoing values, e.g. 100-400 Hz, 10-300 Hz, 20-500 Hz, etc.

In another embodiment, routers described herein comprise or are implemented in cooperation with charged droplet steering apparatus that encapsulates beads in aqueous droplets in an oil stream. The droplets may be given a net charge. The routers may be used to route the charged droplets, for example steer them at a sorting junction, such as by affecting attraction toward and/or repulsion by charged plates. In various embodiments, routers acting on charged droplets may be configured to route units within microfluidic devices described herein at, at about, or at greater than 100, 200, 300, 400, 500, 600, 700, 800, 900, 1000, 2000 Hz or higher. Routers acting on charged droplets may be configured to route units within the microfluidic devices described herein at rates less than 2000, 1000, 900. 800. 700. 600, 500, 400, 300, 200, 100, 75, 50, 25, 20, 10 Hz or less. Routers acting on charged droplets may be configured to route units within the microfluidic devices described herein at a rate that falls within a range bounded by any of the foregoing values, e.g. 100-1000 Hz, 10-2000 Hz, 20-500 Hz, etc.

In another embodiment, routers described herein comprise or are implemented in cooperation with an electrostrictive apparatus. For example, electrostrictive apparatus may comprise sources of positive and negative potentials applied to opposing sides of a layer of an elastomeric polymer. Without being bound by theory, such positive and negative potentials may be used to apply forces that cause the polymer to compress. The elastomeric polymer may be coupled to or integrated with a wall of a chamber, such that the applied forces cause the chamber volume to expand and/or contract. In various embodiments, multiple chambers configured to be under the control of electrostrictive apparatus may be coupled to a flow channel via a cross channel (e.g., as described above). A first chamber that may be actuated to pull fluid from the flow channel into the first chamber. If a second chamber fluidically connected to the cross-channel junction is deactivated, fluid may be released from the second chamber to the flow channel.

In another embodiment, routers described herein comprise or are implemented in cooperation with thermal bubble forming apparatus. Thermal generation of microbubbles can rapidly generate gasses that displace liquid volume. Microbubbles may be used for routing of units, (e.g. beads) in a flow stream, for example, by displacing liquid around a unit and thereby creating a flow stream. In related embodiments, routers comprise or are implemented in cooperation with electrochemical bubble forming apparatus. Electrochemical generation of microbubbles can rapidly generate gasses that displace liquid volume and can be used for routing of units (e.g. beads) in a flow stream.

Various embodiments of routers described herein comprise microheaters or microactuators configured to generate bubbles. Use of microheaters and microactuators for bubble generation is further described in aus der Wiesche, S. Rembe, C., Maier, C., and Hofer, E. P. Dynamics in Microfluidic Systems with Microheaters (1999) and Chen, C., Wang, J. and Solgaard, O. Micromachined bubble-jet cell sorter with multiple operation modes. Sensors and Actuators B. 2006; 117: 523-529, both of which are herein incorporated by reference in their entirety. See also, Vercruysse, D., Liu, C., Dusa, A. d Wijs, K., Majeed, B. Miyazaki, T. Peeters, S., and Lagae, L. A High-Speed Miniaturized Cell Sorter with Lens-Free Imaging and Thermal Bubble Based Jet Flow Sorting. 18th International Conference on Miniaturized Systems for Chemistry and Life Sciences 2014: 382-384; UK Patent Application No. GB 2561587; and European Patent Application No. EP2602608, all of which are herein incorporated by reference in their entirety. Without being bound by theory, bubbles generated within a fluid of substantially laminar flow may cause a displacement of the fluid and/or unit(s) within the fluid laterally with respect to the direction of flow, e.g. by a force that disturbs the fluid and/or unit(s) within the fluid laterally with respect to the direction of flow.

In some embodiments, routers described herein comprise a vortex element or elements configured to generate a vortex in a flow stream within a desired distance from the microactuator, e.g., within about 1 μm, 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 350 μm, 400 μm, 450 μm, or 500 μm or more from the microactuator. Without being bound by theory, a vortex generated downstream from a microactuator configured to generate bubbles in the fluid moving along a channel may be used to amplify the displacement of the fluid and/or unit(s) within the fluid and/or the force that disturbs the fluid and/or unit(s) within the fluid. For example, a displacement and/or force generated by a microactuator configured to generate bubbles upstream from the vortex element may be amplified by the vortex. In some cases, the vortex elements configured to generate a vortex may comprise a recess, turn, and/or protrusion in a channel within a microfluidic device (e.g., a triangular recess on the channel wall). The generated vortex may travel downstream with the unit to be sorted and may cause routing of the unit into a branch channel. In some embodiments the vortex generating element is located between a microheater or microactuator configured to generate bubbles, and a branch channel.

In some embodiments, microfluidic devices described herein comprise a microactuator configured to generate bubbles, one or more vortex elements configured to generate a vortex and/or a branch point configured to route a unit in flow into one of a plurality of branch channels, located within 100 μm to 10 mm along the direction of flow. The path comprising a microactuator, one or more vortex elements configured to generate a vortex, and/or a branch point configured to route a unit into a branch channel may have a length of at least 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 1000 μm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.5 mm, 4.0 mm, 4.5 mm, 5.0 mm, 6.0 mm, 7.0 mm, 8.0 mm, 9.0 mm, 10.0 mm, or more. The path comprising a microactuator, one or more vortex elements configured to generate a vortex, and/or a branch point configured to route a unit into a branch channel may have a length of at most 10.0 mm, 9.0 mm, 8.0 mm, 7.0 mm, 6.0 mm, 5.0 mm, 4.5 mm, 4.0 mm, 3.5 mm, 3.0 mm, 2.9 mm, 2.8 mm, 2.7 mm, 2.6 mm, 2.5 mm, 2.4 mm, 2.3 mm, 2.2 mm, 2.1 mm, 2.0 mm, 1.9 mm, 1.8 mm, 1.7 mm, 1.6 mm, 1.5 mm, 1.4 mm, 1.3 mm, 1.2 mm, 1.0 mm, 900 μm, 800 μm, 700 μm, 600 μm, 500 μm, or less. The length of the path comprising a microactuator, one or more vortex elements configured to generate a vortex, and/or a branch point configured to route a unit into a branch channel may fall within a range bound by any of the foregoing values, e.g. 1.6-8.0 mm, 750 μm-2.3 mm, or 100 μm-3.5 mm.

In some embodiments, microfluidic devices comprising routers comprising or implemented in conjunction with a thermal bubble forming apparatus comprise one unit delivery channel and one or more (e.g. two) fluid delivery channels that all open into a switch chamber with two branch outlet channels. The fluid delivery channels may be connected to a common fluid source. In some embodiments, the fluid delivery channels terminate in a firing chamber and a nozzle connected to the switch chamber. In some embodiments, one or more microactuator(s) (e.g. microheater(s)) is incorporated into the wall of the firing chamber. The microactuator may be used to generate a bubble, e.g. following application of an electrical pulse. Growth of the bubble may force the incoming fluid from a fluid delivery channel to pass through the nozzle and form a jet that pushes a selected unit toward the desired (e.g. the farther) branch outlet channel. Timing of the application of the electrical pulse may be calibrated to cause incoming units to enter into a designated branch outlet channel.

The routers comprising or implemented in cooperation with a thermal bubble forming apparatus described herein may be fabricated using any suitable method known in the art, including without limitation photolithography and deep reactive ion etching (DRIE) to form microfluidic channels and etch on an opposite side of a silicon wafer housing the microfluidic channels openings providing connections to the channels and access to actuator pads. Optical access may be provided by any suitable material known in the art, such as by Pyrex wafers covering the microfluidic channels. Bubble actuator circuits may be patterned on a suitable medium known in the art, e.g, Pyrex. In one example, trenches about 1 μm deep are etched on Pyrex wafers using hydrofluoric acid (HF); a layer of about 400 Å titanium is sputtered on the Pyrex and patterned by a lift-off process to construct micro-heaters; conducting wires are made by successive sputtering and lift-off of 3000 Å gold; an insulating layer of 3000 Å silicon nitride is deposited on Pyrex by plasma-enhanced chemical vapor deposition (PECVD) and patterned by plasma etch; and Pyrex wafers are anodically bonded to Si wafers. Heaters, conductors and/or insulators may be patterned in the Pyrex trenches. The construction of routers comprising or implemented in cooperation with a thermal bubble forming apparatus (e.g., bubble-jet distributors) are described in Chen, C., Wang, J. and Solgaard, O. Microma-chined bubble-jet cell sorter with multiple operation modes. Sensors and Actuators B. 2006; 117: 523-529, which is incorporated herein by reference in its entirety.

In another embodiment, routers described herein comprise or are implemented in cooperation with acoustic steering apparatus. An acoustic steering apparatus may be configured to generate sound/pressure waves and apply such waves to flow within the system (e.g. in a way that produces standing waves of low and/or high pressure). Standing acoustic waves may be used to route units, e.g. beads in the microfluidic devices described herein. In some embodiments, transient surface acoustic waves are used to route units.

In another embodiment, routers described herein comprise or are implemented in cooperation with electrowetting apparatus that generates electric fields/electric charges. Electric fields and/or charges may be configured to modulate surface tension at corresponding liquid-gas, liquid-solid, and/or liquid-liquid interfaces. Modulation of surface tension may be used to maintain or release pressure gradients that cause fluids to remain still or move under resulting modified pressures provided by the electrowetting apparatus, thereby routing units (e.g. beads in fluid communication with the modulated fluids).

Routers as described further herein may be configured to merge one or more units from different channels or branch channels. For example, a router may be configured to merge one or more units from a first channel to a second channel, from two or more channels into a single channel, or from two or more branch channels to a second channel. A single type of router or any combination of routers may be used in a single device. The sequencing of moving specific individual units or sets of units into specific locations within a device, or from one channel to another, or from two or more branch channels into a single destination channel may be controlled by a single type of router or a combination of different types of routers as described in further detail herein. The movement of units into one or more channels may be verified by one or more detectors.

The microfluidic device described herein may be configured to distribute one or more units from one channel to one or more channels or branch channels via any appropriate distribution mechanism known in the art. The devices described herein may comprise one or more types of distributors. Distributors in a microfluidic device can be configured to stop, hold, direct, or redirect units or fluid in the device. A distributor may be used to close off sections of the channel(s) or branch channels, or to impede progress of the units through or into a channel or branch channel.

Distributors in a microfluidic device may be configured to distribute one or more units from a primary channel into one or more branch channel(s) based on the positional order of the unit(s) in the primary channel. Distributors may also be configured to distribute one or more units into one or more branch channel(s) based on a label on a unit. The distribution of one or more units to a branch channel may be predesig-nated according to an intended sequence of reactions and/or treatments. The intended sequence of reactions and/or treatments may be preassigned to the one or more unit. The channels to which the one or more units may be distributed may also be randomly assigned to the one or more unit. Methods to distribute one or more units into a channel or branch channel include, but are not limited to, altering the position of a unit within the laminar or laminar-like flow at or before a branch point; the presence of one or more moving or non-moving mechanical devices at or before a branch point to direct units into a channel or branch channel; any method that alters the amount or pressure of the fluid flow through branch channels such that units are directed into one or more branch channel(s), or any combination thereof or any other suitable method known in the art. The correct distribution of one or more units into one or more branch channel(s) may be verified using detectors. Incorrectly distributed units may be subjected to an error correction mechanism described elsewhere herein, for example, by directing and/or holding one or more units into a side channel and/or redirecting the one or more units in a side channel back into a primary channel holding positionally ordered units, and/or any other suitable error correction mechanism known in the art.

In some embodiments, the units are distributed by altering the position of the unit within the fluid. Such methods can alter the position of the unit within ordered flow, for example within laminar or laminar-like flow, of a channel. Lateral movement of a unit within flow may cause the unit to be directed into a desired channel at a branch point, typically the channel located at the same side as the unit's relative position within flow prior to the branch point. Methods that alter the position of a unit within the flow include the application of electrostatic or electrokinetic forces such as electrophoresis, dielectrophoresis, and electroosmotic flow; acoustic forces such as bulk standing waves, standing surface acoustics waves, and traveling waves; optical manipulation(s) or optical radiation with focused laser beam(s), also known as optical tweezers; application of side flow or cross flow at an angle to the flow direction of a unit to move the unit laterally within the flow; gravity; magnetophoresis if the units contain ferromagnetic materials; flow focusing; via the application of any other suitable type of force known in the art; or combinations thereof. In some embodiments, application of side flow or cross flow is performed by application of pressure, electroosmosis, or displacement via pistons or actuators, such as those comprising piezoelectric, electro-static or electroactive polymers, or pumps such as electoos-motic pumps.

In some embodiments, the units are distributed by moving mechanical distributors. Moving mechanical distributors that may be configured to distribute units include, but are not limited to, rotary valves, ratchet mechanisms, pins, flippers, gates, flow switching mechanisms, or channel actuation via application of heat to a thermoreversible gelation polymer.

In some embodiments, the units are distributed by methods that alter the fluidic pressure of a channel, including without limitation a branch channel. This method can be used to cause increased or decreased fluid from one channel to flow into another specified channel at the branch point. For example, as the relative pressure is increased in one channel and decreased in a second, connecting channel, the carrier fluid and units carried therein can be directed into the second channel with the lower relative pressure.

Routers, e.g. distributors, having suitable configurations as described in further detail herein may also be used as mergers to merge units from at least q channels into q-j channel(s), where q>j. For example, units from two channels may be merged into one merger channel, or units from four channels may be merged into three, two, or one merger channels. Differential pressures may be utilized to cause release of units from two or more branch channels into one or more channels in a designated order. By application of a lower relative pressure into a first branch channel, units therein may be kept from entering the branch point and/or an adjacent merger channel while units from a second branch channel leading to the same branch point may be released from the second branch channel into and/or past the branch point. Such units may be routed into the merger channel prior to the release of units from the first branch channel into the branch point and/or merger channel.

In various embodiments, dedicated routers, e.g. distributors, are used to facilitate the movement and/or merging of mobile units. For example, a router, e.g. a distributor, placed at the branch point of two channels can be configured to direct one or more unit into one or more channel(s) or branch channel(s) during distribution. In the reverse direction, the same router may block, hold, or impede the movement of units from a first branch channel while allowing the movement of units from a second branch channel into a single channel, thus allowing the controlled and/or orderly distribution of units as well as the controlled and/or orderly merging of units. Distribution of units into branch channels may comprise distributors that act on one or more units with spacing between them. Units may be merged from p channels into p-b channels, where p>b, via use of any router, e.g distributor, to route one or more units in a first channel and then route one or more units from a second channel.

In various embodiment, microfluidic devices and systems comprise one or more of the following: high-speed routers, e.g. distributor(s), for directing units into one of the multiple branch channels, e.g. for parallel synthesis; high-speed unit counting sensor(s) configured to detect units prior to a distribution step; and device integration that combines discrete components, for example unit router(s), unit detector(s), multiple capillaries, and/or reagent mixing chips into a complete device.

The position of the units in the device may be maintained by a variety of methods. For example, the position of the units in the device may be maintained by placing physical constraints on the units in a channel(s) to preserve the relative position of the units or by spacing the units in a channel(s) under continuous flow or by a combination of both within the same device. To place physical constraints on units, a channel width may be selected to be sufficiently narrow so that units cannot pass one another in the channel. To maintain order of units in flow, e.g. in laminar or laminar-like flow, the units may be separated in continuous or stopped flow with sufficient space between the units that they do not pass one another during the flow or during stopped flow. While uncontrolled migration of the units due to factors like, but not limited to, diffusion, or sedimentation may eventually cause units to pass one another, stopped flow for short periods of time can maintain order of sufficiently spaced units for desired periods of time.

The microfluidic device described herein may also correct unit position errors introduced during the operation of a microfluidic device described herein, for example during operation for nucleic acid synthesis. Additional routers and channels may be added to the system to handle units that have been incorrectly distributed. Units incorrectly distributed at a first router may be routed into a second channel where correct distribution can be performed immediately. For example, a channel comprising a loop can return a unit to a position before the distribution router such that the unit can be correctly routed. Units can also be routed into branch channels and held for either the remainder of device operation, or they can be held temporarily and subsequently routed back to into position to be distributed.

In some cases, two or more neighboring units may exchange position while not affecting other units on either side of the exchanged units. In various embodiments, such units getting out of positional order are identified by a detector. This type of error may result in incorrect reactions, treatments, or modifications being applied to the units, e.g. incorrectly synthesized molecules on affected units. In some embodiments, this error occurs at less than 0.000001 times, 0.00001 times, 0.0001 times, 0.001 times, 0.0025 times, 0.005 times, 0.0075 times, 0.01 times, 0.025 times, 0.05 times, 0.075 times, 0.1 times, 0.25 times, 0.5 times, 0.75 times, 1 times, 2 times, 3 times, 4 times, 5 times, 10 times, 15 times, 20 times, or 30 times per unit per 100 cycles of modification.

In some cases, one or more units may be incorrectly distributed through mis-routing at a branch point. In various embodiments, mis-routed units can be identified by a detector. In some embodiments mis-routing can be detected in the channel in which reactions or treatments occur. In some embodiments, mis-routing can be detected after mis-routing by detectors placed after the branch point. In some embodiments detection of the mis-routing event can occur at any point between the branch point and the channel in which the reactions or treatments occur. The effect of this type of an error may be limited to only the mis-routed units. Subsequent units may be correctly routed, and only the mis-routed unit may be affected by the mis-routing. In some embodiments, the mis-routing is detected, and the positions of all units is updated accordingly so that the history of each unit is known and units with the desired sequence of treatments can be identified and/or from those without the desired sequence of treatments, e.g. nucleic acid synthesis steps.

In various embodiments, additional routers and channels may be added to the microfluidic device system to hold units that have been incorrectly distributed. In some embodiments, a mis-routed unit may be detected and routed into a branch channel for holding until the unit can be routed back, for example for further distribution. In some embodiments, treatments and chemical reactions are reserved from mis-routed units held in such channels. Units can also be routed into branch channels and held for either the remainder of device operation or discarded. Units incorrectly distributed at a first router, e.g. a distributor, may be re-routed into a second channel where correct distribution can be attempted immediately, such as a channel comprising a loop that returns a unit to a position before the distributor such that another attempt at correctly routing the unit can be made. In various embodiments, the positional information of the mis-routed units and all other units is updated, such that the position and history of all or a subset of the units throughout the device remains known. In some embodiments, these types of errors may be tracked or corrected such that they do not result in a loss of correct sequence of treatments or modifications applied to or to be applied to some or all units.

In some embodiments, this type of a mis-routing error occurs at, less than or less than about 0.000001 times, 0.00001 times, 0.0001 times, 0.001 times, 0.0025 times, 0.005 times, 0.0075 times, 0.01 times, 0.025 times, 0.05 times, 0.075 times, 0.1 times, 0.25 times, 0.5 times, 0.75 times, 1 times, 2 times, 3 times, 4 times, 5 times, 10 times, 15 times, 20 times, or 30 time per unit per 100 cycles of modification. Values for the error rates may range between any of the potential values set forth for the error rates herein. In some embodiments, mis-routed units may escape detection. This type of error may result in incorrect synthesis history for units that are out of positional order. In some embodiments, labeled units capable of labeling units, for example beads that can be colored with pigment or imbued with fluorescent properties, are used to verify routing. Detectors at any point in the device or on any cycle of operation may be used to verify such labeled units are in the expected relative position. In one embodiment for example, one in 100 beads in a device may be labeled with a fluorescent dye. During device operation, the relative positional ordering of these labeled and distinguishable beads may be verified against their expected position based on predesignated routing paths for each of the units. In some embodiments, the verification occurs in reaction channels after each cycle of device operation. In other embodiments verification occurs on each cycle in the initial channel prior to distribution. In further embodiments verification occurs only once after all cycles are complete and all modifications have taken place.

In various embodiments, devices and systems described herein are operated for multiple cycles, where all or substantially all of the units within a microfluidic device are returned to a common area, such as a channel. Unit detection, identification of mis-routing events, corrective routing may be performed one or more times during each cycle of operation.

Unit Spacing

In various embodiments, units are held and moved together in a group having units adjacent to each other in a channel. This "stacked regime" may comprise units that are held or flowed in direct contact with (e.g. end-to-end and/or with their geometric centers offset) or in close vicinity of each other. In various embodiments, the order of units within a channel is maintained by the restrictive width of the channel holding the units, preventing units from swapping positions outside of their order. The ratio of unit diameter and/or sizes to channel diameter, cross-section, or widths can be selected to maintain positional ordering and/or to prevent wedging of units within a channel which may lead to clogging.

Without wishing to be bound by theory, units moving through a microfluidic device in a stacked regime can contact each other and the channel at acute angles, creating a force that may push the units into the channel walls. This may result in the likelihood of the units wedging and clogging the channel. Such forces may become so great as to distort or compress the units such that the units stop moving in the channel. In addition, imperfection in the unit surface may likewise prevent movement through the channel. Without wishing to be bound by theory, a solution to units clogging in the stacked regime includes the use of straight and sufficiently smooth channels, and/or units that are sufficiently smooth and/or round. Channels that are straight and sufficiently smooth can support movement of beads in the stacked regime. In addition, unit spacers may be incorporated into the microfluidic devices described herein to separate stacked beads in channels with changing dimensions, e.g. at width transitions, or at branch points.

Units in the stacked regime may be abutting or touching one another in the channel(s). In some embodiments, units are less than 1 unit length apart in the direction of the flow, e.g. due to the offset geometric centers within a channel. Units may be a fraction of a unit length apart. In some embodiments, units are about, less than, or less than about 2, 1.9, 1.85, 1.8, 1.75, 1.7, 1.65, 1.6, 1.55, 1.5, 1.45, 1.4, 1.35, 1.3, 1.25, 1.2, 1.15, 1.1, 1.05, 1, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05 or fewer unit lengths apart, center to center, in the direction of the flow. Center to center unit spacing in the direction of the flow may fall within any range bound by the foregoing values, including for example 0.1-0.2, 0.1-1, 0.2-0.3, 0.2-1.5, 0.3-0.4, 0.4-0.5, 0.5-0.6, 0.6-0.7, 0.7-0.8, 0.8-0.9, or 0.9-2 unit lengths. Values for the unit spacing may range between any of the potential values set forth for the unit spacing herein.

In various embodiments, units are separated by space from each other. This "separated regime" may facilitate proper distribution by allowing various routers, e.g. distributors, to act on units individually, without interference from other units; may allow units to navigate various features or aspects of the device that could briefly or temporarily slow or impede the movement of a unit such as a corner, constriction, edge, expansion, or combination thereof without risk of clogging due to interference or contact by adjacent units; and may allow units to move to and from areas of the device in ordered flow, e.g. in laminar or laminar-like flow. Flow-based unit ordering, e.g. in laminar or laminar-like flow can be used to allow the use of channels that are greater in width than those allowed in a stacked regime. Ordered flow may be maintained in separated regime in channels having greater widths than widths that allow for maintaining unit order by physically constraining unit mixing, including without limitations widths that are about, more than, or more than about 2 times the width of unit size.

In a flow-based unit ordering regime, units may be maintained within channels having widths that are about, more than, or more than about 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 5, 6, 7, 8, 9, 10, 15, 20, 25, 30, 35, 40, 45, 50, 55, 60, 65, 70, 75, 80, 85, 90, 95, 100 or more times the average or nominal diameter and/or size of the units. Values for the channel widths may range between any of the potential values set forth for the channel widths herein.

Also provided herein are methods for separating units. A spacer or ejector device may be configured to apply a fluidic shear force that results in a first unit accelerating away from a second unit as the first unit passes through the spacer or ejector device. The acceleration of the first unit may introduce space and/or additional fluid volume between the first and second unit.

Units may be moved through a channel feeding into a unit spacer in various configurations, including, without limitation, individually or as a stacked column. When a unit reaches a unit spacer, e.g. at a T-intersection, an in-line spacer channel, or any suitable cross-channel geometry, units may be separated by the additional flow, or "cross flow," in the main channel. The additional flow(s) for spacing fluids (e.g., for a T-intersection, for a cross-channel, for an inline-spacer channel for other geometries, etc.) entering from side channels may be created without additional pressure sources. For instance, a bypass channel with low fluidic resistance may be used to redirect fluid upstream of a stacked unit (e.g. bead) column and into the spacer. The lower fluidic resistance may be configured to yield a higher flow rate through the bypass channel than along the unit stack. Increased flow rates may be used to induce high shear and a degree of unit separation. Unit separation may be influenced by channel geometries near the spacer.

Additionally or alternatively, in associated embodiments, the systems described herein comprise one or more spacers (e.g., spacers having independent pressure control a bypass channel) fluidly interfaced with the channels of a microfluidic device. Such spacers may be used to restack beads or other units in a controlled manner. In operation, such a spacer may be used to reduce the spatial extent of a collection of beads or other units in a portion of the system. In various embodiments, such spacers are configured in conjunction with or without unit (e.g. bead) stops. In more detail, the system can allow fluid flow, with beads or other units, through such spacers in reverse, such that one or more beads can be returned in reverse manner through the spacer to allow restacking or re-ordering of beads in a controlled manner. Additionally or alternatively, such spacers may be used with a bypass channel and an element (e.g., valve, check-valve, variable flow restriction unit, one-way flow restriction unit, etc.) that prevents return flow through the bypass channel, such that beads or other units can be removed from a stack, and not re-stacked. Any of the above spacer embodiments can include wall geometries designed to ensure that beads enter the exit channel without jamming. In one example of a wall geometry that mitigates jamming, the wall geometry can include a narrow gap or slit in the channel wall (e.g., primary channel wall, cross-flow channel wall, etc.). Such a gap or slit may have a width that is less than the diameter of one unit, e.g. bead or other characteristic dimension of a bead or other unit. In examples, the gap or slit width can be less than 20 nm, 100 nm, 500 nm, 1 μm, 2 μm, 3 μm, 4 μm, 5 μm, 6 μm, 7 μm, 8 μm, 9 μm, 10 μm, 20 μm, 30 μm, 35 μm, 40 μm, 50 μm, 60 μm, 70 μm, 80 μm, 90 μm, 100 μm, etc. Those of skill in the art will appreciate that the slit or gap width may have a value that is within any range bound by any of these values, for example 20-100 nm, 100-500 nm, 500-1000 nm, 1-10 μm, 10-20 μm, 20-30 μm, 30-40 μm, 40-50 μm, 50-60 μm, 60-70 μm, 70-80 μm, 80-90 μm, 90-100 μm, etc., with associated tolerances as described above.

Figure 22A:
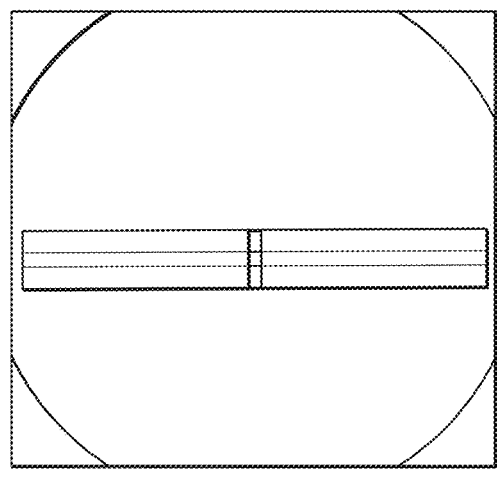
FIG. 22A-D provides images of a unit stop (A), a unit spacer (B), a unit spacer with polished capillaries inserted (C) and a cross channel unit spacer (D).
Figure 22B:
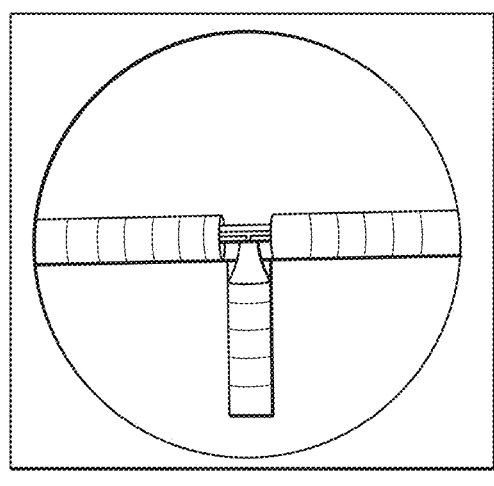
Figures 22C, 22D:
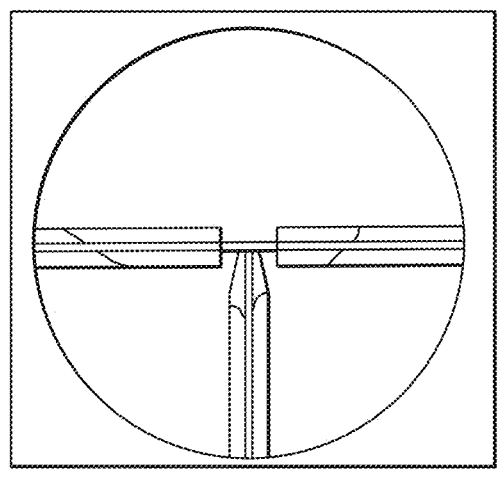

In one example, units entering a unit spacer having a cross-channel geometry from a feeding channel may enter into a cross-flow incoming laterally to the unit's flow. FIG. 22D provides an illustrative implementation of a unit spacer with cross-flow geometry constructed in accordance with the embodiments herein. The cross-flow may be generated by flow from opposing or substantially opposing directions. The cross-flow may be perpendicular or substantially perpendicular or have a component of velocity perpendicular or substantially perpendicular to the units' path through the unit spacer. The cross-flow may be provided by two or more channels leading into the cross-channel geometry of a unit spacer. A first unit may flow past the cross-channel geometry, followed by a mix of fluid from each side of the cross-flow. In some embodiments, the pressures in channels generating the cross-flow are adjusted such that they are equal and greater than the pressure in the downstream portion of the entering unit's path and less than the pressure in the feeding channel. The pressures in channels generating the cross-flow need not be equal. Unequal flows may be used according to various embodiments, for example to bias flowing units laterally with respect to the units' direction of flow. Suitable pressures, pressure differentials, and/or flow rates, flow rate differentials for causing a desired movement of a unit within the microfluidic devices described herein may be selected as described in further detail elsewhere herein or as is otherwise known in the art.

A spacing may be generated between the first unit and a second unit entering the unit spacer subsequent to the first unit by the mix of fluid from each side of the cross-flow being introduced between the first and the second channel as they move past the unit spacer. In some embodiments, e.g. for a T-intersection type unit spacer, the cross-flow is provided by one channel. The spacing introduced between units may be used to facilitate subsequent distribution of each unit at a branch channel, various embodiments of which are described in further detail elsewhere herein, by allowing that the router, e.g. a distributor, act on units individually for each distribution event. Therefore, entry of a plurality of units into a router at once may be prevented by introducing a space between units moving in channels of the devices described herein.

Units may also be spaced from each other in the channel. The units may be spaced by a spacer length of about, more than, or more than about 1, 2, 3, 4, 5, 6, 7, 8, 9, 10, 12, 14, 15, 16, 18, 20, 25, 50, 75, 100, 200, 300, 400, 500, 600, 700, 800, 900, 1000, 2000, 3000, 4000, 5000, 6000, 7000, 8000, 9000, 10,000, 50,000, 100,000 or more unit diameter and/or sizes apart. The units may be spaced by a spacer length of about, less than, or less than about 100,000, 50,000, 10,000, 9000, 8000, 7000, 6000, 5000, 4000, 3000, 2000, 1000, 900, 800, 700, 600, 500, 400, 300, 200, 100, 90, 80, 70, 60, 50, 40, 30, 20, 15, 10, 9, 8, 7, 6, 5, 4, 3, 2, 1 or less unit diameter and/or size apart. The spacer length between units may fall within any range bounded by the foregoing limits, including without limitation, between 1-10, 20, 20-30, 30-50, 50-100, 100-250, 250-500, 500-1000, 1000-2500, 2500-5000, 5000-7500, 7500-10,000, 10,000-50,000, 50,000-100,000 unit diameter and/or sizes. The units may be spaced by a spacer length of about, more than, or more than about 1 μm, 2 μm, 3 μm, 4 μm, 5 μm, 6 μm, 7 μm, 8 μm, 9 μm, 10 μm, 12 μm, 14 μm, 15 μm, 16 μm, 18 μm, 20 μm, 25 μm, 50 μm, 75 μm, 100 μm, 200 μm, 300 μm, 400 μm, 500 μm, 600 μm, 700 μm, 800 μm, 900 μm, 1000 μm, 2000 μm, 3000 μm, 4000 μm, 5000 μm, 6000 μm, 7000 μm, 8000 μm, 9000 μm, 10,000 μm, 50,000 μm, 100,000 μm or more. The units may be spaced by a spacer length of about, less than, or less than about 100,000 μm, 50,000 μm, 10,000 μm, 9000 μm, 8000 μm, 7000 μm, 6000 μm, 5000 μm, 4000 μm, 3000 μm, 2000 μm, 1000 μm, 900 μm, 800 μm, 700 μm 600 μm, 500 m, 400 μm, 300 μm, 200 μm, 100 μm, 90 μm, 80 μm, 70 μm, 60 μm, 50 μm, 40 μm, 30 μm, 20 μm, 15 μm, 10 μm, 9 μm, 8 μm, 7 μm, 6 μm, 5 μm, 4 μm, 3 μm, 2 μm, 1 μm or less. The spacer length between units may fall within any range bounded by the foregoing limits, including without limitation between 0-10 μm, 20 μm, 20-30 μm, 30-50 μm, 50-100 μm, 100-250 μm, 250-500 μm, 500-1000 μm, 1000-2500 μm, 2500-5000 μm, 5000-7500 μm, 7500-10,000 μm, 10,000-50,000 μm, 50,000-100,000 μm. Values for the unit spacing may range between any of the potential values set forth for the unit spacing herein.

Pressure Differentials

Figures 31A, 31B, 31C, 31D, 31E, 31F:
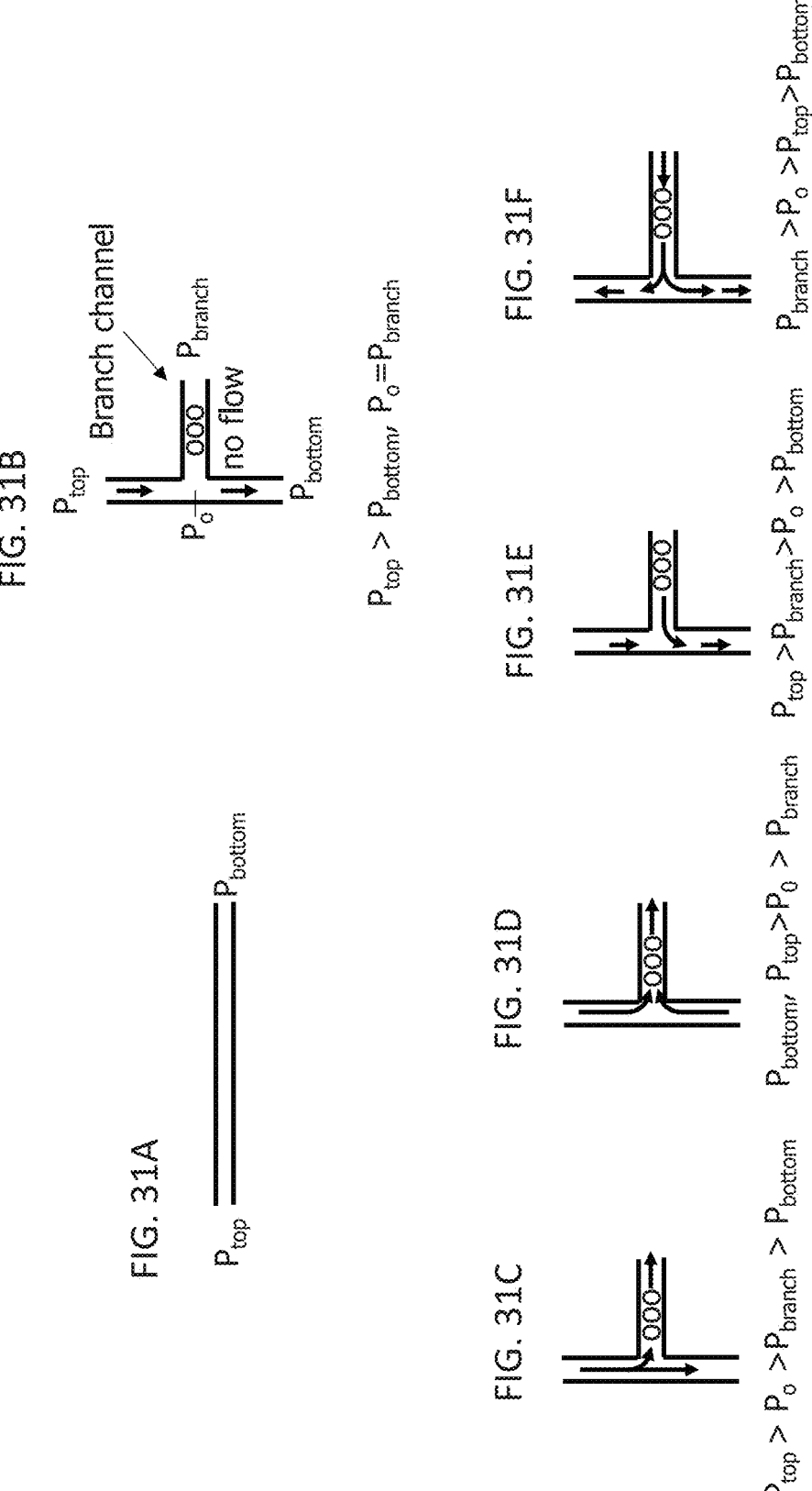
FIG. 31A-F provides diagrams of differential pressure for distributing units in a single T junction.

In various embodiments, units flowing through the channels and branch points of the microfluidic devices described herein, may be routed in a designated direction by adjusting pressures and/or flow rates within channels that connect through branch points. FIG. 31 shows exemplary pressure settings in channels connected through one branch point. Without being bound by theory, fluid within microfluidic devices flows down a gradient in pressure. Further, in various channel configurations, pressure drops continuously along the direction of flow. Further without being bound by theory, flow rates through channels of microfluidic devices correlate with the pressure differential between two points $(P_{top}-P_{bottom})$ divided by the channel length between such two points (FIG. 31A).

In a branch point of a main channel intersecting with a branch channel (FIG. 31B-F), pressures at locations a distance away from the branch point may be adjusted to set a pressure value at the branch point $P_0$. In FIG. 31B, pressures are adjusted such that $P_{top} > P_{bottom}$ in the main channel and the pressure value at the branch point $P_0$ is equal to $P_{branch}$ ($P_0 = P_{branch}$). In FIG. 31C, pressures at the corresponding locations are adjusted such that $P_{top} > P_{bottom}$ and $P_0 > P_{branch}$, leading to flow from top to bottom of the main channel as well as from branch point into the branch channel. In FIG. 31D, pressures at the corresponding locations are adjusted such that $P_{top} > P_0 > P_{branch}$ and $P_{bottom} > P_0 > P_{branch}$, leading to flow from the top and the bottom of the main channel into the branch channel from the branch point. In FIG. 31E, pressures at the corresponding locations are adjusted such that $P_{top} > P_{branch} > P_0 > P_{bottom}$, leading to flow from the top of the main channel as well as the branch channel toward the bottom of the channel. In FIG. 31F, pressures at the corresponding locations are adjusted such that $P_{branch} > P_0 > P_{top}$ and $P_{branch} > P_0 > P_{bottom}$, leading to flow from the branch channel to the top as well as the bottom of the main channel. Pressure differentials can be created by setting pressures in a variety of location within microfluidic devices described herein to route flow and/or units carried therein in designated directions following a pressure gradient.

FIG. 32 provides further exemplary embodiments using pressure differentials to route units within microfluidic devices described herein. A branch point configuration with a main channel and two branch channels B1 and B2 is illustrated describing pressure values at the top and the bottom of the main channel $P_{top}$, $P_{bottom}$, respectively, at the intersection of the main channel with the first branch channel B1 and B2, $P_1$, $P_2$, respectively, and at the distal ends of branch channels B1 and B2, $P_{B1}$, $P_{B2}$, respectively. FIG. 32B-E provide exemplary values for each of these pressures and resulting flow patterns. For example, flow between the intersection of the main channel with branch channel B1 and the intersection of the main channel with branch channel B2 is governed by the pressure differential $P_1 - P_2$. Where $P_1 - P_2 = 0$, there is no flow between these points (FIG. 32B). Similarly, flow into and out of the first branch channel B1 is governed by the pressure differential $P_1 - P_{B1}$; flow into and out of the second branch channel B2 is governed by the pressure differential $P_2 - P_{B2}$; and flow between the top of the main channel and the intersection of the main channel with branch channel B1 is governed by the pressure differential $P_{top} - P_1$; and flow between the bottom of the main channel and the intersection of the main channel with branch channel B2 is governed by the pressure differential $P_{bottom} - P_2$.

Using the pressure differentials exemplified with the pressure values shown in FIG. 32B-E, units may be selectively loaded into branch channel B1 (FIG. 32B) or into branch channel B2 (FIG. 32C). Similarly units can be unloaded selectively from either branch channel. FIG. 32D shows a pressure differential setting for unloading selectively from branch channel B2 toward the top of the main channel. Similar pressure values are set in FIG. 32E as FIG. 32D, except that $P_{bottom} > P_2$ in FIG. 32E, allowing for flow from the bottom of the main channel past the intersection of the main channel with branch channel B2. Thus, as units are unloaded from branch channel B2 toward the top of the main channel, fluid flowing from the bottom of the main channel is introduced between units creating spacer lengths of fluid (FIG. 32E). In contrast, $P_{bottom} = P_2$ in FIG. 32D, resulting in no flow from the bottom of the main channel toward the intersection of the main channel with the second channel B2. Such a setting allows the spacing between units to be maintained as the units enter the main channel from the branch channel (FIG. 32D).

Those skilled in the art will note that similar applications of pressure differentials between various points in microfluidic channels can be used to route, including without limitation to hold, units within microfluidic devices described herein and/or adjust spacing between units.

Multi-Branch Channels

Figure 39:
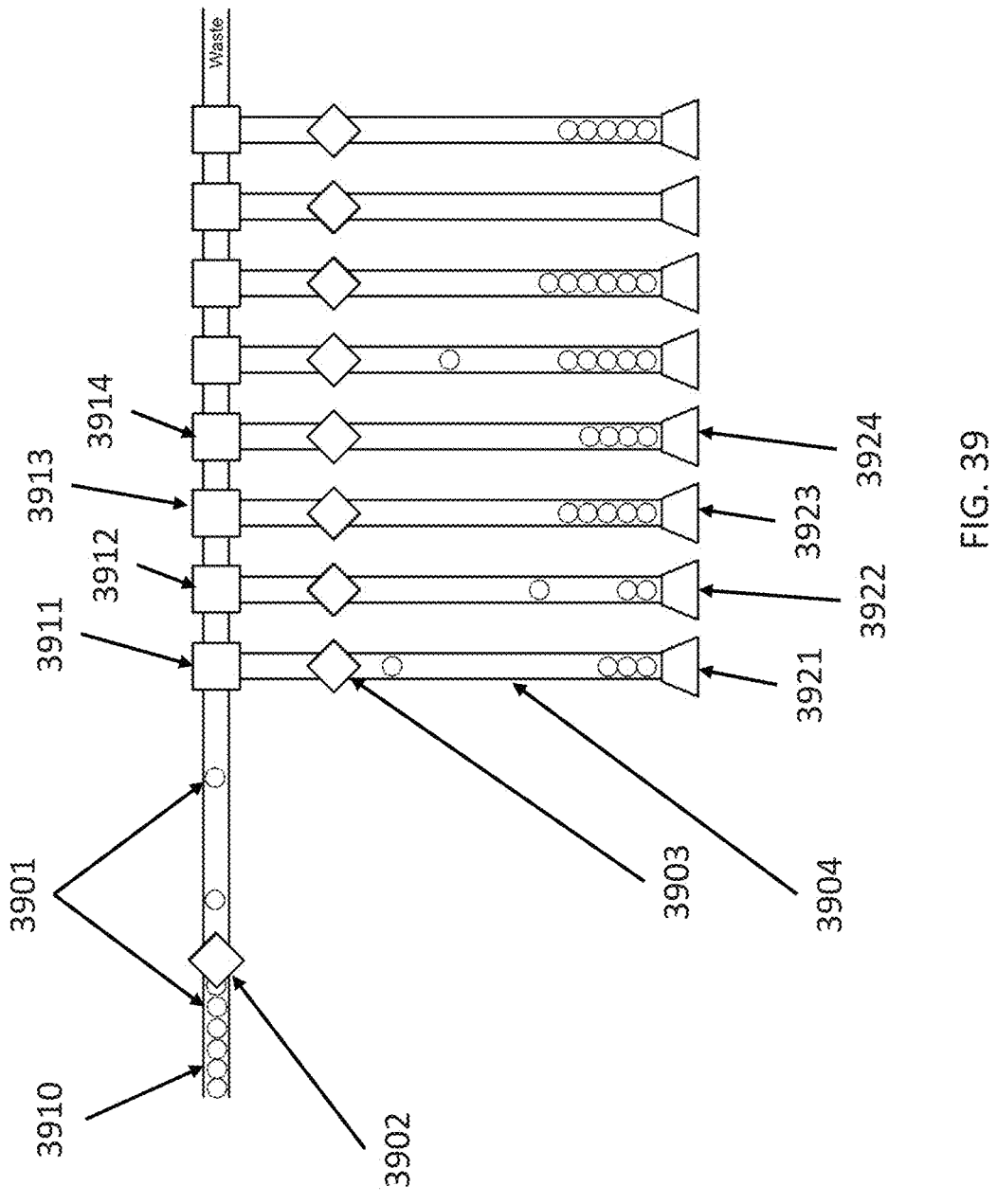
FIG. 39 depicts an exemplary illustration of a router configured to distribute beads into a plurality of branch channels and/or merge beads from a plurality of branch channels.

In various embodiments, the microfluidic devices described in further detail herein, comprise routers and branch points with multiple branch channels. In some embodiments, such branch points comprise multiple "sub-branch points" allowing for units to be sorted into branch channels that branch off in consecutive sub-branch points. FIG. 39 depicts an exemplary illustration of a router configured to distribute beads into a plurality of branch channels and/or merge beads from a plurality of branch channels. Incoming units, e.g beads 3901 as depicted in FIG. 39, as they move from the unit spacer 3902 toward the first router 3911, may be routed into a branch channel 3904, via one of the routers 3911, 3912, 3913, 3914. The units may be stopped with a unit stop (e.g. a bead stop) 3921, 3922, 3923, 3924, within and/or at the end of the branch channel. The units may be merged back into the main flow, for example through a spacer 3903, and/or a router 3911, 3912, 3913, 3914. As the units are distributed from and/or merged into the main flow in the main capillary 3910, fluids may be flowed past the branch point, e.g. into a waste reservoir.

Units

The units may be solid or porous. They may or may not carry an attached library product. The units may be glass, polymeric beads, droplets, or cells. The units may be directly modified by the modification procedures described herein. In some embodiments, both a unit and an associated product is modified by one or more modification procedures described herein. Large collections of units can be generated with specific properties such as color, surface chemistries, labels using the various modification procedures described herein. Some or all of the units within a microfluidic device or a channel thereof may be uniquely encoded, without redundancy. The units may be randomly assigned or assigned based on some physical, chemical, or optical characteristic of each unit. A series of modification procedures may be applied sequentially, in a loop or in series, such that each unit is exposed to a particular set of modification procedures. The positional encoding according to the various embodiments of the invention allows the elimination of redundancy. Accordingly, large numbers of physically encoded library units may be generated at low cost. Such library units may be encoded uniquely. Physically encoded library units may be used in downstream procedures. A first procedure where units are physically encoded may be coupled with a second procedure where products are generated on the units, while preserving the positional encoding between the first and second procedures. This approach can be used to associate physical unit encodings with products. By associating the physical encodings with products, the units can be directed into unrelated procedures where the positional information/encoding may be lost, but physical encoding can be detected.

The units used in various embodiments can be made from a range of materials. In some embodiments, the units are solid. In some embodiments, the units are porous. In some embodiments, the units do not carry an attached library product. The units may be glass, polymeric beads, droplets, bubbles, slugs, or cells. Materials used for beads can include polymers such as polystyrene, melamine resin, polyacrylonitrile, or agarose; hydrogels such as alginate or chitosan; silica, glass, or controlled porous glass (CPG); and metals such as gold, silver, GaAs, GaP, or iron. Silica may be fused silica (amorphous pure silica), quartz (crystalline pure silica), or other generic glass (silica crystalline or amorphous). Many beads can be purchased from vendors such as ThermoFisher or Sigma Aldrich with or without the functionalized coatings, including functionalized coatings with reactive chemistries, affinity tags such as biotin or streptavidin, and/or dyes, such as fluorescent dyes. Units may already have a molecule, for example a nucleic acid on their surface while a second, distinct, chemical or molecular compound is added to their surface, or to such molecule during device operation.

In some embodiments, the units comprise superparamagnetic beads. Without being bound by theory, use of superparamagnetic beads may reduce the number of fluidic connections. In some embodiments, superparamagnetic beads have a high magnetic susceptibility, and are mechanically sound, chemically functionalized, and/or monodisperse.

Barcodes

Units may be barcoded with physical properties, molecular properties, color or pigment, metal, or spectral properties, or any combination thereof. Physical properties include, but are not limited to, etching or shape, or metal bars or deposits. Molecular properties include, but are not limited to, chemical functionalization and chemical compounds, nucleic acids, or biotin or streptavidin affinity tags. Color or pigments include, but are not limited to, fluorescent or non-fluorescent dyes. Barcodes could be used before, after, or during to establish the identity of units prior to commencing operation, during operation to verify the identity of units, or after completion of operation to enable tracking of units after removal from the device and disordering. The identify of barcoded beads may detected and mapped to a unit position so that barcodes need only be read once while positional information is used during operation. Barcodes may be detected at the end of operation to verify correct position.

Units with or without barcodes or labels may be randomly arranged initially. Units may also be arranged in a known pattern, either due to a deliberate arrangement initially, or as a result of a previous round of synthesis performed using positional encoding. In various embodiments, barcodes (labels) comprise nucleic acids. Barcodes may differ in a variety of chemical or physical feature, such as optical or spectral features, including features described herein or any suitable features known in the art. In some embodiments, barcode differ in more than one type of a feature. For example, a barcode having an optical feature may also comprise an oligonucleotide feature. Multiple features of a barcode can be used in combination to identify one or more features about a unit and/or molecules associated with a unit. For example, one feature of a barcode may be used for identification of a unit. Another feature of a barcode may be used for identification of a target associated with the unit.

In various embodiments, barcodes are known nucleic acid sequences that allow some feature of a polynucleotide with which the barcode is associated to be identified. In some embodiments, a barcode comprises a nucleic acid sequence that when associated with a target polynucleotide serves as an identifier of the sample from which the target polynucleotide was derived.

Nucleic acid barcodes can be designed at suitable lengths to allow sufficient degree of identification, e.g. at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or more nucleotides in length. Multiple barcodes, such as 2, 3, 4, 5, 6, 7, 8, 9, 10, or more barcodes, may be used on the same molecule, optionally separated by nonbarcode sequences. In some embodiments, barcodes are shorter than 10, 9, 8, 7, 6, 5, or 4 nucleotides in length. In some embodiments, barcodes associated with some polynucleotides are of different length than barcodes associated with other polynucleotides. In general, barcodes are of sufficient length and comprise sequences that are sufficiently different to allow the identification of samples based on barcodes with which they are associated. In some embodiments, each barcode within a plurality of barcodes differ from every other barcode in the plurality at at least three nucleotide positions, such as at least 3, 4, 5, 6, 7, 8, 9, 10, or more positions.

In some embodiments, units described herein, such as all or some of the units within a microfluidic device described herein, are associated with one or more of a) a unit-specific barcode uniquely identifying the unit, b) a target specific barcode, and c) a target, e.g. an oligonucleotide. Unit-specific barcodes may be associated with the unit alone or with the unit and the target-specific barcode and/or target. For example, a unit-specific barcode may be attached to a unit and a target-specific barcode and the target-specific barcode may be attached to the target. In some embodiments, unit-specific barcodes are associated with the unit, but are not attached to the target-specific barcode and/or the target. In some embodiments, unit-specific barcodes and target-specific barcodes are linked, e.g. covalently. Target-specific barcodes may be associated with targets in a variety of ways, for example covalently. In some embodiments, a first end of a unit-specific barcode is attached to a unit, the second end of the unit-specific barcode is attached to the first end of a target-specific barcode and the second end of the target-specific barcode is attached to a target. In some embodiments, unit-specific barcodes are attached directly to targets associated with the unit. Target-specific barcodes may also be attached to the target, e.g. through the opposite end of the target from the unit-specific barcode. In some embodiments, unit-associated target-specific barcodes continue to be associated with and/or identify targets after being separated from a unit. In various embodiments, target-specific barcodes for each of the targets on a unit are different. In various embodiments, the unit-specific barcode for each of the targets associated with a unit is the same. Unit-specific barcodes and target-specific barcodes can facilitate methods of target analysis, such as analysis comprising counting. Such analysis may comprise sequencing, hybridization and/or any suitable method known in the art. Such analysis may follow an amplification step. For example, upon amplification of the target along with one or more barcodes described herein, the number of different target-specific barcodes can indicate the number of pre-amplification target molecules. In various embodiments, upon amplification of the target along with one or more barcodes described herein, the number of different unit-specific barcodes is used to analyze the number of units the pre-amplification targets were associated with. Such amplification and/or analysis steps, such as sequencing, may follow a hybrid capture step. For example, nucleic acids in a sample may be hybridized to targets associated with units in a hybrid capture step. One or more barcode sequences may be incorporated to hybridized nucleic acids, for example by a nucleic acid extension elongation reaction. The hybridized nucleic acids may be amplified and/or analyzed. The number of hybridized nucleic acids from the sample may be analyzed by counting the number of different barcodes. The identity of barcodes described herein may be probed using hybridization, sequencing, or any suitable method known in the art. Barcodes described herein may be generated through an oligomer synthesis method (such as nucleic acid synthesis or peptide synthesis), e.g. a number of rounds of monomer, (such as nucleotide) incorporation, such as random incorporation. In some embodiments, barcodes are generated through oligomer synthesis of, of about, or of at least 1, 2, 3, 4, 5, 6, 7, 8, 9, 10, 15, 20, 25, 30, 35, 40, 45, 50 or more rounds of monomer incorporation. Barcodes may be synthesized through oligomer synthesis wherein the number of rounds of monomer incorporation falls within any range bound by the foregoing values, e.g. 2-30 rounds, 8-10 rounds etc. In some embodiments, presynthesized barcodes attached to units. Barcodes described herein may comprise oligonucleotides. Synthesis of barcodes may be achieved through oligomer synthesis methods described herein. For example, units may be routed iteratively through reaction chambers or channels of the microfluidic devices described herein. One or more monomers (or dimers or longer building blocks) may be incorporated to the a nascent chain of a barcode in each routing cycle.

Cells may be bacterial cells or eukaryotic cells, for example cells derived from cell culture, animals, or human subjects, such as cells derived from patient samples. Droplets may be formed by the mixture of immiscible fluids, such as water and oil or other organic solvents, to form an emulsion. Droplet formation for use in microfluidic devices is described in U.S. Pat. Nos. 8,528,589, 9,364,803, 8,658,430, WO2014001781, and US20080286751, which are herein incorporated by reference in their entirety with respect to droplet formation in microfluidic devices.

The methods described herein can take advantage of beads or other types of units maintaining their order throughout an iterative modification process. In some embodiments, the beads or other types of units cannot pass each other or stick together. The bead or other type of unit distribution may be adjusted to be fairly monodisperse throughout the process. In some embodiments, units are passed through a size selection mechanism generating a population of units that substantially or entirely fall within a predesignated size range, for example by passing units through a size sorter. Units may be size sorted such that the likelihood of detected or undetected undesired unit mixing within the channels of the devices described herein, e.g. within channels having widths that physically prevent mixing of units of a selected average or nominal diameter and/or size, is minimized.

Figure 36:
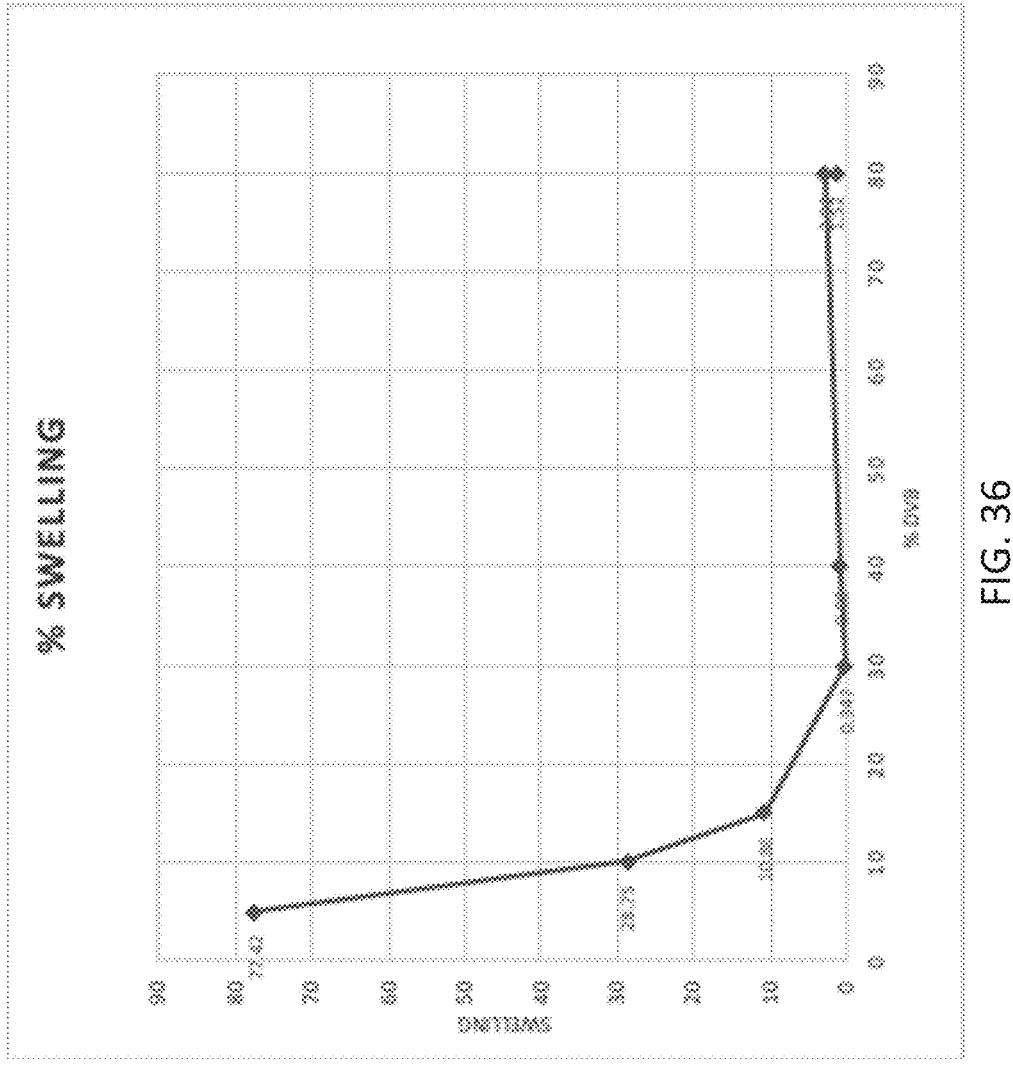
FIG. 36 depicts swelling response of divinylbenzene-cross-linked polystyrene (PS) beads in organic solvent versus percent divinylbenzene (DVB) cross-linking agent.
Figures 37A, 37B:
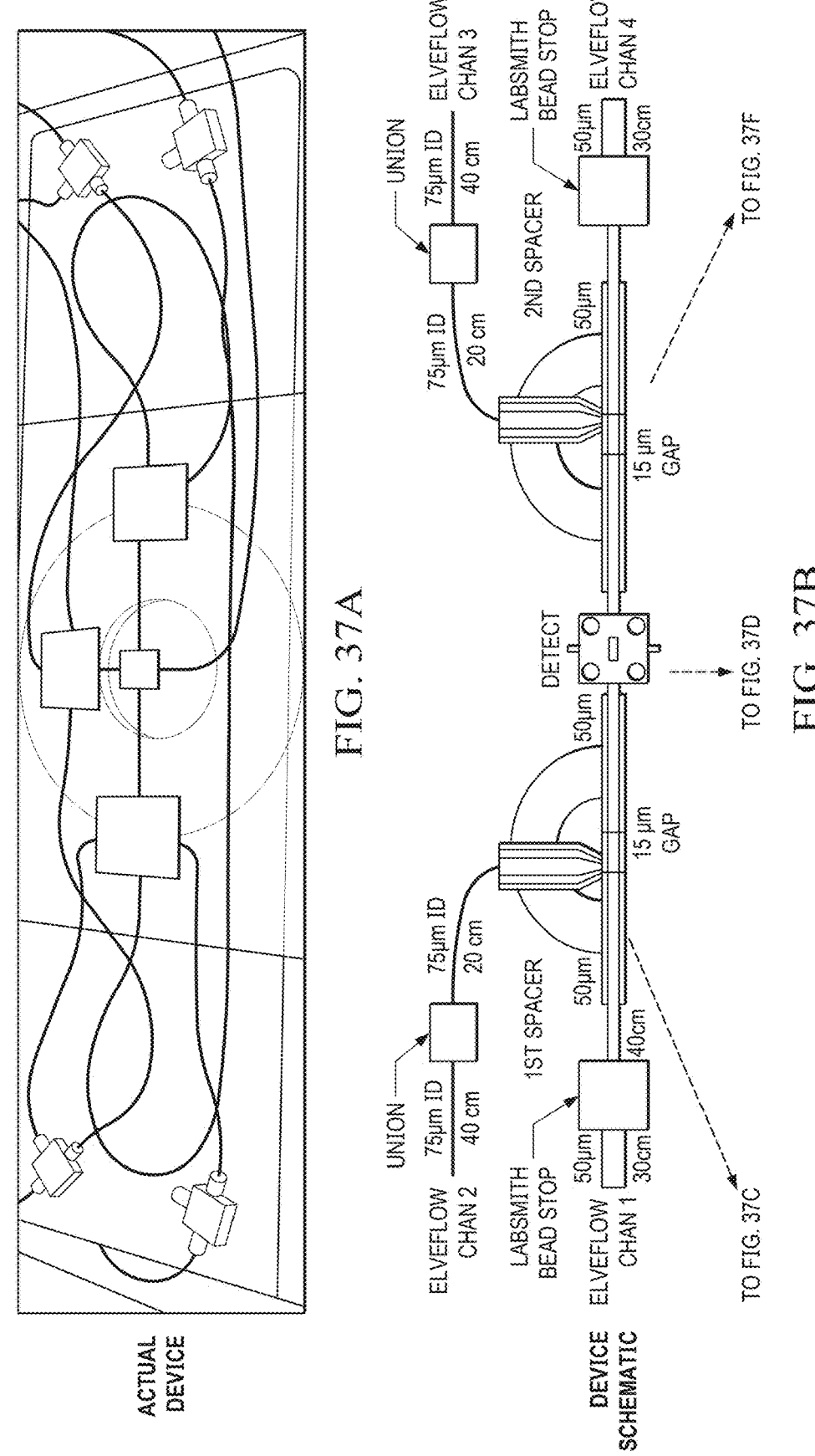
FIG. 37A-F depict images and schematics of an example device portion for spacing and re-stacking beads without permanent jams.
Figure 37D:
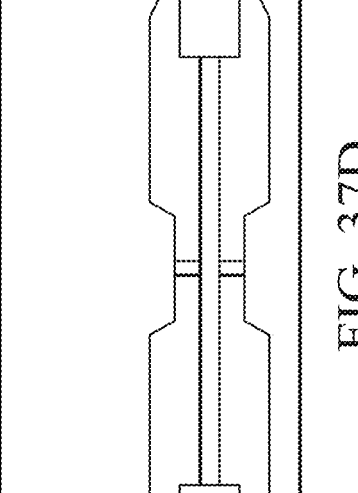
Figure 37F:
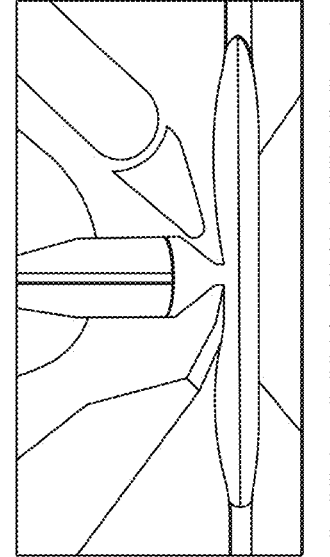
Figure 37C:
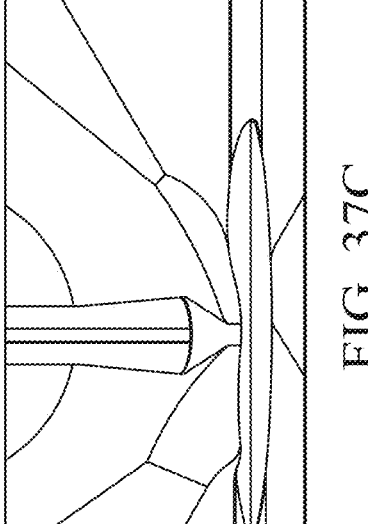
Figure 37E:
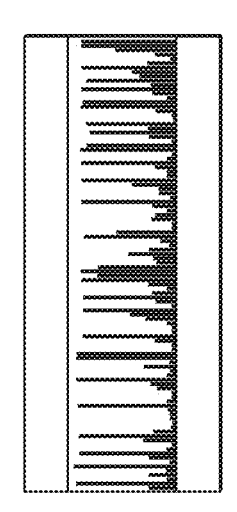

The beads or other types of units may swell when exposed to non-aqueous reagents, such as toluene, used in DNA synthesis. A swollen bead may stick to capillary walls and impede flow. Various materials, such as divinylbenzene (DVB) cross-linking of polymeric beads can mitigate swelling at an appropriate concentration. Introduction of surfactants may be used to reduce bead/unit adhesion. In more detail, one or more embodiments of the method(s) and/or system(s) described can implement beads or other types of units configured to be non-swelling, non-brittle, monodisperse, and/or porous, and devoid of outlier (in relation to morphological uniformity) beads or other types of units. Outlier units (e.g. beads may be removed by filtering, sieving, suspension processes, processes involving removal of a supernatant of smaller-than-desired particles, or by any suitable method known in the art. FIG. 36 depicts swelling response of divinylbenzene-cross-linked polystyrene (PS) beads in organic solvent versus percent divinylbenzene (DVB) cross-linking agent (in terms of molar ratio between PS and DVB). Beads were put in toluene to quantify swelling response of cross-linked beads in organic solvents. In various embodiments, swelling response of beads can be similarly measured in alternative solvents, such as acetonitrile, toluene, dichloromethane, tetrahydrofuran (THF), pyridine, N-methyl pyrrolidinone (NMP), 2,6-lutidine, carbon disulfide, 1,2-dichloroethane, 1,1-dichloroethane, chloroform, dimethylformamide, dimethylacetamide, dimethylsulfoxide (DMSO), ethylene carbonate, 1,4-dioxane, DME (1,2-dimethoxyethane), nitromethane, methyl tert-butyl ether, methyl ethyl ketone (butanone), or dichloromethane. Without being bound by theory, beads cross-linked in high cross-linker ratios may be brittle and/or be subject to surface solvation (e.g., as in the range from 60-80% DVB cross-linking in FIG. 36), while beads cross-linked in lower cross-linker ratios exhibit acceptable performance in terms of minimal swelling, brittleness, and solvation (e.g., as in the range from 30-60% DVB cross-linker in FIG. 36). Cross-linked beads may be functionalized by a variety of suitable moieties described elsewhere herein or otherwise known in the art, such as by amine or carboxyl groups.

In various embodiments, units may be filtered by size to provide a uniformly sized unit population. For example, units having a diameter greater than an upper threshold may be filtered out by a suitable method described herein or is known in the art. Amine functionalized polystyrene beads were cross-linked with 35% DVB. Cross-linked beads had a diameter of 34.4 μm with a coefficient of variation of 2.6%. Particles larger than 40 μm were removed by sieving through a 40 μm electroformed mesh. In some embodiments, particles smaller than a desired size are removed by a suitable method described herein or otherwise known in the art, such as by an electroformed mesh of appropriate size. Such size filtering methods may be applied on cross-linked beads of any suitable kind, which may be functionalized by one or more suitable moieties described elsewhere herein or otherwise known in the art, such as by amine or carboxyl groups. In a related variation, small particles, particle fragments, dust, and other contaminants may be removed by suspending the monodisperse PS beads in solution and letting the desired particles settle for a period of time, after which the supernatant with undesired particles and fragments may be removed. In another variation, small particles, particle fragments, dust, and other contaminants may be removed by centrifugation and removal of the supernatant with undesired particles and fragments. In any of the examples and variations described, one or more successive washing steps, optionally intercalated by other filtering steps, such as settling steps, may be implemented to remove undesired particles.

In embodiments, cross-linking can be performed using one or more of chemical cross-linking agents (e.g., DVB, glutaraldehyde, formaldehyde, epoxy compounds, dialdehyde, dichloroethane, etc.), radiation-induced cross-linking procedures, oxidative cross-linking procedures, and other cross-linking procedures.

In embodiments, beads used according to the methods described herein are crosslinked at a molar cross-linker ratio of, of about, or of greater than 1%, 2%, 3%, 4%, 5%, 6%, 7%, 8%, 9%, 10%, 20%, 30%, 40%, 50%, 60%, 70%, 80%, 90% or higher. Beads used according to the methods described herein may be crosslinked at a molar cross-linker ratio of less than 90%, 80%, 70%, 65%, 60%, 55%, 50%, 45%, 40%, 35%, 30%, 25%, 20% or lower. Beads used according to the methods described herein may be cross-linked at a molar cross-linker ratio that falls within a range bounded by any of the foregoing values (e.g. 10-60%, 3-60%, 45-55%, etc.). Ranges of cross-linking and/or different types of cross-linking agents can be selected to tune swelling behavior, brittleness, and/or solvation as desired.

For example, aforementioned parameters may be selected to limit swelling to, to about, or to less than 10%, 9% 8%, 7%, 6%, 5%, 4%, 3%, 2%, or less.

Units, such as bead units can range in size according to the various embodiments described herein. For example, all or substantially all (e.g. more than 80%, 90%, 95%, 96%, 97%, 98%, 99%, 99.5%, 99.6%, 99.7%, 99.8%, 99.9%, 99.95%, 99.99%, 99.995%, 99.999% or more) units used in the methods and devices described herein may have a diameter and/or size from about, at least, or at least about 20 nm, 100 nm, 500 nm, 1000 nm, 1 μm, 2 μm, 3 μm, 4 μm, 5 μm, 6 μm, 7 μm, 8 μm, 9 μm, 10 μm, 20 μm, 30 μm, 35 μm, 40 μm, 50 μm, 60 μm, 70 μm, 80 μm, 90 μm, 100 μm. Those of skill in the art will appreciate that the unit diameter and/or size may have a value that falls within any range bound by any of these values, for example 20-100 nm, 100-500 nm, 500-1000 nm, 1-10 μm, 10-20 μm, 20-30 μm, 30-40 μm, 40-50 μm, 50-60 μm, 60-70 μm, 70-80 μm, 80-90 μm, 90-100 μm. The coefficient of variation for the size or cross-section of the units can be about, at least, or at least about 1%, 2%, 3%, 4%, 5%, 6%, 7%, 8%, 9%, 10%, 11%, 12%, 13%, 14%, 15%, 16%, 17%, 18%, 19%, 20% or more. The coefficient of variation for the size or cross-section of the units can be about less than, or about less than 20%, 19%, 18%, 17%, 16%, 15%, 14%, 13%, 12%, 11%, 10%, 9%, 8%, 7%, 6%, 5%, 4%, 3%, 2%, 1% or less. The units can also be oval. Droplet volume may be about, at least or at least about 10 femtoliters (fl), 100 fl, 1 pl, 10 pl, 100 pl, 500 pl, 1 nanoliter (nl), 10 nl, 50 nl, 100 nl, 300 nl, 400 nl, 500 nl, 600 nl, 700 nl, 800 nl, 900 nl, 1 μl, 2 μl, 3 μl, 4 μl, 5 μl, 6 μl, 7 μl, 8 μl, 9 μl, 10 μl, 50, pl, 100 μl, or more. The droplet volume may fall in a range bounded by any of the foregoing values, e.g. 10-100 femtoliters (fl), 100-1000 fl, 1-10 picoliters (pl), 10-100 pl, 100-500 pl, 500-1000 pl, 1-10 nanoliter (nl), 10-100 nl, 100-200 nl, 200-300 nl, 300-400 nl, 400-500 nl, 500-600 nl, 600-700 nl, 700-800 nl, 800-900 nl, 900-1000 nl, 1-10 μl, 10-50 μl, or 50-100 μl. Values for the unit or droplet size may range between any of the potential values set forth for the unit or droplet size herein.

In various embodiments, screening procedures may be applied to a library of products (or a subset thereof having selected properties) associated with units for which positional encoding is maintained. The positional encoding of the units can be used to identify products of interest. For example, after a library of products is made, the associated units, arranged in a 1d-array with known absolute or relative positions, can be exposed to a set of screening reagents. In various embodiments, screening reagents are delivered in the same or a similar manner as the reagents for modification procedures. Screening reagents may be moved through channels holding the products to be screened, such as channels holding the associated units in an ordered 1d-array. The units or the associated products may be evaluated for their reactivity to screening interactions, for example by optical analysis of the units in place or by flowing the units past a detector, such as an optical or magnetic detector. Units or associated products displaying features of interest, such as an ability to interact with a target compound, can be detected. A product associated with a unit detected for a screened feature can be identified, for example by the position of the unit.

In some embodiments, the physical encoding on the units may be associated with the units' positional encoding within a system. For example, the physical encoding of units may be read once in the beginning or end of one or more procedures within a system maintaining positional encoding and the physical and positional encodings of the units may be associated. This association between physical encodings and products can be used in downstream procedures even in the case where the positional encoding of the units is lost, for example when the units have been removed from an ordered 1d-array or otherwise disordered with respect to one another.

Pumps

The systems and devices described in further detail elsewhere herein may contain pumps, for example for moving solutions or units through the channels of microfluidic devices, or for delivery of reagents into the reaction chambers of microfluidic devices. These pumps may be mechanical or non-mechanical, and utilize driving forces such as piezoelectrical, electrostatic, electro-osmotic, solenoid, thermo-pneumatic, pneumatic, magnetic, vacuum, or passive gravity or capillary forces, or other appropriate forces known to those of skill in the art (see Iverson B D et al, 2008, incorporated herein by reference in its entirety). The pumps may comprise peristaltic, syringe, vacuum, piezoelectric, or passive, or other appropriate pumps known to those of skill in the art. The pump may be connected to a flow rate sensor and a pressure controller.

In various embodiments, pumps are used for routing (e.g. steering units through several junctions, e.g. Y-junctions, to destination(s), e.g. a microfluidic destination, such as intone or more reaction chambers. The pump described herein may be used to generate pulses of about 100 pl over <10 msec. In some embodiments, pumps described herein are configured to generate pulses of about, at least, or at least about 1 pl, 2 pl, 3 pl, 4 pl, 5 pl, 6 pl, 7 pl, 8 pl, 9 pl, 10 pl, 20 pl, 30 pl, 40 pl, 50 pl, 60 pl, 70 pl, 80 pl, 90 pl, 100 pl, 200 pl, 300 pl, 400 pl, 500 pl, 600 pl, 700 pl, 800 pl, 900 pl, 1000 pl, 1 nl, 2 nl, 3 nl, 4 nl, 5 nl, 6 nl, 7 nl, 8 nl, 9 nl, 10 nl, or more. The pumps described herein may be configured to generate less than or less than about 500 μl, 400 μl, 300 μl, 200 μl, 100 μl, 90 μl, 80 μl, 70 μl, 60 μl, 50 μl, 40 μl, 30 μl, 20 μl, 10 μl, 1000 nl, 900 nl, 800 nl, 700 nl, 600 nl, 500 nl, 400 nl, 300 nl, 200 nl, 100 nl, 90 nl, 80 nl, 70 nl, 60 nl, 50 nl, 40 nl, 30 nl, 20 nl, 10 nl, 9 nl, 8 nl, 7 nl, 6 nl, 5 nl, 4 nl, 3 nl, 2 nl, 1 nl, 900 pl, 800 pl, 700 pl, 600 pl, 500 pl, 400 pl, 300 pl, 200 pl, 100 pl, 90 pl, 80 pl, 70 pl, 60 pl, 50 pl, 40 pl, 30 pl, 20 pl, 10 pl, 9 pl, 8 pl, 7 pl, 6 pl, 5 pl, 4 pl, 3 pl, 2 pl, 1 pl or less. Those of skill in the art will appreciate that the pumps described herein may be used to generate pulses of a volume that falls within any range bound by any of these values, for example 10-50 pl, 10-100 pl, 50-100 pl, 100-200 pl, 200-300 pl, 300-400 pl, 400-500 pl, 500-600 pl, 600-700 pl, 700-800 pl, 800-900 pl, 900-1000 pl, or 1-10 pl. Values for the pulse volumes generated by the pumps described herein may range between any of the potential values set forth for the pulse volumes herein. In some embodiments, pumps described herein are configured to generate pulses of volumes described herein in over about, less than or less than about 500 msec, 400 msec, 300 msec, 200 msec, 100 msec, 90 msec, 80 msec, 70 msec, 60 msec, 50 msec, 40 msec, 30 msec, 25 msec, 20 msec, 10 msec, 9 msec, 8 msec, 7 msec, 6 msec, 5 msec, 4 msec, 3 msec, 2 msec, 1 msec, 0.9 msec, 0.8 msec, 0.7 msec, 0.6 msec, 0.5 msec, 0.4 msec, 0.3 msec, 0.2 msec, 0.1 msec or less.

Any appropriate pump can be used, including, but not limited to, electroosmotic pumps, which are cost-effective, compact, and can achieve high flow rates with a sub-millisecond response time.

Figure 33:
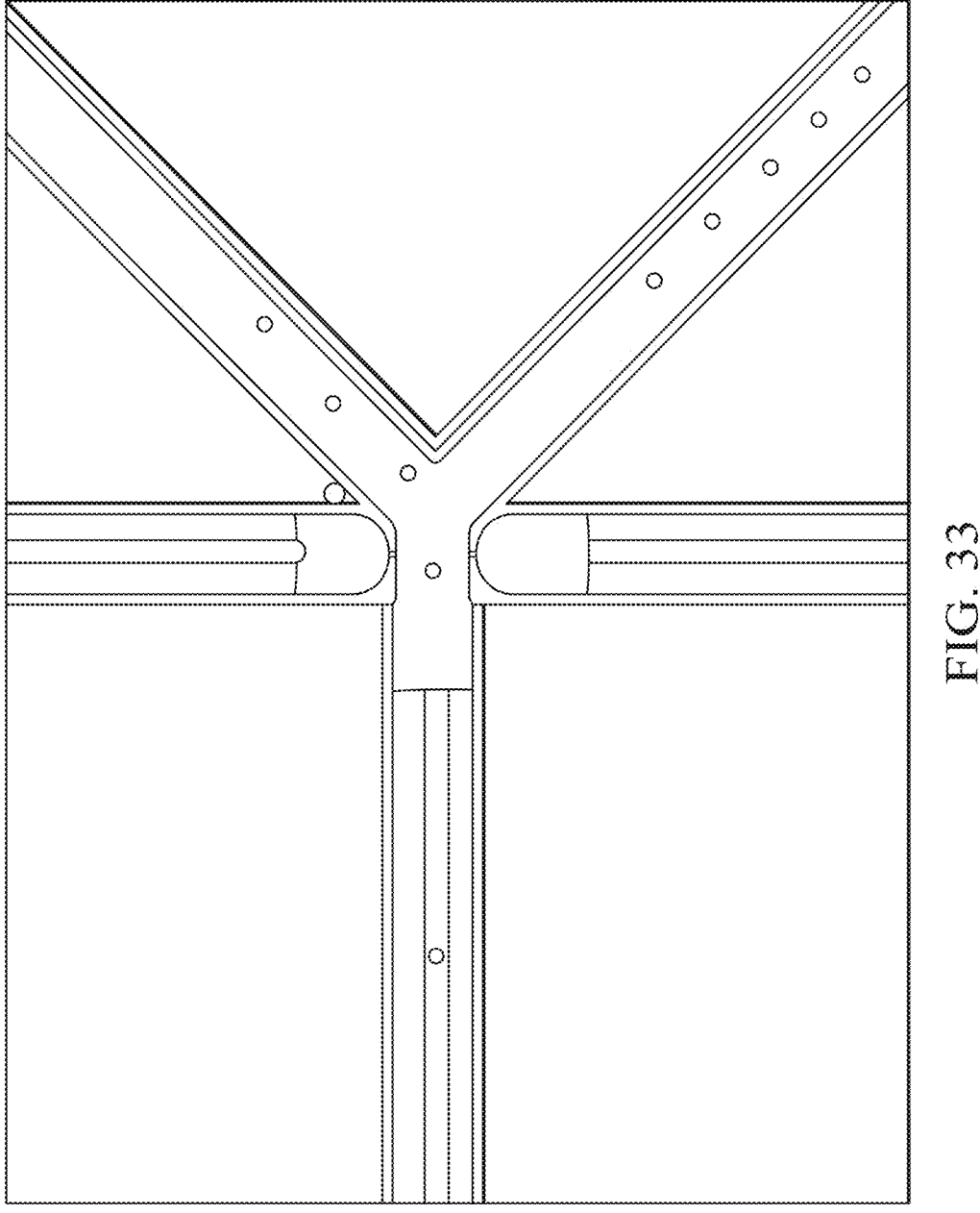
FIG. 33 provides a close-up image of a cross-flow routing junction. Glass capillaries are inserted into 3D printed routing device. Units, e.g. beads, spaced 40 μm from each other enter from left and a cross-flow current from the vertically oriented capillaries deflect the units into the upper or lower bifurcation.

A pump may be used to route (e.g. steer) units, e.g. microbeads via cross-flow routing. In some embodiments, the units within the microfluidics devices described herein are passed through a primary channel, which branches into at least two side channels, e.g. in a Y-shaped geometry. At least two additional cross-flow channels may be configured to intersect the main channel near the junction. As a unit, e.g. passes the cross-flow channels, a pulse of fluid may be delivered perpendicular to the unit's velocity. This pulse may be used to cause the unit to be deflected to the side of the channel. Laminar flow within the microfluidic devices described herein may be used to enable the unit to continue its forward motion in the same relative position in the channel adopted after deflection. Such deflected units may be caused to deterministically enter the side channel towards which it was deflected. FIG. 33 provides an illustration of a junction with cross-flow routing. Pneumatic pumps were used to move bead position laterally within laminar flow as individual beads were flowed from the left channel into the junction, thereby moving the beads' position within cross-section of the laminar flow toward one of the two branch channels on the right. Beads that were moved upward within the cross-section of the laminar flow followed a path into the upper branch channel and beads that were moved downward within the cross-section of the laminar flow followed a path into the lower branch channel.

Figure 34B:
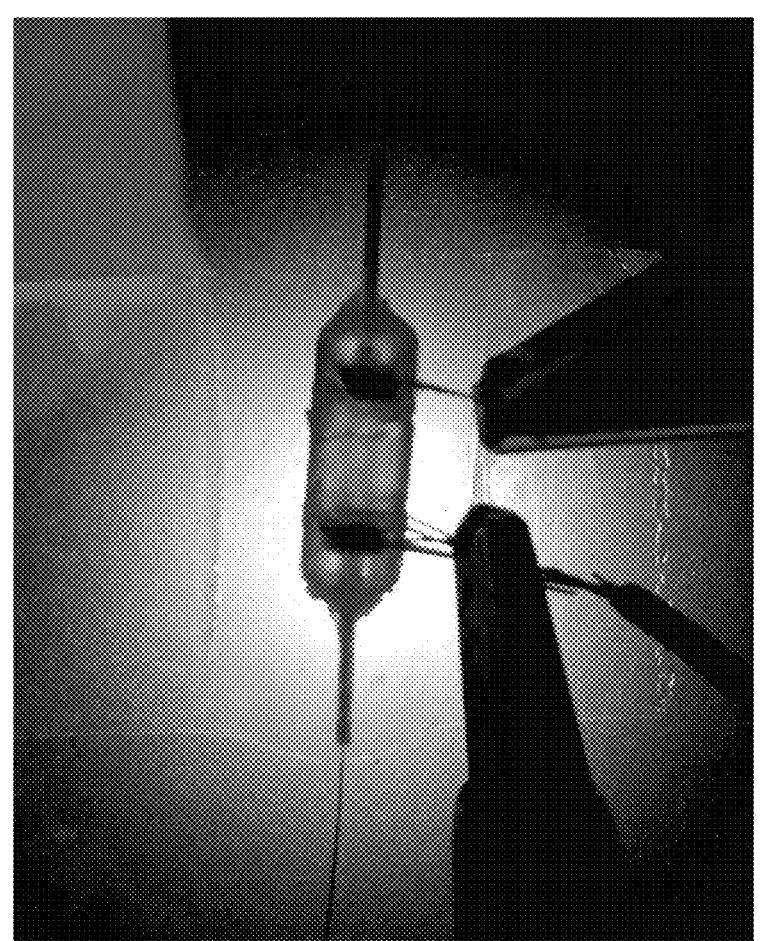
FIG. 34A-B provide a schematic (34A) of electroosmotic flow and a close up of an electroosmotic pump (34B). Voltage across two porous electrodes drives electroosmotic flow through a nanoporous pump medium. Electrical leads drive fluidic flow through connected glass capillaries.
Figure 34A:
Figures 35A, 35B, 35C:
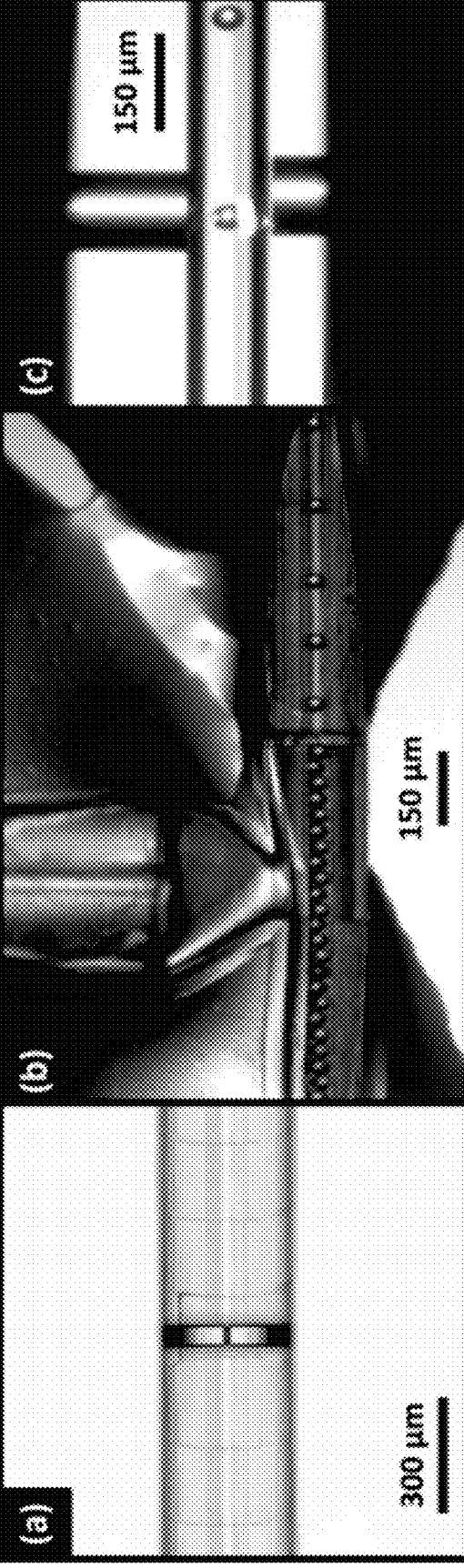
FIG. 35A-C provide close up images on a unit trap (35A), a unit spacer (35B), and a laser detector (35C).

FIG. 34B provides and exemplar electroosmotic pump. Electroosmotic pump elements of suitable configurations (such as a cylindrical frit 5 mm long and 1 mm in diameter) may be used to produce high pressures. In various embodiments, electroosmotic pump elements comprise a "pancake" design, for example one comprising a frit 5 mm in diameter and 1 mm long. Suitable pump elements may be selected in order to improve ability to prime, (such as by decreasing resistance to flow; to increase flow rates; and/or to improve ease of assembly. Any suitable method known in the art may be used to fabricate such electroosmotic pump elements.

Also provided herein is a high-speed pump, such as an electroosmotic high-speed pump, capable of sorting beads into reaction chambers. In various embodiments, such pumps may be configured to route units, e.g. beads, at, at about, or at least 1 Hz, 5 Hz, 10 Hz, 15 Hz, 20 Hz, 25 Hz, 30 Hz, 35 Hz, 40 Hz, 42 Hz, 45 Hz, 50 Hz, 60 Hz, 70 Hz, 80 Hz, 90 Hz, 100 Hz, 200 Hz, 300 Hz, 400 Hz, 500 Hz, 600 Hz, 700 Hz, 800 Hz, 900 Hz, 1 kHz, 2 kHz, 3 kHz, 4 kHz, 5 kHz, 6 kHz, 7 kHz, 8 kHz, 9 kHz, 10 kHz, or greater. Such pumps may be configured to achieve such routing frequencies with an accuracy of, of about, or of at least 95%, 96%, 97%, 98%, 99%, 99.5%, 99.9%, 99.95%, 99.99%, 99.993%, 99.995% 99.999%, 99.9995% 99.9999% or greater. In some embodiments, the pump is configured to have a flow rate of, of about, or of at least 25 nl/s and/or a switching rate of, of about, or of at least 30 Hz for at least 1 hour. In some embodiments, the pump is configured to have a flow rate of, of about, or of at least 10 nL/s and/or rise times (t) of, of about, or of at least 10 msec, 9 msec, 8 msec, 7 msec, 6 msec, 5 msec, 4 msec, 3 msec, 2 msec, 1 msec, 900 μsec, 800 μsec, 700 μsec, 600 μsec, 500 μsec, 400 μsec, 300 μsec, 200 μsec, 100 μsec, 50 μsec, 10 μsec, 5 μsec, or 1 μsec, or less when integrated into a fluidic system.

In some embodiments, microfluidic devices comprising such pumps may be configured to result the synthesis of, of about, or of at least 10,000 oligonucleotides. Such oligonucleotides may be, be about, or be at least 5, 10, 20, 30, 40, 50, 60, 70, 75, 80, 90, 100, 125, 150, 175, 200, 250, 300, 400, 500, 600, 700, 800, 900, 1000, 1500, 2000, 2500, 3000, 4000, 5000, 10,000 nucleotides long, or longer. In various embodiments, microfluidic devices comprising such pumps may be used to synthesize such oligonucleotides in, in about, or in less than 50, 40, 30, 25, 20, 15, 12, 10, 9, 8, 7, 6, 5, 4, 3, 2, 1 hours or less. Such microfluidic devices may be configured to achieve such oligonucleotide synthesis with, with about, or with fewer than 1000, 500, 400, 300, 200, 150, 125, 100, 90, 80, 70, 60, 50, 40, 30 20, 10, 5, 4, 3, 2 or fewer errors (i.e. units, such as beads, with an incorrect sequence).

In some embodiments, the pump has at least a single microfluidic bifurcation and manual or semi-manual switched routing, e.g. steering, of, of about, or of at least 100 particles with, with about or with at least 95%, 96%, 97%, 98%, 99%, 99.5%, 99.9%, 99.95%, 99.99%, 99.995%, or 100% accuracy. In some embodiments, the pump has automated routing, e.g. steering, of, of about, or of at least 100 individual particles at, at about, or at at least 1 Hz through a single bifurcation with at least 95%, 96%, 97%, 98%, 99% 99.5%, 99.9%, 99.95%, 99.99%, 99.995%, or 100% accuracy. In some embodiments, the pump has automated routing, e.g. steering, of, of about, or of at least 1000 individual particles at, at about or at at least 5 Hz through two serial bifurcations into four outlets with, with about, or with at least 95%, 96%, 97%, 98%, 99% 99.5%, 99.9%, 99.95%, 99.99%, 99.995% accuracy. In some embodiments, the pump has automated routing, e.g. steering, of, of about, or of at least 1000, 5,000, 10,000, 50,000, 100,000, 500,000 or 1,000,000 individual particles at, at about or at least 5, 10, 50, 100, 250, 500, 750, 1000, 1250, 1500, 200, 2500, 3000, 3500, 4000, 4500, or 5000 Hz through two serial bifurcations into at least one, two, or four outlets with, with about, or with at least 95%, 96%, 97%, 98%, 99% 99.5%, 99.9%, 99.95%, 99.99%, 99.995% accuracy.

In some embodiments, the pump is a piezo or solenoid driven pump.

The mobile units may be in a fluid or solution. Pumps may be used to control the flow rate and/or pressure of the fluid and thereby control the flow rate of the units. Pumps may also be used to control the direction of the fluid or solution flow in the device and thereby control the flow direction of the unit. Changes in the flow direction of a fluid may be used to distribute the mobile units into secondary channels, branch channels, branch points, or reaction chambers. For example, a pump at the first end of a channel may apply a flow rate such that the units move down the channel to a branch point that branches into two, three, or more channels. The branch point may comprise a router, e.g. a distributor, or may not comprise a router. As the units approach the branch point, the pump at the first end of the channel is shut off or slowed, and a second pump at the end of one of the branch channels is turned on, resulting in flow of the fluid comprising the mobile units towards the second pump and down the chosen branch channel. Each branch channel may have a separate pump that can be controlled independently. Mobile units can be routed into the individual branch channels by turning on the appropriate pump for each branch channel as the unit approaches or passes through the branch point. Individual units or groups of units may be routed into branch channels.

Units in a fluid may be passed through the channels or the path of a detector at a flow rate of about, at least, or at least about 10 nl/min, 20 nl/min, 30 nl/min, 40 nl/min, 50 nl/min, 60 nl/min, 70 nl/min, 80 nl/min, 90 nl/min, 100 nl/min, 200 nl/min, 300 nl/min, 400 nl/min, 500 nl/min, 600 nl/min, 700 nl/min, 800 nl/min, 900 nl/min, 1 μl/min, 2 μl/min, 3 pl/min, 4 μl/min, 5 μl/min, 6 μl/min, 7 μl/min, 8 μl/min, 9 μl/min, 10 μl/min, 20 μl/min, 30 pl/min, 40 μl/min, 50 μl/min, 60 μl/min, 70 μl/min, 80 μl/min, 90 μl/min, 100 μl/min, or faster. In some cases, units in a fluid may be passed through the path of a detector at a flow rate of at most, or at most about 100 μl/min, 90 μl/min, 80 μl/min, 70 μl/min, 60 μl/min, 50 pl/min, 40 μl/min, 30 μl/min, 20 μl/min, 10

μl/min, 9 μl/min, 8 μl/min, 7 μl/min, 6 μl/min, 5 pl/min, 4 μl/min, 3 μl/min, 2 μl/min, 1 μl/min, 100 nl/min, 90 nl/min, 80 nl/min, 70 nl/min, 60 nl/min, 50 nl/min, 40 nl/min, 30 nl/min, 20 nl/min, 10 nl/min, or slower. Those of skill in the art appreciate that the flow rate may fall within any range bound by any of these values, for example 10-100 nl/min, 100-500 nl/min, or 500-1000 nl/min. Units and/or carrier fluid may also be passed through the device at a flow rate of about, at least, or at least about 0.1 cm/min, 0.5 cm/min, 1 cm/min, 2 cm/min, 3 cm/min, 4 cm/min, 5 cm/min, 6 cm/min, 7 cm/min, 8 cm/min, 9 cm/min, 10 cm/min, 20 cm/min, 30 cm/min, 40 cm/min, 50 cm/min, 60 cm/min, 70 cm/min, 80 cm/min, 90 cm/min, 1 m/min, 2 m/min, 3 m/min, 4 m/min, 5 m/min, 6 m/min, 7 m/min, 8 m/min, 9 m/min, 10 m/min, 20 m/min, 30 m/min, 40 m/min, 50 m/min, 60 m/min, 70 m/min, 80 m/min, 90 m/min, 100 m/min, or faster. In some cases, carrier fluid and/or units in a fluid may be passed through the channels or the path of a detector at a flow rate of at most, or at most about 100 m/min, 90 m/min, 80 m/min, 70 m/min, 60 m/min, 50 m/min, 40 m/min, 30 m/min, 20 m/min, 10 m/min, 9 m/min, 8 m/min, 7 m/min, 6 m/min, 5 m/min, 4 m/min, 3 m/min, 2 m/min, 1 m/min, 90 cm/min, 80 cm/min, 70 cm/min, 60 cm/min, 50 cm/min, 40 cm/min, 30 cm/min, 20 cm/min, 10 cm/min, 9 cm/min, 8 cm/min, 7 cm/min, 6 cm/min, 5 cm/min, 4 cm/min, 3 cm/min, 2 cm/min, 1 cm/min, 0.5 cm/min, 0.1 cm/min, or slower. Those of skill in the art appreciate that the carrier fluid and/or flow rate may fall within any range bound by any of these values, for example 10-100 cm/min, 100-500 cm/min, or 500-1000 cm/min. Values for the flow rate may range between any of the potential values set forth for the flow rate herein.

In various embodiments, pumps may be used to facilitate movement of mobile units. A pump may be attached to a channel to manipulate the flow rate of the fluid in the channel. The flow can be stopped, started, or the flow rate modulate via the speed of the pump, resulting in stopping, starting, or modulation of the unit movement through the device. Pump-controlled fluid flow may also be used to route, e.g. distribute, the mobile units by creating low pressure or vacuum conditions in the desired direction of travel for the mobile unit.

The methods and compositions described herein may be used to order units within a microfluidic device. Any suitable type of distributing algorithm can be used to distribute units in a first order into a second order. For example, units in a device may be distributed so that the correct units could be dispensed at the correct time or order. A first group of units may be dispensed followed by a second group of units and so on. In some embodiments, the exact order of the units within each such group is unimportant. Accordingly, units may be distributed so that the correct units are grouped into a first group of a desired size, a second group of a desired size etc. For example, the first group in a given grouping may have a size of 5 units whereas the second group in the grouping may have a size of 1 unit.

Valves and Bead Stops

The device may contain elastomeric valves that close off sections of the channel(s). These valves may be mechanical or pressure-actuated. The valves may be deflected into or retracted from one channel or channel section in response to a force applied to another channel or channel section. The valves may be upwardly-deflecting, downwardly deflecting, side actuated, normally-closed, or some other type of valve. Elastomeric valves for use in microfluidic devices are described in US 20050072946, U.S. Pat. No. 6,408,878, US 20020127736, and U.S. Pat. No. 6,899,137, all which are herein incorporated by reference in their entirety, in particular with respect to the description of elastomeric valves. The device may have a combination of valve types. The valves may be operated by injecting gases, liquids, ionic solutions, or polymer solutions. A non-exclusive list of such solutions includes air, nitrogen, argon, water, silicon oils, perfluoropolyalkylether or other oils, salt solutions, polyethylene glycol, glycerol, and carbohydrates. Valves may also be operated by applying a vacuum to the channel(s).

The device may also contain valves that are physically separated from the reaction chamber(s) and/or branch channel(s). Reagents may be routed to the reaction chamber(s) and/or branch channel(s) via a delivery channel or an inlet directly or indirectly via a network of channels. In some embodiments, the delivery channel and/or inlet is about the same size or smaller than the reaction chamber(s), branch channel(s), and/or other channel(s) connecting the delivery channel and/or inlet to where reagents are designated to be delivered. In some embodiments, a delivery channel and/or an inlet interfaces with the reaction chamber(s), branch channel(s), and/or other connected channel(s) via a frit, a nozzle, a weir, a bead stop, or any other physical structure that enable fluid to pass through the structure but not units.

Valves and valve membranes can be constructed from any appropriate elastomeric material known in the art, including poly dimethylsiloxane (PDMS), polyisoprene, polybutadiene, polychloroprene, polyisobutylene, poly(styrene-butadiene-styrene), the polyurethanes, and silicones. A non-exclusive list of elastomeric materials which may be utilized in connection with the present invention includes polyisoprene, polybutadiene, polychloroprene, polyisobutylene, poly(styrene-butadiene-styrene), the polyurethanes, and silicone polymers; or poly(bis(fluoroalkoxy)phosphazene) (PNF, Eypel-F), perfluoropolyalkylether siloxane block copolymer, poly(carborane-siloxanes) (Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly(vinylidene fluoride), poly(vinylidene fluoride-hexafluoropropylene) copolymer (Viton), elastomeric compositions of polyvinylchloride (PVC), polysulfone, polycarbonate, polymethylmethacrylate (PMMA), and polytertrafluoro-ethylene (Teflon).

In some embodiments, the device includes one or more microfluidic check valves. A microfluidic check valve can be used to direct solution flow in only one direction through the valve. Any suitable check valve known in the art may be used in the systems and devices described herein.

Valve membranes separating flow channels may have a thickness of between about 0.01 and 1000 microns. Membrane thicknesses can be about, at least, or at least about 0.01 μm, 0.02 μm, 0.03 μm, 0.04 μm, 0.05 μm, 0.06 μm, 0.07 μm, 0.08 μm, 0.09 μm, 0.1 μm, 0.2 μm, 0.3 μm, 0.4 μm, 0.5 μm, 0.6 μm, 0.7 μm, 0.8 μm, 0.9 μm, 1 μm, 2 μm, 3 μm, 4 μm, 5 μm, 6 μm 7 μm, 8 μm, 9 μm 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm. Membrane thicknesses can be less than or less than about 100 μm, 90 μm, 80 μm, 70 μm, 60 μm, 50 μm, 40 μm, 30 μm, 20 μm, 10 μm, 9 μm, 8 μm, 7 μm, 6 μm, 5 μm, 4 μm, 3 μm, 2 μm, 1 μm, 0.9 μm, 0.8 μm, 0.7 μm, 0.6 μm, 0.5 μm, 0.4 μm, 0.3 μm, 0.2 μm, 0.1 μm, 0.09 μm, 0.08 μm, 0.07 μm, 0.06 μm, 0.05 μm, 0.04 μm, 0.03 μm, 0.02 μm, 0.01 μm. Those of skill in the art will appreciate that the membrane thickness may have a size that falls within any range bound by any of these values, for example 0.01-0.1 μm, 0.1-1 μm, 1-10 μm, 10-20 μm, 20-30 μm, 30-40 μm, 40-50 μm, 50-60 μm, 60-70 μm, 70-80 μm, 80-90 μm, 90-100 μm. Values for the valve membrane thickness may range between any of the potential values set forth for the valve membrane thickness herein.

In some embodiments, the device described herein includes unit stops, such as a frit, wire, or weir. Unit stops may be used to halt the flow of single or multiple mobile units in one direction. Any appropriate unit stop known in the art may be used. Unit stops may be manufactured by inserting a wire within a channel, 3D printing a capillary connector that introduces a constriction or frit, and/or using photolithography to create a weir structure in a glass device or any suitable method known in the art. Unit stops may be used to halt the flow of single or multiple mobile units in one direction. The stopped mobile units may then be held, or the flow of the stopped mobile units may be reversed by altering the fluid flow or pressure e.g. via a pressure controller, pump, or vacuum. Unit stops may be used at any point in the device, such as at the beginning or end of a channel or branch channel, at a branch point, at the beginning or end of a reaction chamber, or any combination thereof.

Detectors and Optical Detection Systems

The microfluidic devices described in various embodiments herein may include one or more detection systems for positionally tracking units within the microfluidic device. Each detection system may have one or more detectors. One or more detectors may be placed at any point in the device, for example to track units in a channel or the device, such as at any point in a channel or branch channel, before or after any or every branch point, before or after any or every router, e.g. distributor, before or after any or every reaction chamber, or before or after any or every outlet or inlet. One or more detectors may be used to ensure the correct number of units are distributed or steered into a channel or branch channel. In various embodiments, the one or more detectors are not be restricted to particular points or junctions of the systems described herein. For instance, the one or more detectors can be configured globally or regionally relative to a particular system. In one such embodiment, a charge-coupled device (CCD)/complementary metal oxide semiconductor (CMOS) or other wide-field imaging detector could monitor some or all of the units in a fluidic network of the system, or could be used to observe a region-of-interest (ROI) (e.g. to improve detection speed or reduce data volume). Additionally or alternatively, linear CCD arrays can be used to track beads in multiple channels (e.g., parallel channels, non-parallel channels). Additionally or alternatively, regional detectors, including but not limited to CCDs, can incorporate machine vision to identify and track beads as they move through the device. Additionally or alternatively, conductivity-based detection may be used to identify the presence and/or quantity of units, e.g. beads along a fluidic path between electrode probe points. In any embodiment, detectors may also be configured in any orientation relative to the channel(s) of the microfluidic devices described herein (e.g., above, below, laterally).

A detection system may be configured to execute steps for serial or parallel interrogation of the units using a variety of interrogatory devices, such as interrogatory devices using lasers or cameras, real time classification, and rapid, command driven distributing. The detection system may comprise a multiple part system, having, for example, one or more of a scanner that emits light at a particular excitation wavelength or set of wavelengths over the units in the microfluidic device, a detector that receives the emitted light or diffraction pattern from the units and converts it into a digital electrical signal that corresponds to the unit, a decoder that translates the signal into data which can then be sent to an associated computer for storage, and/or any other suitable component known in the art. Light illumination and detection devices may include fluorescence, surface plasmon resonance, total internal reflection fluorescence (TIRF), Raman spectroscopy, or any other suitable light illumination and/or detection technique known in the art. Detectors may include non-optical detectors such as magnetic detectors, conductivity sensors such as Coulter counters, capacitive sensors, dielectric spectroscopy, or any other non-optical detector known in the art, or any combination thereof. Multiple detectors, and multiple types or classes of detectors may be used in the device as described herein. For example, a device may have both one or more optical detectors and one or more non-optical detectors.

The detector may comprise a lamp (e.g. mercury, xenon, halogen), a laser (e.g. argon, krypton, helium neon, helium cadmium, diode laser), a light emitting diode (LED) or a diode laser coupled to a wavelength filter and a photon detector. The detector may also include a photomultiplier tube, a photodiode, or an avalanche photodiode. The detector may be optical fiber coupled or free-space optics coupled. The detector may also be a charge-coupled device (CCD) camera. Multiple detectors can be joined consecutively to read units that have multiple labels or to track a given unit through a device. Detectors configured to interrogate various locations within a device may collect information in parallel or in series.

Optical and non-optical detectors may detect and evaluate size, shape, orientation, positions, color, color spectra, interference patterns, barcode patterns, charge, magnetic or paramagnetic labels, or capacitance or conductivity of the units, or any combination thereof. Detectors may distinguish units from other non-unit elements such as dust, bubbles, unit fragments, or other contaminants. Detectors may be configured to collect location and speed information of units, which may be used for feedback control for the operation of the devices described herein, such as by increasing or decreasing the pressure of a carrier fluid to move the units, or to distribute the units. Detectors may be located in any channel, including without limitation a main channel, feeder channel, branch channel, reaction chamber or outlet channel and may be used to verify correct distributing or steering of the units, for example by determining the presence or absence of a unit, or by counting units to determine whether the correct number of units have been distributed or steered. Information collected by a detector may be used to identify an error in distributing and/or correct the distribution of a unit into the incorrect channel, as described in further detail elsewhere herein. As an example, a mis-distributed unit may be re-distributed into the correct channel, or a unit may be distributed into a channel to be held until it can be distributed into the correct channel.

An exemplary detector may comprise a single-mode or multimode source fiber and a receiver fiber placed adjacent or nearly adjacent to a channel. Such a detector is shown in FIG. 18. The source fiber provides an incident light and a receiver fiber receives light scattered or directed from the source fiber.

Figure 16A:
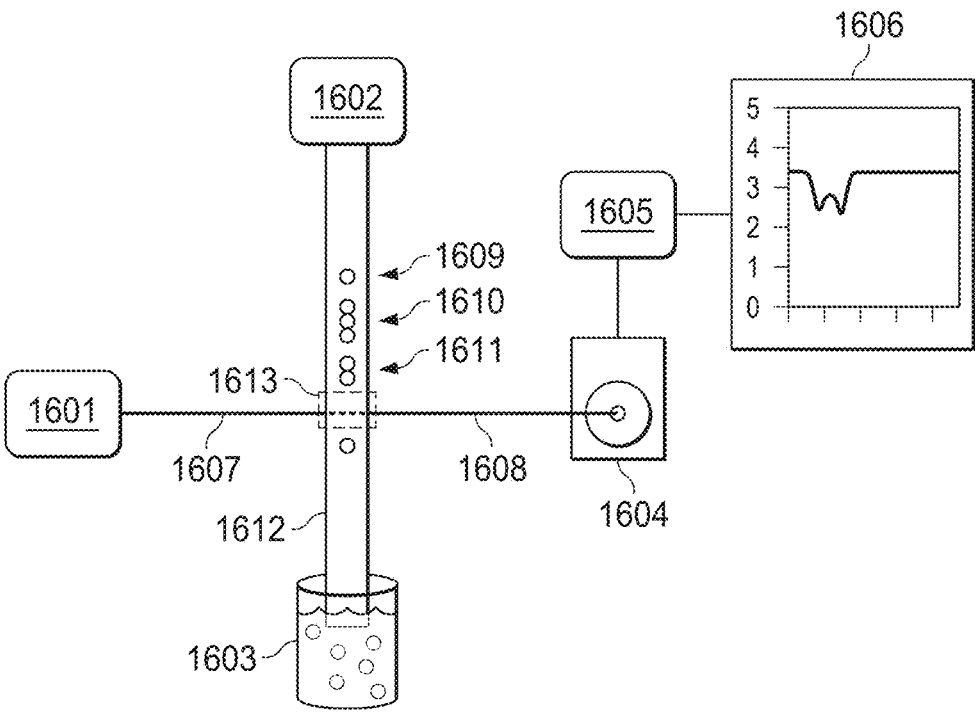
FIG. 16A provides an illustrative example of a detection system.

Highly accurate detection and counting of units can be achieved by using a detection system, such as an optical system to distinguish single units, even if closely spaced, from adjacent two (doubles), three (triplets), or more units (n-tuplets) as they traverse the detection system in the device. Two adjacent units (a double) can be distinguished from one or more units through a characteristic detection patterns, for example a detection pattern comprising a characteristic light transmission pattern as shown in FIG. 16A. Single, double, triple, and n-tuple units are shown to each result in a different characteristic signal shape that can be used to distinguish the number of units or beads passing through the detector. Detecting these characteristic patterns allows for positionally tracking the units or beads as they move through the device.

Complex combinations of single, double, triple, and n-tuple units can be distinguished by a detection system, including, without limitation, an optical detection system. Optical detection systems described herein may be used to analyze signal patterns of transmitted light, as shown in shown in FIG. 16A as units pass through a detection path as described previously or elsewhere herein. Single, double, triple, and n-tuple units traversing through an optical detection system may be identified by a characteristic intensity signal signature, including, without limitation, the characteristic "W" pattern obtained by single beads passing through the optical detection system described in Example 4. Characteristic signal patterns for two or more adjacent units may be established using the detection systems described herein. Signal patterns may be used to distinguish single, double, triple, and n-tuple units, including for example 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more adjacent units. Values for the adjacent units may range between any of the potential values set forth for the adjacent units herein. Detectors described herein may be used to detect and/or count units in a stacked configuration or unstacked configuration and can be used to count an arbitrarily large number of units. Based on the identification of a plurality of adjacent units, systems and methods described herein may be used to take an action on the plurality of adjacent beads. Such an action may include corrective mechanisms, including without limitation, directing one or more units, such as one or more of the detected adjacent units, to a holding chamber, applying a separating force on one or more units, such as one or more of the detected adjacent units, reprogramming of downstream directions of one or more units, such as one or more of the detected adjacent units, or combinations of one or more of the foregoing. One or more units, such as one or more beads that miss the application of designated application of reaction conditions, may be redirected immediately or at a later point such that the missed application of reaction conditions can be applied.

Without being bound by theory, the optical detection signals may be generated by the incident light being scattered (FIGS. 17A and 17B), and transmission intensity decreasing from baseline intensity as the leading edge of a first unit enters the optical path of an optical detection system (a) (FIG. 17B). Then, as the center of the first unit aligns with the optical path, the transmitted light momentarily increases, likely due to lensing of some, but not all of the light through the unit and into the receiving fiber (b). Transmitted light intensity decreases even further as the trailing edge of the first unit and leading edge of the second bead directly align with the optical path (c). Then, the transmitted light momentarily increases again, likely due to lensing as the center of the second unit aligns with the optical path (d). Transmitted light then momentarily decreases one last time as the trailing edge of the second unit traverses the optical path (e). This results in a characteristic "W" shape of the signal.

Figures 18A, 18B:
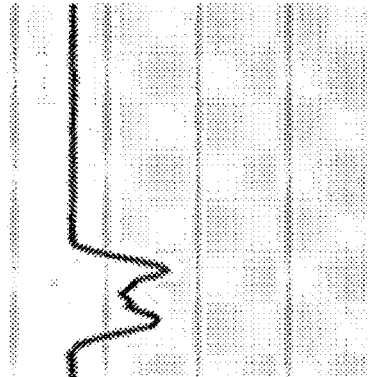
FIG. 18A-B provides examples of signals generated by single units (18A) and bubbles (18B).

In various embodiments, methods and systems described herein are configured to distinguish bubbles from units in order to detect bubbles within the microfluidic devices described herein. Without being bound by theory, bubbles may interfere with device operation and/or cause miscounting of units. Bubbles traveling through a detector, such as an optical path lens, may cause a similar signal at the detector as that of a unit, for example a bead. In various embodiments, detectors, including without limitation, the optical detection systems described herein may be designed to distinguish bubbles from units using various characteristics. For example, bubbles may have a lower index of refraction than units, for example beads. The use of a sufficiently sensitive optical sensing system allows discrimination between the change in signal intensity from baseline caused by a bubble from that caused by a unit, for example a bead. In addition, a narrow size distribution of the units within the systems described herein reduces variation in unit signals, including for example the variation in signal width of a unit passing through the path of a detector at a selected speed. Without being bound by theory, greater bubble size variation can cause a greater variation in bubble signals. The combination of signal width variation and signal intensity differences can be combined to discriminate bubbles from other types of units in methods and systems described herein (FIGS. 18A and 18B).

Detectors may be configured to collect information from units passing the detector's path at a rate of about, at least, or at least about $1 \times 10^{-1}$ units/sec (u/sec), $1 \times 10^{1}$ u/sec, $1 \times 10^{2}$ u/sec, $2 \times 10^{2}$ u/sec, $3 \times 10^{2}$ u/sec, $4 \times 10^{2}$ u/sec, $5 \times 10^{2}$ u/sec, $6 \times 10^{2}$ u/sec, $7 \times 10^{2}$ u/sec, $8 \times 10^{2}$ u/sec, $9 \times 10^{2}$ u/sec, $1 \times 10^{3}$ u/sec, $2 \times 10^{3}$ u/sec, $3 \times 10^{3}$ u/sec, $4 \times 10^{3}$ u/sec, $5 \times 10^{3}$ u/sec, $6 \times 10^{3}$ u/sec, $7 \times 10^{3}$ u/sec, $8 \times 10^{3}$ u/sec, $9 \times 10^{3}$ u/sec, $1 \times 10^{4}$ u/sec, $2 \times 10^{4}$ u/sec, $3 \times 10^{4}$ u/sec, $4 \times 10^{4}$ u/sec, $5 \times 10^{4}$ u/sec, $6 \times 10^{4}$ u/sec, $7 \times 10^{4}$ u/sec, $8 \times 10^{4}$ u/sec, $9 \times 10^{4}$ u/sec, $1 \times 10^{5}$ u/sec, $2 \times 10^{5}$ u/sec, $3 \times 10^{5}$ u/sec, $4 \times 10^{5}$ u/sec, $5 \times 10^{5}$ u/sec, $6 \times 10^{5}$ u/sec, $7 \times 10^{5}$ u/sec, $8 \times 10^{5}$ u/sec, $9 \times 10^{5}$ u/sec, $1 \times 10^{6}$ u/sec, $2 \times 10^{6}$ u/sec, $3 \times 10^{6}$ u/sec, $4 \times 10^{6}$ u/sec, $5 \times 10^{6}$ u/sec, $6 \times 10^{6}$ u/sec, $7 \times 10^{6}$ u/sec, $8 \times 10^{6}$ u/sec, $9 \times 10^{6}$ u/sec, $1 \times 10^{7}$ u/sec, $2 \times 10^{7}$ u/sec, $3 \times 10^{7}$ u/sec, $4 \times 10^{7}$ u/sec, $5 \times 10^{7}$ u/sec, or more. In some cases, detectors may be configured to collect information from units passing through the detector's path at a rate of at most, or at most about $5 \times 10^{7}$ u/sec, $4 \times 10^{7}$ u/sec, $3 \times 10^{7}$ u/sec, $2 \times 10^{7}$ u/sec, $1 \times 10^{7}$ u/sec, $9 \times 10^{6}$ u/sec, $8 \times 10^{6}$ u/sec, $7 \times 10^{6}$ u/sec, $6 \times 10^{6}$ u/sec, $5 \times 10^{6}$ u/sec, $4 \times 10^{6}$ u/sec, $3 \times 10^{6}$ u/sec, $2 \times 10^{6}$ u/sec, $1 \times 10^{6}$ u/sec, $9 \times 10^{5}$ u/sec, $8 \times 10^{5}$ u/sec, $7 \times 10^{5}$ u/sec, $6 \times 10^{5}$ u/sec, $5 \times 10^{5}$ u/sec, $4 \times 10^{5}$ u/sec, $3 \times 10^{5}$ u/sec, $2 \times 10^{5}$ u/sec, $1 \times 10^{5}$ u/sec, $9 \times 10^{4}$ u/sec, $8 \times 10^{4}$ u/sec, $7 \times 10^{4}$ u/sec, $6 \times 10^{4}$ u/sec, $5 \times 10^{4}$ u/sec, $4 \times 10^{4}$ u/sec, $3 \times 10^{4}$ u/sec, $2 \times 10^{4}$ u/sec, $1 \times 10^{4}$ u/sec, $9 \times 10^{3}$ u/sec, $8 \times 10^{3}$ u/sec, $7 \times 10^{3}$ u/sec, $6 \times 10^{3}$ u/sec, $5 \times 10^{3}$ u/sec, $4 \times 10^{3}$ u/sec, $3 \times 10^{3}$ u/sec, $2 \times 10^{3}$ u/sec, $1 \times 10^{3}$ u/sec, $9 \times 10^{2}$ u/sec, $8 \times 10^{2}$ u/sec, $7 \times 10^{2}$ u/sec, $6 \times 10^{2}$ u/sec, $5 \times 10^{2}$ u/sec, $4 \times 10^{2}$ u/sec, $3 \times 10^{2}$ u/sec, $2 \times 10^{2}$ u/sec, $1 \times 10^{2}$ u/sec, $1 \times 10^{1}$ u/sec, $1 \times 10^{-1}$ u/sec or less. Those of skill in the art appreciate that the unit passing rate may fall within any range bound by any of these values, for example $1 \times 10^{2}$-$1 \times 10^{3}$ u/sec, $1 \times 10^{3}$-$5 \times 10^{3}$ u/sec, or $5 \times 10^{3}$-$1 \times 10^{4}$ u/sec. Values for the information collection rate may range between any of the potential values set forth for the information collection rate herein.

Nucleic Acid Synthesis

In one embodiment, the synthesis of large library of specific DNA or other nucleic acid molecules is achieved according to the methods and compositions described herein. A set of units begin in a primary channel and are directed according to a preassigned program to one of four distinct channels. Direction into these channels may be achieved by a multiway distributor, by two sequential bifurcations and corresponding two-way distributors, or by any other suitable method known in the art. Reagents, such as various phosphoramidites may be delivered to the channels.

The units may be combined maintaining their positional encoding and reassigned and delivered into one of the four distinct channels. Accordingly, nucleotides may be added in iterative steps to a nascent chain on each unit.

In various embodiments, nucleic acid synthesis is performed in or on the units described herein within the microfluidic devices described herein. In some cases, nucleic acid synthesis is achieved using the phosphoramidite method. Alternative nucleic acid synthesis methods may also be used, such as H-phosphonate, phosphate triester, phosphodiester, phosphotriester, and phosphite triester methods. A non-exclusive list of reagents for these methods that may be delivered to the units comprises nucleotide phosphoramidite monomers; non-nucleoside phosphoramidite monomers; B-cyanoethyl; 4,4'-dimethoxytrityl (DMT); tricholroacetic acid and/or dochloroacetic acid; an acedic azole catalyst, such as 1H-tetrazole, 5-ethylthio-1H-tetrazole, 2-benzylthiotetrazole, 4,5-dicyanoimidazole, or other similar compounds; acetic anhydride, 1-methylimidazole, and/or DMAP; iodine; water; a weak base such as pyridine, lutidine, or collidine; tert-Butyl hydroperoxide or (1S)-(+)-(10-camphorsulfonyl)-oxaziridine (CSO); 3-(Dimethylaminomethylidene)amino-3H-1,2,4-dithiazole-3-thione, 3H-1,2-benzodithiol-3-one 1,1-dioxide, and/or N,N,N'N'-Tetraethylthiuram disulfide; and controlled porous glass. Reagents for nucleic acid synthesis are available from purchase from numerous commercial sources, including American International Chemical (Natick Mass.), BD Biosciences (Palo Alto Calif.), and others. The specific reagents used may vary depending on the method of nucleic acid synthesis, e.g phosphoramidite or non-phosphoramidite reactions.

In some embodiments, nucleotides with suitable modifications for phosphoramidite or non-phosphoramidite chemistry are deposited on a functionalized unit(s) in the device. These nucleotides can be mononucleotides, dinucleotides, or longer oligonucleotides. Phosphoramidite-based nucleic acid synthesis chemistry typically involves the following steps in order: 1) coupling, 2) capping, 3) oxidation and/or sulfurization, 4) deblocking, and 5) desalting. Either oxidation or sulfurization may be used as one of the steps. Successive rounds of chemistry performed in the device may result in step-wise synthesis of high-quality polymers on units. In various embodiments, units described herein are subjected to one or more steps of nucleic acid synthesis in the microfluidic devices described herein. For example, one or more units in a reaction chamber may be contacted with reagents and solutions through one or more reagent channels that connect to the reaction chamber.

Methods of quickly synthesizing n-mer, such as about or at least about 100-, 150-, 200, 250-, 300, 350-, or longer nucleotide, oligonucleotides on units is further described herein in various embodiments. Such methods can use units functionalized with a chemical moiety suitable for nucleotide coupling. In various embodiments, the surface of the units described herein is chemically modified to provide a proper site for the linkage of a growing oligomer to the surface.

In some embodiments, a trialkoxysilyl amine (e.g. (CH3CH20)3Si—(CH2)2-NH2) is allowed to react with glass or silica surface SiOH groups, followed by reaction with succinic anhydride with the amine to create an amide linkage and a free OH on which the nucleotide chain can grow. In some embodiments, beads, such as polymeric beads e.g. polystyrene beads or divinylbenzene-cross-linked polystyrene beads comprise amino functionalization, hydroxyl functionalization, or other suitable functionalization known in the art.

In some embodiments, photocleavable linkers are used. A photocleavable linker may allow for a synthesized oligonucleotide to be removed from the units (e.g. by irradiation with light, e.g. ~350 nm light) without cleaving the protecting groups on the nitrogenous functionalities on each base. The use of photocleavable linkers of this sort is described at www.glenresearch.com. Various other suitable cleavable linker groups are known in the art and may alternatively be used.

In some embodiments, adenine, guanine, thymine, cytosine, or uridine building blocks, or analogs/modified versions thereof are used as described in further detail elsewhere herein. In some cases, the added building blocks comprise dinucleotides, trinucleotides, or longer nucleotide based building blocks, such as building blocks containing about or at least about 4, 5, 6, 7, 8, 9, 10, 11, 12, 13, 14, 15, 16, 17, 18, 19, 20, 25, 30, 35, 40, 45, 50, or more nucleotides. In some embodiments, large libraries of n-mer oligonucleotides are synthesized in parallel on units, e.g. about or at least 100, 1000, 10000, 100000, 1000000, 2000000, 3000000, 4000000, 5000000 units hosting oligonucleotide synthesis. Individual units may host synthesis of oligonucleotides that are different from each other.

A common method for the preparation of synthetic nucleic acids is based on the fundamental work of Caruthers and is known as the phosphoramidite method (M. H. Caruthers, Methods in Enzymology 154, 287-313, 1987; incorporated herein by reference in its entirety).

In some embodiments, the synthesis of DNA oligomers by the methods of the invention is achieved through phosphoramidite chemistry, reviewed in Streyer, Biochemistry (1988) pp 123-124 and U.S. Pat. No. 4,415,732, herein incorporated by reference. In various embodiments, the chemical synthesis of nucleic acids is performed using variations of the phosphoramidite chemistry developed for solid surfaces (Beaucage S L, Caruthers M H. Deoxynucleoside phosphoramidites—a new class of key intermediates for deoxypolynucleotide synthesis. Tetrahedron Lett. 1981; 22: 1859-1862; Caruthers M H. Gene synthesis machines—DNA chemistry and its uses. Science. 1985; 230:281-285., both of which are incorporated herein by reference in their entirety). For instance, phosphoramidite based methods can be used to synthesize abundant base, backbone and sugar modifications of deoxyribo- and ribonucleic acids, as well as nucleic acid analogs (Beaucage S L, Iyer R P. Advances in the synthesis of oligonucleotides by the phosphoramidite approach. Tetrahedron. 1992; 48:2223-2311; Beigelman L, Matulic-Adamic J, Karpeisky A, Haeberli P, Sweedler D. Base-modified phosphoramidite analogs of pyrimidine ribonucleosides for RNA structure-activity studies. Methods Enzymol. 2000; 317:39-65; Chen X, Dudgeon N, Shen L, Wang J H. Chemical modification of gene silencing oligonucleotides for drug discovery and development. Drug Discov. Today. 2005; 10:587-593; Pankiewicz K W. Fluorinated nucleosides. Carbohydrate Res. 2000; 327:87-105; Lesnikowski Z J, Shi J, Schinazi R F. Nucleic acids and nucleosides containing carboranes. J. Organometallic Chem. 1999; 581: 156-169; Foldesi A, Trifonova A, Kundu M K, Chattopadhyaya J. The synthesis of deuterionucleosides. Nucleosides Nucleotides Nucleic Acids. 2000; 19: 1615-1656; Leumann C J. DNA Analogues: from supramolecular principles to biological properties. Bioorg. Med. Chem. 2002; 10:841-854; Petersen M, Wengel J. LNA: a versatile tool for therapeutics and genomics. Trends Biotechnol.

2003; 21:74-81; De Mesmaeker A, Altmann K-H, Waldner A, Wendebom S. Backbone modifications in oligonucleotides and peptide nucleic acid systems. Curr. Opin. Struct. Biol. 1995; 5:343-355), all of which are incorporated herein by reference in their entirety.

In various embodiments, nucleic acids, e.g. nucleic acid double strands, are synthesized and/or assembled while attached on a unit. Methods of preparation of nucleic acid on a common solid support, are discussed in U.S. Pat. No. 7,790,369 and Pub. No. 2007-0087349, both of which are herein incorporated by reference in their entirety.

Oligonucleotides

As used herein, the terms "preselected sequence", "predefined sequence" or "predetermined sequence" are used interchangeably. The terms mean that the sequence of the polymer is known and chosen before synthesis or assembly of the polymer. Various aspects of the invention are described herein primarily with regard to the preparation of nucleic acids molecules, the sequence of the oligonucleotide or polynucleotide being known and chosen before the synthesis or assembly of the nucleic acid molecules. In one embodiment, oligonucleotides are short nucleic acid molecules. For example, oligonucleotides may be from about 10 to about 300 nucleotides, from about 20 to about 400 nucleotides, from about 30 to about 500 nucleotides, from about 40 to about 600 nucleotides, or more than about 600 nucleotides long. Those of skill in the art appreciate that the oligonucleotide lengths may fall within any range bounded by any of these values (e.g., from about 10 to about 400 nucleotides or from about 300 to about 400 nucleotides etc.). Suitably short or long oligonucleotides may be used as necessitated by the specific application. Individual oligonucleotides may be designed to have a different length from another in a library. Oligonucleotides can be relatively short, e.g. shorter than 200, 100, 80, 60, 50, 40, 30, 25, 20, 15, 12, 10, 9, 8, 7, 6, 5, or 4 nucleotides, more particularly. Relatively longer oligonucleotides are also contemplated; in some embodiments, oligonucleotides are longer than or equal to 7, 8, 9, 10, 11, 12, 13, 14, 15, 16, 17, 18, 19, 20, 25, 30, 35, 40, 50, 60, 70, 80, 90, 100, 125, 150, 200, 250, 300, 350, 400, 500, 600 nucleotides, or longer. In some embodiments, oligonucleotides are single-stranded DNA or RNA molecules.

In some embodiments, oligonucleotides described herein are associated to the units described herein through an attachment via the oligonucleotides' 5' end. In some embodiments, oligonucleotides described herein are associated to the units described herein through an attachment via the oligonucleotides' 3' end. In some embodiments, the attachment is through a covalent bond or an affinity binding pair. In some embodiments, a second strand complementary to a first strand associated with a unit is synthesized. In some embodiments, the second strand is attached to the unit via its 3' end. In some embodiments, the second strand is attached to the unit via its 5' end. In some embodiments, oligonucleotides associated with a unit have a free 3' end. In some embodiments, oligonucleotides associated with a unit have a free 5' end. Oligonucleotides described under this paragraph may be synthesized using any synthesis method described herein or any suitable method known in the art.

In some embodiments, oligonucleotides attached to a unit are inverted to reverse the orientation with respect to the units, e.g. from 3'-bound to 5'-bound. Oligonucleotides described herein may be attached to units described herein through a cleavable linker, e.g. a cleavable linker arm of a branched linker attached to a unit. In various embodiments, a branched linker is attached to units described herein. Such branched linkers may comprise a first branch, e.g. a first branch comprising a first alkyne and a second branch, e.g. a second branch comprising a cleavable linker. An oligonucleotide may be attached to the cleavable linker via a first end, e.g. via its 3' end. The other end, e.g. the 5' end, of the oligonucleotide, may be attached to an azide group. In some embodiments, the oligonucleotide is circularized through the branched linker, e.g. by binding the free end of the oligonucleotide to the second branch. In some embodiments, the circularization is achieved by Cu(I) Click chemistry. For example, the azide group on the free end of the oligonucleotide may be reacted with the alkyne on the first branch of the branched linker. Upon circularization, the cleavable linker may be cleaved, e.g. using standard deprotection conditions, such as treatment with $NH_4OH$ at 55° C. for 15 hours, thereby releasing the first end, e.g. 3' end of the oligonucleotide. Methods relating to inversion of oligonucleotides on solid supports are further discussed in U.S. Pat. Pub. 2017/0050162, which is incorporated herein by reference in its entirety.

In one aspect of the invention, a device for synthesizing a plurality of nucleic acids having a predetermined sequence is provided. The device can include units as described in further detail herein having a plurality of oligonucleotides. In some embodiments, the oligonucleotides are linked through their 3' end to the units described herein. Yet, in other embodiments the oligonucleotides are linked through their 5' end to the units described herein. Oligonucleotide linkages may be in a variety of forms, such covalent linkages or linkages comprising affinity binding.

An oligonucleotide may be immobilized on the units described herein via a nucleotide sequence (e.g., a degenerate binding sequence), a linker or spacer (e.g., a moiety that is not involved in hybridization). In some embodiments, the oligonucleotide comprises a spacer or linker to separate the oligonucleotide sequence from the unit. Useful spacers or linkers include photocleavable linkers, or other traditional chemical linkers. In one embodiment, oligonucleotides may be attached to a unit through a cleavable linkage moiety. For example, the unit may be functionalized to provide cleavable linkers for covalent attachment to the oligonucleotides. The linker moiety may be of six or more atoms in length. Alternatively, the cleavable moiety may be within an oligonucleotide and may be introduced during synthesis. A broad variety of cleavable moieties are available in the art of oligonucleotide synthesis (see e.g., Pon, R., Methods Mol. Biol. 20:465-496 (1993); Verma et al, Annu. Rev. Biochem. 67:99-134 (1998); U.S. Pat. Nos. 5,739,386, 5,700,642 and 5,830,655; and U.S. Patent Publication Nos. 2003/0186226 and 2004/0106728). A suitable cleavable moiety may be selected to be compatible with the nature of the protecting group of the nucleoside bases, the choice of unit material, and/or the mode of reagent delivery, among others. In an exemplary embodiment, the oligonucleotides cleaved from the unit contain a free 3'-OH end. Alternatively, the free 3'-OH end may also be obtained by chemical or enzymatic treatment, following the cleavage of oligonucleotides. In various embodiments, the invention relates to methods and compositions for release of unit bound oligonucleotides into solution. The cleavable moiety may be removed under conditions which do not degrade the oligonucleotides. The linker may be cleaved using a variety of approaches, for example simultaneously under the same conditions as a deprotection step or subsequently utilizing a different condition or reagent for linker cleavage after the completion of a deprotection step.

As used herein, the term "duplex" may refer to a nucleic acid molecule that is at least partially double-stranded. The terms "nucleoside" or "nucleotide" may refer to those moieties which contain not only the conventional purine and pyrimidine bases, i.e., adenine (A), thymine (T), cytosine (C), guanine (G) and uracil (U), but also other heterocyclic bases that have been modified. Such modifications include methylated purines or pyrimidines, acylated purines or pyrimidines, alkylated riboses or other heterocycles or any other suitable modifications described herein or otherwise known in the art. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the terms "nucleoside" and "nucleotide" may refer to protected forms of nucleosides and nucleotides, e.g., wherein the base is protected with a protecting group such as acetyl, difluoroacetyl, trifluoroacetyl, isobutyryl or benzoyl, and purine and pyrimidine analogs.

Suitable nucleotide and nucleoside analogs will be known to those skilled in the art. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methyl guanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylanminomethyl)uracil, 5-(carboxymethylaminomethyl)-uracil, 2-thiouracil, 5-methyl-2-thiouracil, 5-(2-bromovinyl)uracil, uracil-5-oxy acetic acid, uracil-5-oxy acetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

As used herein, the term "oligonucleotide" shall include poly deoxynucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones (for example PNAs). Thus, these terms include known types of oligonucleotide modifications, for example, substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.). There is no intended distinction in length between the term "polynucleotide" and "oligonucleotide," and these terms may be used interchangeably.

The term "attached," as in, for example, a unit having a moiety "attached" thereto, includes covalent binding, adsorption, and physical immobilization. The terms "binding" and "bound" are identical in meaning to the term "attached."

Oligonucleotides on units may be cleaved from their solid surface and optionally pooled to enable new applications such as, gene assembly, nucleic acid amplification, sequencing libraries, shRNA libraries etc. (Cleary M A, Kilian K, Wang Y Q, Bradshaw J, Cavet G, Ge W, Kulkami A, Paddison P J, Chang K, Sheth N, et al. Production of complex nucleic acid libraries using highly parallel in situ oligonucleotide synthesis. Nature Methods. 2004; 1:241-248), gene synthesis (Richmond K E, Li M H, Rodesch M J, Patel M, Lowe A M, Kim C, Chu L L, Venkataramaian N, Flickinger S F, Kaysen J, et al. Amplification and assembly of chip-eluted DNA (AACED): a method for high-throughput gene synthesis. Nucleic Acids Res. 2004; 32:5011-5018; Tian J D, Gong H, Sheng N J, Zhou X C, Gulari E, Gao X L, Church G. Accurate multiplex gene synthesis from programmable DNA microchips. Nature. 2004; 432: 1050-1054) and site-directed mutagenesis (Saboulard D, Dugas V, Jaber M, Broutin J, Souteyrand E, Sylvestre J, Delcourt M. High-throughput site-directed mutagenesis using oligonucleotides synthesized on DNA chips. BioTechniques. 2005; 39:363-368), all of which are herein incorporated by reference in their entirety. In some embodiments, reactions comprising such oligonucleotides may be performed without detaching the oligonucleotide from its unit."

Other Oligomers

In various embodiments, the invention relates to the synthesis, such as chemical synthesis, of molecules other than nucleic acids. The terms "peptide," "peptidyl" and "peptidic" as used throughout the specification and claims are intended to include any structure comprised of two or more amino acids. The peptides synthesized according to the methods described herein may comprise about 5 to 10,000 amino acids, preferably about 5 to 1000 amino acids. The peptides synthesized according to the methods described herein may comprise, comprise about or comprise at least 2, 3, 4, 5, 6, 7, 8, 9, 10, 11, 12, 13, 14, 15, 16, 17, 18, 19, 20, 25, 30, 40, 50, 60, 70, 80, 90, 100, 200, 300, 400, 500, 600, 700, 800, 900, 1000 amino acids or more. The peptides synthesized according to the methods described herein may comprise a number of amino acids falling within the range bounded by any of the foregoing values, such as 2-900, 90-10,000, etc. The amino acids forming all or a part of a peptide may comprise any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y) or amino acids, e.g. non-naturally occurring amino acids. The term "non-conventional amino acid" refers to amino acids other than conventional amino acids, and includes, for example, isomers and modifications of the conventional amino acids (e.g., D-amino acids), non-protein amino acids, post-translationally modified amino acids, enzymatically modified amino acids, constructs or structures designed to mimic amino acids (e.g., $\alpha,\alpha$-disubstituted amino acids, N-alkyl amino acids, lactic acid, $\beta$-alanine, naphthylalanine, 3-pyridylalanine, 4-hydroxyproline, O-phosphoserine, N-acetylserine, N-formylmethionine, 3-methylhistidine, 5-hydroxylysine, and nor-leucine), and peptides having the naturally occurring amide —CONH— linkage replaced at one or more sites within the peptide backbone with a non-conventional linkage such as N-substituted amide, ester, thioamide, retropeptide (—NHCO—), retrothioamide (—NHCS—), sulfonamido (—S02NH—), and/or peptoid (N-substituted glycine) linkages. Accordingly, the peptidic molecules of the array include pseudopeptides and peptidomimetics. The peptides of this invention can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

The term "oligomer" may encompass any polynucleotide or polypeptide or other chemical compound with repeating moieties such as nucleotides, amino acids, carbohydrates and the like.

In some examples, all or some of the units in a group of units, e.g. units within a microfluidic device described herein each are attached to a different composition, such as a different oligonucleotide.

Amplification of Nucleic Acids

In various embodiments, the methods and systems relate to amplification of single stranded nucleic acids.

The single stranded nucleic acids may be amplified using adaptors incorporated into the target sequence. Polymerase chain reaction in conjunction with primers corresponding to these adaptors, or any amplification method described herein or any other suitable amplification method known in the art, can be used to amplify the target.

The single stranded nucleic acids may be circularized upon hybridization with an adaptor. A single stranded nucleic acid may be circularized by joining its 5' and 3' ends, forming a contiguous circle. Various ligation methods and enzymes are suitable for the reaction as described elsewhere herein and otherwise known in the art. Circularized nucleic acids may be attached to units described herein. In some embodiments, nucleic acids are circularized while being associated with, e.g. attached to, units. For example, a unit may be isolated within a microfluidic device, for example, in a channel or chamber of a microfluidic device, nucleic acids associated with the unit may be released from the unit may be circularized, e.g. through the use of an adaptor. In some embodiments, the circularized nucleic acids are attached to the unit, e.g. covalently or through affinity binding.

Adaptors, according to the various embodiments of the invention, can be extended using the circularized single stranded nucleic acid as a template. Alternatively, one or more different primers may be used to anneal elsewhere on the circle in addition or instead of the adaptor and can be extended with a polymerase enzyme. The extension reaction, such as rolling circle amplification, multi-primer rolling circle amplification or any other suitable extension reaction, can facilitate the creation of one long and linear single stranded amplicon nucleic acids comprising alternating replicas of the single stranded template nucleic acid and the adaptor hybridization sequences. In some embodiments, the combined replicas of the adaptor hybridization sequences are copies of the adaptor sequence, or differ by less than 8, 7, 6, 5, 4, 3, or 2 nucleotides. These sequences will together be referred to as "adaptor copies" for ease, but it is understood that they may refer to a number of different types of sequences generated from the extension reaction using the circle as a template. Nucleotide extension products produced using templates described herein, such as circularized single stranded nucleic acid templates, may be attached to units described herein. In some embodiments, nucleic acid extension products are attached to the same unit as the template nucleic acid that is used as a template to produce the nucleic acid extension product.

Nucleic acids, e.g. the extension and/or amplification products produced from template nucleic acids described herein, may be cleaved using the methods described herein or by any suitable method known in the art. For example, extension and/or amplification products may be cleaved at the 5' end of a recognition site by Type II endonucleases. The cutting site may be 1, 2, 3, 4, 5, 6, 7, 8, 9, 10, 11, 12, 13, 14, 15, 16, 17, 18, 19, 20, 21, 22, 23, 24, 25 nucleotides or more upstream from the first nucleotide of the recognition site. The 5' or 3' end of a recognition site may form a 0-, 1-, 2-, 3-, 4-, or 5-nucleotide overhang. Blunt Type II endonucleases which cleave with a 0-nucleotide overhang include Mlyl and Schl. Exemplary Type IIS endonucleases which generate 5' overhangs (e.g., 1, 2, 3, 4, 5 nucleotides overhangs) include, but are not limited to, Alwl, Bed, BceAI, BsmAI, BsmFI, Fokl, Hgal, Plel, SfaNI, BfuAI, Bsal, BspMI, BtgZI, Earl, BspQI, Sapl, Sgel, BceFI, BslFI, BsoMAI, Bst71I, Faql, Acelll, Bbvll, Bvel, and Lgul. Nicking endonucleases which remove the recognition site and cleave on the 5' site of the recognition site include, but are not limited to Nb.BsrDI, Nb.BtsI, AspCNI, BscGI, BspNCI, EcoHI, Finl, Tsui, UbaFl 1I, Unbl, Vpakl 1AI, BspGI, Drdll, Pfll 108I, and UbaPI.

Nucleic acids, e.g. the extension and/or amplification products produced from template nucleic acids described herein, may be cleaved by non-Type IIS endonucleases which cleave at the 5' end of the recognition site on both strands to generate a blunt end. The amplification product may be cleaved by non-Type IIS endonucleases which cleave at the 5' end of the recognition site on one strand and in the middle of the recognition site on the other strand, generating a 5' overhang. Examples of endonucleases which generate a 5' overhang include, but are not limited to, BfuCI, DpnII, Fatl, Mbol, MluCI, Sau3AI, Tsp509I, BssKI, PspGI, StyD4I, Tsp45I, Aoxl, BscFI, Bspl43I, BssMI, BseENII, BstMBI, Kzo9I, Nedll, Sse9I, Tasl, TspEI, Ajnl, BstSCI, EcoRII, Maelll, NmuCI, and Psp6I.

Nucleic acids, e.g. the extension and/or amplification products produced from template nucleic acids described herein, may be cleaved by nicking endonucleases which cleave at the 5' end of a recognition site to produce a nick. The nicking site may be 1, 2, 3, 4, 5, 6, 7, 8, 9, 10, 11, 12, 13, 14, 15, 16, 17, 18, 19, 20, 21, 22, 23, 24, 25 nucleotides or more upstream from the first nucleotide of the recognition site. Exemplary nicking endonucleases include, but are not limited to, Nb.BsrDI, Nb.BtsI, AspCNI, BscGI, BspNCI, EcoHI, Finl, Tsui, UbaF 1I, Unbl, Vpakl 1AI, BspGI, Drdll, Pfll 108I, and UbaPI.

Nucleic acids, e.g. the extension and/or amplification products produced from template nucleic acids described herein, may be cleaved at the 3' end of a recognition site by Type IIS endonucleases. The 5' or 3' end of a recognition site may form a 0-, 1-, 2-, 3-, 4-, or 5-nucleotide overhang. The cutting site may be 1, 2, 3, 4, 5, 6, 7, 8, 9, 10, 11, 12, 13, 14, 15, 16, 17, 18, 19, 20, 21, 22, 23, 24, 25 nucleotides or more downstream from the last nucleotide of the recognition site. Type IIS endonucleases which cleave at 0 nucleotides downstream of the last nucleotide of the recognition site include Mlyl and Schl. Exemplary Type IIS endonucleases which generate 3' overhangs (e.g., 1, 2, 3, 4, 5 nucleotide overhangs) include, but are not limited to, Mnll, BspCNI, Bsrl, BtsCI, Hphl, HpyAV, Mboll, Acul, BciVI, Bmrl, Bpml, BpuEI, BseRI, Bsgl, Bsml, BsrDI, Btsl, Ecil, Mmel, NmeAIII, Hin4II, TscAI, Bce83I, Bmul, Bsbl, and BscCI. Non-Type II endonucleases which remove the recognition site on one strand and generate a 3' overhang or blunt end on the other strand include, but are not limited to Nlalll, Hpy99I, TspRI, Fael, Hinlll, Hsp92II, Setl, Tail, Tscl, TscAI, and TseFI. Nicking endonucleases which remove the recognition site and cut on the 3' end of the recognition site include Nt.AlwI, Nt.BsmAI, Nt.BstNBI, and Nt.BspQI.

The adaptor sequences described herein may comprise one or more restriction recognition sites. In some embodiments, the recognition site is at least 4, 5, or 6 base pairs long. In some embodiments, the recognition site is non-palindromic. In some embodiments, the adaptor oligonucleotide comprises two or more recognition sites. Two or more recognition sites may be cleaved with one or more restriction enzymes. Exemplary pairs of recognition sites in an adaptor sequence include, but are not limited to, Mlyl-Mlyl, Mlyl-Nt.AlwI, Bsal-Mlyl, Mlyl-BciVI, and BfuCI-Mlyl.

Sequencing

In any of the embodiments, the detection or quantification analysis of polynucleotides described herein, e.g. polynucleotides synthesized on units described herein or polynucleotides captured thereby or produced based thereon, such as amplification products using such polynucleotides as templates, can be accomplished by sequencing. The subunits or entire synthesized oligonucleotides can be detected via full sequencing of all oligonucleotides by any suitable methods known in the art, e.g., Illumina HiSeq 2500, including the sequencing methods described herein.

Sequencing can be accomplished through classic Sanger sequencing methods which are well known in the art. Sequencing can also be accomplished using high-throughput systems some of which allow detection of a sequenced nucleotide immediately after or upon its incorporation into a growing strand, i.e., detection of sequence in real time or substantially real time.

In some embodiments, high-throughput sequencing involves the use of next-generation sequencing (NGS) technology available by Illumina Genome Analyzer II, MiSeq personal sequencer, or HiSeq systems, such as those using HiSeq 4000, HiSeq 3000, HiSeq 2500, HiSeq 1500, HiSeq 2000, or HiSeq 1000.

In some embodiments, NGS comprises the use of technology available by ABI SOLiD System. This genetic analysis platform may be used for massively parallel sequencing of clonally-amplified DNA fragments linked to beads. The sequencing methodology may utilize sequential ligation with dye-labeled oligonucleotides.

The NGS may comprise ion semiconductor sequencing (e.g., using technology from formerly Life Technologies, now Thermo Fisher (Ion Torrent)). Ion semiconductor sequencing can take advantage of the fact that when a nucleotide is incorporated into a strand of DNA, an ion can be released.

In some embodiments, NGS comprises the use of the Single Molecule Sequencing by Synthesis (SMSS) method, discussed in further detail in U.S. Pub. Nos. 2006/002471 I; 2006/0024678; 2006/0012793; 2006/0012784; and 2005/0100932.

High-throughput sequencing of oligonucleotides can be achieved using any suitable sequencing method known in the art, such as those commercialized by Pacific Biosciences, Complete Genomics, Genia Technologies, Halcyon Molecular, Oxford Nanopore Technologies and the like. The sequencing of polynucleotides may be performed using a next generation sequencing technique, e.g. real-time (SMRT™) technology by Pacific Biosciences. In some embodiments, the next generation sequencing comprises nanopore sequencing (See e.g., Soni G V and Meller A.

(2007) Clin Chem 53: 1996-2001). The nanopore sequencing technology from Oxford Nanopore Technologies; e.g., a GridION system is used in various embodiments. Nanopore sequencing technology from Roche (formerly GENIA) can be used. The next generation sequencing may comprise DNA nanoball sequencing (as performed, e.g., by Complete Genomics; see e.g., Drmanac et al. (2010) Science 327: 78-81).

Genes

The methods and compositions of the invention in various embodiments allow for the construction of gene libraries comprising a collection of individually accessible polynucleotides of interest. The polynucleotides can be linear, can be maintained in vectors (e. g., plasmid or phage), cells (e. g., bacterial cells), as purified DNA, or in other suitable forms known in the art. Library members (variously referred to as clones, constructs, polynucleotides, etc.) can be stored in a variety of ways for retrieval and use, including for example, in multiwell culture or microtiter plates, in vials, in a suitable cellular environment (e.g., *E. coli* cells), as purified DNA compositions on suitable storage media (e.g., the Storage IsoCodeD ID™ DNA library card; Schleicher & Schuell Bioscience), or a variety of other suitable library forms known in the art. A gene library may comprise about or at least 10, 100, 200, 300, 400, 500, 600, 750, 1000, 1500, 2000, 3000, 4000, 5000, 6000, 7500, 10000, 15000, 20000, 30000, 40000, 50000, 60000, 75000, 100000 members, or more.

In various embodiments, the methods and compositions of the invention allow for production of synthetic (i.e. de novo synthesized) genes. Libraries comprising synthetic genes may be constructed by a variety of methods described in further detail elsewhere herein, such as PCA, non-PCA gene assembly methods or hierarchical gene assembly, combining ("stitching") two or more double-stranded polynucleotides (referred to here as "synthons") to produce larger DNA units (i.e., multisynthons or chassis). Libraries of large constructs may comprise polynucleotides that are about or at least 1, 1.5, 2, 3, 4, 5, 6, 7, 8, 9, 10, 15, 20, 30, 40, 50, 60, 70, 80, 90, 100, 125, 150, 175, 200, 250, 300, 400, 500 kb long or longer. The large constructs may be shorter than 50000, 20000, 10000 or 5000 base pairs. The synthesis of any number of polypeptide-segment encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, as well as non-coding DNA or RNA, such as regulatory sequences e.g. promoters, transcription factors, enhancers, siRNA, shRNA, RNAi, miRNA, small nucleolar RNA derived from microRNA, or any functional or structural DNA or RNA unit of interest is contemplated according to the embodiments of the invention. The term "gene" as used herein may refer broadly to any type of coding or non-coding, long polynucleotide or polynucleotide analog.

In some embodiments, nucleic acids and/or nucleic acid libraries described herein comprise genes encoding for a part or all of the genome of a synthetic organism, e.g. a virus or a bacterium. The terms "gene", "polynucleotide", "nucleotide", "nucleotide sequence", "nucleic acid" and "oligonucleotide" are used interchangeably and refer to a nucleotide polymer. Unless otherwise limited, the same include known analogs of natural nucleotides that can function in a similar manner (e.g., hybridize) to naturally occurring nucleotides. They can be of polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), microRNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. A polynucleotide may comprise one or more of the modified nucleotides described herein or any other modified nucleotides known in the art, such as methylated nucleotides and nucleotide analogs. Modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term nucleic acid encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing non-nucleotidic backbones, for example, poly-amide (e.g., peptide nucleic acids (PNAs)) and polymorpholino (commercially available from the AntiVirals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, which are incorporated herein by reference in their entirety for their disclosure of LNAs.

As used herein, the term "complementary" refers to the capacity for precise pairing between two nucleotides. Without being bound by theory, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial", in which only some of the nucleotides bind, or it may be complete when total complementarity exists between the single-stranded molecules. The degree of complementarity between nucleic acid strands has significant effects on the efficiency and strength of hybridization between nucleic acid strands.

"Hybridization" and "annealing" may refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of a PCR or other amplification reactions, or the enzymatic cleavage of a polynucleotide by a ribozyme. A first sequence that can be stabilized via hydrogen bonding with the bases of the nucleotide residues of a second sequence is said to be "hybridizable" to said second sequence. In such a case, the second sequence can also be said to be hybridizable to the first sequence.

The term "hybridized" as applied to a polynucleotide may refer to a polynucleotide in a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. The hybridization reaction may constitute a step in a more extensive process, such as the initiation of a PCR reaction, or the enzymatic cleavage of a polynucleotide by a ribozyme. A sequence hybridized with a given sequence is referred to as the "complement" of the given sequence.

"Specific hybridization" may refer to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

The "complement" of a given sequence may refer to a sequence that is fully or substantially complementary to and hybridizable to the given sequence. In general, a first sequence that is hybridizable to a second sequence or set of second sequences is specifically or selectively hybridizable to the second sequence or set of second sequences, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, or about or at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity.

The term "primer" may refer to an oligonucleotide that is capable of hybridizing (also termed "annealing") with a nucleic acid and serving as an initiation site for nucleotide (RNA or DNA) polymerization under appropriate conditions (e.g., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but in various embodiments, primers are at least 7 nucleotides long and, range from 10 to 30 nucleotides, or range from 15 to 30 nucleotides, in length. Other primers can be somewhat longer, e.g., about or at least 30 to 50 or 40-70 nucleotides long. Those of skill in the art appreciate that the primer length may fall within any range bounded by any of these values (e.g., from 7 to 70 or from 50 to 70). Oligonucleotides of various lengths as further described herein can be used as primers or building blocks for amplification and/or gene assembly reactions. In this context, "primer length" refers to the portion of an oligonucleotide or nucleic acid that hybridizes to a complementary "target" sequence and primes nucleotide synthesis. A primer need not reflect the exact sequence of the template but must be sufficiently complementary to hybridize with a template. The term "primer site" or "primer binding site" refers to the segment of the target nucleic acid to which a primer hybridizes. A construct presenting a primer binding site is often referred to as a "priming ready construct" or "amplification ready construct".

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence.

Gene Assembly

In various embodiments, the present invention relates to the preparation of a polynucleotide sequence (also called "gene") using assembly of overlapping shorter oligonucleotides synthesized or spotted in or on units, e.g. beads. The shorter oligonucleotides may be patchworked together on the same strand using annealing oligonucleotides with complementary regions to consecutive assembled oligonucleotides, e.g. using a polymerase lacking strand displacement activity, a ligase, Click chemistry, or any other suitable assembly method known in the art. In this fashion, the sequence of the annealing nucleic acid may be replicated between the consecutive oligonucleotides of the opposing strand. In some embodiments, consecutive oligonucleotides annealed to a strand or or consecutive oligonucleotides forming portions of a strand are not immediately linked, e.g. through gap-filling using a polymerase. In some cases, consecutive oligonucleotides of the same strand may be stitched together without the introduction of sequence elements from an annealing oligonucleotide, for example using a ligase, Click chemistry, or any other suitable assembly chemistry known in the art. In some cases, longer polynucleotides can be synthesized hierarchically through rounds of assembly involving shorter polynucleotides/oligonucleotides.

Various embodiments of the methods, devices and systems described herein may be used to synthesize genes or genomes de novo from oligonucleotides by assembling large polynucleotides as described in the synthesis of a viral genome (7.5 kb; Cello et al, Science, 2002, 297, 1016), bacteriophage genome (5.4 kb; Smith et al, Proc. Natl. Acad. Sci. USA, 2003, 100, 15440), and a gene cluster as large as 32 kb (Kodumal et al, Proc. Natl. Acad. Sci. USA, 2004, 101, 15573), all of which are herein incorporated by reference in their entirety. Libraries of long synthetic DNA sequence can be manufactured, following the methods described in the 582 kb the genome assembly of a bacterium (*Mycoplasma genitalium*) by Venter and co-workers (Gibson et al, Science, 2008, 319, 1215), which is incorporated herein by reference in its entirety. Furthermore, large DNA biomolecules can be constructed with oligonucleotides, as described for the case of a 15 kb nucleic acid (Tian et al, Nature, 2004, 432, 1050; incorporated herein by reference in its entirety). The methods and compositions of the invention contemplate large libraries of de novo synthesized polynucleotide sequences using gene assembly methods described herein or known in the art. The synthesis of such sequences may be performed in parallel in high densities on suitable subsets of units in microfluidic devices described in further detail elsewhere herein.

Genes may be assembled from large numbers of synthesized oligonucleotides that are pooled. In some embodiments, some or all of the pooled oligonucleotides comprise oligonucleotides in or on units, e.g. beads described in further detail elsewhere herein. Pooled oligonucleotides may comprise about or at least 2, 3, 4, 5, 6, 7, 8, 9, 10, 20, 30, 40, 50, 60, 70, 80, 90, 100, 200, 300, 400, 500, 600, 700, 800, 900, 1000 or more different oligonucleotides. The length of the assembled genes can be further extended by using longer oligonucleotides. For even larger genes and DNA fragments, for example larger than about 0.5, 1, 1.5, 2, 3, 4, 5 kb, or more, more than one rounds of synthesis may be applied, typically within a hierarchical gene assembly process. PCR assembly and synthesis from oligonucleotides as disclosed herein may be adapted for use in series, as described below.

Figure 11:
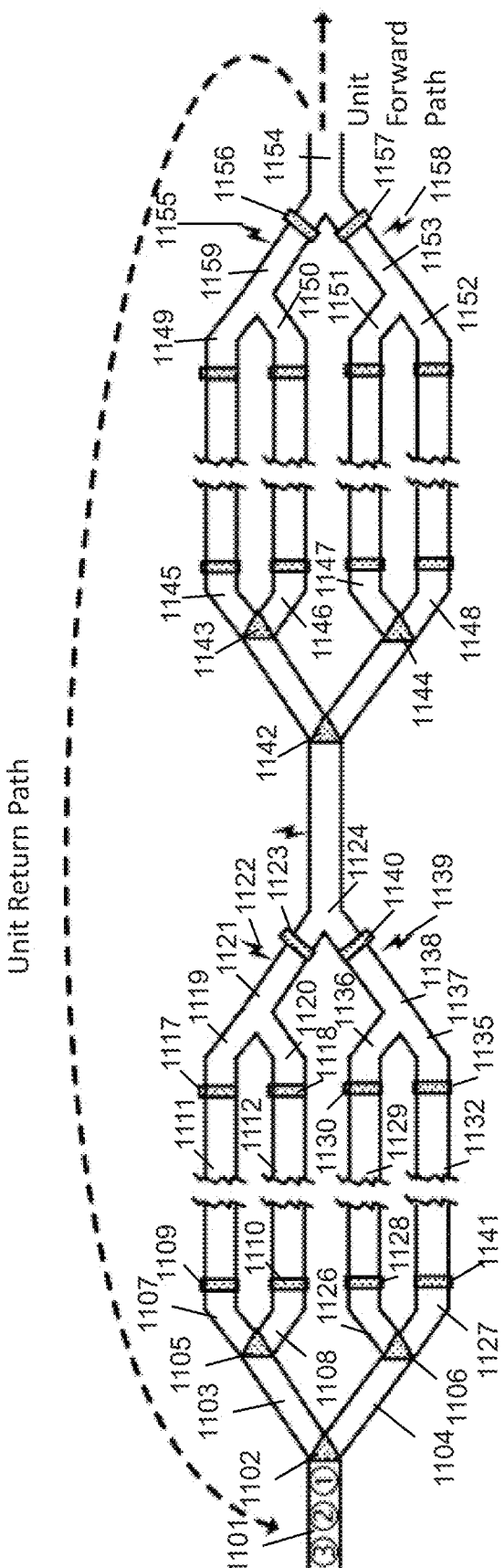
FIG. 11 provides an illustrative example of a microfluidic device with two consecutive reaction clusters.

A variety of gene assembly methods may be used, including without limitation ligase-chain reaction (LCR) (Chalmers and Curnow, Biotechniques, 30(2), 249-52, 2001; Wosnick et al, Gene, 60(1), 115-27, 1987) to suites of PCR strategies (Stemmer et al, 164, Gene, 49-53, 1995; Prodromou and L. H. Pearl, 5(8), Protein Engineering, 827-9, 1992; Sandhu et al, 12(1), BioTechniques, 14-6, 1992; Young and Dong, Nucleic Acids Research, 32(7), e59, 2004; Gao et al, Nucleic Acids Res., 31, e143, 2003; Xiong et al, Nucleic Acids Research, 32(12), e98, 2004) (FIG. 11). In various applications of LCR, an initial oligonucleotide population having phosphorylated 5' ends that allow a ligase, e.g. Pfu DNA ligase, may be covalently connected as "building blocks" to form an initial template. In various applications of PCR assembly, unphosphorylated oligonucleotides may undergo repetitive PCR cycling to extend and create a full length template.

Heaters and coolers described in further detail herein may be used to provide for time regulated heating of the devices described herein to allow PCR amplification or PCA reactions to occur. The time varying thermal field may be applied externally, for example by placing a device substrate with reactors, or integrated within a microfluidic device, for example as a thin film heater located immediately below a PCA or PCR chambers. A temperature controller can vary the temperature of the heating element in conjunction with a temperature sensor linked to a heater element, or integrated into the reaction chamber. A timer can vary the duration of heat applied to the reaction chambers.

In various embodiments, enzymes that incorporate nucleoside triphosphates, or deoxynucleoside triphosphates, to extend a 3' hydroxyl terminus of a PCR primer, an oligonucleotide or a DNA fragment are utilized. For a general discussion concerning polymerases, see Watson, J. D. et al, (1987) Molecular Biology of the Gene, 4th Ed., W. A. Benjamin, Inc., Menlo Park, Calif. Suitable polymerases that can be used in various embodiments of the invention include, but are not limited to, KOD polymerase; Pfu polymerase; Taq-polymerase; *E. coli* DNA polymerase I, "Klenow" fragment, T7 polymerase, T4 polymerase, T5 polymerase and reverse transcriptase, all of which are known in the art. A polymerase having proof-reading capability, such as Pfu and Pyrobest may be used to replicate DNA with high fidelity. Pfu DNA polymerase possesses 3' to 5' exonuclease proof-reading activity, thus it may correct nucleotide misincorporation errors. In various embodiments of the invention, the nucleic acid fragments are joined together preferably by a specific hybridization reaction between overlapping regions of mutually complementary segments of the nucleic acid fragments, thereby obtaining longer synthetic double-stranded nucleic acids. The individual sequence segments used for building up longer nucleic acids can have a length of, e.g. 20-200, 50-300, 75-350 or 100-400 nucleotide building blocks. Those of skill in the art appreciate that the sequence segment length may fall within any range bounded by any of these values (e.g., 20-350 or 200-350).

In various embodiments, polymerase chain reaction (PCR)-based and/or non-polymerase-cycling-assembly (PCA)-based strategies are used for chemical gene synthesis. In addition, non-PCA-based chemical gene synthesis using different strategies and methods, including enzymatic gene synthesis, annealing and ligation reaction, shotgun ligation and co-ligation, gene synthesis via one strand of DNA, template-directed ligation, ligase chain reaction, microarray-mediated gene synthesis, Blue Heron solid unit technology, Sloning building block technology, PCR-based thermodynamically balanced inside-out (TBIO), two-step total gene synthesis method that combines dual asymmetrical PCR (DA-PCR), overlap extension PCR, PCR-based two-step DNA synthesis (PTDS), successive PCR method, or any other suitable method known in the art can be used in connection with the methods and compositions described herein, for the assembly of longer polynucleotides from shorter oligonucleotides.

In various embodiments, variations of the polymerase-mediated assembly techniques, collectively termed polymerase construction and amplification, are used for chemical synthesis of polynucleotides.

PCR Assembly (PCA)

Various embodiments of the invention incorporate PCR assembly by using polymerase-mediated chain extension in combination with at least two oligonucleotides having complementary ends which can anneal such that at least one of the polynucleotides has a free 3'-hydroxyl capable of polynucleotide chain elongation by a polymerase (e.g., a thermostable polymerase such as Taq polymerase, VENT™ polymerase (New England Biolabs), KOD (Novagen) and the like). Overlapping oligonucleotides may be mixed in a standard PCR reaction containing dNTPs, a polymerase, and buffer. The overlapping ends of the oligonucleotides, upon annealing, create regions of double-stranded nucleic acid sequences that serve as primers for the elongation by polymerase in a PCR reaction. Products of the elongation reaction may serve as substrates for formation of a longer double-strand nucleic acid sequences, eventually resulting in the synthesis of full-length target sequence.

Various PCR based methods can be used to synthesize genes from oligonucleotides. These methods include, but are not limited to, the thermodynamically balanced inside-out (TBIO) method (Gao et al, Nucleic Acids Research, 31:e143, 2003), successive PCR (Xiong et al, Nucleic Acids Research, 32:e98, 2004), dual asymmetrical PCR (DA-PCR) (Sandhu et al, Biotechniques, 12: 14, 1992), overlap extension PCR (OE-PCR) (Young and Dong, Nucleic Acids Research, 32:e59, 2004; Prodromou and Pearl, Protein Eng., 5:827, 1992) and PCR-based two step DNA synthesis (PTDS) (Xiong et al, Nucleic Acids Research, 32:e98, 2004), all of which are incorporated by reference herein in their entirety and can be adapted to assemble a PCR template in a microfluidic device.

Various embodiments of the invention utilize DA-PCR as a one-step process for constructing synthetic genes. In one example, four adjacent oligonucleotides of, e.g. 17-100 bases in length with overlaps of, e.g. 15-17 bases are used as primers in a PCR reaction. Other suitable oligonucleotide and overlap sizes are within the bounds of the invention as further described herein. Without being bound by theory, because the quantity of the two internal primers is highly limited, the resultant reaction may cause an asymmetric single-stranded amplification of the two halves of the total sequence due to an excess of the two flanking primers. In subsequent PCR cycles, these dual asymmetrically amplified fragments, which overlap each other, may yield a double-stranded, full-length product.

In some embodiments, TBIO synthesis is performed using only sense-strand primers for the amino-terminal half and only antisense-strand primers for the carboxy-terminal half of a gene sequence. In addition, the TBIO primers may contain identical regions of temperature-optimized primer overlaps. Complementation of successive pairs of outside primers with the termini of a fully synthesized inside fragment may follow. TBIO bidirectional elongation may be completed for a given outside primer pair before the next round of bidirectional elongation takes place.

Successive PCR may comprise a single step PCR approach in which half the sense primers correspond to one half of the template to be assembled, and the antisense primers correspond to the second half of the template to be assembled.

PDTS may be performed two steps. First individual fragments of the DNA of interest are synthesized: In some embodiments of the invention, 10-12 oligonucleotides, such as oligonucleotides of length of about 60, 80, 100, 125, 150, 175, 200, 250, 300, 350, or more nucleotides, with about 20 bp overlap are mixed and a PCR reaction is carried out with a polymerase, such as pfu DNA, to produce longer DNA fragments. And second, the entire sequence of the DNA of interest is synthesized: 5-10 PCR products from the first step are combined and used as the template for a second PCR reaction with a polymerase, such as pyrobest DNA polymerase with two outermost oligonucleotides as primers.

In some embodiments, nucleic acids are synthesized in series. In this scheme, multiple smaller DNA segments are synthesized in parallel in separate compartments, chambers or in or on separate units, or in series and then introduced together as precursors for the PCA reaction for assembly into a "larger" DNA fragment for subsequent PCR amplification. PCR assembly using such oligonucleotides may result in a template (a first-run template) for PCR amplification. A number of first-run templates so produced may serve as precursors for PCA assembly of DNA fragments larger than the first-run templates, thus producing second-run templates. In turn, the second-run templates may serve as the precursors for the assembly of a third-run template, and so on.

Larger genes may be synthesized combining gene assembly methods hierarchically. A number of genes of intermediary length, for example about 2 kb, can be assembled using a first gene assembly method, such as PCA. A second gene assembly method, e.g. Gibson Assembly (Gibson et al, Science, 2008, 319, 1215) may be utilized to combine the genes of intermediary length into larger genes, e.g. about 5 or 10 kb. The first and second assembly method may be the same or different. Hierarchical assembly can be applied in stages. In vitro recombination techniques may be used to assemble cassettes of gene of intermediary length into increasingly longer sequences, e.g. more than 5, 10, 15, 20, 25, 30, 40, 50, 60, 70, 80, 90, 100, 125, 150, 175, 200, 250, 300, 400, 500, 600, 700, 800, 900, 1000 kb or longer.

Non-polymerase-cycling-assembly-based strategies, such as annealing and ligation reaction, gene synthesis via one strand, template-directed ligation (TDL), ligase chain reaction, microarray-based gene synthesis technology, Blue Heron solid unit technology, or Sloning building block technology, or any suitable assembly method known in the art may also be used for chemical synthesis of polynucleotides.

Enzymatic Gene Assembly

Enzymes that repair single-stranded breaks in double-stranded DNA, can be used to join chemically synthesized oligonucleotides, such as deoxyribopolynucleotides, to form continuous bihelical structures. In another example, the Klenow fragment of DNA polymerase I can be used to join oligonucleotides to longer polynucleotides. Oligonucleotides can further be joined together via ligation, for example using a ligase, such as using phage T4 polynucleotide ligase. In some cases, oligonucleotides can be ligated hierarchically, forming longer and longer polynucleotides in each step.

Annealing and Ligation Reaction

Another approach for the facile synthesis of genes comprises assembly of a polynucleotide from many oligonucleotides through annealing and ligation reaction. In the first, both strands of the desired sequences can be divided with short cohesive ends so that adjacent pairs of complementary oligonucleotides can anneal. The synthesized oligonucleotides can be phosphorylated, for example using a kinase, and annealed before ligation into a duplex.

Shotgun Ligation and Co-Ligation

The shotgun ligation approach comprises the assembly of a full gene from several synthesized blocks. Accordingly, a gene may be sub-assembled in several sections, each constructed by the enzymatic ligation of several complementary pairs of chemically synthesized oligonucleotides with short single strands complementary to that of an adjacent pair. Co-ligation of the sections can achieve the synthesis of the final polynucleotide.

Gene Synthesis Via One Strand

Gene synthesis via one strand refers to a method to synthesize a gene via one stand (Chen et al.; 1990). A plus-stranded DNA of the target gene can be assembled by a stepwise or single-step T4 DNA ligase reaction with several, for example 2, 3, 4, 5, 6, 7, 8, 9, 10 or more, oligonucleotides in the presence of multiple, for example two, terminal complementary oligonucleotides and multiple, for example 2, 3, 4, 5, or more, short interfragment complementary oligonucleotides. The use of fewer synthesized bases, in comparison to the double-strand or overlap methods can reduce costs.

Template-Directed Ligation

Template-directed ligation refers to a method to construct large synthetic genes by ligation of oligonucleotide modules, by partial annealing with a single-stranded DNA template. Oligonucleotides comprising only one strand can be synthesized, in contrast to other technologies that require synthesis of two strands. A ligase, such as the Pfu DNA ligase, can be used to perform thermal cycling for assembly, selection and ligation of full-length oligonucleotides as well as for linear amplification of the template-directed ligation (TDL) product.

Ligase Chain Reaction

A ligase chain reaction (LCR) can be used for synthesis of polynucleotides. Fragments can be assembled from several oligonucleotides via ligation, using a ligase, for example Pfu DNA ligase. After LCR, the full-length gene can be amplified with the mixture of fragments which shared an overlap by denaturation and extension using the outer two oligonucleotides.

Microarray-Mediated Gene Synthesis

Microarray-mediated gene synthesis, as a general concept, is based on the capacity to immobilize tens of thousands of specific probes on a small solid surface (Lockhart and Barlow, 2001). For the production of arrays, DNA can either be synthesized directly on the solid unit (Lipshutz et al., 1999; Hughes et al., 2001) or can be deposited in a presynthesized form onto the surface, for example with pins or ink-jet printers (Goldmann and Gonzalez, 2000). The oligonucleotides obtained can be used in ligation under thermal cycling conditions to generate longer nucleic acids. Another microchip-based technology for accurate multiplex gene synthesis, the modified array-mediated gene synthesis technology, is similar to amplification and assembly of chip-eluted DNA AACED), a method developed for high-throughput gene synthesis. Pools of thousands of 'construction' oligonucleotides and tagged complementary 'selection' oligonucleotides can be synthesized on photo-programmable microfluidic chips, released, ligation amplified, and selected by hybridization to reduce synthesis errors.

Blue Heron Technology

The Blue Heron technology, developed by Blue Heron Biotechnology, is based on a solid-phase support strategy based on the GeneMaker platform. The GeneMaker protocol may generally comprise a user sequence data entry, an algorithm designing suitable oligonucleotides for the assembly of entered sequence, oligonucleotides synthesis and hybridization into duplexes, automated ligation based solid-phase assembly through automated sequential additions inside a column on a solid support matrix, and/or cloning and sequence verification. The Blue Heron technology relies on the sequential addition of building blocks to lower errors.

Various embodiments of the invention make use of serial and hierarchical assembly methods as exemplified in the implementation of the Blue Heron technology.

Sloning Building Block Technology

Sloning building block technology (Slonomics™; Sloning Biotechnology GmbH, Puchheim, Germany) is another method using a ligation-based strategy for chemical gene synthesis. In contrast to ligating oligonucleotides specifically designed and synthesized for a given gene construct, Sloning technology and variations thereof use a library of standardized building blocks that can be combined to form a desired sequence.

Golden Gate Assembly

The Golden-gate method (see, e.g., Engler et al. (2008) PLoS ONE, 3(11): e3647; Engler et al. (2009) PLoS ONE 4(5): e5553) offers standardized, multi-part DNA assembly. The Golden-gate method can use Type IIs endonucleases, whose recognition sites are distal from their cutting sites, for example BsaI. The Golden-gate method is further discussed in U.S. Pat. Pub. 2012/0258487, which is incorporated herein by reference in its entirety.

Nonenzymatic Chemical Ligation of DNA

Other approaches include, nonenzymatic chemical ligation of DNA, for example with cyanogen bromide as a condensing agent. In some embodiments, assembly of oligonucleotides comprises the use of CLICK chemistry. Suitable methods to link various molecules using CLICK chemistry are known in the art (for CLICK chemistry linkage of oligonucleotides, see, e.g. El-Sagheer et al. (PNAS, 108:28, 11338-11343, 2011). Click chemistry may be performed in the presence of Cu(l).

In some cases, the methods and compositions for gene assembly may involve a combination of specifically synthesized building blocks and presynthesized building blocks. Libraries of presynthesized oligonucleotides may be stored and assembly processes for desired target nucleic acids may be optimized for maximum use of presynthesized oligonucleotides, minimizing the need for new synthesis. Specifically synthesized oligonucleotides may fill in parts of a target nucleic acid, for which there is no coverage in libraries of presynthesized oligonucleotides.

In some embodiments, gene assembly is performed with one or more of the oligonucleotides associated with its unit. In some embodiments, an assembled double-stranded nucleic acid, e.g. dsDNA, is attached to the unit of one of the oligonucleotide components.

Oligonucleotides for assembly of a nucleic acid may be provided in an isolated location, such as within a chamber or channel of a microfluidic device. Oligonucleotides may be provided associated with units. Some or all oligonucleotides may be provided free in solution.

One or more oligonucleotide-holding units may be provided associated with oligonucleotides. In some embodiments, each such oligonucleotide-holding unit is associated with a different oligonucleotide. One or more oligonucleotide-transferring units may be provided associated with oligonucleotides. In some embodiments, each such oligonucleotide-transferring unit is associated with a different oligonucleotide. Oligonucleotides may be released from oligonucleotide-transferring units via any cleavage method described herein or any suitable method known in the art. For example, cleavage may be performed by enzymatic methods, photocleavage of a photolabile linker, or ammonia gas. In some embodiments, cleavage is performed by ammonia gas and DNA is not carried away after cleavage. In some embodiments, unit are provided as a mixture of reversible and irreversible linkers for attaching oligonucleotides. Oligonucleotides may be synthesized on such linkers. For example, a unit having 1:1 mix of reversible and irreversible linkers for attaching oligonucleotides would allow 50% of such synthesized oligonucleotides to be cleaved. A unit would act as an oligonucleotide-holding unit with respect to the uncleaved oligonucleotides and as an oligonucleotide-transferring unit with respect to oligonucleotides cleaved through this process. Any suitable ratio of reversible and irreversible linkers for attaching oligonucleotides may be used. In some embodiments, two different types of units are used: units with reversible linkers and units with irreversible linkers that are not susceptible to a subsequent cleavage reaction. In some embodiments, a cleavable linker is introduced to oligonucleotides associated with some units through a cleavable nucleic acid sequence, such as a restriction enzyme site.

One or more oligonucleotide holding units may be combined with one or more oligonucleotide transferring units or oligonucleotides retrieved from one or more oligonucleotide transferring units. Such units and/or oligonucleotides may be isolated in a reaction chamber or channel within the microfluidic devices described herein.

Oligonucleotides may be released, e.g. by cleaving, from oligonucleotide transferring units. Combined oligonucleotides may cover all or a portion of a gene. Nucleic acid assembly may be performed according to a method described herein or any suitable method known in the art, resulting in an assembled nucleic acid on one or more oligonucleotide holding unit. Upon oligonucleotide hybridization and/or assembly, free oligonucleotides may be washed. Reagents may be exchanged. A polymerase or ligase may be added to fill in remaining nucleotides and/or to ligate oligonucleotides according to methods described herein or any suitable method known in the art.

In some embodiments, assembled nucleic acids hay undergo an error correction using MutS as described in further detail elsewhere herein, related methods or any suitable error correction method known in the art. Exonuclease VIII or a similar nuclease may be used to cleave assembled nucleic acids, e.g. DNA with apurininc or apyrimidinic sites. In some embodiments, exchange or wash of cleaved error products and/or reagent exchange is accomplished by flowing appropriate liquids and reagents in and out of reaction chambers or channels. Attachment of the assembled nucleic acid to an oligonucleotide holding unit may allow retention of error corrected assembled nucleic acids.

Amplification, e.g. PCR amplification of assembled target nucleic acids may be performed using primer sites corresponding to the start and end of the assembled target nucleic acid. The design of the assembled target nucleic acid and primers may be performed such that only full length assembled sequences will exponentially amplify, e.g. by having priming sites capping the target sequence to be assembled. Amplification reactions may be accomplished inside a reaction chamber or channel of a microfluidic device. The amplification products may not be attached to a unit.

In some embodiments, the assembled nucleic acid is cleaved from the oligonucleotide holding unit. In some embodiments, cleavage of the assembled nucleic acids from the oligonucleotide holding unit is performed by a mechanism distinct from the cleavage mechanism for releasing oligonucleotides from the oligonucleotide transferring units. Released assembled nucleic acids may be flowed to a separate location, such as a different reaction chamber or channel or a vessel outside of the microfluidic device. Amplification, e.g. PCR may be performed at such second location. In some embodiments, the assembled nucleic acids remain associated with the units. Assembled nucleic acids may be replicated by single strand extension using a polymerase and a single primer. The extension product may be flowed to a different location, e.g. a different reaction chamber or channel or a vessel outside of the microfluidic device. Other amplification reactions, e.g. PCR may be performed at such different location, amplifying the full length assembled nucleic acid.

In some embodiments, nucleic acid assembly comprises combining, combining about or combining at least 1, 2, 3, 4, 5, 6, 7, 8, 9, 10 or more oligonucleotide holding units with one or more oligonucleotide transferring units in a single location. In some embodiments, nucleic acid assembly comprises combining, combining about or combining at least 1, 2, 3, 4, 5, 6, 7, 8, 9, 10, 11, 12, 13, 14, 15, 16, 17, 18, 19, 20, 25, 30, 35, 40, 45, 50, 55, 60, 70, 80, 90, 100 or more oligonucleotide transferring units with one or more oligonucleotide holding units in a single location. The nucleic acid assembly may combine a number of oligonucleotide holding units and/or oligonucleotide transferring units falling in a range bounded by any of the foregoing values, e.g.

1-45, 2-18 etc. In some embodiments, more than one target nucleic acid is assembled in a single location, such as reaction chamber or channel.

In some embodiments, larger nucleic acids are assembled by iteratively combining and assembling assembly products of previous assembly reactions. Cleavage from units may be controlled such that unit associated nucleic acids are cleaved during the correct iteration of nucleic acid assembly. Rounds of assembly reactions may be performed iteratively within microfluidic devices described herein. In some embodiments, a plurality of assembly reactions are performed in parallel within the microfluidic devices described herein. In some embodiments, the number of parallel assembly reactions performed in a microfluidic device is, is about, or is at least 2, 3, 4, 5, 6, 7, 8, 9, 10, 11, 12, 13, 14, 15, 16, 17, 18, 19, 20, 30, 40, 50 or more. The number of parallel assembly reactions performed in parallel in a microfluidic device may fall within any range bounded by the foregoing values, such as 2-8, 4-20 etc. All or a subset of such parallel assembly reactions may each result in a distinct assembly product. Assembly products of the parallel assembly reactions may be routed according to the methods described herein and/or combined within the microfluidic devices described herein. In various embodiments, unpaired nucleotides during nucleic acid assembly are filled, e.g. using a polymerase, and/or ligated.

Enzymatic Cleavage of Nucleic Acids

Cleavage of oligos from units, e.g. beads, e.g. after synthesis steps, may be achieved by enzymatic approaches. A specific nucleotide sequence may be included in the oligonucleotide comprising a target oligonucleotide sequence, e.g. proximal to the unit. Such a nucleotide sequence may enable cleavage of the target sequence without a scar, i.e. inclusion or deletion of undesired bases or sequences to or from the cleaved target oligonucleotide.

In one example, a leader nucleotide sequence, e.g. a 10-nucleotide leader nucleotide sequence, is positioned directly adjacent to a target oligonucleotide sequence, e.g. a target oligonucleotide sequence synthesized in the 3' to 5' direction, and proximal to an associated unit. Position 10 of the leader nucleotide sequence may be placed immediately adjacent to the first nucleotide of the target oligonucleotide sequence. Positions leading to the final leader nucleotide sequence, e.g. positions 7-10, may contain a recognition sequence for a restriction endonuclease, such as the restriction endonuclease Mbo I, in reverse orientation such that the end position of the leader nucleotide sequence, e.g. position 10 of a 10-nucleotide leader nucleotide sequence, is the 5' end of the recognition sequence for the restriction endonuclease, e.g. the 5' guanine of the four base Mbo I recognition sequence (5'-GATC-3'). A hybridization oligonucleotide may be flowed into the chamber or channel holding the associated unit and allowed to hybridize to nucleic acids associated to such unit, forming a duplex, with the leader nucleotide sequence, e.g. upon completion of nucleic acid synthesis steps for the synthesis of the unit associated nucleic acids. Once formed, the duplex may be incubated with the restriction endonuclease, e.g. Mbo I and, optionally, any appropriate buffer (e.g. CutSmart® Buffer, New England Biolabs) to allow for efficient cleavage at the recognition site. The orientation of the recognition site may be arranged such that upon cleavage, the target oligonucleotide is released without a scar. For example, due to the orientation of the Mbo I recognition sequence described above, the target oligonucleotide may be cleaved 5' of the leader nucleotide sequence, for example 5' of the Mbo I recognition sequence. Cleavage of a target oligonucleotide 5' of the leader nucleotide sequence may release the target oligonucleotide from an associated unit without a scar.

The leader nucleotide sequence may be longer or shorter than 10 nucleotides. Any typical restriction endonuclease may be used to cleave oligonucleotides from units. In various embodiments, endonucleases that cleave 5' of their recognition sequence are used such that the cleaved target sequences contains no scar. The hybridization oligonucleotide may be selected to be long enough to form a sufficiently stable duplex at the restriction endonuclease of the restriction endonuclease. In some embodiments, longer hybridization oligonucleotides are selected to allow for greater specificity of binding. For oligonucleotides synthesized in the 3'-5' direction, a reversed orientation may be used for leader nucleotide sequences, recognition sites and hybridization oligonucleotides to allow for cleavage of the target oligonucleotide 3' to the leader nucleotide sequence.

The hybridization oligonucleotide may have an end, such as a 3' end, that extends beyond the recognition site toward or overlapping with the target oligonucleotide sequence, e.g. to improve efficiency of cleavage. If necessary, mixtures of hybridization oligonucleotides may be used such that at least one of the hybridization oligonucleotides is perfectly or sufficiently complementary to the leader nucleotide sequence on the unit to allow for cleavage of the target oligonucleotide.

A mixture of hybridization oligonucleotides may be used. In some embodiments, one or more target oligonucleotides are cleaved by hybridization to a first hybridization oligonucleotide, while one or more other target oligonucleotides are cleaved by hybridization to a second hybridization oligonucleotide. In some embodiments target oligonucleotides cleavable by hybridization to separate hybridization oligonucleotides are associated with separate units.

A leader nucleotide sequence may be attached to a unit, e.g. a bead prior to the synthesis of a target oligonucleotide. The leader nucleotide sequence may be synthesized during initial rounds of nucleic acid synthesis on a unit prior to incorporation of a target oligonucleotide sequence.

Enzymatic Nucleic Acid Synthesis

In various embodiments, de novo nucleic acid synthesis is achieved using enzymes in a template dependent or template independent manner. In some cases, nucleic acid synthesis is achieved using transferase enzymes that allow the enzymatically mediated synthesis of de novo polynucleotides. A variety of transferase enzymes may be used, including but not limited to, terminal deoxynucleotidyl transferase (TdT), a thermostable DNA polymerase such as DNA polymerase theta, poly(A) polymerase, Therminator, and variants thereof (See, e.g., WO2015159023, US 20160046974, and US 20180274001, each of which is incorporated by reference in its entirety). In some cases, the transferase enzyme is a modified transferase enzyme having improved efficiency of catalysis and/or optimized enzymatic function for use in generating long oligonucleotide chains. For example, the transferase may have modified characteristics such as improved binding affinity for nucleotides, e.g. modified nucleotides for use in enzymatic synthesis. The transferase enzyme may have modified characteristics allowing it to accept a nucleotide with a blocking moiety at the 3' position (See, e.g., US 20160108382 and WO2017216472, both of which are herein incorporated by reference in their entireties).

The transferase enzyme may catalyze the formation of a covalent bond between naturally occurring or modified nucleotides (e.g., nucleotides that comprise the nucleic acid bases adenine (A), cytosine (C), guanine (G), thymine (T), and uracil (U)); non-natural nucleotides (e.g., nucleotides that comprise bases such as 3-nitropyrrole 2'-deoxynucloside and 5-nitroindole 2'-deoxynucleoside, alpha phosphorothiolate, and phosphorothioate nucleotide triphosphates); nucleotide analogs (e.g., a nucleotide triphosphate such as deoxynucleotide triphosphate (dNTP) or ribonucleotide triphosphate (rNTP) attached to an inhibitor via a cleavable linker); or nucleotides conjugated to a transferase enzyme such as TdT (See, e.g., Palluk et al., *Nature Biotechnology*, vol. 7, (2018) p. 645-650 and Jensen and Davis, *Biochemistry*, vol. 57, (2018) p. 1821-32, both of which are incorporated herein by reference in their entireties).

One or more reagents for enzymatic nucleic acid synthesis may be delivered to the units described herein in the microfluidic devices described herein. Reagents for enzymatic nucleic acids may comprise one or more of nucleotide analogs with at least one attached removable binding moiety (e.g., 3'-aminoalkoxy-N4-acyl-dCTP, 3'-aminoalkoxy-N4-acyl-rCTP, 3'-aminoalkoxy-N2-acyl-dGTP, or 3'-aminoalkoxy-N2-acyl-rGTP), TdT, thermostable DNA Polymerase theta, magnesium (Mg$^{2+}$), sodium nitrite, anhydrous DMF, phosphoryl chloride, tris(2-carboxyethyl) phosphine (TCEP), dithiothreitol (DTT), potassium hydroxide (KOH) solution, Tris-HCl, ammonium hydroxide (NH$_4$OH) solution, alkaline phosphatase, a steric inhibitor such as a polymer or peptoid, a restriction nuclease, an initiator nucleic acid, and any other suitable reagent known in the art. Reagents for enzymatic nucleic acid synthesis are available from various commercial sources, including Glen Research (Sterling, VA), ThermoFisher Scientific (Pittsburgh, PA) and others. The specific reagents used may vary depending on the method of enzymatic nucleic acid synthesis (e.g., DNA or RNA synthesis).

Enzymatic nucleic acid synthesis chemistry may be performed in the microfluidic devices described herein by performing one or more of: 1) providing a plurality of functionalized units comprising an initiator nucleic acid; 2) performing a coupling reaction by catalyzing the formation of a covalent bond between the terminal nucleotide of a nascent oligonucleotide and a new nucleotide or nucleotide analog in the presence of a nucleotidyl transferase enzyme; 3) performing a deblocking reaction to remove the blocking moiety of the newly incorporated nucleotide or nucleotide analog; and 4) washing the unit-bound oligonucleotide. Steps 2-4 can be repeated successively to produce high-quality oligonucleotides on units. Additional washing, modification, and/or cleaving steps may be included. In various embodiments, units described herein are subjected to one or more steps of nucleic acid synthesis in the microfluidic devices described herein. For example, one or more units in a reaction chamber may be contacted with reagents and solutions through one or more reagent channels that connect to the reaction chamber. In various embodiments, units described herein may be associated with nascent oligonucleotides being elongated through enzymatic addition of nucleotides. Units may be routed through the microfluidic devices described herein between individual steps of a single nucleotide addition and/or between successive additions of nucleotides. Oligonucleotides and or units associated with oligonucleotides having an undesired nucleotide incorporation may be capped, error corrected, and/or sorted out of a population.

In some embodiments, nucleotide analogs suitable for enzymatic nucleic acid synthesis are delivered on unit(s) in the devices described herein. In some cases, an initiator nucleic acid is associated with some or all of the unit(s) in a microfluidic device. Nucleotide analogs having blocking moieties may be flowed into a branch channel or reaction chamber holding the units. A nucleotidyl transferase may be combined with a nucleotide analog having a blocking moiety in an aqueous solution in the branch channel or reaction chamber. The nucleotidyl transferase may catalyze the formation of a covalent bond between the nucleotide analog and the free 3'-OH group of the terminal nucleotide on the initiator and/or nascent nucleic acid. The presence of a blocking moiety on the nucleotide analog may prevent strand elongation by blocking the transferase from attaching additional nucleotides or nucleotide analogs. Subsequent removal of the blocking moiety by a deblocking reaction may allow conversion of the analog to a naturally-occurring nucleotide or a to structure resembling a naturally-occurring nucleotide and/or permit strand elongation by the addition of another nucleotide analog to the nascent strand. Successive rounds of enzymatic nucleic acid elongation performed in the devices described herein may result in efficient synthesis of long oligonucleotides. Oligonucleotides synthesized associated with units described herein by enzymatic synthesis methods alone or in combination with other methods may be, be about or be at least 5, 6, 7, 8, 9, 10, 11, 12, 13, 14, 15, 16, 17, 18, 19, 20, 25, 30, 35, 40, 50, 60, 70, 80, 90, 100, 200, 300, 400, 500, 600, 700, 800, 900, 1000, 1250, 1500, 2000, 3000, 4000, 5000 bases long or longer. In some embodiments, synthesis methods, such as enzymatic nucleic acid synthesis are combined with gene assembly methods described herein or any suitable gene assembly method known in the art, to synthesize desired polynucleotides described herein. In some embodiments, synthesis methods are combined with error correction methods. Such synthesized polynucleotides may have low error rates described elsewhere herein in further detail. In some embodiments, the synthesized oligonucleotide are cleaved from the unit(s), for example by a chemical or enzymatic method or by any suitable method known in the art. In some cases, an enzyme may be used to digest a portion of an oligonucleotide associated with a unit, such as the initiator nucleic acid.

The nucleotide analog may be attached to a removable blocking moiety that blocks attachment of additional nucleotides or nucleotide analogs to the nascent oligonucleotide on the unit. The nucleotide analog may have an unmodified 3' hydroxyl and/or may be attached to a removable blocking moiety via one or more of the carbon atoms at the 2', 3', and 4' positions of the ribose ring or to the nucleobase. In some embodiments, the removable blocking moiety is attached via the 3' position in the ribose ring of the nucleotide analog. The removable blocking moiety may be a substituent at the 3' position of the ribose ring that prevents formation of a phosphodiester bond at the 3' position. The removable blocking moiety may be a substituent at the 2' and/or 4' positions of the ribose ring that sterically interferes with formation of a phosphodiester bond at the 3' position. The removable blocking moiety may be an aminooxy derivative such as a 3'-aminoalkoxy group or a 3'-O-azidomethyl group. Examples of blocking moieties at the 3' position of the ribose ring include, but are not limited to, the 3'-O-allyl, 3'-O-azidomethyl (3'-OCH$_2$N$_3$), 3'-aminoalkoxyl (3'-ONH$_2$), and 3'-OCH$_2$CN blocking groups.

Alternatively, the nucleotide analog may be attached to a removable blocking moiety via the pyridine or pyrimidine of the base of the nucleotide analog. For example, the removable blocking moiety may be attached via N4 of cytosine, N3 of thymine, O4 of thymine, N2 of guanine, N3 of guanine, N6 of adenine, N3 of uracil, or O4 of uracil. The nucleotide analogs may be 3'-aminoalkoxy dNTPs or 3'-aminoalkoxy rNTPs. For example, the nucleotide analogs may be 3'-aminoalkoxy-N4-acyl-dCTP, 3'-aminoalkoxy-N4-acyl-rCTP, 3'-aminoalkoxy-N2-acyl-dGTP, or 3'-amino-alkoxy-N2-acyl-rGTP. The nucleotide analog may be linked to a blocking moiety at the base of the nucleotide analog by a cleavable linker. The blocking moiety may prevent strand elongation by sterically interfering with the enzyme used for nucleic acid synthesis (e.g., DNA polymerase, TdT, or other nucleotidyl transferase) and/or physically block the addition of a nucleotide or nucleotide analog onto the oligonucle-otide. Blocking moieties that sterically interfere with the transferase enzyme may include but are limited to polymers, nanoparticles, poly-N-substituted glycines (peptoids), and proteins. In some cases, a blocking moiety may sterically inhibit access to the active site of the transferase.

Nucleotide analogs may be linked to any blocking moiety that prevents the coupling of subsequent nucleotides or nucleotide analogs to the nascent oligonucleotide by the transferase enzyme. The blocking moiety may comprise a charged group such as a charged amino acid, or may comprise a group that can become charged under certain conditions. The blocking moiety may comprise a peptide or pseudopeptide comprising amino acids or amino acid ana-logs. In some embodiments, the blocking moiety comprises a group that reacts with residues at or near the active site of the transferase, and may thus inhibit coupling of nucleotides or nucleotide analogs by the transferase.

A suitable method of removing the blocking moiety may be selected according to the type of moiety and/or the bonds by which it is attached to the nucleotide analog. In various embodiments, for example where the blocking moiety is attached to the nucleotide at the 3' carbon of the ribose ring, the blocking moiety may be removed by addition of a reagent, including, but not limited to sodium nitrite, tris (2-carboxyethyl) phosphine (TCEP), potassium hydroxide (KOH), hydrochloric acid (HCl), dithiothreitol (DTT), and/or mercaptoethanol. In some embodiments, the blocking moiety, for example a blocking moiety attached at the 3' carbon, is removed by use of a palladium catalyst at elevated temperature, UV radiation, alkaline phosphatase, enzymatic or chemical deacetylation, and/or enzymatic glycositic cleavage.

Suitable methods for removal of blocking moieties, for example a blocking moiety that is attached via a base of the nucleotide analog, may be selected according to the type of attachment. In some embodiments, embodiments, for example where the blocking moiety is attached by a cleav-able linker, removal may occur by chemical, electrochemi-cal, enzymatic, or photolytic cleavage of the linker. In some cases, the blocking moiety may be removed by adjusting the pH of the solution surrounding the nucleotide analog, adjust-ing the temperature of the solution surrounding the nucleo-tide analog, for example to activate a proteolytic enzyme, or reducing disulfide bonds by addition of a reducing agent. In some cases, the blocking moiety may be attached via a photocleavable linker. Blocking moieties attached via a photocleavable linker may be removed by exposing the nucleotide analog to a specific wavelength of light. The blocking moiety may also be attached via a linker that is susceptible to nucleophilic or electrophilic cleavage.

In other embodiments, nucleotide analogs tethered to a transferase molecule are flowed into the branch channel or reaction chamber. A transferase incorporates its tethered nucleotide into an initiator nucleic acid attached to a unit in the device. The transferase molecule covalently attached to the 3' end of a ribose may prevent strand elongation by blocking the transferase from attaching additional nucleo-tides or nucleotide-enzyme conjugates. The linker attaching the nucleotide and the enzyme molecule may be subse-quently cleaved, exposing the 3' end of the oligonucleotide on the unit and thus allowing for incorporation of another nucleotide or nucleotide analog and/or subsequent elonga-tion of the oligonucleotide.

Removal of a nucleotide-tethered transferase molecule by cleaving the linker or removal of a blocking moiety from an oligonucleotide incorporated nucleotide may result in addi-tional atoms on each nucleotide that may differ from the desired nucleotides ("scarred bases"). Such "scars" may prevent the nucleotides from being structurally identical to naturally-occurring nucleotides. Nucleic acids comprising scarred bases can serve as templates for directed synthesis of complementary nucleic acids, for example using a template-dependent polymerase, such as Taq polymerase.

In some embodiments a synthesized nucleic acid sequence may be prepared for cleaving from a unit by addition of a uracil nucleobase in the first position or near the start of the sequence being synthesized. Upon comple-tion of synthesis, the generated sequence may be cleaved from the unit by addition of UDG, Endonuclease VIII, a short oligo complementary to the position where the uracil was incorporated, and buffers well known in the art. UDG will cleave the uracil base and then endonuclease VIII will subsequently cleave the backbone at the abasic site, thus cleaving the target. The uracil may be incorporated at the first position of a synthesized sequence or at any position proximal to the unit. The number of nucleotides or nucleo-tide analogs between the uracil and the unit may be any number of nucleotides or nucleotide analogs, preferably 5 to 20 nucleotides or nucleotide analogs to allow UDG and Endonuclease VIII sufficient physical access to the position of the uracil base.

In some embodiments UDG and Endonuclease VIII may be added in combination. In some embodiments UDG and Endonuclease VIII may be added separately.

In some embodiments the synthesized nucleic acid sequence may be cleaved from the unit by incorporation of a restriction enzyme site into the first part of the synthesized sequence. Upon completion of synthesis the synthesized sequence may be cleaved from the unit by addition of (1) a short oligo complementary to the position where the restric-tion site is incorporated, (2) a restriction enzyme that targets the double stranded sequence formed by the oligo and the synthesized DNA, and (3) buffers well known in the art.

In some embodiments, the synthesized nucleic acid sequences can be programmed to be cleaved from their attached units. In some embodiments the synthesized nucleic acid sequences may not be programmed to be cleaved from their attached units.

In some embodiments, one or more reagents selected from reagents described herein for enzymatic nucleic acid synthesis, e.g. a terminal transferase, and any other suitable reagent known in the art for enzymatic nucleic synthesis is provided in a microfluidic channel. In some embodiments, such microfluidic channel holds one or more units described in further detail herein. In some embodiments, such units are functionalized to allow synthesis of a nucleic acid in situ on such units. In some embodiments, the units are arranged in such microfluidic channel as column restricting exchange of the order of the units. In some embodiments, the reagents comprise a terminal transferase and/or a nucleotide. In some embodiments, a building block of an oligomer, such as a nucleotide monomer, dimer, trimer, or multimer, is incorpo-rated to a functional group on the unit and/or an oligonucle-otide attached to the unit.

Peptide Synthesis

In one embodiment, the synthesis of individual peptides or a large library of peptides is achieved according to the methods and compositions described herein. A set of units may begin in a primary channel and may be directed according to a preassigned program to one of a plurality of branch channels, e.g. 20 branch channels. Direction into these channels may be achieved by a multiway distributor, by two sequential bifurcations and corresponding two-way distributors, or by any other suitable method known in the art. Reagents, such as various carbodiimides may be delivered to the channels. The units may be combined maintaining their positional encoding and reassigned and delivered into one of a plurality of branch channels. Accordingly, amino acids may be added in iterative steps to a nascent chain on each unit.

In various embodiments, the peptides synthesized by the methods and compositions described herein comprise 5 to 10,000 amino acids, preferably 5 to 1,000 amino acids. The peptides synthesized according to the methods described herein may comprise, comprise about or comprise at least 2, 3, 4, 5, 6, 7, 8, 9, 10, 11, 12, 13, 14, 15, 16, 17, 18, 19, 20, 25, 30, 40, 50, 60, 70, 80, 90, 100, 200, 300, 400, 500, 600, 700, 800, 900, 1000 amino acids or more. The peptides synthesized according to the methods described herein may comprise a number of amino acids falling within the range bounded by any of the foregoing values, such as 2-900, 90-10,000, etc.

The amino acids forming the peptides synthesized by the methods and compositions described herein comprise 5 to 10,000 amino acids, preferably 5 to 1,000 amino acids. The peptides synthesized according to the methods described herein may comprise, comprise about or comprise at least 2, 3, 4, 5, 6, 7, 8, 9, 10, 11, 12, 13, 14, 15, 16, 17, 18, 19, 20, 25, 30, 40, 50, 60, 70, 80, 90, 100, 200, 300, 400, 500, 600, 700, 800, 900, 1000 amino acids or more. The peptides synthesized according to the methods described herein may comprise a number of amino acids falling within the range bounded by any of the foregoing values, such as 2-900, 90-10,000, etc.

The amino acids forming all or part of a peptide may comprise any of the twenty conventional, naturally occurring amino acids (e.g., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y)). Any of the amino acids in the peptides synthesized by the methods and compositions described herein may be replaced by a non-conventional amino acid. The term "non-conventional amino acid" refers to amino acids other than conventional amino acids, and include, for example, isomers and modifications of the conventional amino acids (e.g., D-amino acids), non-protein amino acids, post-translationally modified amino acids, enzymatically modified amino acids, constructs or structures designed to mimic amino acids (e.g., α,α-disubstituted amino acids, N-alkyl amino acids, lactic acid, β-alanine, naphthylalanine, 3-pyridylalanine, 4-hydroxyproline, O-phosphoserine, N-acetylserine, N-formylmethionine, 3-methylhistidine, 5-hydroxylysine, and norleucine), and peptides having the naturally occurring amide —CONH— linkage replaced at one or more sites within the peptide backbone with a non-conventional linkage such as N-substituted amide, ester, thioamide, retropeptide (—NHCO—), retrothioamide (—NHCS—), sulfonamide (—SO$_2$NH—), and/or peptoid (N-substituted glycine) linkages. Accordingly, the peptides synthesized by the methods and compositions described herein include pseudopeptides and peptidomimetics.

In various embodiments, peptide synthesis is performed in or on the units described herein within the microfluidic devices described herein. In some cases, peptide synthesis is achieved using solid-phase peptide synthesis. Peptide synthesis methods used according to various embodiments may comprise microwave-assisted peptide synthesis and methods that utilize a photolabile linker and UV irradiation for peptide synthesis (See, e.g., Qvortrup et al., *Organic Letters* 2014, 16:4782-85. One or more reagents for peptide synthesis may be delivered to the units described herein in the microfluidic devices described herein. Reagents for peptide synthesis may comprise one or more of carbodiimides such as dicyclohexylcarbodiimide (DCC), diisopropylcarbodiimide (DIC); triazoles such as 1-hydroxybenzotriazole (HOBt), 1-hydroxy-7-aza-benzotriazole (HOAt); ethyl cyanohydroxyiminoacetate (oxyma); Hexafluorophosphate Azabenzotriazole Tetramethyl Uronium (HATU); Hexafluorophosphate Benzotriazole Tetramethyl Uronium (HBTU), 2-(1H-Benzotriazole-1-yl)-1,1,3,3-tetramethylaminium tetrafluoroborate (TBTU); 2-(6-Chloro-1H-benzotriazole-1-yl)-1,1,3,3-tetramethylaminium hexafluorophosphate (HCTU); benzotriazol-1-yl-oxytripyrrolidinophosphonium hexafluorophosphate (PyBOP); (7-Azabenzotriazol-1-yloxy)tripyrrolidinophosphonium hexafluorophosphate (PyAOP); tert-butyloxycarbonyl (Boc), fluorenylmethyloxycarbonyl (Fmoc), or benzyl (Bzl) protected amino acids; anhydrous hydrogen fluoride; piperidine in dimethylformamide (DMF); dichloromethane (DCM); trifluoroacetic acid (TFA); triisopropylsilane (TIPS); hydrogen bromide (HBr); trifluoromethane sulfonic acid (TFMSA); phenol; water; insoluble porous resin; and any other suitable reagent known in the art. Reagents for peptide synthesis are available for purchase from numerous commercial sources, including Sigma-Aldrich (St. Louis, MO) and others. The specific reagents used may vary depending on the method of peptide synthesis.

In some embodiments amino acids with suitable modifications for solid-phase peptide synthesis are delivered to a functionalized unit(s) in the devices described herein. The amino acids may be single amino acids, dipeptides, or longer peptides. Solid-phase peptide synthesis may be performed in the microfluidic devices described herein by performing one or more of: 1) coupling; 2) washing; 3) capping; 4) deprotecting; and 5) cleaving. Successive rounds of peptide synthesis chemistry performed in the devices described herein may result in step-wise synthesis of high-quality polymers associated with units. In various embodiments, units described herein are subjected to one or more steps of peptide synthesis in the microfluidic devices described herein. For example, one or more units in a reaction chamber may be contacted with reagents and solutions through one or more reagent channels that connect to the reaction chamber.

In some embodiments the unit(s) are functionalized by the addition of one or more reactive groups to the unit. The reactive groups may comprise, for example, one or more of an amine, hydroxyl, chloromethyl, aminomethyl, and benzhydrylamino.

Materials.

Materials used to manufacture the microfluidic device may be chosen from any suitable material known in the art, including but not limited to glass; silicon; silicon dioxide; off-stoichiometric thiol-ene (OSTE); thermoset polymers such as polydimethylsiloxane (PDMS) and perfluoropolyether (PEPE); and thermoplastic polymers such as polymethylmethacrylate (PMMA), polycarbonate (PC), cyclic olefin (co)polymers, polytetrafluoroethylene (PTFE), polyamide, and polystyrene (PS).

The microfluidic device may be manufactured by any method described herein or any suitable method otherwise known in the art. Manufacturing process may include lithography or photolitgography; 3-D printing; etching techniques such as wet chemical, dry, and photoresists removal; microelectromechanical systems (MEMS) manufacturing techniques including microfluidics/lab-on-a-chip, optical MEMS (also called MOEMS), RF MEMS, PowerMEMS, and BioMEMS techniques and deep reactive ion etching (DRIE); nanoelectromechanical (NEMS) techniques; thermal oxidation of silicon; electroplating and electroless plating; diffusion processes such as boron, phosphorus, arsenic, and antimony diffusion; ion implantation; film deposition such as evaporation (filament, electron beam, flash, and shadowing and step coverage), sputtering, chemical vapor deposition (CVD), epitaxy (vapor phase, liquid phase, and molecular beam), electroplating, screen printing, and lamination. Glass or silicon devices can be wet or dry etched, and bonded via direct bonding (e.g. plasma activate or fusion), anoding bonding, or adhesive bonding.

The microfluidic device may be manufactured from optically transparent materials or a combination of optically transparent and opaque materials, such that the units within the channel(s) may still be detected and tracked.

In various embodiments, optical procedures are applied in or on the fluidic channel(s). The characteristics of the channel or units may be selected to enhance the effectiveness of optical modification procedures. For example, the channel(s) or one or more side of the channel(s) may utilize a transparent material, such as optically clear glass.

Modification procedures may comprise mechanical operations. For example, one or more units may be physically manipulated by an integrated or external mechanism.

In various embodiments, modification procedures comprise one or more of chemical, optical and mechanical procedures.

Multi-Component Units

In various embodiments, units described herein are attached to molecules or molecular groups with one or more components. Such components may be of the same kind (e.g. polynucleotide) or may have different types (e.g. polynucleotides and polypeptides). In some embodiments, each component of a molecular group is attached to a unit individually. In some embodiments, one or more of the components of a molecular group is attached to a unit, whereas one or more of the components are attached to the unit indirectly, through other components. Components of a molecular group may be linked to each other through a linker. Linkers linking components of a molecular group may be universal, allowing for the linking of any building block. In some embodiments, linkers may be designed to permit linking of desired pairs or groups of components. For example, linkers linking components of a molecular group may comprise complementary nucleic acid sequences attached to or associated with such components or affinity binding pairs, e.g. streptavidin-biotin. In some embodiments, components of a molecular group are assembled by linking the unit attached to or associated with some or all of the components of a molecular group.

In various embodiments, a plurality of independent molecules or molecular groups or a plurality of attached or associated molecular group components are synthesized attached to or associated with a single unit. Such combinations of molecules, molecular groups and/or molecular group components may be achieved in a predetermined fashion or randomly. Component-specific barcodes may be associated with each component. Molecular group-specific barcodes may be associated with each molecular group. Components described herein may comprise any small or macro-molecule, e.g. small molecules such as small organic molecules, nucleic acids such as any DNA or RNA, and/or polypeptides such as antibodies. In various embodiments, polypeptides associated with units are synthesized by in situ methods, such as nucleic acid programmable protein array (NAPPA; see e.g. Ramachandran, N., E. Hainsworth, et al. (2004). "Self-assembling protein microarrays." Science 305 (5680): 86-9), Protein in situ array (PISA; see e.g. He, M. and MI J. Taussig (2001). "Single step generation of protein arrays from DNA by cell-free expression and in situ immobilisation (PISA method)." Nucleic Acids Res 29(15): E73-3), in situ puromycin capture (see e.g. Tao, S. C. and H. Zhu (2006). "Protein chip fabrication by capture of nascent poly peptides." Nat Biotechnol 24(10): 1253-4), in each case as suitably modified for application on units described herein, or any suitable cell-free polypeptide synthesis method known in the art. In some embodiments, polypeptide synthesis comprises a solid phase peptide synthesis method described herein or a suitable solid phase peptide synthesis method known in the art. In some embodiments, a nucleic acid sequence encoding a target protein and a barcode, such as a target- or unit-specific barcode, e.g. a peptide tag (or epitope), is synthesized associated with units described herein. Such nucleic acid may be used for the in situ synthesis of a protein fused to the barcode. In some embodiments, a nucleic acid-polypeptide hybrid is provided by attaching, e.g. via a covalent bond or affinity binding, a barcode, such as a target- or unit-specific, e.g. a nucleic acid, such as DNA, barcode to a polypeptide target, for example a polypeptide target synthesized according to the methods described herein. Polypeptide associated barcodes, such as target- or unit-specific barcodes, may be used to locate the polypeptide target to a desired location, e.g. on an array of oligonucleotides (or on a unit) comprising an oligonucleotide complementary or hybridizable to the barcode or a binding partner, e.g. and antibody, having an affinity for the barcode. In some embodiments, barcode linked nucleic acid targets are synthesized associated with units described herein. Nucleic acid associated barcodes may be used to locate the target nucleic acid to a desired location, such as on an array of oligonucleotides (or on a unit) comprising an oligonucleotide complementary or hybridizable to the barcode, e.g. upon release of such target nucleotides from units.

Methods

In various embodiments, microfluidic devices and systems described herein are configured as automated desk-top laboratory nucleic acid synthesizers.

In various embodiments, nucleic acids synthesized using the microfluidic devices described herein are used for diagnostic or therapeutic applications, for example, for genetic testing, such as pre-natal non-invasive diagnostics, diagnostic tests for cancer recurrence, for inherited diseases, therapeutic RNA, aptamers, antibodies, gene therapy, or gene editing. Such nucleic acids may also be used to produce exome capture kits, for example exome capture kits incorporating a pool of, of about or at least 500,000 distinct oligonucleotides or be deployed in PCR assays, gene synthesis, synthetic biology, directed evolution of enzymes or high-throughput screening applications.

The methods and compositions of the invention may be used for nucleic acid hybridization studies such as gene expression analysis, genotyping, single nucleotide polymorphism (SNP) genotyping, heteroduplex analysis, nucleic acid sequencing determinations based on hybridization, synthesis of DNA, RNA, peptides, proteins or other oligomeric or non-oligomeric molecules, combinatorial libraries for evaluation of candidate drugs.

DNA and RNA synthesized in accordance with the invention may be used in any application including, by way of example, probes for hybridization methods such as gene expression analysis, genotyping by hybridization (competitive hybridization and heteroduplex analysis), sequencing by hybridization, single strand extension, probes for Southern blot analysis (labeled primers), probes for array (either microarray or filter array) hybridization, "padlock" probes usable with energy transfer dyes to detect hybridization in genotyping or expression assays, and other types of probes. The DNA and RNA prepared in accordance with the invention may also be used in enzyme-based reactions such as polymerase chain reaction (PCR), as primers for PCR, templates for PCR, allele-specific PCR (genotyping/haplotyping) techniques, real-time PCR, quantitative PCR, reverse transcriptase PCR, and other PCR techniques. In various embodiments, one or more of the foregoing are performed in situ using nucleic acids associated with units described herein The DNA and RNA may be used for various ligation techniques, including ligation-based genotyping, oligo ligation assays (OLA), ligation-based amplification, ligation of adapter sequences for cloning experiments, Sanger dideoxy sequencing (primers, labeled primers), high throughput sequencing (using electrophoretic separation or other separation method), primer extensions, mini-sequencings, and single base extensions (SBE). The DNA and RNA produced in accordance with the invention may be used in mutagenesis studies, (introducing a mutation into a known sequence with an oligo), reverse transcription (making a cDNA copy of an RNA transcript), gene synthesis, introduction of restriction sites (a form of mutagenesis), protein-DNA binding studies, and like experiments. Various other uses of DNA and RNA produced by the subject methods will suggest themselves to those skilled in the art, and such uses are also considered to be within the scope of this disclosure.

Genotyping

In various embodiments, nucleic acids described herein, such as the nucleic acids synthesized insitu, associated with units described herein, may be used for genotyping applications, e.g. SNP genotyping. Genotyping methods may be performed on the device, e.g. using nucleic acids associated with units. Methods allowing for identification of units based on methods utilizing absolute or relative position of units may be combined with genotyping methods to link the identity or history of a unit to the results of a genotyping reaction. In some embodiments, genotyping is performed on nucleic acids detached from units, e.g. through a cleavage reaction. Nucleic acids used in genotyping methods described herein may be associated with barcodes, such as target- and/or unit-specific barcodes, e.g. nucleic acid barcodes. In some embodiments, nucleic acids used in genotyping methods described herein are incorporated in a separate genotyping device, such as an oligonucleotide array.

In some embodiments, genotyping comprises SNP genotyping via primer extension. A probe, e.g. a nucleic acid synthesized according to the methods described herein associated with units described herein, may be hybridized to a test nucleic acid with a SNP nucleotide. Probe sequences may be selected such that the 3' end of the probe would be located immediately upstream of the SNP location of the test nucleic acid upon hybridization. Nucleotide extension reaction may be carried out with a DNA polymerase to allow extension of the hybridized probe by adding a nucleotide complementary to the SNP nucleotide. The incorporated base may be detected and used to determine the SNP allele (See e.g. Pastinen, T. et al. A system for specific, high-throughput genotyping by allele-specific primer extension on microarrays. *Genome Res.* 10, 1031-1042 (2000); Syvänen, A. ACCESSING GENETIC VARIATION: GENOTYPING SINGLE NUCLEOTIDE POLYMORPHISMS LINKAGE. 2, 930-942 (2001)).

In some embodiment, genotyping comprises SNP genotyping via oligonucleotide ligation assay. The oligonucleotide ligation assay may be used to interrogate a SNP allele by hybridizing two probes directly over a test nucleotide, such as a known SNP polymorphic site, such that ligation is substantially limited to probes that are identical to the target DNA at the SNP location. For example; an allele-specific probe may be designed so that its 3' base is situated directly over the SNP nucleotide. The second probe may be designed such that it hybridizes to a test nucleic acid downstream from the allele-specific probe. A ligation reaction may be performed. Results of the ligation reaction may be used to identify presence of a SNP polymorphism at the test nucleotide. In some embodiments, oligonucleotide ligation assay-based genotyping is performed in microfluidic devices described herein, such as using probes synthesized in situ associated with units described herein. In some embodiments, one or more of the oligonucleotide ligation assay probes remain associated with a unit during the genotyping assay.

In some embodiment, genotyping comprises SNP genotyping via DNA mismatch binding proteins. Without being bound by theory, DNA mismatch-binding proteins can distinguish single nucleotide mismatches and thus facilitate differential analysis of SNPs. For example, MutS protein from *Thermus aquaticus* binds different single nucleotide mismatches with different affinities and can be used, for example in capillary electrophoresis to differentiate all six sets of mismatches (Drabovich & Krylov 2006).

In some embodiment, genotyping comprises SNP genotyping via a Surveyor nuclease assay. Without being bound by theory, Surveyor nuclease is part of a family of mismatch-specific endonucleases that were discovered in celery (CEL nucleases; pubs.acs.org/doi/abs/10.1021/bi992376z). Surveyor nuclease can be used to detect single-base mismatches or small insertions or deletions ("indels"). Surveyor nuclease may be used to recognize nucleotide substitutions and indels. The 3' site of such mismatched sites in both strands may be cleaved using the Surveyor nuclease with high specificity (See e.g. Qiu, Peter; Shandilya, Harini; D'Alessio, James M.; O'Connor, Kevin; Durocher, Jeffrey; Gerard, Gary F. (2004-04-01), "Mutation detection using Surveyor nuclease". *BioTechniques.* 36 (4): 702-707.)

In some embodiment, genotyping comprises SNP genotyping via the use of stem-loop probes, such as stem-loop probes attached to molecular beacons. Stem-loop probes may be designed with a first hybridization sequence attached to a fluorophore on one end, a second hybridization sequence attached to a fluorophore quencher on another end, and a probe sequence in the middle. The probe and the hybridization sequences may be designed such that availability of a test nucleic acid, such as a test nucleic acid with a desired SNP allele would lead to preferential hybridization of the test nucleic acid to the probe such that the first and second hybridization sequences denature. Denaturation of the hybridization sequences would permit the fluorophore and quencher to lose close proximity, allowing the fluorophore to fluoresce at its emission wavelength. In some embodiments, stem-loop probes are designed such that, even where the probe sequence encounters a test sequence with as little as one non-complementary nucleotide, the hybridization sequences would preferentially stay hybridized, preventing the fluorophore from fluorescing at its emission wavelength. (See e.g. Tyagi, S. & Kramer, F. R. Molecular beacon probes that fluoresce on hybridiztion. *Nat. Publ. Gr.* 14, 303-308 (1996); K., A. et al. Molecular beacons as diagnostic tools: Technology and applications. *Clin. Chem. Lab. Med.* 41, 468-474 (2003).)

In some embodiment, genotyping comprises SNP genotyping via, SNP microarrays. Probes generated associated with units described herein in the microfluidic devices described herein may be cleaved from the units. Cleaved probes may be positioned on a microarray chip. A plurality of SNPs may be tested simultaneously on the SNP microarrays using methods described herein or a suitable method known in the art. Probes may be positioned on the microarray via a target-specific unique barcode associated with the probe. The target-specific barcode may be hybridized to a specific location on the microarray. In some embodiments, SNP genotyping on such microarrays is performed using in the Affymetrix Human SNP GeneChips or Illumina Infinium arrays.

Nucleic Acid Amplification

In some embodiments, the nucleic acids described herein are amplified and/or used for amplification of other nucleic acids, e.g. as primers. Nucleic acids described herein may be amplified in situ associated with units described herein, for example through bridge PCR or variations thereof. In some embodiments, amplification products are released from units, e.g. under certain conditions, such as conditions allowing denaturation of double-stranded nucleic acids. Amplification can be performed by any means known in the art. In some cases, the nucleic acids are amplified by polymerase chain reaction (PCR). Various PCR methods are known in the art, as described in, for example, U.S. Pat. Nos. 5,928,907 and 6,015,674, the complete disclosures of which are hereby incorporated by reference for any purpose. Other methods of nucleic acid amplification include, for example, ligase chain reaction, oligonucleotide ligations assay, and hybridization assay. Other amplification methods that can be used herein include those described in U.S. Pat. Nos. 5,242,794; 5,494,810; 4,988,617; and 6,582,938, all of which are incorporated herein in their entirety.

In some aspects of the invention, exponential amplification of nucleic acids or polynucleotides is used. These methods often depend on the product catalyzed formation of multiple copies of a nucleic acid or polynucleotide molecule or its complement. The amplification products are sometimes referred to as "amplicons." One such method for the enzymatic amplification of specific double stranded sequences of DNA is polymerase chain reaction (PCR).

Other amplification techniques that can be used in the methods of the provided invention include, e.g., allele-specific PCR (see e.g., Saiki R K, Bugawan T L, Horn G T, Mullis K B, Erlich H A (1986). Analysis of enzymatically amplified beta-globin and HLA-DQ alpha DNA with allele-specific oligonucleotide probes Nature 324: 163-166), Alu PCR, assembly PCR (see e.g., Stemmer W P, Crameri A, Ha K D, Brennan T M, Heyneker H L (1995). Single-step assembly of a gene and entire plasmid from large numbers of oligodeoxyribonucleotides Gene 164: 49-53), asymmetric PCR (see e.g., Saiki R K supra), colony PCR, helicase dependent PCR (see e.g., Myriam Vincent, Yan Xu and Huimin Kong (2004). Helicase-dependent isothermal DNA amplification EMBO reports 5 (8): 795-800), hot start PCR, inverse PCR (see e.g., Ochman H, Gerber A S, Hartl D L. Genetics. 1988 November; 120(3):621-3), in situ PCR, intersequence-specific PCR or IS SR PCR, digital PCR, linear-after-the-exponential-PCR or Late PCR (see e.g., Pierce K E and Wangh L T (2007). Linear-after-the-exponential polymerase chain reaction and allied technologies Real-time detection strategies for rapid, reliable diagnosis from single cells Methods Mol. Med. 132: 65-85), long PCR, nested PCR, real-time PCR, duplex PCR, multiplex PCR, quantitative PCR, quantitative fluorescent PCR (QF-PCR), multiplex fluorescent PCR (MF-PCR), restriction fragment length polymorphism PCR (PCR-RFLP), PCK-RFLPIRT-PCR-IRFLP, polony PCR, in situ rolling circle amplification (RCA), bridge PCR, picotiter PCR and emulsion PCR, or single cell PCR. Other suitable amplification methods include, transcription amplification, self-sustained sequence replication, selective amplification of target polynucleotide sequences, consensus sequence primed polymerase chain reaction (CP-PCR), arbitrarily primed polymerase chain reaction (AP-PCR), and degenerate oligonucleotide-primed PCR (DOP-PCR). Another method for amplification involves amplification of a single stranded polynucleotide using a single oligonucleotide primer. The single stranded polynucleotide that is to be amplified contains two non-contiguous sequences that are substantially or completely complementary to one another and, thus, are capable of hybridizing together to form a stem-loop structure.

Another method for achieving the result of an amplification of nucleic acids is known as the ligase chain reaction (LCR). This method may use a ligase enzyme to join pairs of preformed nucleic acid probes. The probes can hybridize with each complementary strand of the nucleic acid, and ligase is employed to bind the pair of probes together resulting in two templates that can serve in the next cycle.

Another method for achieving nucleic acid amplification is the nucleic acid sequence based amplification (NASBA). This method may comprise a promoter-directed, enzymatic process that induces in vitro continuous, homogeneous and isothermal amplification of a specific nucleic acid to provide RNA copies of the nucleic acid. The reagents for conducting NASBA include a first DNA primer with a 5'-tail comprising a promoter, a second DNA primer, reverse transcriptase, RNase-H, T7 RNA polymerase, NTPs and dNTPs.

Another method for amplifying a specific group of nucleic acids is the Q-beta-replicase method, which relies on the ability of Q-beta-replicase to amplify its RNA substrate exponentially. The reagents for conducting such an amplification include "midi-variant RNA" (amplifiable hybridization probe), NTP's, and Q-beta-replicase.

Another method for amplifying nucleic acids is known as 3SR and is similar to NASBA except that the RNase-H activity is present in the reverse transcriptase. Amplification by 3SR is an RNA specific target method whereby RNA may be amplified in an isothermal process combining promoter directed RNA polymerase, reverse transcriptase and RNase H with target RNA. See for example Fahy et al. PCR Methods Appl. 1:25-33 (1991).

Another method for amplifying nucleic acids is the Transcription Mediated Amplification (TMA) used by Gen-Probe. The method is similar to NASBA in utilizing two enzymes in a self-sustained sequence replication. See U.S. Pat. No. 5,299,491, which is herein incorporated by reference in its entirety.

Another method for amplification of nucleic acids is Strand Displacement Amplification (SDA) (Westin et al 2000, Nature Biotechnology, 18, 199-202; Walker et al 1992, Nucleic Acids Research, 20, 7, 1691-1696), which is an isothermal amplification technique based upon the ability of a restriction endonuclease such as Hindi or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand.

Another method for amplification of nucleic acids is Rolling Circle Amplification (RCA) (Lizardi et al. 1998, Nature Genetics, 19:225-232). RCA can be used to amplify single stranded molecules in the form of circles of nucleic acids. In its simplest form, RCA may comprise the hybridization of a single primer to a circular nucleic acid. Extension of the primer by a DNA polymerase with strand displacement activity may yield the production of multiple copies of the circular nucleic acid concatenated into a single DNA strand.

In some embodiments of the invention, RCA is coupled with ligation. For example, a single oligonucleotide can be used both for ligation and as the circular template for RCA. This type of polynucleotide can be referred to as a "padlock probe", "Molecular Inversion Probe" (MIP), or a "RCA probe." For a such probes, both termini of the oligonucleotide contain sequences complementary to a domain within a nucleic acid sequence of interest. The first end of the padlock probe is substantially complementary to a first domain on the nucleic acid sequence of interest, and the second end of the probe is substantially complementary to a second domain, adjacent to the first domain near the first domain. Hybridization of the oligonucleotide to the target nucleic acid results in the formation of a hybridization complex. Ligation of the ends of the probe results in the formation of a modified hybridization complex containing a circular polynucleotide. In some cases, prior to ligation, a polymerase can fill in the gap by extending one end of the probe. The circular polynucleotide thus formed can serve as a template for RCA that, with the addition of a polymerase, results in the formation of an amplified product nucleic acid. A portion of the circular polynucleotide thus formed may be amplified, e.g. by PCR or PCR related techniques using binding sites within the probes. In some embodiments, the probes are first cleaved following an exonuclease step to digest uncircularized probes and then amplified, e.g. by PCR or PCR related techniques using binding sites within the probes. The methods of the invention described herein can produce probes with defined sequences on both the 5'- and 3'-ends. Such amplified products can be used as padlock, MIP, or RCA probes.

Some aspects of the invention utilize the linear amplification of nucleic acids or polynucleotides. Linear amplification generally refers to a method that involves the formation of one or more copies of the complement of only one strand of a nucleic acid or polynucleotide molecule, usually a nucleic acid or polynucleotide analyte.

In some embodiments, amplification may comprise solid-phase amplification, polony amplification, colony amplification, emulsion PCR, bead RCA, surface RCA, or surface SDA. In some embodiments, amplification methods that results in amplification of free DNA molecules in solution or tethered to a suitable matrix by only one end of the DNA molecule can be used. Methods that rely on bridge PCR, where both PCR primers are attached to a surface (see, e.g., WO 2000/018957, which is incorporated by reference in its entirety) can be used. In some cases, the methods of the invention can create a "polymerase colony technology," or "polony." referring to a multiplex amplification that maintains spatial clustering of identical amplicons. These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003).

In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, 3' end extension (e.g. adaptor fill-in), primer annealing, primer extension, and strand denaturation. Steps can be of any duration, including but not limited to about, less than, or more than 1, 5, 10, 15, 20, 25, 30, 35, 40, 45, 50, 55, 60, 70, 80, 90, 100, 120, 180, 240, 300, 360, 420, 480, 540, 600, or more seconds. Cycles of any number comprising different steps can be combined in any order. In some embodiments, different cycles comprising different steps are combined such that the total number of cycles in the combination is about, less than, or more than 5, 10, 15, 20, 25, 30, 35, 50, or more cycles. Amplification can be performed at any point during a multi reaction procedure using the methods and compositions of the invention.

In various embodiments, amplification reactions may be performed while a template polynucleotide is attached to a unit.

Ligation Reactions

In some embodiments, groups of oligonucleotides can be ligated or linked to each other, to adaptors. In various embodiments, an adaptor may comprise one or more barcodes as described in further detail elsewhere herein. The linking agent can be a ligase. In some embodiments the ligase is T4 DNA ligase, using well known procedures (Maniatis, T. in Molecular Cloning, Cold Spring Harbor Laboratory (1982)). Other DNA ligases may also be used. With regard to ligation, other ligases, such as those derived from thermophilic organisms may be used thus permitting ligation at higher temperatures allowing the use of longer oligonucleotides which could be annealed and ligated simultaneously under the higher temperatures normally permissible for annealing such oligonucleotides.

The terms "joining" and "ligation" as used herein, with respect to two polynucleotides, may refer to the covalent attachment of two separate polynucleotides to produce a single larger polynucleotide with a contiguous backbone. Methods for joining two polynucleotides are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adaptor oligonucleotide is joined to a target polynucleotide by a ligase, for example a DNA ligase or RNA ligase. Multiple ligases, each having characterized reaction conditions, are known in the art, and include, without limitation $NAD^+$-dependent ligases including tRNA ligase, Taq DNA ligase, Thermus filiformis DNA ligase, Escherichia coli DNA ligase, Tth DNA ligase, Thermus scotoductus DNA ligase (I and II), thermostable ligase, Ampligase thermostable DNA ligase, VanC-type ligase, 9°N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. Ligation can be between polynucleotides having hybridizable sequences, such as complementary overhangs. Ligation can also be between two blunt ends. In some embodiments, a 5' phosphate is utilized in a ligation reaction. The 5' phosphate can be provided by the target polynucleotide, the adaptor oligonucleotide, or both. 5' phosphates can be added to or removed from polynucleotides to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some embodiments, both of the two nucleic acid ends joined in a ligation reaction (e.g. an adaptor end and a target polynucleotide end) provide a 5' phosphate, such that two covalent linkages are made in joining the two ends. In some embodiments, only one of the two ends joined in a ligation reaction (e.g. only one of an adaptor end and a target polynucleotide end) provides a 5' phosphate, such that only one covalent linkage is made in joining the two ends. In some embodiments, only one strand at one or both ends of a target polynucleotide is joined to an adaptor oligonucleotide. In some embodiments, both strands at one or both ends of a target polynucleotide are joined to an adaptor oligonucleotide. In some embodiments, 3' phosphates are removed prior to ligation. In some embodiments, an adaptor oligonucleotide is added to both ends of a target polynucleotide, wherein one or both strands at each end are joined to one or more adaptor oligonucleotides. Joining may be followed by a cleavage reaction that leaves a 5' overhang that can serve as a template for the extension of the corresponding 3' end, which 3' end may or may not include one or more nucleotides derived from the adaptor oligonucleotide. In some embodiments, a target polynucleotide is joined to a first adaptor oligonucleotide on one end and a second adaptor oligonucleotide on the other end. In some embodiments, the target polynucleotide and the adaptor to which it is joined comprise blunt ends. In some embodiments, separate ligation reactions are carried out for each target polynucleotide, using a different first adaptor oligonucleotide comprising at least one barcode sequence for each target polynucleotide, such that no two identical barcode sequences are joined to the target polynucleotides of more than one sample. A target polynucleotide that has an adaptor/primer oligonucleotide joined to it is may be referred to as "tagged" by the joined adaptor.

In some embodiments, nucleic acids described herein are linked making use of CLICK chemistry. Suitable methods to link various molecules using CLICK chemistry are known in the art (for CLICK chemistry linkage of oligonucleotides, see, e.g. El-Sagheer et al. (PNAS, 108:28, 11338-11343, 2011). Click chemistry may be performed in the presence of Cu(I).

In various embodiments, ligation reactions may be performed while one or more of the linked polynucleotides are attached to a unit.

In various embodiments, error-containing sequences in a synthesized gene are removed from error-free sequences. A DNA mismatch-binding protein, MutS (from *Thermus aquaticus*), can be employed to remove failure products from synthetic genes using different strategies (Schofield and Hsieh, 2003; Carr et al., 2004; Binkowski et al., 2005).

Some other strategies (Pogulis et al., 1996; Ling and Robinson, 1997; An et al., 2005; Peng et al., 2006b) use site-directed mutagenesis by overlap extension PCR to correct mistakes, and can be coupled with one or more rounds of cloning and sequencing, and/or additional synthesis of oligonucleotides.

In some embodiments, error correction is achieved by utilizing Surveyor endonuclease (IDT), a mismatch-specific DNA endonuclease to scan for known and unknown mutations and polymorphisms in heteroduplex DNA. Surveyor nuclease may be used to cleave with high specificity at the 3' side of any base-substitution mismatch and other distortion site in both strands of a double stranded nucleic acid, e.g. DNA.

Heating and Cooling

The microfluidic devices described herein may contain elements for heating and cooling. Any suitable types of temperature controls known in the art can be combined in the systems and devices described in further detail elsewhere herein. Heaters and coolers may include an external enclosure which can be heated and chilled; a thermal plate and a thermoelectric element; secondary microfluidic channels that flow liquid between a hot source such as a thermal element and a cold sink; reagents in branch channels, e.g. branch channels that may run parallel to the channels of a microfluidic device, such as linear, serpentine, or spiral channels, that undergo exothermic and endothermic reactions, such as $H_2SO_4$ mixed with water to provide an exothermic reaction or acetone with air to provide an endothermic reaction; use of conductive liquids in branch channels, e.g. branch channels that may run parallel to the channels of a microfluidic device, such as linear, serpentine, or spiral channels, that are heated or cooled, e.g. with AC current; integrated platinum or gold resistor heaters; integrated metal wires that carry current; microwave dielectric heating via metal electrodes; or laser diodes; or other such appropriate elements known to those of skill in the art (see Miralles V et al, 2013 incorporated herein in its entirety by reference). Branch channels for heating a cooling may be within or outside the microfluidic device. Temperature can also be spatially controlled, e.g. multiple reaction chambers may have thermal zones of different temperature such that the fluid carrying the units undergo multiple temperature changes by flowing through channels. These thermal zones may be gradient temperature changes or sudden temperature changes. The temperature in the microfluidic device may be not constant, instead it may be a gradient from one point in a channel to another point in the same channel or in a different channel. Heaters and/or coolers of the same or different type may be combined in the systems and devices described herein. For example, the systems and devices described herein, including without limitation microfluidic devices, may contain multiple heater elements of the same or different temperature control type, such as a resistor heater and a metal electrode for microwave heating.

The temperature of thermal fields generated by the heater and cooler components described herein may vary according to the desired parameters of a temperature sensitive reaction, for example according to denaturation, annealing and extension steps of PCR or PCA reactions. As an example, nucleic acids may be denatured at about 95° C. for 2 min, followed by 30 or more cycles of denaturation at 95° C. for 30 secs, annealing at 40-60° C. for 30 sec and extension at about 72° C. for 30 secs, and a last extension of 72° C. for 10 min. The duration and temperatures used may vary depending on the composition of oligonucleotides, PCR primers, amplified product size, template, and the reagents used, for example the polymerase.

Fiducial Marks and Stages

In various embodiments, the methods and compositions described herein relate to fiducial marks. Fiducial marks on a microfluidic device may be used for positioning the device with respect to an ancillary equipment such as a detector, a temperature controller, a computer, or a system comprising one or more thereof. Fiducial marks may also be used to track the absolute or relative position of one or more units inside a microfluidic device.

Fiducial marks may be placed on the microfluidic devices described herein to facilitate alignment of such devices with other components of a system. Microfluidic devices of the invention may have one or more fiducial marks, e.g. 2, 3, 4, 5, 6, 7, 8, 9, 10, or more fiducial marks. A fiducial mark may be located at any position on or within the microfluidic device. In some embodiments, a fiducial mark is located near an edge or corner of a device. The fiducial mark may be located from about 0.1 mm to about 10 mm from the edge or corner of a device. In some embodiments, the fiducial mark is located about, at least, or at least about 0.1 mm, 0.2 mm, 0.3 mm, 0.4 mm, 0.5 mm, 0.6 mm, 0.7 mm, 0.8 mm, 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, 9 mm, or 10 mm from the edge of a device. In some embodiments, the fiducial mark is located about, at most, or at most about 10 mm, 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, 0.3 mm, 0.2 mm, or 0.1 mm from the edge of the device. Those of skill in the art appreciate that the distance of the fiducial mark from the edge of the devices described herein may fall within any range bound by any of these values, for example 0.1 mm-5 mm.

The fiducial mark may have any width or cross-section suitable for function. In some embodiments the width or cross-section of a fiducial mark is about, at least, or at least about 0.1 mm, 0.2 mm, 0.3 mm, 0.4 mm, 0.5 mm, 0.6 mm, 0.7 mm, 0.8 mm. 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, 9 mm, or 10 mm. In some embodiments, the width or cross-section of a fiducial mark at most, or at most about 10 mm, 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, 0.3 mm, 0.2 mm, or 0.1 mm. The fiducial mark width or cross-section may range between 0.1-10 mm, 0.2-9 mm, 0.3-8 mm, 0.4-7 mm, 0.5-6 mm, 0.1-6 mm, 0.2-5 mm, 0.3-4 mm, 0.4-3 mm, or 0.5-2 mm long. Those of skill in the art appreciate that the width or cross-section of the fiducial mark may fall within any range bound by any of these values, for example 0.1 mm-5 mm.

The microfluidic device described herein may be mounted on a static or movable stage. The fiducial marks as described elsewhere herein may be used to align the device on a stage. The stage may be moved by manual, electrical, or piezo-electrical means, or other suitable means known to those of skill in the art. The stage may or may not be mounted on a microscope device. Other auxiliary devices used with the microfluidic device may also be mounted on the stage and/or microscope. Such auxiliary devices include, but are not limited to, cameras, lasers, light sources, detectors, temperature regulators, flow rate sensors, pumps, and computer connections, among other devices.

In various embodiments, one or more properties for units such as color, surface chemistry, label, or any suitable property known in the art, on one or more units may be used to detect, track, and/or correct the order of units within a microfluidic device. In various embodiments, properties of only a subset of units are utilized for these purposes. In some embodiments, fiducial units with detectable properties are mixed in with other units that are not tracked or lack detected or tracked properties of the fiducial units. For example, knowledge about the specific properties of one or more units within a set of units may be used as a check to assess specific errors or error rate in the order of the units as controlled or tracked by the methods and compositions described herein. A decision can be made about whether to redo detection, calibrate control systems and/or reorder the units to correct deviations from the predicted or expected order of units within a microfluidic device. In various embodiments, a decision about whether to redo detection, calibrate control systems, and/or reorder the units is made based on an assessment of specific errors and/or error rate, and/or one or more suitable factors or determinations.

Any of the steps, operations, or processes described herein may be performed or implemented with one or more hardware or software components, alone or in combination with other devices. In one embodiment, a software component is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a tangible computer readable storage medium or any type of media suitable for storing electronic instructions, and coupled to a computer system bus. Furthermore, any computers and computing systems referred to in the specification may include a single processor or may be architectures employing multiple processor designs for increased computing capability. Computers and computing systems described herein may comprise a microcontroller and/or cards or processors using staggered pin grid array (SPGA) or field programmable gate array (FPGA) technology. Computers and computing systems described herein may be connected to one or more output devices, including without limitation, one or more user interfaces, one or more printers, or any combination thereof. Computers or computing systems may be embedded inside the devices and/or systems described in further detail herein.

Embodiments of the invention may also relate to a computer data signal embodied in a carrier wave, where the computer data signal includes any embodiment of a computer program product or other data combination described herein. The computer data signal may be a product that is presented in a tangible medium or carrier wave and modulated or otherwise encoded in the carrier wave, which is tangible, and transmitted according to any suitable transmission method.

The data may also be analyzed and processed by computer programs and algorithms. The data analysis and processing may include image analysis and use of image analysis software. Such programs may include publically or commercially available programs, including, but not limited to, ImageJ, MatLab, Imaris, or Metamorph.

Exemplary Microfluidic Devices and Methods of Distributing Units

FIG. 1 provides an illustrative example of a microfluidic device comprising a first primary channel 101 having a plurality of ordered mobile units, such as beads. A router, e.g. a distributor, 102 at the connection of the first channel with the two branch channels 103, 104 can be configured serve to direct each of the mobile units into one of the two branch channels. Valves 105, 113, 106, 114 in the two branch channels can be configured to control entry and exit of the mobile units and form a reaction channel or chamber 107, 108. Reagents may be delivered to the two reaction channels or chambers via reagent delivery channels 110, 112 as shown by the arrows. Delivery of reagents may be controlled with a valve 109, 111. This configuration can be representative of the many configurations that can move a plurality of units through the microfluidic devices described herein, including without limitation, iteratively. The foregoing flow patterns and arrangements are not meant to be limiting.

Microfluidic devices described herein may have one or more clusters comprising a plurality branch channels and/or reaction chambers in temporary or permanent fluidic communication with one channel, such as a primary inlet channel or an outlet channel, that splits into a plurality of branch channels and/or chambers. Reaction chambers may be configured by temporary or permanent barriers, such as physical barriers, e.g. a physical valve, at one or more outlets of a channel, such as a branch channel. Routers may be present at the branch points of channels. 1, 2, 3, 4, 5, 6, 7, 8, 9, 10, 20, 30, 40, 50, 60, 70, 80, 90, 100 or more reaction chambers may be accessible from one or more routers, e.g. distributors, for example, the two reaction chambers accessible after one router, e.g. a distributor, illustrated in FIG. 1 or the four reaction chambers accessible after two sets of successive distributors illustrated in FIG. 5. Two or more reaction clusters may be connected to each other via channels. In some embodiments, some or all of the reaction clusters of a microfluidic device are disconnected from each other.

Units may be moved through the microfluidic device of FIG. 1 and distributed into the different channels randomly or in a deterministic method (e.g., according to an algorithm). Algorithms for deterministic movement may be updated during operation of the microfluidic devices described herein, including without limitation, based on the outcome of routing steps during one or more previous stages of operation. In either case, the collection of units may start in an entry channel in a particular order, for example units 1, 2, 3, 4, 5, 6, 7, 8, and 9 as illustrated in FIG. 1. In some embodiments, the entire collection of units enters one channel after passing through the distributor. In some embodiments, the units are distributed into different channels, e.g. in the case of a two-way split, the distributor may allow unit 1 to enter the left channel, unit 2 to enter the right channel, and unit 3 to enter the left channel according to an algorithm or randomly. After being distributed, the units may travel down the channels. The units may be distributed again by a second distributor according to an algorithm or randomly. In one illustrative example, a channel cluster has two channels, but some clusters may have more than two channels. After the distributing step, the units are held in each channel by a valve which may be configured to halt the flow of the units. The valve may be opened to allow the units to enter a reaction chamber with a further valve at the end of the channel. The first valve may close behind the units to form a reaction chamber. In some embodiments, each reaction chamber holds a single unit. In other embodiments, some or all reaction chambers in a cluster hold multiple units.

After the units have been distributed into the reaction chambers, reagents may be flowed into the chamber by opening a valve abutting the reaction chamber to release reagents and begin a reaction cycle. A reaction cycle may comprise the delivery of reagents, treatment with a light or laser, or physical treatment. A reaction cycle may also comprise no delivery of reagents, treatment with a light or laser, or physical treatment. The units may be subjected to selected reaction conditions for a specified time for each reaction cycle. Reagents may be selected in order to chemically modify the units in a prescribed manner. The reagents in some or all of the reagent channels connected to the different reaction chambers of a cluster may be different, for example delivered reagents may comprise different nucleotide building blocks for oligonucleotide synthesis.

Reaction conditions are not limited chemical reactions and can include enzymatic treatments, such as enzymatic DNA synthesis, physical treatment such as heating or cooling or applying pressure or shear forces; or light treatments, such as ultraviolet (UV), infrared (IR), or any light in the visible spectrum, approximately 390 to 700 nm. Reaction conditions may also include the absence of a reaction or treatment with or without a reagent.

After a reaction cycle, the valves at the end of the reaction chamber may be opened to release the units. The order in which the units may be released may be determined based on the timing and duration of the valve opening, e.g. if there are multiple units in one reaction chamber, they may all be released before the units in the next chamber are released. The units in the chambers may be released such that they are interleaved with units from another chamber, such as by opening the desired chamber router in a prescribed manner, for example periodically, and for an appropriate amount of time to release units in a desired manner.

In various embodiments, units may be released from some or all channels or chambers individually or in sub-batches, as opposed to releasing the entire batch of units within a channel or chamber at once. Further, in various embodiments, a set of units entering a cluster may be partitioned into branch channels and/or reaction chambers in sub-batches. The sub-batches may be subjected to a reaction cycle and released from the cluster before an additional sub-batch from the set of units are partitioned. The partitioning of sub-batches of units from a set of units may be repeated until all of the units within the set are partitioned into the branch channels and/or reaction chambers of a cluster.

Where units have been split into more than two chambers, units from the individual chambers may be recombined successively. For example, after combining units from two chambers, the units may be further combined at a subsequent branch point with units from additional chambers, for example into a single channel. Units at each merging branch point may be recombined in similar or different ways, e.g. in batches by opening the valve at the end of one reaction chamber, releasing all of the units in that chamber, and repeating the process for the units in the remaining channels. The units may also be combined into one channel by opening a valve on some or all reaction chambers periodically in succession to interleave the units. The recombined units may be iteratively routed back to the origin point of a reaction cluster to undergo further reaction cycles. The units may also be flowed into a second reaction cluster with a similar or different arrangement, or flowed into outlets, e.g. collection receptacles for further processing.

FIG. 2 provides an illustrative example of a microfluidic device. Mobile units 1-6 from a first channel 201 may be directed deterministically or randomly into one of two branch channels 203, 204 by using a router, e.g. distributor 202. Units 7-9 are arranged in the first channel, behind the router. The router may be programmed to deliver units 7-9 the positions indicated by the hashed-circles. Once the mobile units are distributed into the branch channels and reaction chambers 207, 208, reagents, such as synthesis reagents may be circulated through the two reaction chambers that are configured to hold the mobile units. After undergoing a reaction cycle, the units may be released from the reaction chamber by opening the valves 213, 214. In some embodiments, the units are flowed iteratively back to the first channel 201 to undergo another distributing step, for example, via the return path 217.

FIG. 3 provides an illustrative example of a snapshot of tracked circulating of mobile units through split channels of a microfluidic device. The order of the mobile units in the channel 301 as the mobile units are about to start a round of distributing is different than the order shown in FIG. 1. The order of the mobile units as they are recirculated back to the first channel may be set in a deterministic manner, for example by distributing and releasing the units into and from reaction chambers in a predetermined manner. The position or relative position of specific mobile units may be known or determinable from the path each mobile unit has taken in a prior round of distributing and recombining. In this illustrative example, the mobile units are being prepared to be distributed again into the branch channels 303, 304 and reaction chambers 307, 308 that may be set to host a pre-assigned sequence of chemistries via dedicated reagent channels 310, 312.

FIG. 4 provides an illustrative example of a microfluidic device wherein mobile units are split into four branch channels 407, 408, 426, 427 passing through two sets of successive routers, e.g. distributors, 402, 405, 406. A device configuration having a reaction cluster comprising four branch channels 407, 408, 426, 427 and four reaction chambers 411, 412, 429, 432 may be used to synthesize molecules, for example nucleic acids, in or on the mobile units by successive circulation of the mobile units through the reaction cluster. Dedicated reagent delivery channels 414, 416, 439, 434 may each provide a selected reagent, for example one of four building blocks for nucleic acid synthesis. After undergoing a reaction cycle, the units may be released from the reaction chambers by opening the valves located in the reaction chambers and combined into one channel 439. The released units may be released in a random or deterministic way according to an algorithm as described in further detail elsewhere herein. The units may be flowed back to the first router 402 and redistributed into the reaction chambers. The unit order of the second distributing may vary from the unit order of the first distributing, such that the same units may or may not undergo a reaction cycle in the same reaction chamber. The units may be flowed iteratively through the reaction cluster for multiple rounds of reaction cycles.

Figure 5:
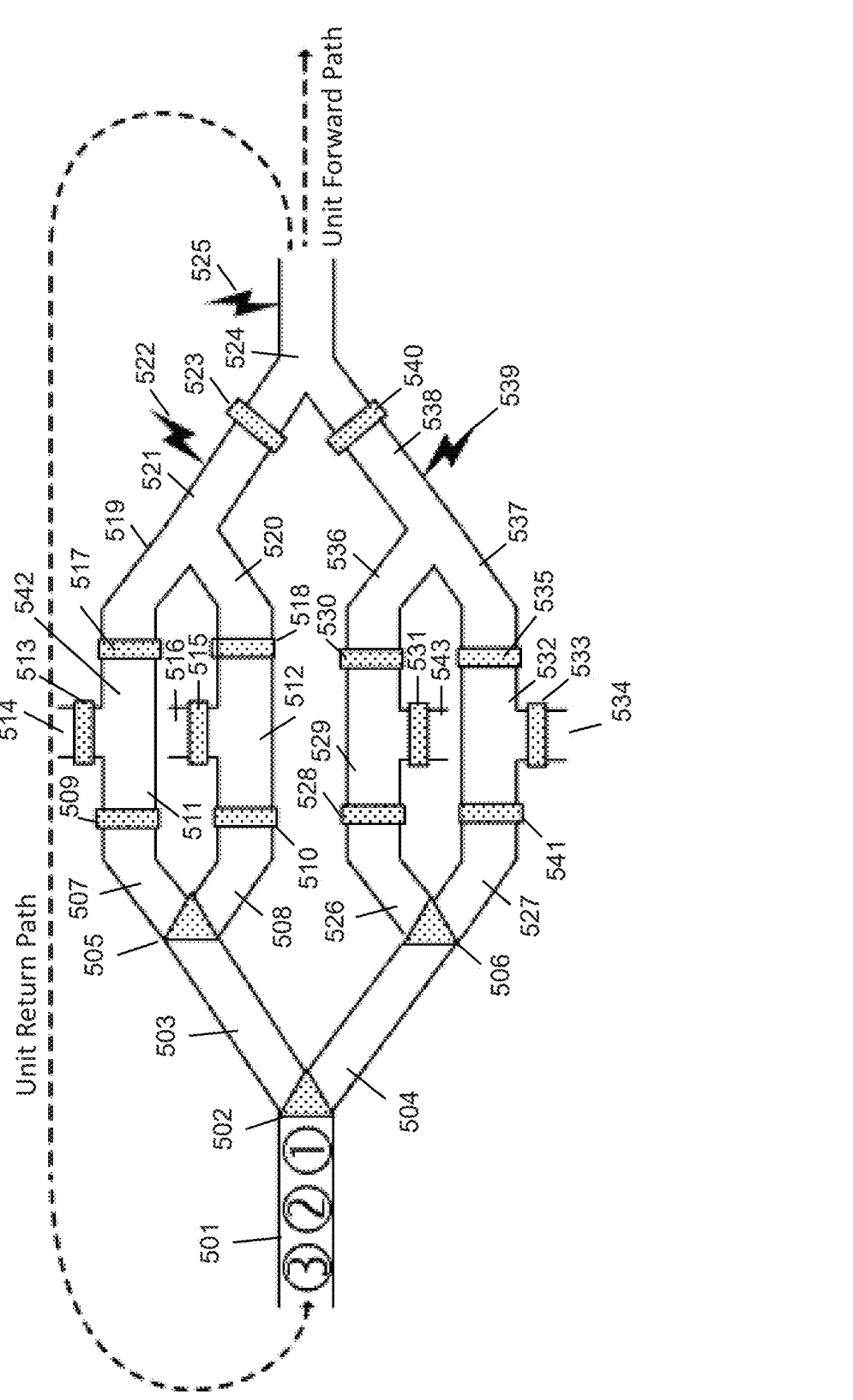
FIG. 5 provides an illustrative example of a microfluidic device wherein mobile units are distributed into four branch channels passing through two sets of successive routers, e.g. distributors. Valves in each of the four channels may control exit and entry of the mobile units and create a reaction chamber for a reaction cycle comprising chemical modification of the units when closed. Units released from one or more of the reagent chambers may be merged with the units released from another reaction chamber at successive branch points, resulting in combination of the units in the four channels into two channels.

FIG. 5 provides an illustrative example of a microfluidic device wherein mobile units are split into four branch channels 507, 508, 526, 527 passing through two sets of successive routers, e.g. distributors, 502, 505, 506. Valves 509, 510, 517, 518, 528, 530, 535, 541 in each of the four channels may control exit and entry of the mobile units and create reaction chambers 542, 512, 529, 532 configured to host a reaction cycle, for example a reaction cycle comprising chemical modification of the units when closed. Dedicated reagent delivery channels 514, 516, 543, 534 may provide reagents to some or all of the reaction chambers in a reaction cluster.

Units released from one or more of the reagent chambers may be merged with the units released from another reaction chamber, for example, in a pairwise fashion, resulting in combination of the units in the four channels into two channels 521, 538. For example, units from the left (top) two channels may be merged with each other and units from the right (bottom) two channels may be merged with each other. The resulting merged units may be merged again to combine units from four channels in a stepwise fashion. Each merging step may combine the units according to a selected algorithm. The combination algorithm may be the same or different in some or all merging branch points. An example of a combination algorithm for merging units from 4 channels may be 1 unit from the right channel, 1 unit from the right middle channel, 2 units from the left middle channel, and 2 units from the left channel. One or more detectors 522, 525, 539 with fields capturing some or all channels may interrogate the released units to capture information, which may or may not include positional information. Detectors may be placed in a variety of locations, for example immediately before and/or after a branch point where units are routed, e.g. distributed or merged, along the unit flow. However, as described above, the detector(s) can also be configured for global or regional detection of regions of interest. A valve 523, 540 at the end of some or all of the merger channels may control release of the units into a single channel 524 according to an algorithm or randomly. Another detector may further interrogate the units in that single channel. The units may then be routed back to the beginning of the reaction cluster, continue to another cluster that has been configured similarly or differently, or be released into outlet(s). A plurality of units in a microfluidic device may go through iterative steps comprising the same or similar configurations as the one depicted in FIG. 5.

To positionally track the units as they move through the devices described herein, one or more detectors may be placed at single or multiple points in the device. In FIG. 5, detectors have been placed on the channels that are formed after the first merge of the reaction chamber channels. Detectors may also be placed on the channel between the final valve that forms the reaction chamber and the merge point of two or more reaction chamber channels. Detectors may also be placed immediately before, after, or in line with routers, e.g. distributors, mergers, or valves, in the microfluidic devices described herein. Detectors may be connected to a computer configured to perform analysis of the signal detected by the detectors. The result of such detector signal analysis may be used to control the fluidic pressure, the velocity of carrier fluids and/or units therein and/or the actuation or timing of routers, e.g. distributors, or actuation or timing of valves, or other types of routers. As the units exit the reaction chambers, a detector may interrogate the unit, for example by scanning the units with a laser, an LED, or by taking multiple pictures of the units with a CCD, CMOS or NMOS camera. Other methods to interrogate the units may also be used. The positional data may be sent to a computer for analysis and storage. The valve at the end of a channel, for example the final merger channel may be opened and closed based on the data from the detectors in order to release the units in a particular order. Or the valves may be opened and closed based on a predetermined or random order to release the units.

Figure 6:
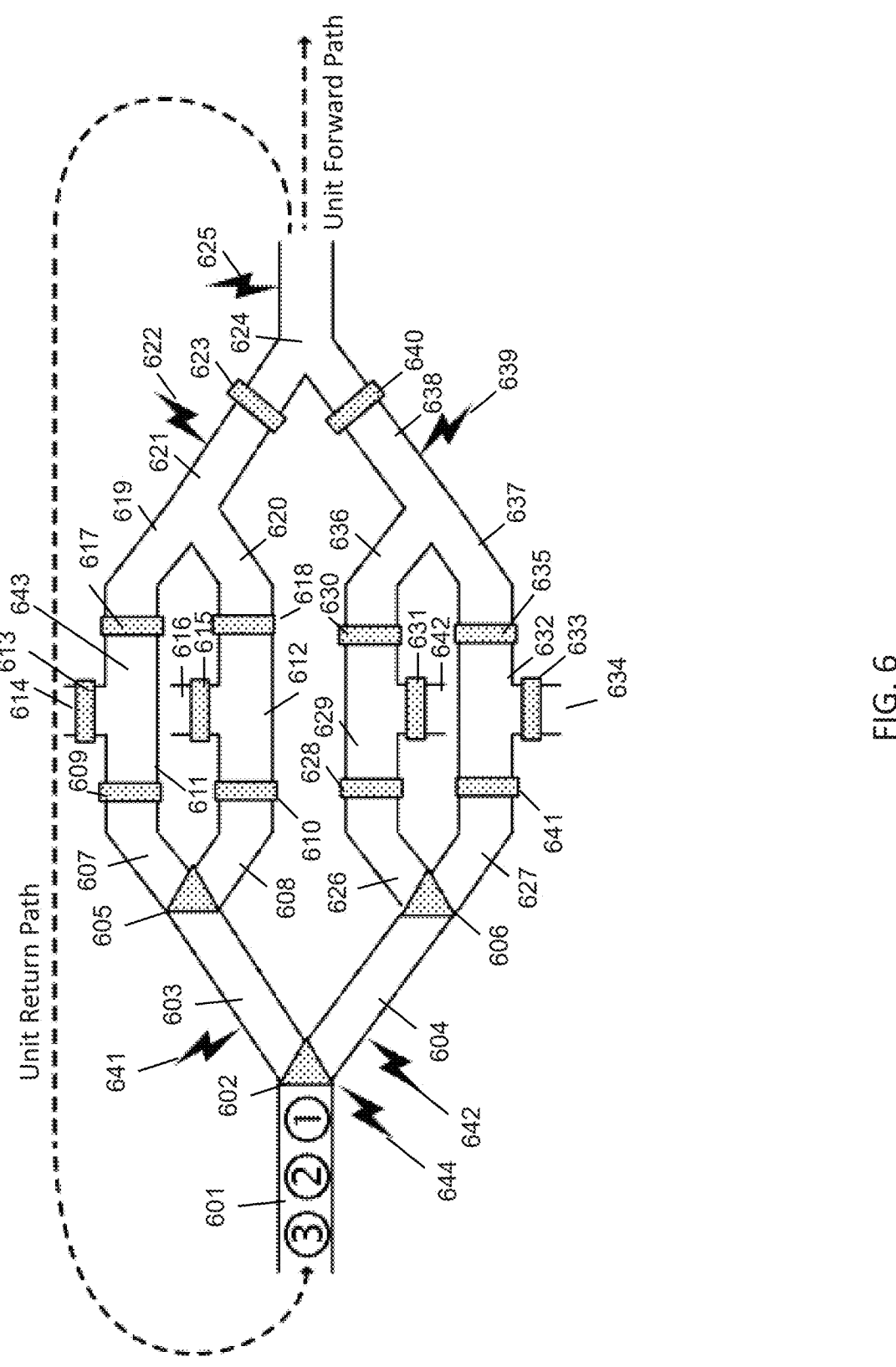
FIG. 6 provides an illustrative example of a microfluidic device wherein mobile units are distributed into four branch channels passing through two sets of successive routers, e.g. distributors. A detector in the two channels after the first router may interrogate the units as they pass through the channels. The data may be sent to a computer for storage and image processing.

FIG. 6 provides an illustrative example of a microfluidic device wherein mobile units are distributed into four branch channels 607, 608, 626, 627 passing through two sets of successive routers, e.g. distributors, 602, 605, 606. A detector 644 in line with the router may interrogate the units as they pass through the router. A detector 641, 642 in the two channels 603, 604 may interrogate the units as they pass through the channels after passing through the first router 602 and before entering a second router 605, 606. The data may be sent to a computer for storage and/or image processing. Valves 609, 610, 617, 618, 628, 630, 635, 641 in each of the different channels may control exit and entry of the mobile units and create reaction chambers 612, 629, 632, 643 configured to host a reaction cycle when closed. Dedicated reagent delivery channels 614, 616, 642, 634 may provide reagents to some or all of the reaction chambers in the reaction cluster. Units released from one or more of the reagent chambers may be merged with the units released from another reaction chamber in pairwise fashion, resulting in combination of the units in the four channels into two channels. For example, units from the left (top) two channels 619, 620 may be merged with each other and the right (bottom) two channels 636, 637 may be merged with each other. Units released from some or all of the reagent chambers may be merged with the units released from another reaction chamber in pairwise fashion, resulting in combination of the units in the four channels into two channels according to an algorithm or randomly. One or more detectors 622, 639 in some or all of the channels may interrogate the released units. A valve 623, 640 at the end of each of the merger channels may control release of the units into a single channel 624. The units may be released individually from each channel or in a batch, as described in further detail elsewhere herein. One or more detectors 625 in a downstream channel may be configured to further interrogate the units. This configuration is representative of one of many iterative steps a plurality of units may undergo through the microfluidic device.

Units may be moved through the microfluidics device of FIG. 6 and distributed into one or more different channels according to an algorithm or randomly as described in further detail elsewhere herein. The combined units may then be iteratively routed back to the origin point of the described reaction cluster to undergo another reaction cycle. The units may also be flowed into a second reaction cluster with a similar or different arrangement, or flowed into outlets, e.g. collection receptacles for further processing. The foregoing flow patterns and arrangements are not meant to be limiting.

Figure 7:
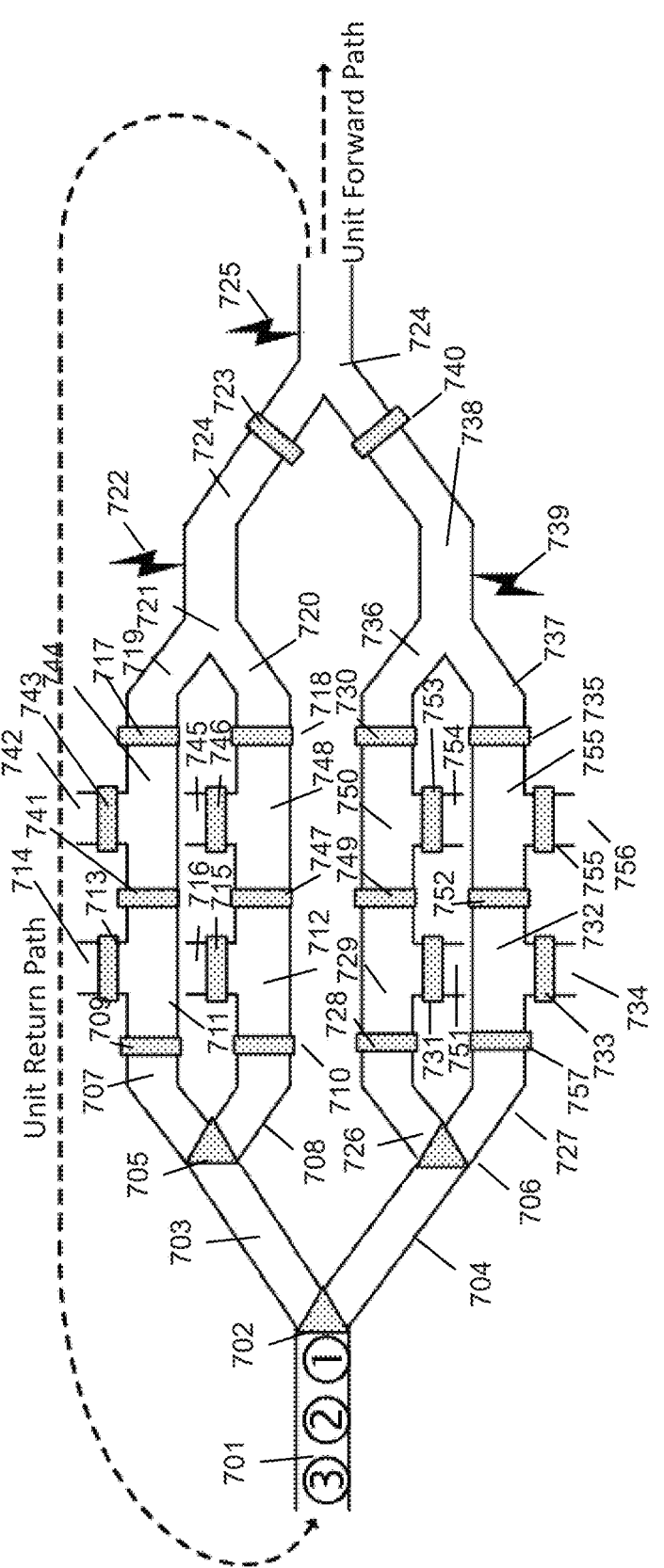
FIG. 7 provides an illustrative example of a microfluidic device wherein mobile units are distributed into four branch channels passing through two sets of successive routers, e.g. distributors. In this example, the units may be distributed into a reaction cluster comprising four reaction chambers with three consecutive valves: a first valve, a middle valve, and a last valve. These valves may form two reaction chambers in each channel, resulting in eight total reaction chambers in the reaction cluster.

FIG. 7 provides an illustrative example of a microfluidic device wherein mobile units are distributed into four branch channels 707, 708, 726, 727 passing through two successive routers, e.g. distributors, 702, 705, 706. In this example, the units may be distributed into a reaction cluster comprising four reaction chambers 711, 744, 712, 748 729, 750, 732, 755, each bounded with three consecutive valves: a first valve 709, 710, 728, 757, a middle valve 741, 747, 749, 752, and a last valve 717, 718, 730, 735. These valves may form two reaction chambers 711, 744, 712, 748 729, 750, 732, 755 in each channel, resulting in eight total reaction chambers in the reaction cluster. In alternative embodiments, 3, 4, 5, 6, 7, 8, 9, 10 or more reaction chambers may be configured within each channel. The reaction chambers may have an individual dedicated reagent channel 714, 742, 716, 745, 751, 754, 734, 756 for delivery of chemical reagents. In this example, consecutive reaction cycles may be performed on the units after they have been distributed into one or more different channels without re-combining and re-distributing the units between reaction cycles. One or more detectors 722, 739 after a first channel intersection and/or a second channel intersection may interrogate the units. The channels may be configured to return the units to the beginning of the cluster or deliver them to a cluster with a similar or a different configuration, for example for additional reaction cycles according to an algorithm or randomly. In some embodiments, reaction chamber may be partitioned into three or more reaction chambers, for example by the use of additional routers. Some or all reaction chambers may have a dedicated reagent channel delivering reagents, for example in a manner controlled by a router 713, 743, 731, 753, 715, 746, 733, 755.

Units may be moved through the microfluidics device of FIG. 7 and distributed into the different channels according to an algorithm or randomly as described in further detail elsewhere herein. In this example, the units may undergo two consecutive reaction cycles without being re-distributed due to the presence of two consecutive reaction chambers in each channel. A reaction cycle may be performed on the distributed units which are then moved to the next reaction chamber by opening the middle valve in the reaction chamber. The reaction cycles may be the same cycle with the same reagents twice or reaction cycles with different reagents. For example, if the reaction cycle is nucleotide synthesis, the device may be used to synthesis two of the same nucleotides in a row or two different nucleotides. A reaction cycle may comprise steps such as rinsing and a reaction chamber may be configured to host such a step. The reaction cycle reagents provided to some or all of the eight example reaction chambers may not be the same. Some or all reaction chambers may not have a dedicated reagent channel, as described in further detail elsewhere herein.

After the units go through a reaction cycle in the reaction chambers, the valves at the end of the reaction chamber may be opened to release the units. The order of the units release may be determined based on the timing and duration of the valve opening according to an algorithm or randomly, as previously described. One or more detectors in the first merger channel(s) 721, 738 may interrogate the units after they are released from the reaction chambers. The units may then be further combined into a single channel 724 according to an algorithm or randomly as described in further detail elsewhere herein. One or more detectors 725 in the second merger channel may interrogate the units. The combined units may then be iteratively routed back to the origin point of the described reaction cluster to undergo another reaction cycle. The units may also be flowed into another reaction cluster with a similar or a different arrangement, or flowed into outlets, for example collection receptacles, for further processing. The foregoing flow patterns and arrangements are not meant to be limiting.

Figure 8:
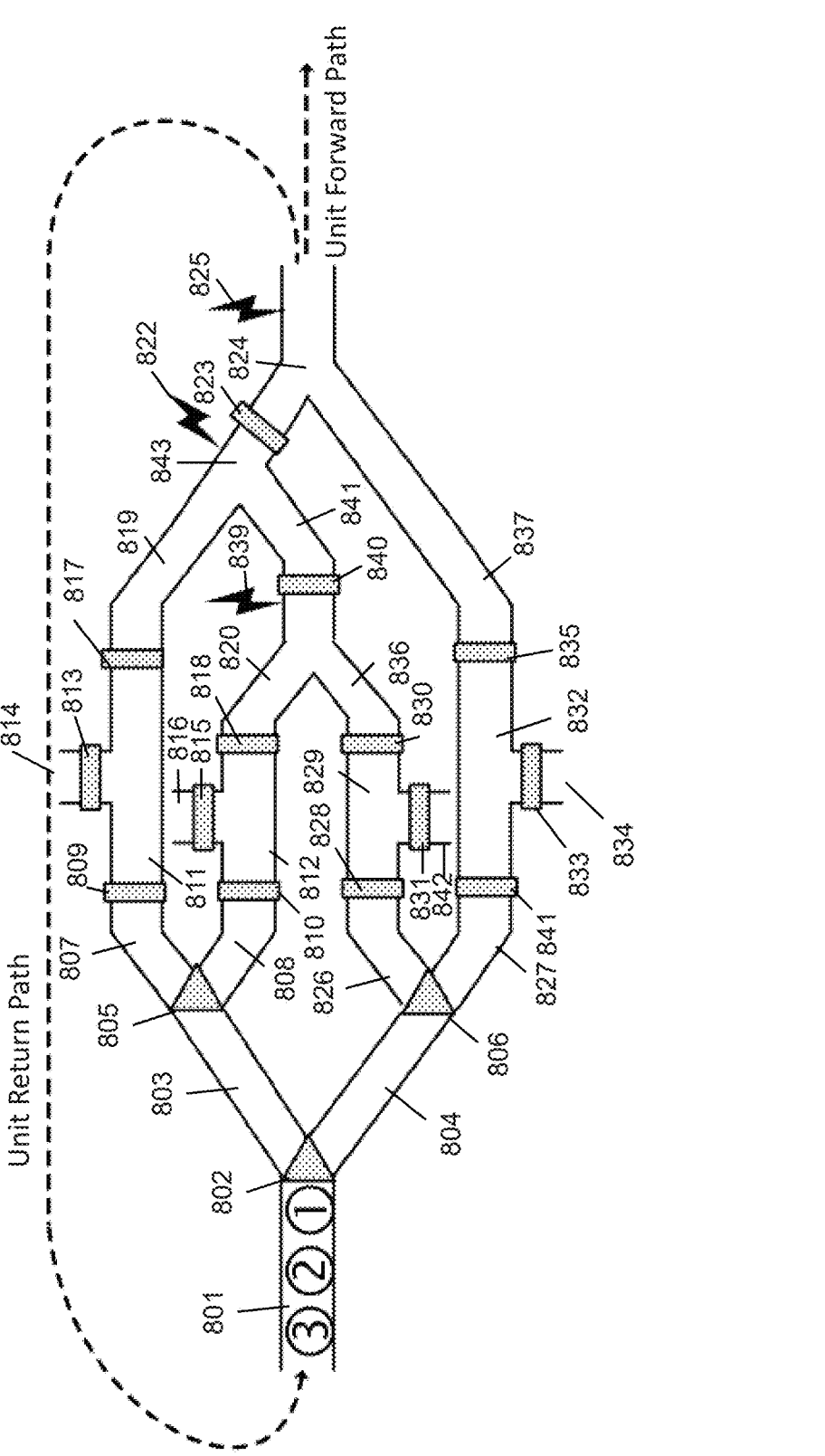
FIG. 8 provides an illustrative example of a microfluidic device wherein mobile units are distributed into four branch channels passing through two sets of successive routers, e.g. distributors. After the units undergo a reaction cycle in some or all of the reaction chambers, the units may be recombined by flowing them through channels that merge, according to an algorithm or randomly. In this example, the two middle channels merge with each other first, before merging with the left (top) and the right (bottom) channels.

FIG. 8 provides an illustrative example of a microfluidic device wherein mobile units are split into four branch channels 807, 808, 826, 827 passing through two successive sets of routers, e.g. distributors, 802, 805, 806. In this example, the units may be distributed via two successive sets of routers, e.g. distributors, into four reaction chambers 811, 812, 829, 832, each with a valve 817, 818, 830, 835 at the end of the chamber. Dedicated reagent channels 814, 816, 842, 834 may provide reagents, for example reagents for chemical modification, to some or all of the reaction chambers. After the units undergo a reaction cycle in some or all of the reaction chambers, the units may be re-combined in merger channels according to an algorithm or randomly. In this example, the two middle channels 820, 836 merge with each other while the left-most 819 and right-most channels 837 remain separate. Individual valves 817, 818, 830, 835 at the end of the reaction chambers may be configured to control the exit of the units from the respective reaction chamber. Some or all of the units in the middle reaction chamber may be released in a batch by opening first one and then the other reaction chamber valves. Or some or all of the units may be released and interleaved by opening the valves in succession periodically according to an algorithm or randomly, as described in further detail elsewhere herein. One or more detectors 839, 822 on the merger channel may interrogate the units as they pass through the merger channel. A valve 840 at the end of the merger channel may control the release of the units in the merger channel. The left-most channel 819 may be configured to merge with the middle channel 841 to form a second merger channel 843 that comprising a valve 823. The middle channel may alternatively merge with the right most channel 837 to form a second merger channel. One or more detectors 822 in the second merger channel may interrogate the units. The remaining channels may then merge to form one channel 824 and one or more detectors 825 on the channel may interrogate the units as they pass by it.

Units may be moved through the microfluidics device of FIG. 8 and distributed into the different channels according to an algorithm or randomly as described in further detail elsewhere herein. The combined units may then be iteratively routed back to the origin point of the described reaction cluster to undergo another reaction cycle. The units may also be flowed into a second reaction cluster with a similar or a different arrangement, or flowed into outlets, e.g. collection receptacles, for further processing. The foregoing flow patterns and arrangements are not meant to be limiting.

Figure 9:
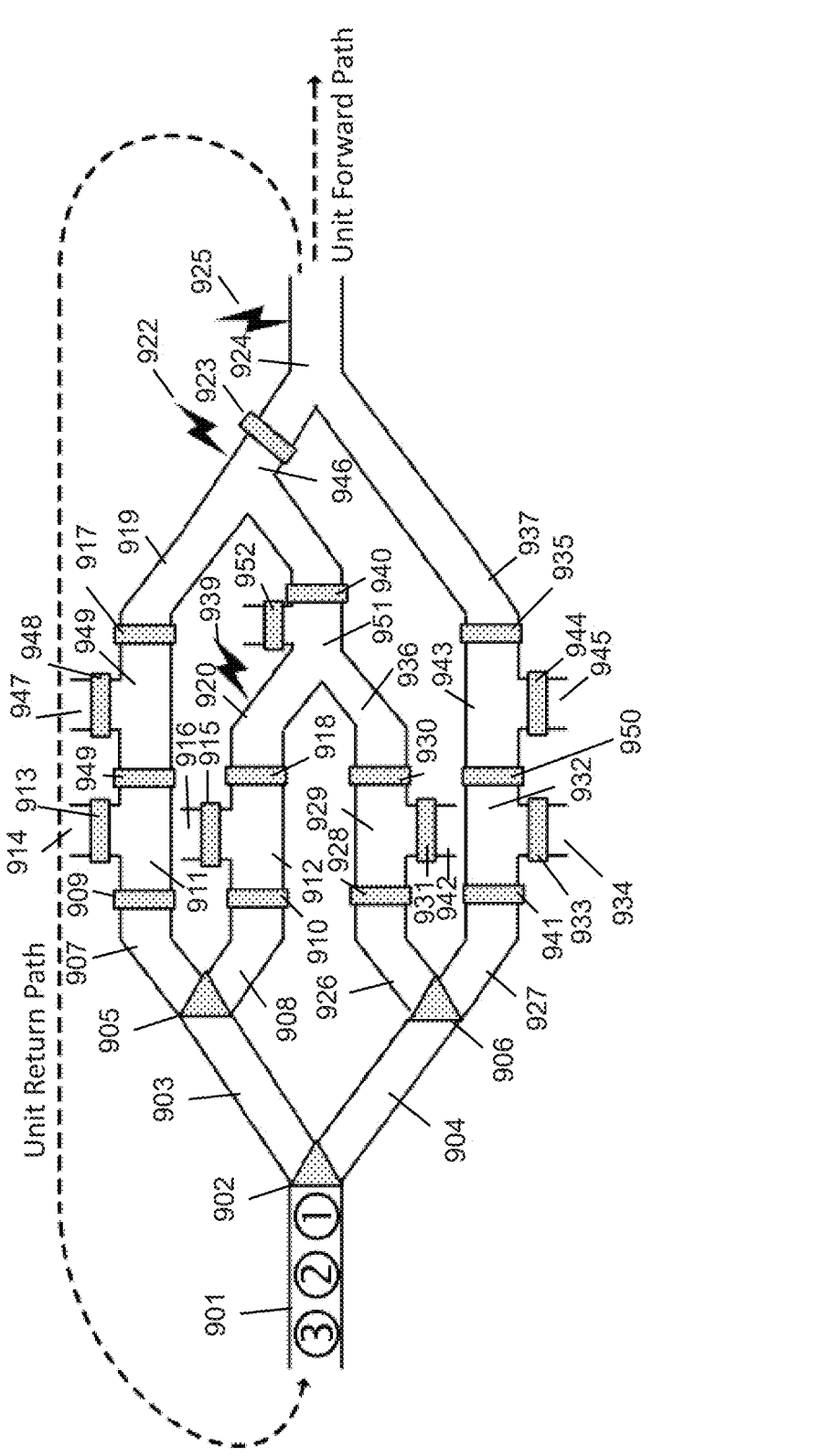
FIG. 9 provides an illustrative example of a microfluidic device wherein mobile units are distributed into four branch channels passing through two sets of routers, e.g. distributors. In this example, the units are distributed into different channels with varying numbers of reaction chambers.

FIG. 9 provides an illustrative example of a microfluidic device wherein mobile units are split into four branch channels 907, 908, 926, 927 passing through two successive sets of routers, e.g. distributors, 902, 905, 906. In this example, the units are distributed into different channels with varying numbers of reaction chambers 911, 949, 912, 929, 932, 943. The channels, for example the channels on the periphery of the device may be configured to have multiple successive reaction chambers formed by three or more valves, as previously described in FIG. 7, while other channels, for example the middle channels, may be configured to have different numbers of reaction chambers, for example one. In other examples, the periphery channels may have one reaction chamber, while the middle channels may contain varying numbers of reaction chambers. In the example in FIG. 9, there are two reaction chambers 911, 949, 932, 943 in the outside channels and one chamber 912, 929 in each of the middle channels. The reaction chambers may be capped by valves 909, 953, 917, 910, 918, 928, 930, 941, 950, 935. The middle channels 920, 936 may be configured to merge after the reaction chambers and form a reaction chamber 951 capped by a valve 940. One or more detectors 939 on the middle merger channel reaction chamber may interrogate the units as they enter or exit the reaction chamber. In this example there are seven total reaction chambers. Dedicated reagent channels 914, 947, 916, 942, 934, 945, 952 may provide reagents for reaction cycles to some or all of the reaction chambers. The reagents delivered may be selected for the same or different chemical modification(s). For example, in the case of nucleotide synthesis, the reagents may be different nucleotides. The reagents in the successive reaction chambers may be the same or different reagents such that the units may undergo two successive reaction cycles that may comprise different modifications. The middle channel may then merge with the left-most channel to form a second merger channel 946. One or more detectors 922 in this channel may interrogate units as they enter or exit the channel. The second merger channel 946 may be configured to merge with the right most channel 937 to form one channel 924. One or more detectors 925 on this channel may interrogate the units as they flow through the channel.

Units may be moved through the microfluidics device of FIG. 9 and distributed into the different channels according to an algorithm or randomly as previously described. The combined units may then be iteratively routed back to the origin point of the described reaction cluster to undergo another reaction cycle. The units may also be flowed into a second reaction cluster with a similar or a different arrangement, or flowed into an outlet(s), e.g. collection receptacles, for further processing or collection. The foregoing flow patterns and arrangements are not meant to be limiting.

Figure 10:
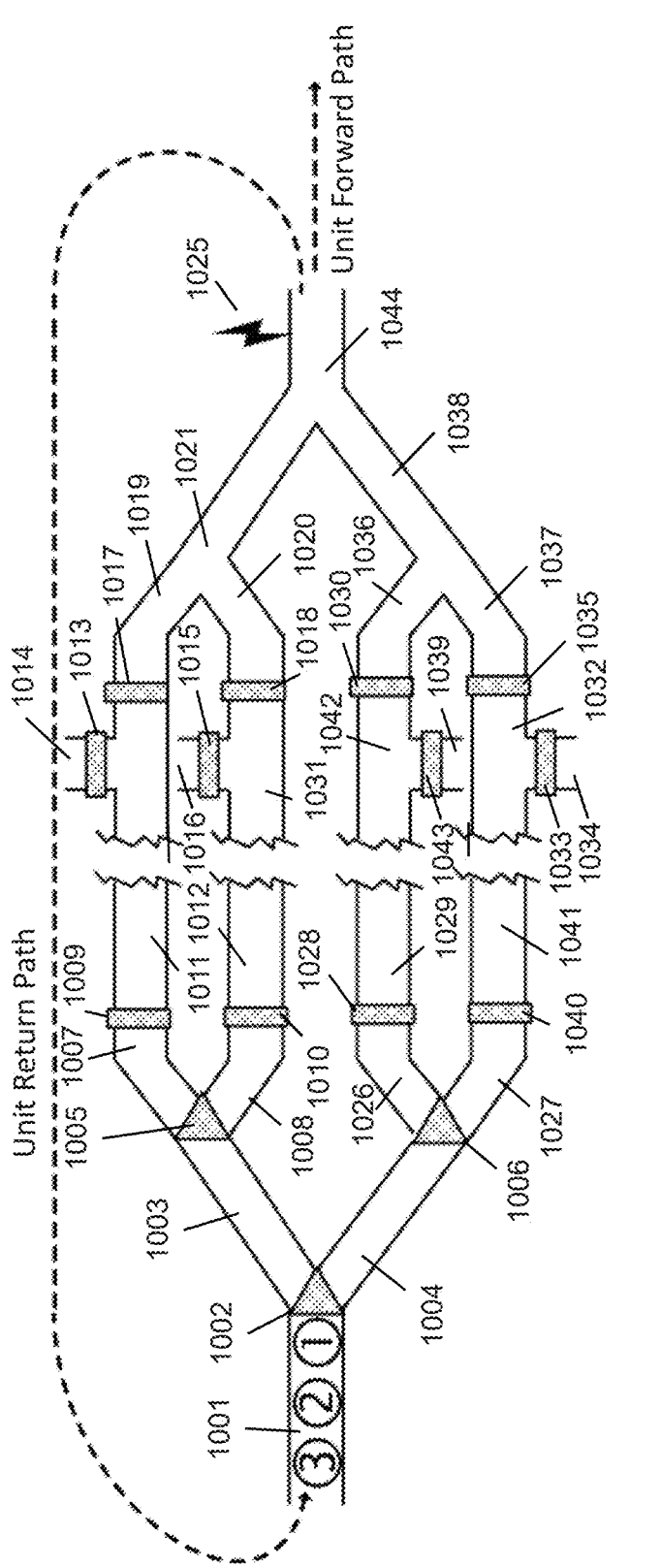
FIG. 10 provides an illustrative example of a microfluidic device wherein mobile units are distributed into four branch channels passing through two sets of successive routers, e.g. distributors. The reaction chambers may include additional features not shown, as indicated by the broken lines in the channel.

FIG. 10 provides an illustrative example of a microfluidic device wherein mobile units are distributed into four branch channels 1007, 1008, 1026 passing through two successive sets of routers, e.g. distributors, 1002, 1005, 1006. Valves 1009, 1017, 1010, 1018, 1028, 1030, 1040, 1035 at the ends of each of the four channels may be configured to cap the channels and form reaction chambers 1011, 1012, 1029, 1041. Reagents may be introduced into the reaction chamber via dedicated reagent channels 1014, 1016, 1039, 1034. The reaction chambers may comprise additional features not shown, as indicated by the broken lines in the channel. Such features may comprise additional valves to form multiple successive reaction chambers, additional detectors, additional branch channels, portions of the reaction chamber walls that are coated with functionalized groups, and/or other structural or non-structural features. The additional features in some or all of the reaction chambers may be the same or different. Units released from some or all of the reaction chambers may be merged with the units released from another reaction chamber, for example in a pairwise fashion, resulting in combination of the units in the four channels into two channels. Or one or more units may be released from one or more reaction chamber according to an algorithm or randomly. The left two channels 1019, 1020 may merge with each other and the right two channels 1036, 1037 may merge with each other. The merger channels may be capped with a valve. These merger channels may be configured to further merge with each other to form one channel 1044. One or more detectors 1025 in the final merger channel may interrogate the released units.

Units may be moved through the microfluidics device of FIG. 10 and distributed into the different channels according to an algorithm or randomly as previously described. The combined units may then be iteratively routed back to the origin point of the described reaction cluster to undergo another reaction cycle. The units may also be flowed into a second reaction cluster with a similar or a different arrangement, or flowed into an outlet, for example collection receptacles for further processing. The foregoing flow patterns and arrangements are not meant to be limiting.

FIG. 11 provides an illustrative example of a microfluidic device with two consecutive reaction clusters. In the first cluster, mobile units are split into four branch channels 1107, 1108, 1126, 1127 passing through two successive sets of routers, e.g. distributors, 1102, 1005, 1106. Valves 1109, 1117, 1110, 1118, 1128, 1130, 1141, 1135 at the ends of each of the four channels may cap the channels and form reaction chambers 1111, 1112, 1129, 1132. In this example, the reaction chambers may comprise additional features not shown, as indicated by the broken lines in the channel. Such features may comprise additional valves to form multiple successive reaction chambers, additional detectors, additional branch channels, portions of the reaction chamber walls that are coated with functionalized groups, and/or other structural or non-structural modifications. The features in some or all of the reaction chambers may be the same or different. The four channels may be configured to merge into two channels 1121, 1138. The channels may each be capped with a valve 1123, 1140. One or more detectors 1122, 1139 may be configured to interrogate the mobile units as they flow through the microfluidic device. The two channels may then merge into a single channel 1124. One or more detector(s) 1125 may be configured to interrogate the mobile units as they flow through the channel. This channel may split again into four branch channels 1145, 1146, 1147, 1148 passing through two successive sets of routers, e.g. distributors, 1142, 1143, 1144. The reaction cluster accessed via these routers may have a similar or a different geometry as the first cluster. Some or all of the reaction chambers in the second cluster may have features in the reaction chambers such that the second cluster is the same as or similar to the first cluster, or different than the first cluster. Some or all of the reaction chambers in the second cluster may have the same features or different features than the other reaction chambers in the second cluster. The channels in the second reaction cluster 1149, 1150, 1151, 1152 may be configured to merge, for example in a pairwise pattern as described in further detail elsewhere herein. The merger channels 1159, 1153 may be capped by valves 1156, 1157. One or more detectors 1155, 1158 on the merger channels may interrogate the units as described in further detail elsewhere herein. The first set of merger channels may be configured to merge again to form a second merger channel 1154. One or more detectors in the second merger channel may interrogate the units as previously described. The units in the second merger channel may be routed back to the first cluster, continue on to a second cluster, continue to an outlet, e.g. a collection receptacle, or continue to an exit. The foregoing description of cluster geometry and arrangement is not meant to be limiting.

Mobile units may be flowed and distributed through the microfluidic device shown in FIG. 11 according to an algorithm or randomly as previously described. Some or all of the units may be distributed individually or in batches of more than one unit. After undergoing a first reaction cycle in a first reaction chamber in a first cluster, the units may be flowed directly into a second reaction chamber in a second cluster for a second reaction cycle. The mobile units may move along the same distribution path in the first and second clusters or a different distribution path in the first and second clusters. For example, unit 1 may be distributed into the upper most reaction chamber 1111 in cluster one, merged back with the collection of units into the channel between the reaction clusters, and distributed into the upper most branch channel 1145 in cluster two. Or, unit 1 may be distributed into the upper most reaction chamber 1111 in cluster one, merged back with the collection of units into the channel between the reaction clusters, and distributed into the bottom most branch channel 1148 in cluster two. The units may be distributed in all possible combinations afforded by the distributing pathways, according to an algorithm or randomly. Units exiting the second cluster may be iteratively routed back to the first cluster, continue on to a third cluster with similar or different geometry, or flowed into an outlet, e.g. collection receptacles for further processing or continue to an exit. The foregoing flow patterns and arrangements are not meant to be limiting.

Figure 12:
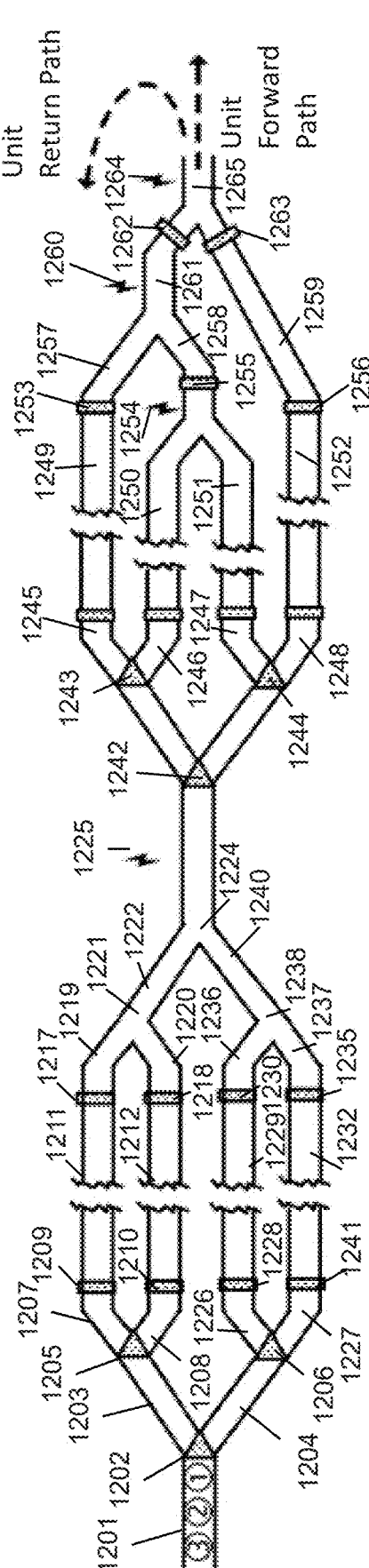
FIG. 12 provides an illustrative example of a microfluidic device with two consecutive reaction clusters. In this example, the reaction chambers may include additional features not shown, as indicated by the broken lines in the channel.

FIG. 12 provides an illustrative example of a microfluidic device with two consecutive reaction clusters, similar to FIG. 11. In the first cluster, mobile units are distributed into four branch channels 1207, 1208, 1226, 1227 passing through two successive sets of routers, e.g. distributors, 1202, 1205, 1206. Valves 1209, 1210, 1217, 1218, 1228, 1230, 1241, 1235 at the ends of each of the four channels may cap the channels and form reaction chambers 1211, 1212, 1229, 1232. In this example, the reaction chambers may include additional features not shown, as indicated by the broken lines in the channel. Such features may comprise, but are not limited to, additional valves to form multiple successive reaction chambers, additional detectors, additional branch channels, portions of the reaction chamber walls that are coated with functionalized groups, and/or other structural or non-structural modifications. The features in some or all of the reaction chambers may be the same or different. The four channels may be configured to merge into two channels 1222, 1240, which may be configured to merge into a single channel. Detector unit(s) 1225 may be positioned at selected locations. This channel may split again into four branch channels 1245, 1246, 1247, 1248 passing through two successive sets of routers, e.g. distributors, 1242, 1243, 1244. The reaction cluster accessed via these routers, e.g. distributors, may have the same or different geometry. Some or all of the reaction chambers in the second cluster may have features in the reaction chamber such that the second cluster is the same as the first cluster, or different than the first cluster. Some or all of the reaction chambers in the second cluster may have the same features or different features than the other reaction chambers in the second cluster. In this example, the first and second reaction chambers have different channel merge geometries. In the first cluster, the channels may be configured to merge in a pairwise fashion with the left most 1219, 1220 and right most 1236, 1237 channels merging with each other. In the second cluster, the middle two reaction chambers 1250, 1251 are configured to merge into a merger channel capped by a valve 1255. One or more detectors 1254 may be configured to interrogate the units passing through the merger channel. The left most channel 1257 and the middle channel 1258 are configured to merge into a second merger channel 1261 capped by a valve 1262. One or more detectors 1260 may be configured to interrogate units passing through the second merger channel 1261. The second merger channel 1261 and the right most channel 1259 are configured to merge into a third and final merger channel 1265. One or more detectors 1264 may be configured to interrogate the units passing through the third merger channel. The mobile units may be routed back to the first cluster, continue on to a second cluster with similar or different geometry, continue to an outlet, for example a collection receptacle, or continue to an exit. The foregoing description of cluster geometry and arrangement is not meant to be limiting.

As the units flow through the channel described in further detail elsewhere, the units may be distributed in all possible combinations that can be facilitated by a collection of routers, e.g. distributors. The units may be distributed according to an algorithm or randomly, as described in further detail elsewhere herein. Units exiting the second cluster may be iteratively routed back to the first cluster, continue on to a third cluster with similar or different geometry, flowed into an outlet, e.g. collection receptacles for further processing, or continue to an exit. The foregoing flow patterns and arrangements are not meant to be limiting.

Figure 13:
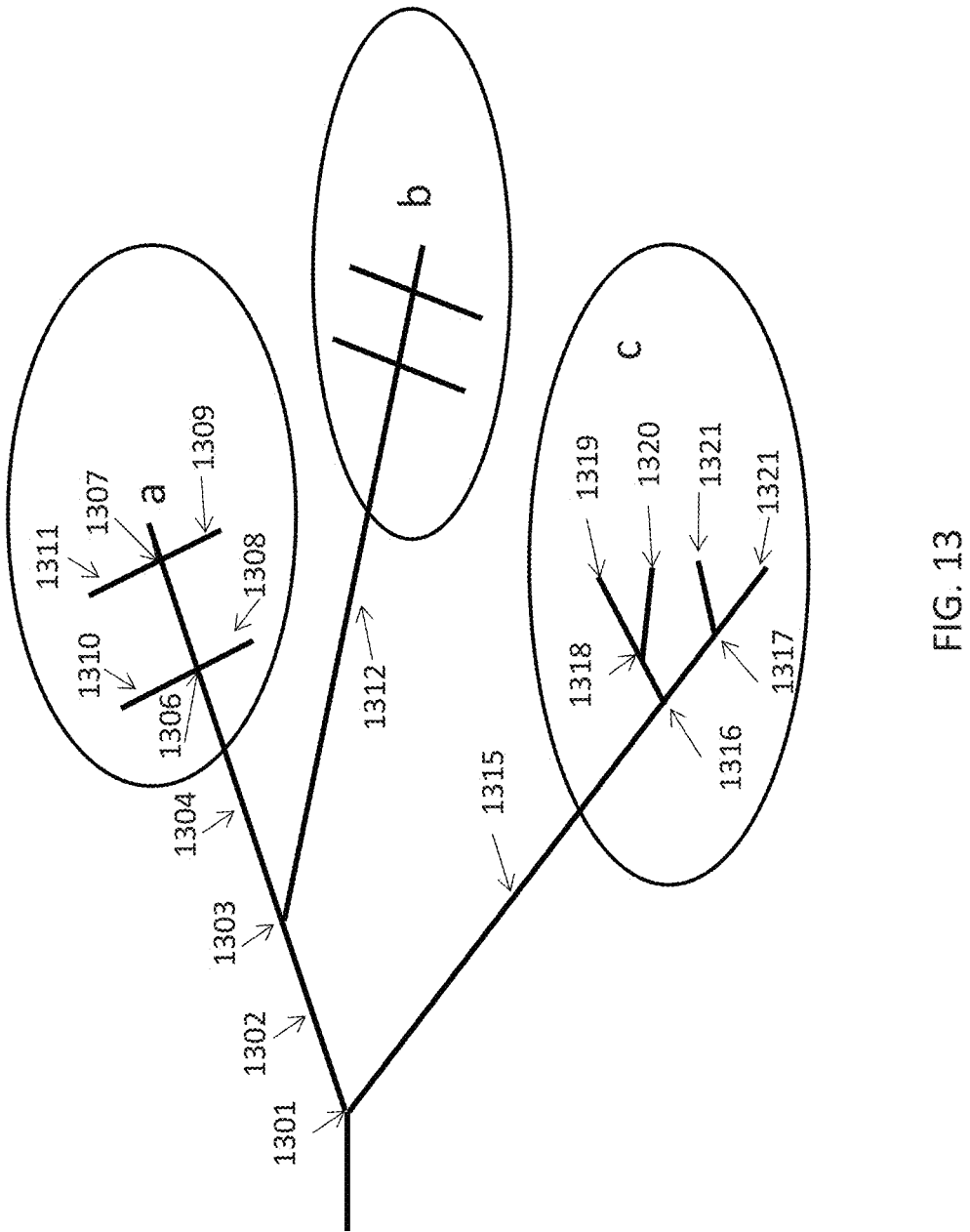
FIG. 13 provides an illustrative example of a microfluidic device with a plurality of reaction zones. Units distributed into the different reaction zones may undergo the same reaction, different reactions, or no reaction. Reactions may occur simultaneously, consecutively, or at different times.

FIG. 13 provides an illustrative example of applying the same or different conditions to units in separate branches or channels. The same, or different, reaction conditions may be applied to each branch or channel. Distributing units into additional branch channels may occur by any of the methods described herein. Distributing units into these additional branch channels may be same or different as methods used in other branches or channels in the same device. For example, FIG. 13 illustrates a device in which units may be distributed at a first branch point 1301, into branch channels 1302 or 13015. Units within branch channel 1302 may be further distributed at branch point 1303 into branch channels 1304 or 1312. Finally units may be further distributed into terminal branches, for example at branch points 1306 and 1307 into terminal branches 1308 or 1310, and 1309 or 1311 respectively (shown in region (a)). Separately units in branch channel 1315 may be further distributed through branch point 1316, 1317, and 1318 into terminal branches 1319, 1320, 1321, 1322 (shown in region (c)). The method of distributing at branch points may be different. For example, branch points 1301, 1303, 1316, 1317, 1318 may use a moving mechanical distributor, whereas distributing at branch points 1306 and 1307, as well as the terminal branches of branch 1312, may be achieved by modulation of the fluidic pressure in the terminal branches via a connected pressure regulator and/or pump.

All of the units within terminal branches 1308, 1309, 1310, 1311 may receive the same treatment or reaction, while all of the units in the terminal branches of branch channel 1312 may receive a different treatment or reaction, and all units of branch 1315 may receive a third treatment or reaction. In some embodiments, all of units in terminal branches 1308, 1309, 1310, 1311, 1319, 1320, 1321, and 1322 may receive the same treatment or reaction. The treatment or reaction in the terminal channels may happen at the same time, or may happen at different times. The treatments or reactions may happen consecutively, e.g., the units in region (a) may undergo a treatment or reaction, then the units in region (b), and then the units in region (c). Some units may not receive any treatment or reaction e.g., the units in region (a) may undergo a treatment or reaction, but not the units in region (b). In some embodiments, differential treatments or reactions are performed in different terminal branches.

Figure 14:
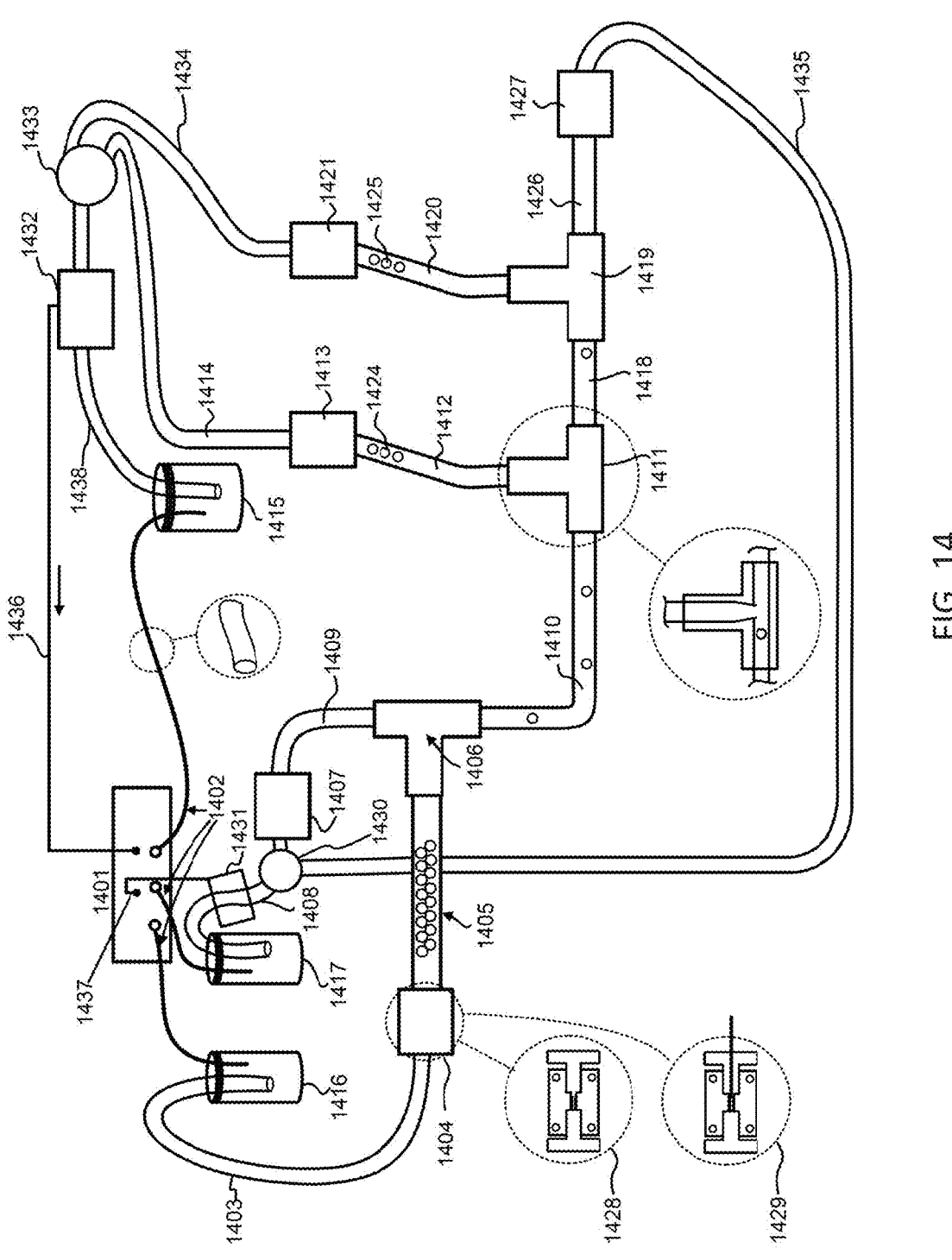
FIG. 14 provides an illustrative example of a microfluidic device with unit spacers wherein mobile units are distributed into two branch channels. The unit spacer(s), unit stop(s), and/or the pressure controller(s) and/or regulator(s) may be used to space and distribute units into branch channels and merge units from the branch channels.

FIG. 14 provides an illustrative example of a portion of a microfluidic device set-up for distributing units into two branch channels. Before being distributed into branch channels 1412 and 1420, units may be passed through two successive branch points 1411, 1419, which may be equipped with a unit spacer. Units may be initially packed and held in a first channel 1405, which may be equipped with a connector and unit stop 1404 at one end and a unit spacer 1406 at the other end. The connector may be connected to a carrier fluid reservoir 1416, for example via polymer tubing 1403. A second tube 1402 may be used to connect a pressure controller or pump to the fluid reservoir.

The polymer tube 1403 may be connected to a first channel 1405 via a connector 1404. The connector may be constructed form commercially available connectors, such as machined connectors (LabSmith), or custom constructed, via a suitable method including 3-D printing or any other suitable method known in the art. Units held in the first channel 1405 may be in a specific order or in a random order. The units may be in a stacked regime, wherein units may be held or flowed in direct contact with or in close vicinity of each other, or in a separated regime, separated by spacers of uniform or non-uniform length. Application of fluid pressure by the pressure controller or pump may result in units moving though the first channel and through the unit spacer 1406 into a second channel 1410. The second channel may be equipped with a connector and unit stop 1407 and may be connected to a fluid reservoir 1417 and the pressure controller, regulator or pump 1401 via additional tubing 1408, 1402. A two-way valve 1430 and a flow sensor 1431 may be placed between the second channel and the fluid reservoir 1417. In some embodiments, data lines are used to connect fluid sensors, such as 1436, 1437, to a pressure controller or regulator 1401. The fluid pressure or flow speed in a first channel 1405 may be the same or different than the pressure or flow speed in a second channel 1409, 1410. Units passing through the unit spacer 1406 into the second channel 1409, 1410 may be guided and separated from one another via the shear force of the flow in the second channel. This separation may be a predesignated distance that may be increased or decreased by increasing or decreasing the speed of the fluid flow in the second channel. The second channel may be long enough to hold a subset of or all of the separated units in the microfluidic device between a first spacer and a branch point or router. The length of the channel may be selected based on the size of the units, the number of the units, and the desired spacer length between units. Spacing the units in the channel may allow for retention of the units in a desired positional order in the device, e.g. as the units move within laminar or laminar-like flow or are stopped for suitable amounts of time that is not long enough to cause diffusion based mixing. Once the units are in the channel with spaces between them, the flow of the fluid from the first channel 1405 may be stopped by turning off or decreasing the pressure and/or pumping speed for that channel. The motion of the units may be stopped by similarly stopping the flow in the second channel. The units may be then moved through the device at a same rate or at a different rate, by turning on or increasing the pressure and/or pumping speed within the second channel 1410. Units moving through the second channel 1410 may be distributed into branch channels 1412, 1420 as they pass through a branch point 1411, 1419. In some embodiments, the branch points have spacer units 1411, 1419. Units may be distributed at branch points based on pressure differentials applied by connected pressure controller(s) and/or regulator(s) and/or by selectively activating flow through a desired branch channel(s) for example by using a two-way valve 1430, 1433. The two-way valve 1430, 1433 may connect to a fluid reservoir 1415. A fluid sensor 1431, 1432 may be placed between the two-way valve 1430, 1433 and the fluid reservoir 1415. To distribute units into the branch channels, as the units approach the first branch point, the pressure controller(s) and/or regulator(s) may be adjusted such that pressure is applied toward branch point 1411, both from the upstream 1410 and downstream 1418 portion of the second channel, focusing the carrier fluid and/or units at branch point 1411. The pressure on branch channel 1412 may be decreased to guide the carrier fluid and/or units toward branch channel 1411. In some embodiments, flow through the selected branch channel is activated while flow through unselected branch channels is de-activated, for example via a selector valve, such as the two-way valve 1430, 1433. In some embodiments, other types of fluids, such as fluids carrying reagents or other components designated for treatments within a branch channel or reaction chamber (e.g. enzymes, solvents etc.) are similarly directed at branch point(s) The unit(s) may be stopped in the branch channel by a unit stop 1413. As a second unit approaches the first branch point, the pressure on the second channel 1410 may be kept at a value such that the unit passing through the branch point passes down the second channel 1418. As the second unit approaches the second branch point 1419, the pressure on the first channel 1410 may be increased or flow through the first branch channel may be de-activated reducing or eliminating flow through the first branch channel. The pressure in the second branch channel 1420 may be decreased relative to the second channel or flow through the second branch channel 1420 may be activated, e.g. via connected pressure controller(s) and/or regulator(s) or selector valves, drawing fluid and/or unit(s) from the second channel into the second branch channel 1420. The unit may be stopped inside the branch channel by a unit stop 1421. In some embodiments, units are held in the branch channels 1412, 1420 by the continuous flow of fluid toward the unit stop via a pump connected to each branch channel. The units may be prevented from progressing farther down the branch channel(s) 1412, 1420 by the use of a physical block, which may be implemented via unit stop(s) 1413, 1421. Units may be prevented from travelling back down to the second channel 1410, 1418, 1426 by the use of forward flow of fluid from the second channel into the branch channel(s).

Single or multiple units may be distributed into the branch channels 1412, 1420. The units may be distributed individually, e.g., one individual unit may be directed into the first branch channel and a following individual unit directed into the second branch channel. In some embodiments, units are distributed into branch channels in groups, e.g., three units in a row may be directed into the first branch channel and the following two units directed into the second branch channel. Alternatively, a single unit may be directed into the first (or second) branch channel and a group of following units may be directed into the second (or first) branch channel. Units distributed into the branch channels need not be equal in numbers, e.g., ten units may be distributed into the first branch channel and 100 units may be distributed into the second branch channel. Each branch channels may be configured to be as long as necessary to hold a desired number of units. The branch channels may or may not be of the same length. Once the units have been distributed into the branch channels, they may be modified via chemical, physical, or light treatments as described elsewhere herein.

Units may be released from the branch channels 1412, 1420 into the second channel. Pumps and/or pressure controllers connected to the branch channels may be adjusted such that the flow is directed toward the second channel 1410, 1418, 1426. Units may be redistributed at the branch points 1411, 1419, e.g. by turning on flow through one branch channel 1412, 1420 at a time and/or by adjusting differential pressures on the branch channels as well as the connecting portions of the second channel and by directing the flow of the fluid and/or the units in the branch point into the desired direction of the second channel. Units in a branch channel may be flowed into the second channel individually or as a group. Units in one branch channel may be merged with units from a second or third branch channel by alternatively flowing units from one branch channel, then from the other branch channel into the second channel.

Figure 15:
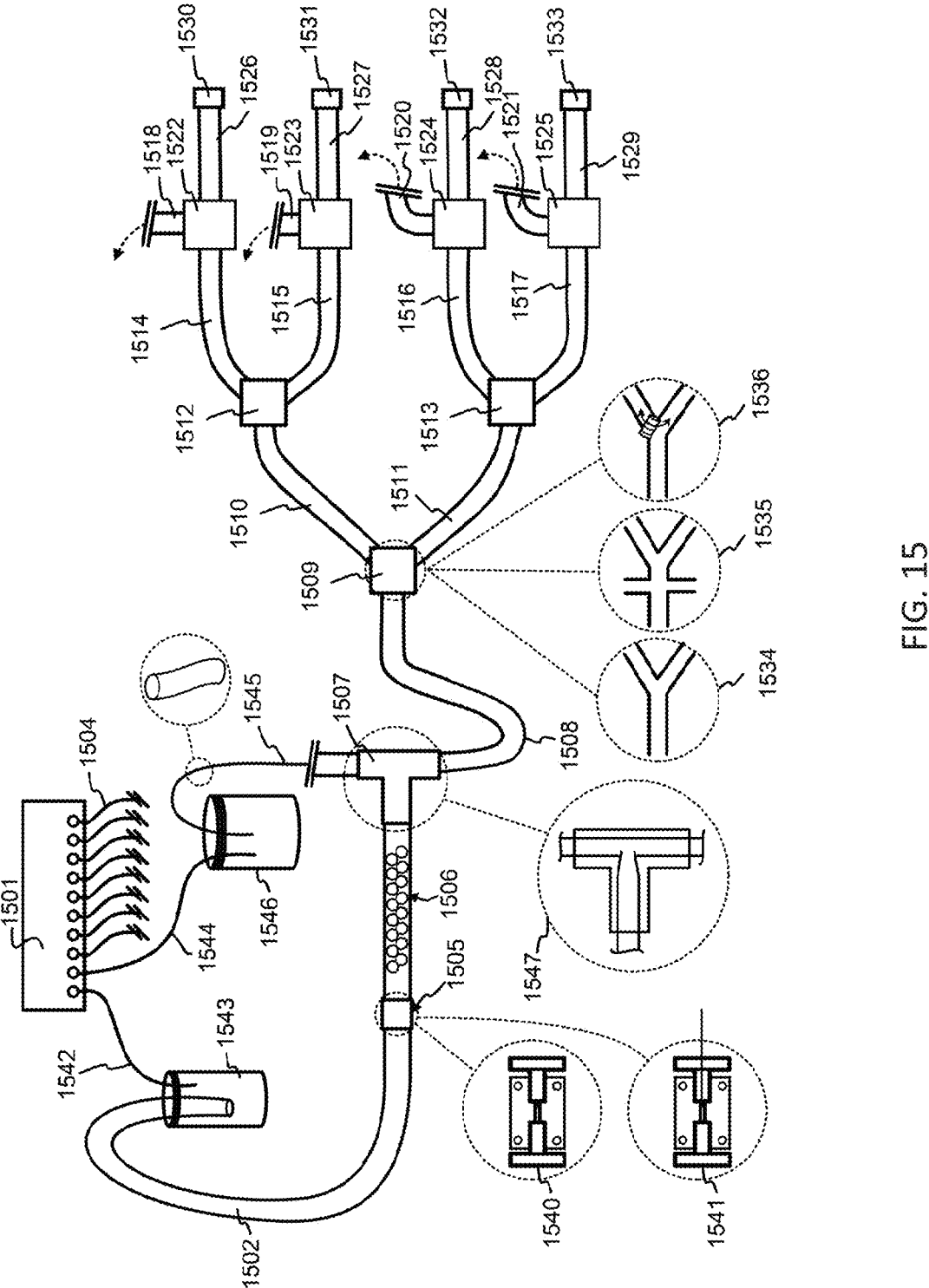
FIG. 15 provides an illustrative example of a microfluidic device wherein mobile units are distributed into four branch channels passing through a spacer and two sets of successive routers, e.g. distributors.

FIG. 15 provides an illustrative example of a microfluidic device wherein mobile units are distributed into four branch channels 1514, 1515, 1516, 1517 passing through two successive branch points 1509, 1512, 1513. Before being distributed into branch channels 1514, 1515, 1516, and 1517, units may be passed through two successive branch points 1509, 1512, 1513. A connector and/or unit stop 1505 may be connected to a carrier fluid reservoir 1543, for example via tubing 1502. A second tube 1542 may be used to connect a pressure controller or pump 1501 to the fluid reservoir 1543. As described for the illustrative example in FIG. 14, the first channel 1506 may hold units in a specific order or in a random order. The units may be in a stacked regime, or in a separated regime, wherein they may be separated by spacers of uniform or non-uniform length. The units may be moved though the first channel and the unit spacer 1507 into a second channel 1508 by the application of fluid pressure by pressure controller 1501 and/or the pump. The second channel may be connected to a pressure controller port 1501 and/or pump as shown in FIG. 15. The pressure on the first channel may be selected to cause positive fluid flow towards the branch point or spacer 1507. The pressure on the second channel may be selected to cause in positive fluid flow towards the first branch point 1509 downstream of the spacer 1507. As the units pass through the spacer 1507 into the second channel 1508, the shear force of the flow in the second channel may result in separation of the units from one another. Similar to the example illustrated in FIG. 14, the length of the second channel may be selected as long as is necessary to hold a subset of or all of the units in the device with spacers of desired length between the units. As the units approach the first branch point 1509, they may be distributed into one of the two branch channels 1510, 1511. Any distributor described herein or any suitable distributor known in the art may be placed and/or used at the branch point 1509. Shown are three exemplary channel arrangements 1534, 1535, 1536 for the branch points 1509, 1512, 1513. 1534 shows an unobstructed branch point configuration in which the units may be distributed, e.g. by altering the lateral position of the unit in the flow via application of electrophoretic, magnetic, optical, or acoustic forces on the unit or by adjusting the relative pressures on channel 1508 and branch channels 1510, 1511. In this arrangement, upstream of the branch point a force may act on a unit approaching the branch point to move it within the flow laterally toward one side of a channel containing the unit, guiding the unit into the desired branch channel. 1535 shows a channel with inlet ports that may be used to apply side flow or pressure on a unit(s), moving the unit(s) laterally to a desired position within the flow. Similar to 1534, the side flow or pressure may be placed upstream of the branch point, prepositioning the unit to move into a desired branch channel. 1536 shows a moving mechanical distributor placed at the branch point. Activation of the moving mechanical distributor may start or stop the flow of fluid, e.g. carrier fluid, reagents etc., and/or any units therein down a branch channel 1510, 1511. Same or different types of routers, e.g. distributors, may be used in each branch point within a microfluidic device according to various embodiments of the methods and systems described herein. As the units approach the branch points 1509, 1512, 1513 activation of the routers, e.g. distributors, may result in distributing or steering of the units into one of the four branch channels 1514, 1515, 1516, 1517. Units may be held in position, e.g. between or behind branch points or inside channels, such as branch channels, by a unit stop 1505, 1530, 1531, 1532, 1533, and/or by the application of suitable pressure differentials in connecting channels through the ports of the pressure controller 1501 to guide units into the branch channels, away from the branch points. Exemplary unit stops are shown in 1540, 1541. 1540 depicts a unit stop configuration comprising a constriction point in a channel, e.g. a weir, allowing for passage of fluids, but blocking units. Unit stops having constriction points may be constructed using a variety of methods, including without limitation by 3D printing a capillary connector. An illustrative implementation of the 1540 unit stop configuration is show in FIG. 22A. 1541 depicts a unit stop configuration by insertion of a volume-exclusionary object, such as a wire, peg or stop. An illustrative implementation of the 1541 unit stop configuration is show in FIG. 24 depicting a unit stop constructed by inserting a wire inside a capillary channel. Lines 1518-1521 and/or lines (not shown) connecting to unit stops 1530-1533 connected to the branch channels 1526, 1527, 1528, 1529 may be used to control or regulate pressure on fluidically connected channels, to deliver reagents, and/or to circulate units within the microfluidic devices described herein. Routers, such as unit spacers 1522-1525 may be used to connect lines 1518-1521 to branch channels 1514-1517. Fluids for the application of treatments and reaction conditions may be added to the branch channels by reagent inlets, e.g. via lines 1518-1521 and/or lines (not shown) connecting to unit stops 1530-1533 connected to the branch channels 1526, 1527, 1528, 1529. In some embodiments, units are held in the branch channels without undergoing a reaction. The units may be released from the branch channels and re-routed or returned to the second channel 1508 and/or the first channel 1506. To return the units from the branch channels, first pressures on the channels connecting to branch points 1512, 1513 may be set such that the pressure differential would allow for a unit from one of the selected branch channels 1514, 1515 and 1516, 1517, respectively, to move into the branch channels 1510 and 1511, respectively. Lines 1518-1521 and/or lines (not shown) connecting to unit stops 1530-1533 connected to the branch channels 1526, 1527, 1528, 1529 may be connected to a pressure controller or regulator, via tubing 1504 and a fluid reservoir (not shown). Pressures may be set, for example, via channels 1518, 1519, 1520, 1521 connected to the branch channels 1514, 1515, 1516, 1517 and/or via channels (not shown) connecting to unit stops 1530, 1531, 1532, 1533 (not shown) connected to the branch channels 1526, 1527, 1528, 1529. The attachment of the inlet channel may be configured such that the positive fluid flow from the inlet channel is directed down the branch channel 1514, 1515, 1516, 1517 towards the branch channels 1510, 1511. Units may be flowed out of the branch channels individually, e.g. by sequentially altering the flow from the inlet channel 1518, 1519, 1520, 1521. Units may also be flowed out of the branch channel in groups, such that, e.g. all the units held in one of the branch channels 1514, 1515 are returned to the branch channel 1510, followed by all the units from a second branch channel, and so on. Units from branch channels need not be released in the order of the branch channel, e.g. branch channel 1514, then 1515, then 1516, and finally 1517, and may be released in any desired order such as e.g., 1516, then 1514, then 1515, and then 117 or in any desired permutation of branch channels.

Units released from the branch channel 1526, 1527, 1528, 1529 may be rerouted, e.g. merged, at the branch points 1512, 1513, 1509 by any routing technique described herein or any suitable routing method known in the art. Once in the second channel 1508 the units may be returned to the first channel 1506, held in second channel 1508, and/or rerouted, e.g. redistributed, back into any branch channel(s) in any order as desired.

Figure 40:
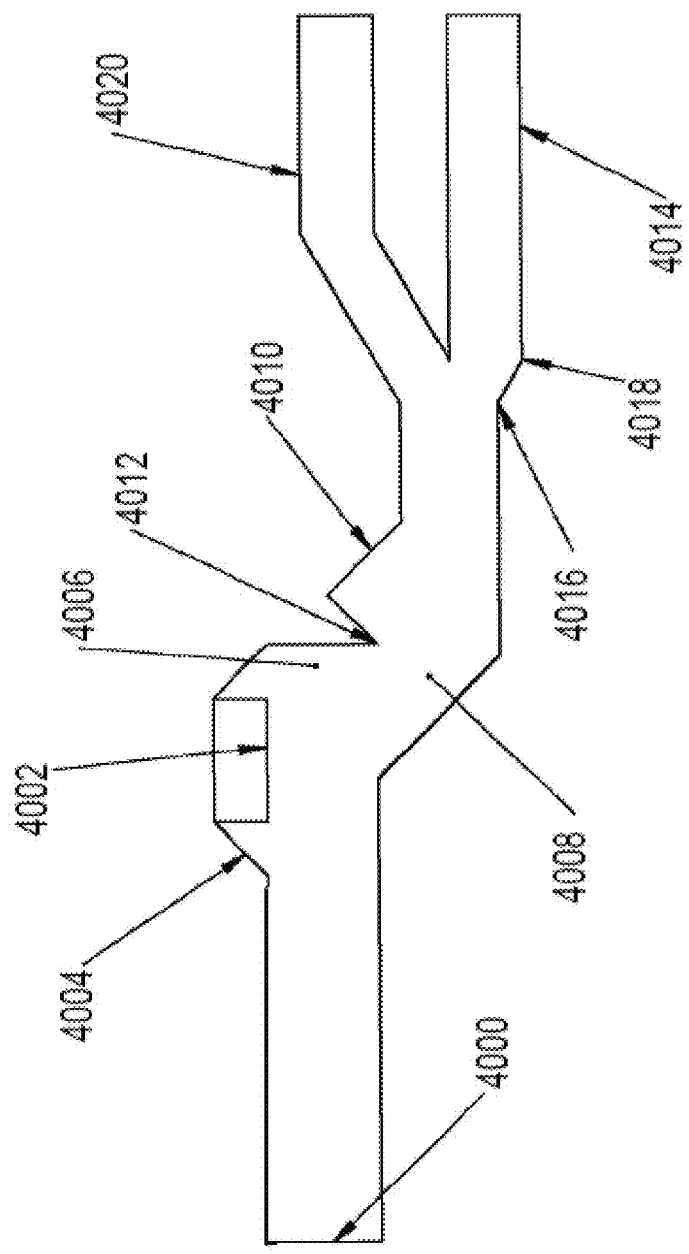
FIG. 40 depicts an exemplary illustration of a router configured to route units into a plurality of branch channels using bubbles generated by a microactuator.

FIG. 40 provides an illustrative example of a microfluidic device comprising a first primary channel 4000 configured for receiving a plurality of mobile units, such as beads. A thermal bubble actuator comprising a microheater 4002 is configured to generate bubbles for selectively displacing liquid around a mobile unit and thereby creating a flow stream. The thermal bubble actuator may comprise a number of thin film layers on top of a glass substrate. The thin film layers may include a first 150 nm thick passivation layer (e.g., silicon nitride), a 100 nm thick resistor (e.g., titanium), a second 150 nm passivation layer (e.g., silicon nitride, and a 250 nm anti-cavitation layer (e.g., tantalum). The microheater 4002 is positioned in a recess 4004 off the top wall of the input channel 4000. Downstream of the recess the top wall of the channel makes a 90° turn 4006 inward toward the center of the channel, continues for 100 μm, then makes a 90° turn 4008 outward toward the outer portion of the channel. Immediately downstream of the turn 4008 there is a triangular recess 4010 on the top wall of the channel such that an acute angle edge 4012 is formed between the turn 4008 and the triangular recess 4010. The triangular recess 4010 is 100 μm long and 40 μm wide. Downstream of the triangular recess 4010 and at the branch point of the branch channels 4014 and 4020, the channel makes a turn creating a pinched region 4018 that is 90 μm wide before reaching an open region 4018 that is 140 μm wide, and then splitting into two symmetric 60 μm wide branch channels 4014 and 4020.

As the units pass through the first primary channel 4000, the units may be aligned in the center of the first primary channel 4000 by flow focusing (e.g., inertial focusing). The velocity of the flow stream is between 1 m/s and 4 m/s, preferably 2 m/s. The thermal bubble actuator may be activated by applying an electrical pulse, e.g. an electrical pulse of 20 volts for 2 μs to the microheater 4002. Following activation of the thermal bubble actuator, the liquid in the channel adjacent to the microheater is rapidly heated. and the liquid may transition to gas, creating a vapor bubble that grows. The vapor bubble may collapse in a short time interval, e.g. in approximately 10 μs. Activation of the thermal bubble actuator may result in displacement of the liquid around the unit such that the unit is moved laterally with respect to the unit's direction of flow. The geometry of the channel and/or pressures in the channels may be biased such that all or substantially all undisturbed flowing units are routed into a branch channel. In the presence of a bubble generated by the thermal bubble actuator, the units may be moved laterally resulting in flow of the units into a second branch channel or chamber. Timing of activation of the thermal bubble actuator may be calibrated to cause incoming units to enter a designated branch channel or chamber. In some embodiments, a plurality of branch channels, e.g. a plurality of or of at least 2, 3, 4, 5, 6, 7, 8, 9, 10 or more branch channels) emerge from a branch point downstream of one or more microactuator(s) configured to selectively route flowing units into a desired one of the plurality of branch channels.

The microfluidic device may optionally comprise a vortex element configured to generate a vortex in a channel (e.g., a recess, turn, or protrusion). The vortex element may be in any form, geometry, or shape suitable for generating a vortex. As a bubble generated by a bubble actuator grows, the flow of the liquid may cause a vortex to form, e.g. near the channel wall at or adjacent to the vortex element, such as at the triangular recess 4010. The vortex may be removed from the flow stream and/or may minimally interact with the units as the bubble grows. When the bubble collapses, the flow stream may create a routing vortex, e.g. around the acute angle edge 4012. As the routing vortex moves downstream with the units in the flow stream, the units may be moved laterally a greater distance than they are moved in the presence of a vapor bubble alone.

FIG. 16A provides an illustrative example of a detection system. A channel, e.g. a capillary channel, 1612 may be configured to allow for flow of units within the channel, for example from a unit suspension 1603 driven by the actuation of a syringe pump 1602 connected to the channel 1612. As the units flow through the channel 1612, they may pass a detection point of a detector, for example and optical detector, comprising a source fiber 1607 and a receiver fiber 1608. The source fiber and receiver fiber may be abutting or touching the channel 1612. In some embodiments, there is a gap between the ends of the source and/or receiver fiber and the channel 1612. The source fiber 1607 may be connected to a source generator such as a laser diode and controller 1601, or any other optical or non-optical component as described elsewhere herein or a suitable component known in the art. The receiver fiber 1608 may be connected to a signal detector 1604 that can be configured to receive the signal generated by the units in channel 1612. For optical detection systems, a laser diode, lamp, or LED may be used to produce a light source. The light source may be transmitted via the source fiber, through the capillary channel at the detection path 1613. The emitted light from the detection 1613 path may be transmitted to the detector via the receiver fiber. The light source may be modified by units passing through the detection path 1613, e.g. by absorption, emission and/or scattering or lensing, resulting in a signal, e.g. the signal shown in 1606. Non-optical detectors may or may not have a source fiber. The detection systems described herein may be configured for detection of units from any region (e.g., point region, region of interest, global region) in the microfluidic devices described herein, such as before or after any branch point, at any point in any channel or branch channel, before or after a unit spacer, before or after a reaction chamber, and/or at a unit output point. The signal detector may be connected to a computer 1605 that may be configured to receive the detection signal generated by the units and detector, and produce a readable signal output 1606 of the units. The signal generated by a single unit 1609, a unit double (i.e. two directly abutting units or units lacking a desired amount of separating spacing) 1611, a unit triplet 1610, or a unit n-tuplet may be recorded by the detector 1604 and computer 1605 and may be distinguishable from each other by the detection systems described herein.

Figure 16B:
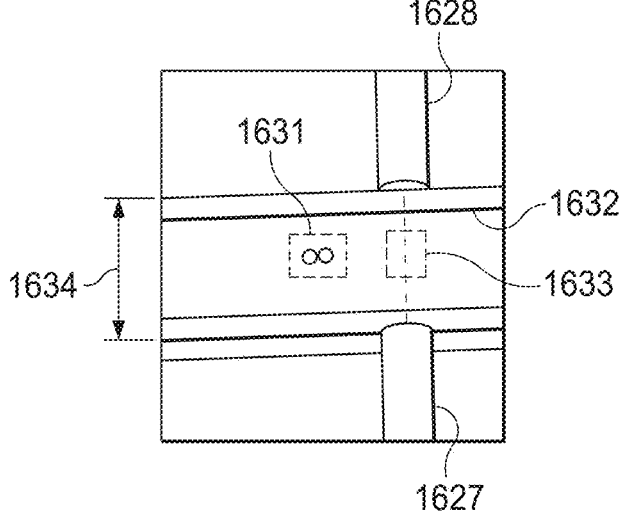
FIG. 16B provides a photograph of a unit doublet traveling through an optical detection system.

FIG. 16B provides a picture of an optical detector set up. A capillary 1634 and interior channel 1632 is shown horizontally, with a source fiber 1627 on the bottom of the figure and a receiver fiber 1638 on the top, each abutting the capillary channel. A unit doublet 1631 is in the capillary channel upstream of the optical path 1633 at the intersection of the capillary channel and laser light produced by the source optical fiber 1627.

Figure 21:
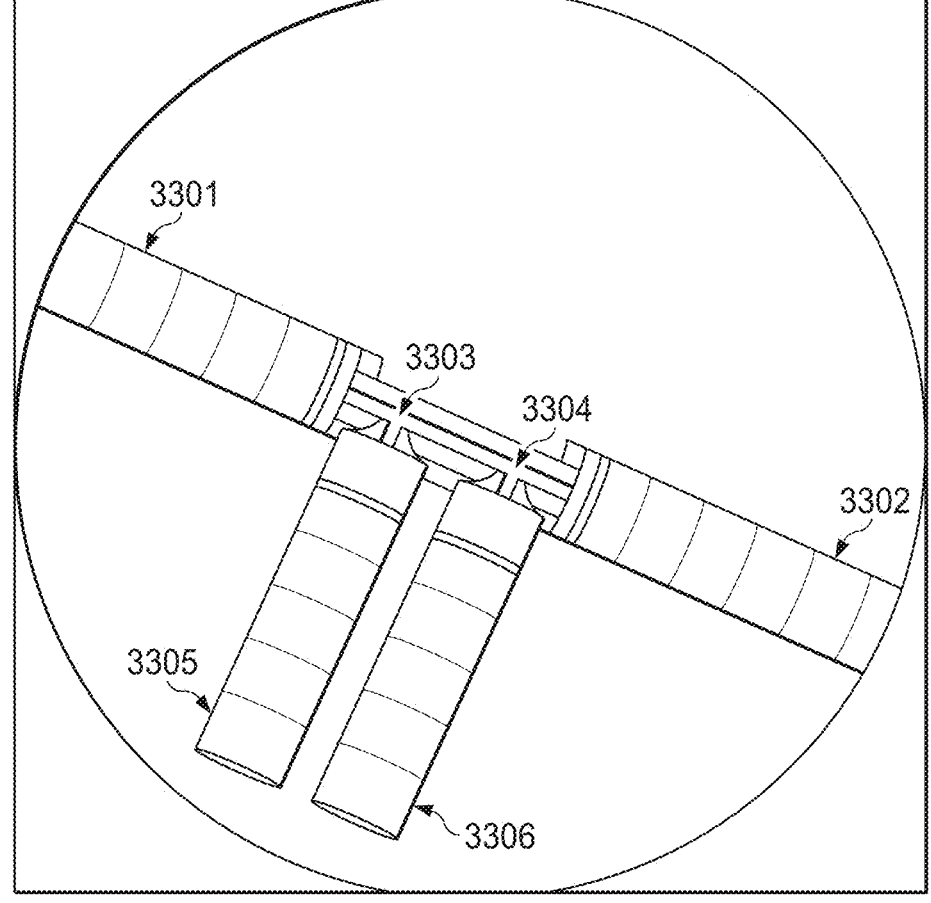
FIG. 21 provides an image of a double T-junction branch point.

FIG. 21 provides an image of a double T-junction spacer and branch point. A capillary can be inserted into a channel sleeve 3301, 3302 with two consecutive branch channel T-junctions 3303, 3304 from the main channel. Branch channel capillaries can be inserted into the branch sleeves 3305, 3306.

FIG. 22 provides images of a unit stop (A), a unit spacer (B), and a unit spacer with polished capillaries inserted (C).

The unit spacer (B) and unit spacer with inserted polished capillaries (C) are illustrative implementations of the unit spacers described in FIGS. 14 and 15.

FIG. 24 provides images of a LabSmith union connector for use as a unit stop. Shown in panel A is the full union connector with a capillary inserted into tubing seat running through the connector. Shown in panel (B) is a close up image of the capillary 2403 inserted in to the tubing seat. On the left side, a wire 2401 has been inserted into the capillary, forming a unit stop. The right side of the capillary 2402 does not have a wire and can be used as a channel to hold carrier fluid and/or units as described in further detail herein. Units flowing into the capillary can be stopped by the wire. Panels (C) and (D) show a capillary without fittings showing an inserted wire that can be used as a unit stop.

Figure 25:
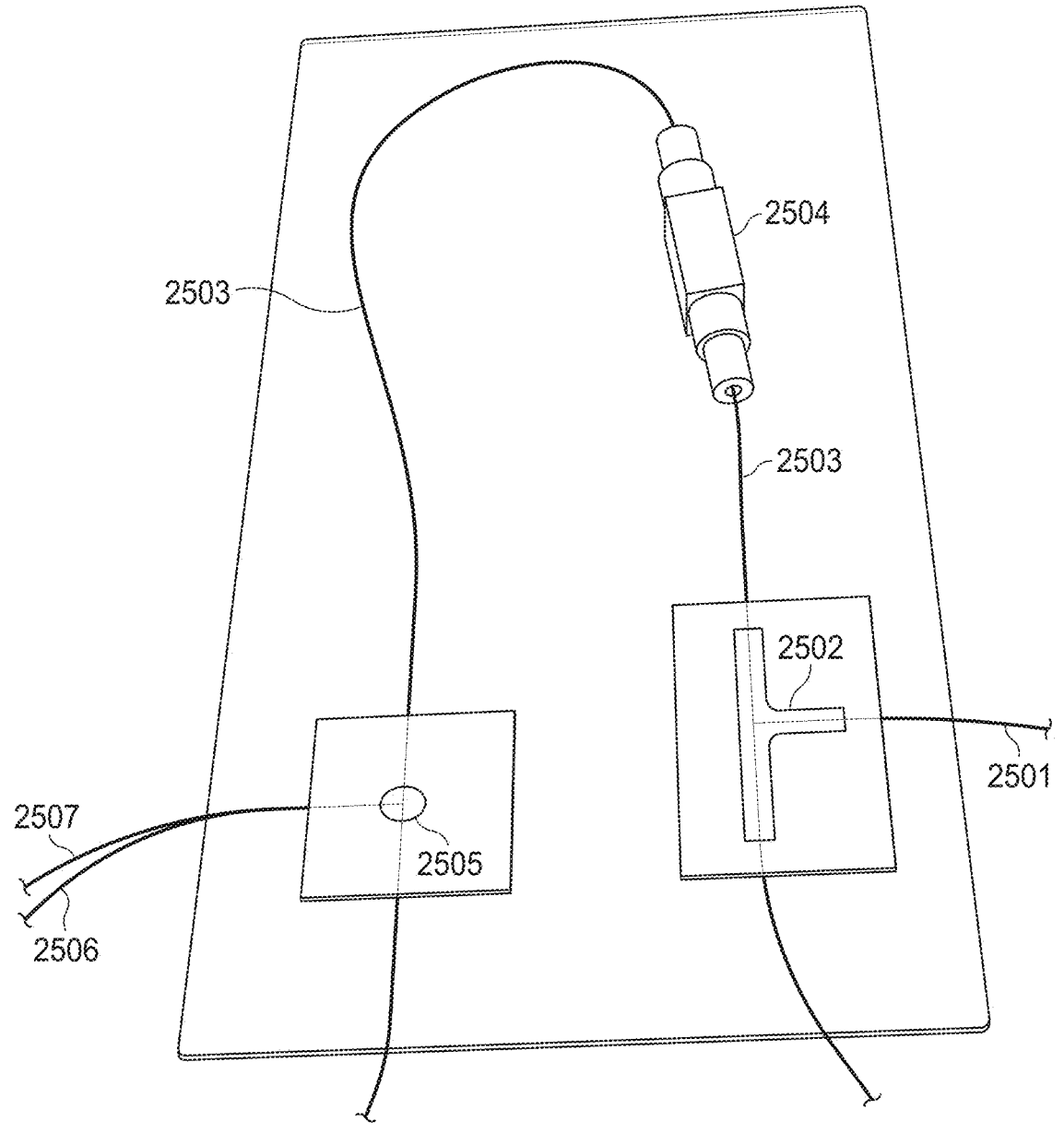
FIG. 25 provides an image of an exemplary positional encoding device.

FIG. 25 provides an image of an exemplary positional encoding device. The device is assembled from fused silica capillary tubing and one T-junction unit spacer and a double T junction branch point. The ends of each channel are connected to controlled fluid lines through unit stops. Units can be loaded into a first channel 2501 and flowed towards a branch point with a unit spacer 2502 which is connected to a second channel 2503. The fluid flow rates in the first and second channel may be different, e.g. the flow or pressure in the first channel may be slower or at a lower rate than the flow in the second channel. When the units reach the unit spacer, if the flow rate in the second channel is faster than the first channel, the unit entering the second channel will flow further before the unit immediately behind it enters the second channel, resulting in spacing of units in the second channel. In FIG. 25, the right ("top") and left ("bottom") portions of the second channel are connected with a union connector 2504. The units may be flowed in the second channel to a branch point. FIG. 25 shows to branch points 2505 configured as a double T-junction connecting the second channel 2503 with branch channels 2506, 2507, respectively. An exemplary double T-junction branch point is shown in FIG. 32. As a unit approaches the branch point 2505, pressure controllers connected to each of the branch channels may be used to adjust differential pressures, resulting in flow of the fluid and units therein into the first branch channel 2507. Alternatively, differential pressures on the connected channels may be adjusted such that the unit may be flowed past the opening to the first branch channel 2506 in the first branch point 2505, and flowed into to the second branch channel 2507 in the branch point 2505. In some embodiments, all the units flowing down second channel 2503 are flowed into the first branch channel 2506 or the second branch channel 2507. In some embodiments, some of the units are distributed into the first branch channel 2506 and some are distributed into the second branch channel 2507. Distribution path of each unit may be predesignated according to a desired algorithm. Unit stops as previously described may be placed in each branch channel to stop the units from travelling further. Units in the first or second branch channels 2506, 2507 may be returned to the main channel 2503 by flowing units in the branch channels toward the second channel. Units in the first and second branch channels 2506, 2507 may be returned to the second channel as a batch, e.g. all of the units in the first branch channel 2506 can be returned to the second channel, then all of the units in the second branch channel 2507 can be returned to the second channel. Alternatively, the units in the first and second branch channel 2506, 2507 may be returned to the second channel individually or a subset of the units in the first and second branch channel 2506, 2507 may be returned to the second channel in groups. Routing of units from the branch channels into the second channel may be accomplished by adjusting differential pressures on the channels. Units in the second channel 2503 may be returned to the first channel 2501 by passing through the unit spacer 2502.

Figure 26:
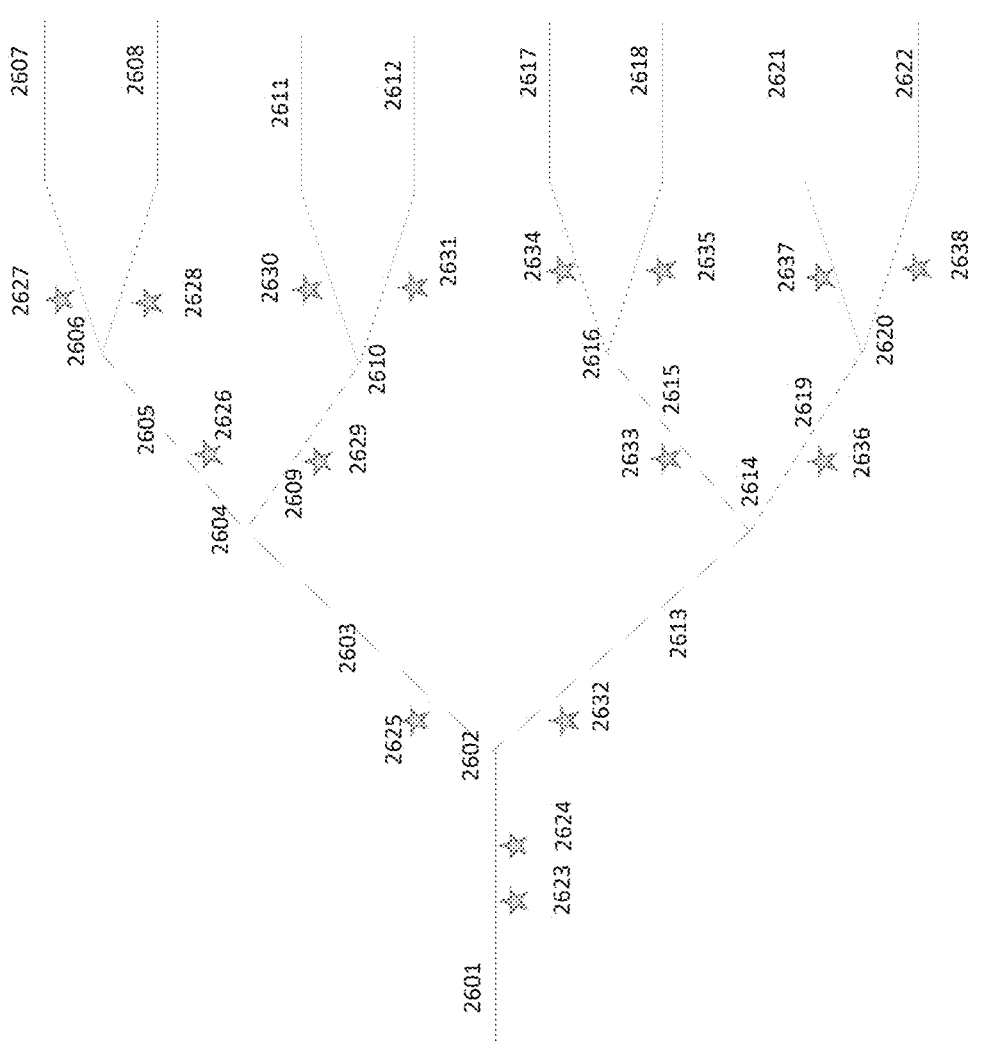
FIG. 26 provides a diagram illustrating exemplary error correction methods and devices in accordance with various embodiments of the invention.
Figure 27:
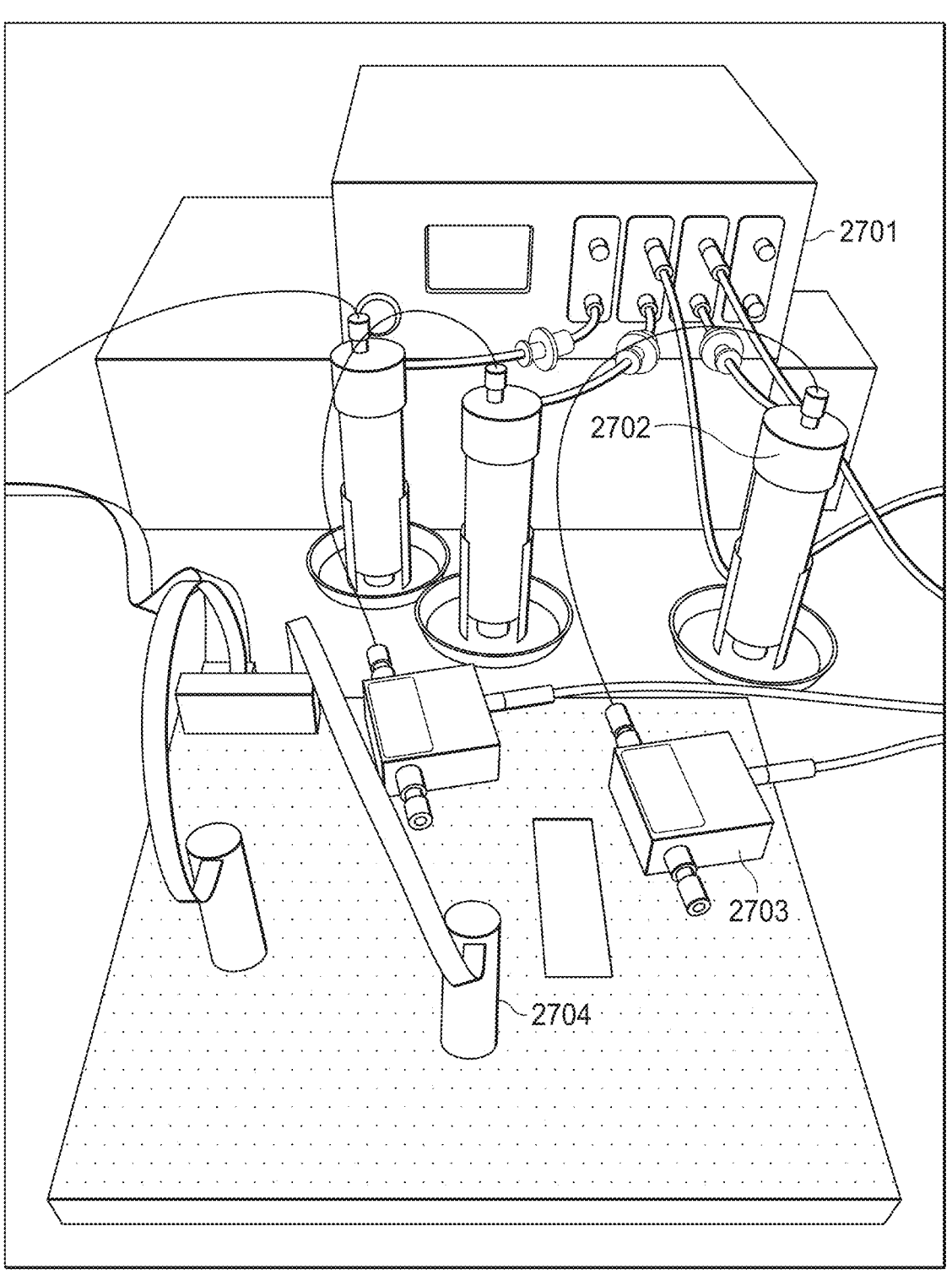
FIG. 27 provides an illustrative example of a microfluidic device and system comprising a multichannel pressure/flow controller (OB1 Mk3, Elveflow), fluid reservoirs, fluid flow sensors, and automated 2-way valves (LabSmith).
Figure 28:
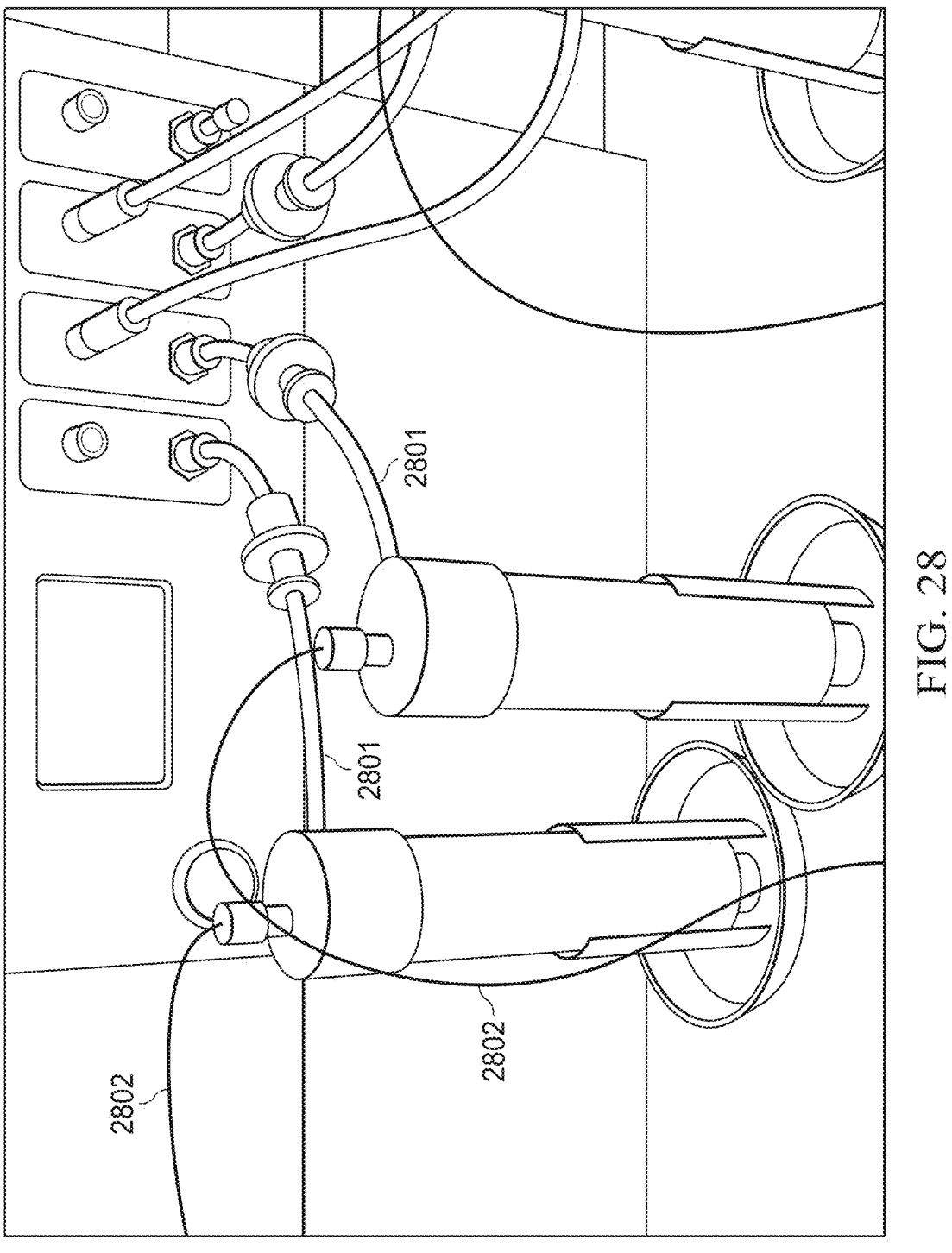
FIG. 28 depicts a close-up image of an illustrative microfluidic device and system focusing on the pressure controller and reservoirs. Shown are tubing from pressure controller outputs to reservoir caps through a filter and/or a liquid stop 2801, which are pneumatic lines that are configured to pressurize the reservoirs; and 360 um fused silica capillary fluid lines leading from top of reservoirs 2802.

FIG. 26 provides illustrative examples of microfluidic device configurations with channels represented by lines for holding units, including mis-routed units. Such mis-routed units may include without limitation units that are distributed in a different channel and/or path than a predesignated channel and/or path and units that flow without a desired spacing between them, such as units flowing in n-tuplets. Devices described herein may be configured to distribute units into branch channels or reaction chambers 2607, 2611, 2617, 2621, e.g. for chemical or physical treatments. Additional branch channels 2608, 2612, 2618, 2622, may be used to hold mis-routed units. The device may comprise detectors as shown by stars in FIG. 26, 2623, 2624, 2625, 2626, 2627, 2628, 2629, 2630, 2631, 2632, 2633, 2634, 2635, 2636, 2637, 2638. Detectors may be used to verify correct unit routing, e.g. distribution, in accordance with a predesignated routing algorithm. The device may have any type of router described herein or any other suitable router known in the art. The device may include various other components, including without limitation control elements, described herein. Detectors, indicated by stars, may be placed at any point before or after a branch point or on a channel.

Units may be loaded into a first channel 2601. The units may be separated (not shown) and routed past detectors 2623, 2624. Detectors 2623, 2624 and/or other detectors in the device may be used to distinguish single units from bubbles or double, triple, or n-tuple units as described in further detail elsewhere herein and/or to determine or verify unit velocity. Once detected, single units can be routed through subsequent branch points. Mis-routed units, including without limitation bubbles and/or double, triple, or n-tuple units, may be routed through branch points 2602, 2604, 2606, 2610, 2614, 2616, 2620 to one or more correction areas, e.g. chambers or outlet channels 2608, 2612, 2618, 2622. Corrective routing algorithms may be used to cause mis-routed units may be held permanently in correction area(s), may be discarded from the correction area(s), e.g. via outlet ports in fluidic communication with the correction areas, and/or may be merged with the remainder of the units within the device. All or a substantial portion of the units may be routed back to the first channel 2601. A corrective routing algorithm may be used to account for the mis-routed units. Corrective algorithms may be used to ensure that mis-routed units are distributed properly, according to a designated algorithm or an updated post-routing algorithm, and/or in a way that would mitigate or eliminate the effect mis-routing, during subsequent cycle(s). A corrective post-routing path may be created for one or more units according to a designated algorithm or an updated post-routing algorithm. Bubbles may be expunged through unit stops (not shown) located at the end of channels 2608, 2612, 2618, 2622. For example, double, triple, or n-tuple units, or bubbles may be routed to channel 2613 at branch point 2602, then to channel 2619, at branch point 2614, then to channel 2622 at branch point 2620. Bubbles are expunged through a bead stop located at the end of this channel (not shown) while units distributed into this channel can be merged with the rest of the units in a controlled manner in preparation for the next cycle. In various embodiments, no treatments or chemical reactions are applied in correction areas, such as the chambers or outlet channels 2608, 2612, 2618, 2622. Routing errors, including without limitation distribution errors, on individual units that occur at subsequent branch points may be detected using the detectors configured to detect signals from points before, at, or after branch points, such as in branch channels. For example, an individual unit with an intended destination of channel 2607 may be incorrectly directed into branch channel 2609 at branch point 2604. This incorrect distribution event may be detected at detector 2629. In response, the post-routing path of this unit may be updated to set a destination of the unit in channel 2612. The unit may be subsequently distributed into channel 2612 at branch point 2610 in accordance with the updated post-routing path and the unit may be registered as having reached its updated destination by detector 2631. In various embodiments, no treatments or chemical reactions are applied in correction areas, such as the chambers or outlet channels 2608, 2612, 2618, 2622. The individual unit may be merged with the remainder of the units in the microfluidic device after passing through channel 2612. The merged may be set up to prepare for a subsequent cycle of routing.

For another example of mis-routing comprising incorrect distribution, a unit intended for channel 2607 may be distributed into the incorrect channel, 2613, at the first branch point 2602. The unit may be assigned a new destination in channel 2622, where it may be held, e.g. in accordance with an updated post-routing algorithm. The unit may again be incorrectly distributed into channel 2621 at branch point 2620. The second incorrect distribution event may be detected by detector 2637. The unit may be subjected to the treatment or chemical reaction that is predesignated for channel 2621 and may be modified unit in an undesired manner and/or in deviation from a predesignated treatment or chemical reaction for the unit. The undesired modification on the unit may be recorded. The unit may be discarded and/or identified to carry the result of an updated set of treatments and/or reaction conditions at the end of the routing process.

EXAMPLES

Example 1: Positional Encoding Device Architecture

We constructed a system configured to perform loading, holding, and manipulating of units as an example of positional encoding within a microfluidic device. The system comprises a fluidic network and a flow control system that controls the fluid flow through the network, as depicted in FIG. 14. The fluidic network is constructed from fused silica capillaries (363 um OD, 50 um ID, Molex), capillary tubing connectors (CapTight connectors, LabSmith), and custom fabricated connectors.

The bead-containing portion of the network begins with a feeder channel 1405 that serves as both a loading channel and a repository for beads prior to bead rearrangement. This channel was connected to a main channel 1410 through a custom-fabricated T-connector 1406 that serves as a bead spacer. Two branch channels 1412, 1420 were connected to the main channel via additional T-connectors that were configured to service as bead spacers. Beads may be distributed into and held in these branch channels during a designated time in the operational cycle of the microfluidic device. During holding periods, the microfluidic device may be used to perform designated actions, such as delivery of reagents to branch channels holding the beads. Both of the branch channels were capped by bead stops 1413, 1421. The bead stops were configured as connectors that allow fluid to pass but not beads. Similarly, the feeder channel was capped with a bead stop 1404, which can be inserted following initial loading of the beads. Similarly, both ends of the main channel are configured with bead stops 1407, 1427.

Fluid flow within the network was controlled using a four-channel pressure control system 1401 (Elveflow OB1). The pressure control system was used to regulate the pressure within up to four fluid reservoirs that were connected via pneumatic lines 1402. The fluid reservoirs were also connected to the bead-containing channel network via additional tubing 1403, 1408, 1438. Two reservoirs 1416, 1417 connected directly to the feeder channel 1405 and the "top" of the main channel 1426, respectively, via bead stops 1404, 1427, respectively. The third reservoir connected via a flow sensor 1432 to a two-way selector valve (MV201, Lab-Smith) 1433 which was connected to branch channels 1412, 1420 via bead stops 1413, 1421, respectively, and which was configured to select through which branch channel 1412, 1420 flow would be activated. By setting the pressures on the channels via the three connected reservoirs and by selectively activated flow through the branch channels, we controlled the fluid and bead flow through the network.

FIG. 25 provides an image of the positional encoding device. The device was assembled from fused silica capillary tubing, one T-junction bead spacer, and one double T junction bead spacer. The ends of each channel were connected to controlled fluid lines through bead stops. Beads loaded into a first channel 2501 can be flowed towards a branch point with a bead spacer 2502, which was connected to a second channel 2503. The right ("top") and left ("bottom") portions of the second channel were connected with a union connector 2504. The beads can be flowed in the second channel to a branch point. FIG. 25 shows to branch point 2505 configured as a double T-junction connecting the second channel 2503 with branch channels 2506, 2507, respectively. An exemplary double T-junction branch point is shown in FIG. 21. As a bead approaches the branch point 2505, pressure controllers connected to each of the channels may be used to adjust differential pressures, resulting in flow of the fluid and beads therein into the branch channel 2506. Alternatively, differential pressures on the connected channels may be adjusted such that the bead may be flowed past the first opening in the double branch point 2505, towards the second opening in the double branch point, and into the second branch channel 2507 by adjusting differential pressures on the channels. Distribution path of each bead may be predesignated according to a desired algorithm. Beads in the first or second branch channels 2506, 2507 may be returned to the main channel 2503 by flowing beads in the branch channels toward the second channel. Routing of beads from the branch channels into the second channel may be accomplished by adjusting differential pressures on the channels. Beads in the second channel 2503 may be returned to the first channel 2501 by passing through the bead spacer 2502.

Figure 29:
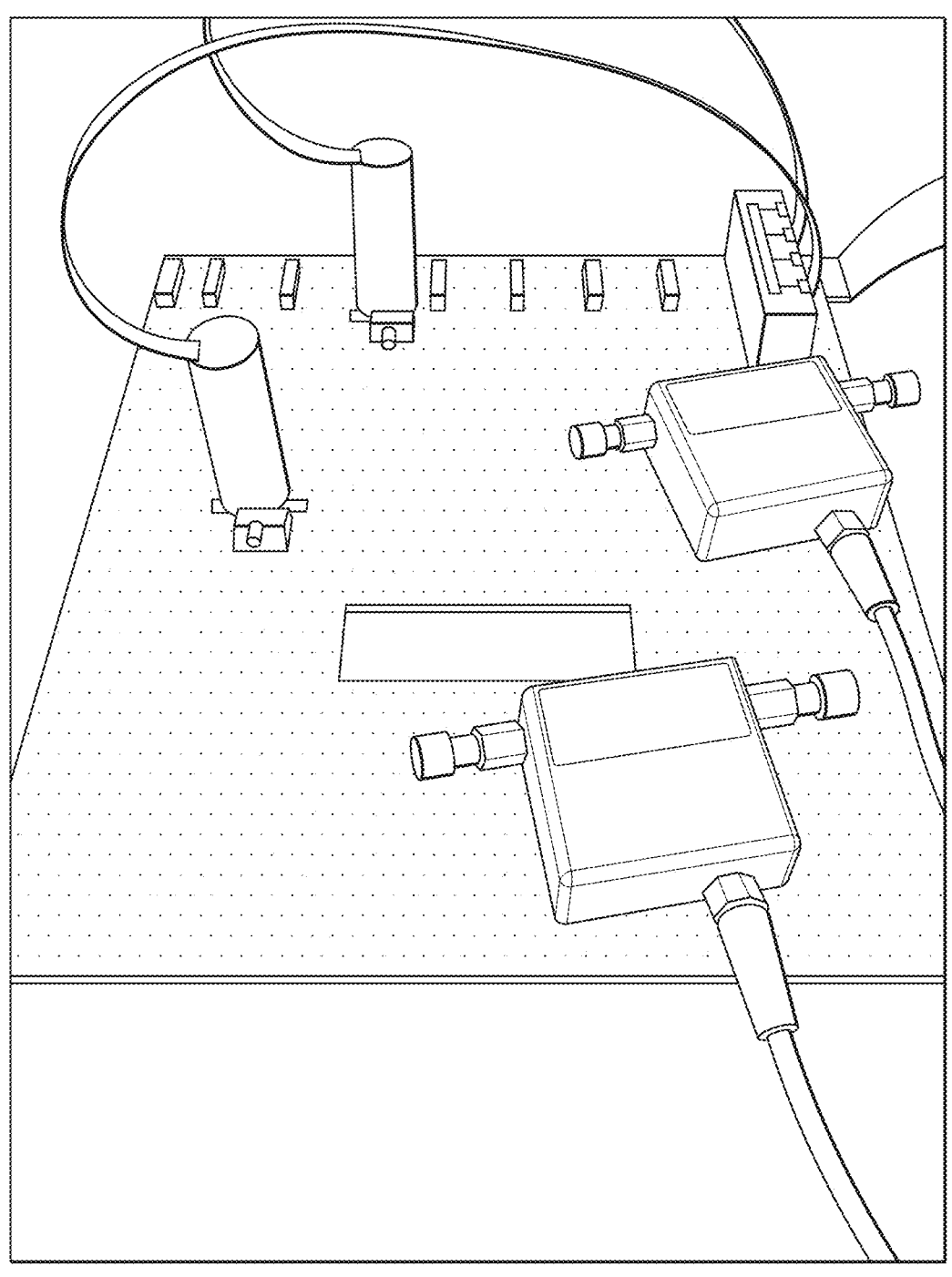
FIG. 29 depicts an illustrative fluidic breadboard with flow sensors and automated valves. Input fluid lines pass through the flow controllers to the two-way valves. Two-way valves route flow to different parts of the fluidic network. The left valve directs flow to the "top" or "bottom" of a main transport channel (the second channel in FIG. 25 described in further detail elsewhere herein.
Figure 30:
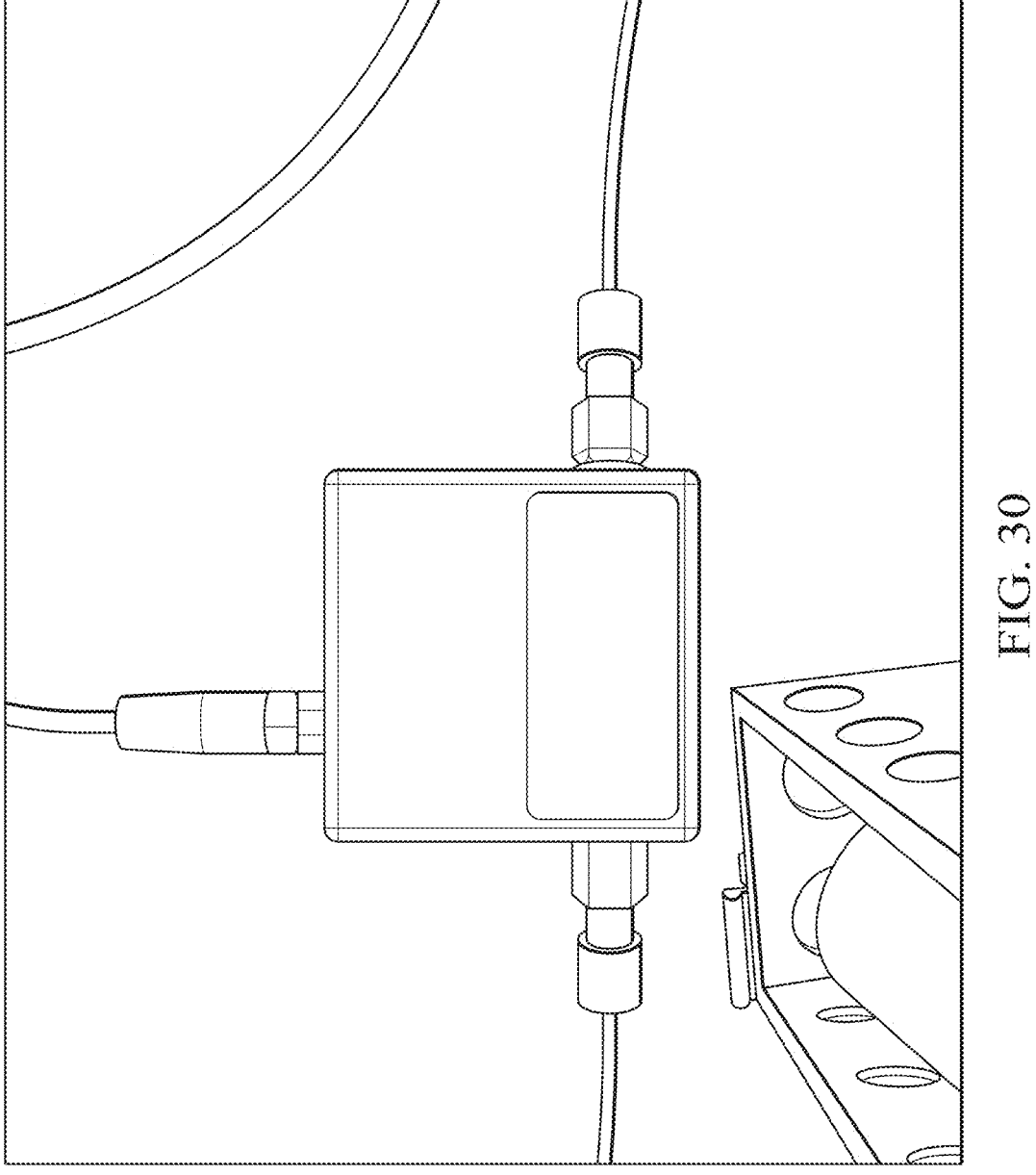
FIG. 30 provides a close-up image of a microfluidic fluid flow sensor (MFS, Elveflow). Top cable is configured to deliver fluid flow data to the multichannel pressure/flow controller depicted in FIG. 27. With the use of the flow sensor, the multichannel pressure/flow controller can be used to perform closed loop control of fluid speed by dynamically adjusting the applied pressure.

FIG. 29 depicts an illustrative fluidic breadboard with flow sensors and automated valves connected to the network shown in FIG. 25. Input fluid lines pass through the flow controllers to the two-way valves. Two-way valves route flow to different parts of the fluidic network. The left valve directs flow to the "top" or "bottom" of the second channel in FIG. 25.

Example 2: Positional Encoding Device—Bead Spacer

We first manually loaded a set of highly monodisperse 40 μm beads into the feeder channel 1405, capped the channel input with a bead stop 1404, and connected the other side of the bead stop to the channel's fluid control line 1403. Then, we directed flow in the main channel toward the top side of the main channel 1410, 1418, 1426 and applied pressure to the feeder channel via the reservoir 1416 and the main channel reservoir 1417.

Beads were fed through the feeder channel in a stacked regime. When abutting beads reached the T-connector, the cross-flow created separation between the beads as they entered the main channel 1410.

Snapshot images from a movie of beads being separated using a T-connector are shown in FIG. 23. We developed a bead spacer to address the challenges of manipulating beads within the stacked regime (i.e., risks of clogging and loss of positional encoding at changes in channel dimension, and difficulty sorting individual beads within a stack). We built spacers using two connector configurations, the T-intersection (FIG. 22B-C) and cross-channel geometries (FIG. 22D). Both geometries were constructed using fused silica capillaries (363 μm OD, 50 μm ID, Molex Inc.) and custom-fabricated connectors. The bead spacers include an input feeder channel, configured to that contains the beads, an exit channel, and at least one cross-channel that was configured to introduces the cross-flow for spacing flow beads. In other implementations (FIG. 22D), we used two cross-channels intersecting with the bead path running from the feeder channel into the exit channel through the cross-section. We built spacers using two connector configurations, the T-channel and cross-channel geometries. Both geometries were constructed using fused silica capillaries (363 um OD, 50 um ID, Molex Inc.) and custom-fabricated connectors. In variations of the embodiment shown FIG. 22D, without loss of generality, the spacing between the input feeder channel and the exit channel can be 1 μm or more, or $\frac{1}{100}^{th}$ of the bead width or more, etc. For instance, the spacing can be 1 μm, 2 μm, 3 μm, 4 μm, 5 μm, 6 μm, 7 μm, 8 μm, 9 μm, 10 μm, 20 μm, 30 μm, 35 μm, 40 μm, 50 μm, 60 μm, 70 μm, 80 μm, 90 μm, 100 μm, 200 μm, 300 μm, 400 μm, 500 μm, 600 μm, 700 μm, 800 μm, 900 μm, 1000 μm, etc.

The custom fabricated connectors were 3D printed by two-photon lithography using a Photonics Professional GT printer (Nanoscribe GmbH). The design of the connectors coupled the internal flow paths with sheaths into which the capillaries were inserted. Sheaths were designed to allow straightforward insertion of the capillaries while still constraining the position of the capillary to avoid occlusion of the 50 μm capillary channel where it mated with the internal channel of the spacer. For the T-connector spacer (FIG. 22C), the internal flow path was a 70 μm diameter channel. The sheaths for the main channel were intended for use with capillary from which the polyimide coating had been removed (diameter of 323 μm), and they tapered from 360 μm at the opening to 334 μm (allowing for a tolerance of 11 μm) where it intersected the main channel, to ease initial insertion yet still provide a tight tolerance on the final capillary position. The sheath for the feeder channel was designed to accept a tapered capillary (360 μm OD, 50 μm ID TaperTip, NewObjective), which intersected with the main channel to inject beads for separation.

To assemble the spacer, we first removed the polyimide coating at the end of the capillaries using a butane micro torch (ST500T, Bernzomatic) and cleaned with isopropyl alcohol. We then inserted each capillary fully into its sheath and applied UV curable adhesive (EMCAST 1823HV, Electronic Materials Inc.) onto the capillary at the edge of the sheath. Once the adhesive had wicked around the capillary within the sheath, it was cured using a 360 nm ultraviolet LED lamp.

In operation, fluid flow was established through the main channel and feeder channels using externally applied pressures from a multichannel pressure controller (OB1 MK3, Elveflow). Outward flow in the feeder channel drove beads toward the main channel. As beads exited the main channel, the shear or drag force from the cross flow in the channel accelerated the bead away from the following bead, introducing spacing. Individually flowing (i.e. spaced) beads could flow from the 70 μm diameter channel of the spacer into the 50 μm diameter lumen of the downstream capillary without issue. In contrast, beads without a spacing flow would typically remained stacked and would clog once they reached the channel contraction at the spacer/capillary interface. Spaced beads entering the 50 μm channel would speed up and become further spaced, as the additional fluid around the beads in the 70 μm channel squeezed incompressibly into the smaller channel.

The degree of spacing and shear force applied to the beads could be adjusted by increasing or decreasing the flow velocities in the main and feeder channels. Higher shear forces could can also be achieved at a given flow rate by decreasing the diameter of the main channel in the separator, subject to the limit of the capillary channel and the positional tolerance in mating the capillary with the separator.

Figure 23A:
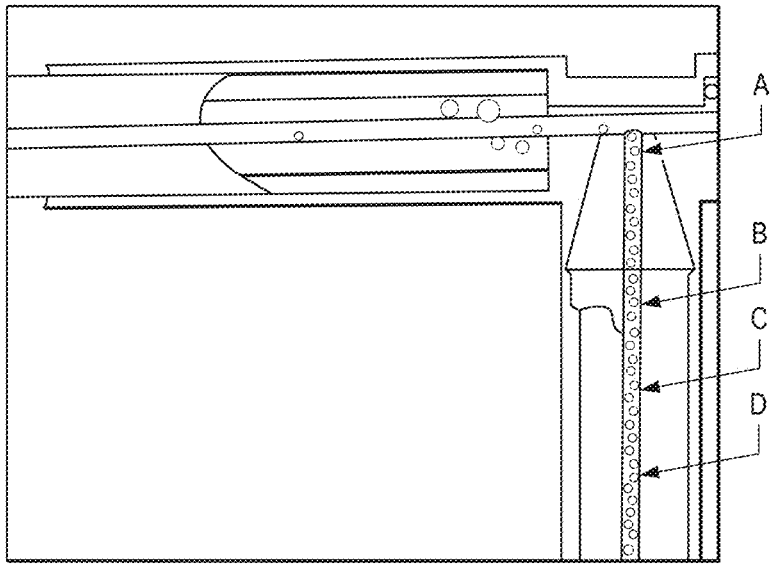
FIG. 23A-D provides snapshots from a movie of beads being separated by a unit spacer.
Figure 23B:
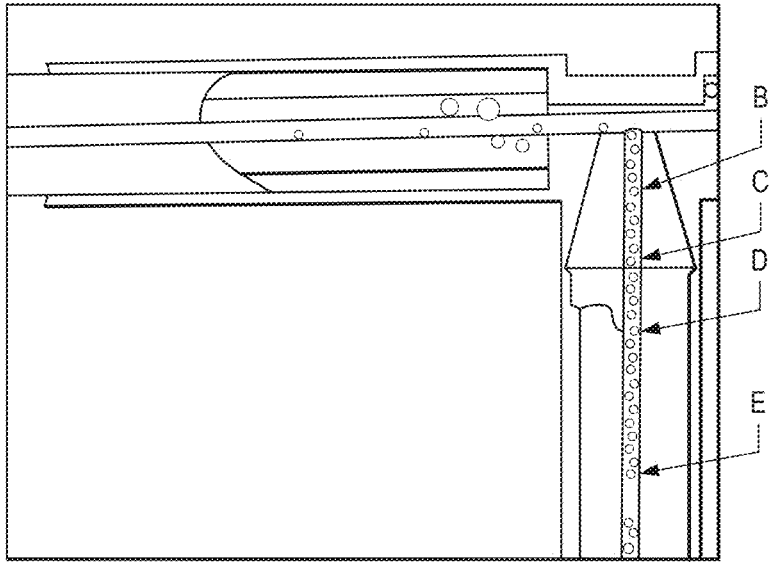
Figure 23C:
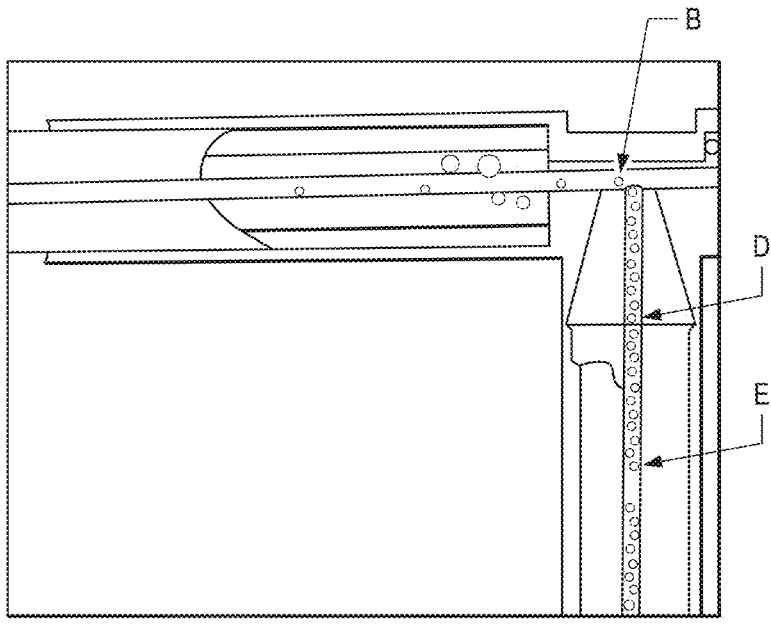
Figure 23D:
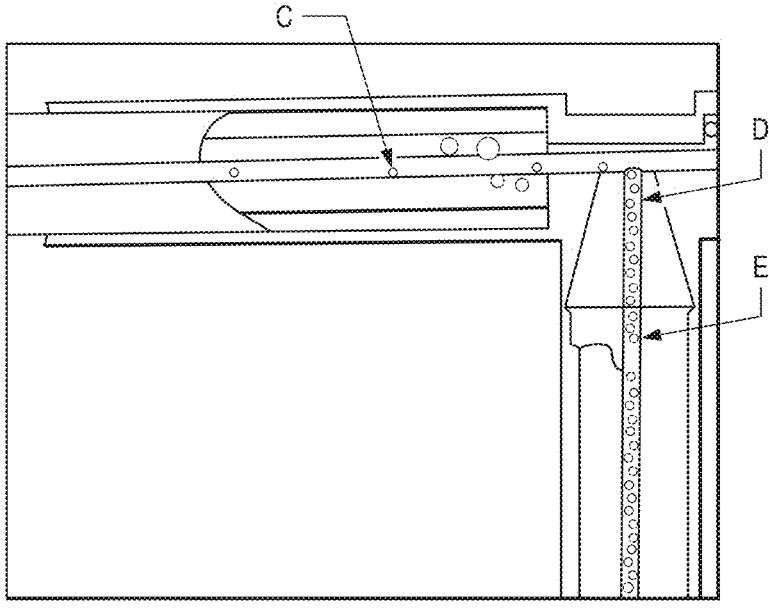
Figure 24A:
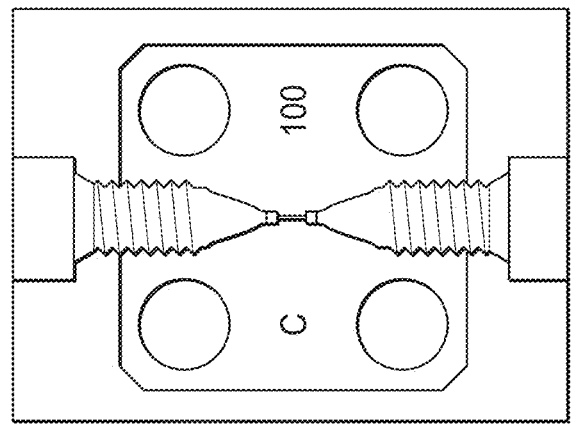
FIG. 24A-D provides pictures of (A) a unit stop constructed from a LabSmith union connector, (B) a close up image of the capillary, tubing, and wires in the unit stop of panel (A), (C)-(D) close up images of a wire inserted into a capillary for use as a unit stop with fitting removed, showing wire.
Figure 24B:
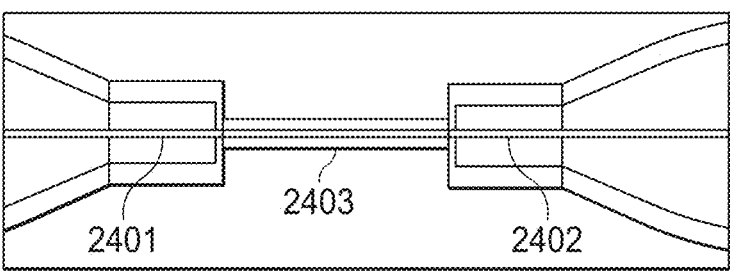
Figure 24C:
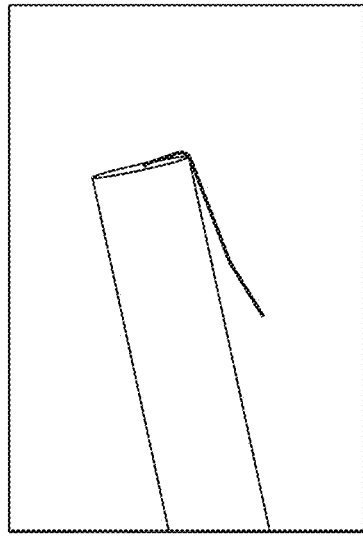
Figure 24D:
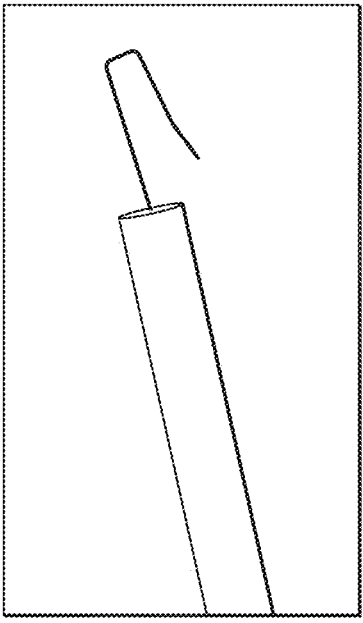

Beads were packed in a capillary in a stacked regime in the feeder channel, which was connected to a second channel via a T-connector. Arrows indicate various beads (a), (b), (c), (d), and (e) in FIG. 23A-D, as the beads were moved through the feeder channel and past the T-connector bead spacer into the second channel. As the units passed through the T-connector spacer, each bead was separated from the preceding and following beads in the second channel. FIG. 23A shows beads (a), (b), (c), and (d). FIG. 23B shows beads (b), (c), (d), and (e) after unit (a) had been flowed into the second channel, past the frame of the movie. FIG. 23C shows bead (b) at the T junction as it entered the second channel. FIG. 23D shows bead (c) further downstream (left) in the second channel with space between it and the beads before and after it. Unit (d) was close to entering the T-connector bead spacer.

Example 3: Positional Encoding Device—Bead Distributing

Beads within the main channel 1410 are flowed towards the branch channels 1412, 1420. We distribute beads into branch channels by adjusting the applied pressure on the main channel upstream and downstream of each branch point 1411, 1419 and by selectively activated flow within the branch channels 1412, 1420 via the two-way selector valve 1433 such that the carrier fluid distributed each bead into its preassigned branch channel. After a first bead enters its designated branch channel, the subsequent pressure configuration and branch channel activation is determined by the branch assignment of the next bead to be distributed. If this second bead is designated for the same branch channel, the applied pressures and the two-way selector valve setting is kept the same. On the other hand, if the second bead was designated for the other branch channel, we adjust the pressures on the main channel and the flow activation of branch channels in order to direct the flow and distribute the bead into the other branch channel. We continue this process until the last of the beads has was moved into its assigned branch channel.

Example 4: Positional Encoding Device—Delivery of Reagents in Branch Channels To demonstrate chemical synthesis, the branch channels 1412, 1420 described in EXAMPLE 1: Positional Encoding Device Architecture are configured such that selected reagents can be flowed into the branch channels.

Reagents are flowed through a network of channels into the desired branch channel by adjusting the pressures on carrier fluids flowing through the channels, similar to the pressure regulated distributing process described in EXAMPLE 3: Positional Encoding Device—Bead distributing. In an alternative device configuration, reagent delivery channels are configured to flow reagents into branch channels via separate access either directly or through access channels (not shown). Such reagent delivery channels can allow for parallel simultaneous application of alternative reaction conditions to multiple branch channels.

Example 5: Positional Encoding Device—Phosphoramidite Synthesis

A device with one of the branch channel configurations described in EXAMPLE: 4 Positional Encoding Device—Delivery of Reagents in Branch Channels is used to perform phosphoramidite synthesis on beads distributed into branch channels.

Controlled porous glass beads or polystyrene beads are functionalized to have reactive chemical groups, such as amino, carboxyl, or hydroxyl groups, for future chemical reactions. In addition, beads with additional, alternative, or secondary functionalization, e.g. beads having specific pre-attached phosphoramidite nucleosides, cleavable phosphoramidites, or cleavable universal phosphoramidites, or other useful initializing chemical moieties or compounds, are commercially available from a variety of vendors, such as AM Chemical, Glen Research, ThermoFisher, Polysciences, or PerkinElmer.

Functionalized beads and/or beads with a phosphoramidite nucleoside already attached are distributed into branch channels or reaction chambers.

De-Blocking (Detritylation)

Protective trityl protection groups attached to phosphoramidite nucleosides (e.g. a 4,4'-dimethoxytrityl group) are removed by flowing into the branch channel or reaction chamber a solution of an acid, such as 2% trichloroacetic acid (TCA) or 3% dichloroacetic acid (DCA), typically in an inert solvent such as dichloromethane or toluene. Depurination is mitigated by adjusting the timing and concentration of acid exposure. The de-blocking acid is removed by washing the beads in the branch channel or reaction chamber, e.g. with acetonitrile wash buffer. For functionalized beads that are not capped, the de-blocking step may be omitted.

Coupling

After deprotection, a coupling reaction is performed by flowing a desired phosphoramidite nucleoside into the branch channel or reaction chamber. A phosphoramidite nucleoside is added to functionalized beads by flowing an activated phosphoramidite nucleoside solution (e.g. 0.02-0.2 M or 1.5-20-fold excess over the bead-bound synthesis material in anhydrous acetonitrile) into the branch channel or reaction chamber that contains the functionalized bead via the reagent delivery channel. The phosphoramidite nucleotide solution may be activated for example by a solution of an acidic azole catalyst, 1H-tetrazole, 5-ethylthio-1H-tetrazole, 2-benzylthiotetrazole, 4,5-dicyanoimidazole, or a similar compound known in the art, in a sufficiently high concentration, e.g. 0.2-0.7 M. After the new phosphoramidite nucleoside has coupled to the nucleoside bound to the beads, any unbound nucleosides and chemical by-products are washed out, e.g. by flowing acetonitrile wash buffer into the branch channel or reaction chamber.

Capping

Next, any remaining reactive hydroxyl groups and any $O^6$ modifications which may have taken place by the reaction of activated phosphoramidites with $O^6$ positions of guanosines are removed. Capping is performed by flowing an acetylating reagent (e.g. a mixture of acetic anhydride and 1-methylimidazole or 4-Dimethylaminopyridine (DMAP)) into the branch channel or reaction chamber. The capping solution is washed out by flowing wash buffer into the branch channel.

Oxidation

The new linkage between the nucleosides is then oxidized and stabilized by an oxidation step. The oxidation step is performed by flowing an iodine and water buffer, typically in the presence of a weak base (e.g. pyridine, lutidine, or collidine) into the branch channel or reaction chamber.

After a final washing step, the beads are ready for another round of phosphoramidite synthesis in the same branch channels or reaction chamber. Alternatively, the beads may be flowed out of the branch channels or reaction chambers into the main channel and re-distributed as described in EXAMPLE 3: Positional Encoding Device—Bead Distributing. Single or multiple cycles of nucleotide synthesis may be performed with the device as described herein.

Example 6: Positional Encoding Device—Phosphoramidite Synthesis, Oligonucleotide Phosphorothioates (OPS)

The synthesis method described in EXAMPLE 5: Positional Encoding Device—Phosphoramidite Synthesis is performed with a sulfurization step. After the coupling step, a sulfur transfer reaction is performed by flowing sulfur transfer agent (e.g. 3-(Dimethylaminomethylidene)amino-3H-1,2,4-dithiazole-3-thione (DDTT), 3H-1,2-benzodithiol-3-one 1,1-dioxide (Beaucage reagent), N, N, N'N'-Tetraethylthiuram disulfide (TETD)) into the branch channel or the reaction chamber. The oxidization step may be omitted.

The sulfurization method may be used for one, some, or all cycles of the nucleotide synthesis as necessary to synthesize the desired oligonucleotide.

Example 7: Positional Encoding Device—Merging Beads

With beads in branch channels, the system is reset for subsequent routing of beads back to the main channel. To accomplish this, we first turn off the pressure applied to each port, stopping the flow of carrier fluid. Next, we set the two-way selector valve 1430 to direct flow to the bottom of the main channel 1409, and set two-way selector valve 1433 to direct flow to the first branch channel 1412. We then apply pressure to the main channel, which generates a flow back towards the bottom of the main channel 1409. We then route the beads in the first branch channel 1412 into main channel 1410. Beads are carried by the resulting flow of the carrier fluid back towards the main channel. As described in EXAMPLE: 2 Positional Encoding Device—Bead Spacer for the first separation step, carrier fluid flow in the main channel is used to separate and space the beads as they emerge from the branch channel. These beads are flowed through the main channel and into the feeder channel 1405 using a differential pressurizing method. We distribute beads from the branch channels by switching the selector valve 1433 to the desired branch channel and adjusting the applied pressure on the selected branch channel and the main channel 1435. With the bottom of the main channel 1409 closed to flow by selector valve 1430, the beads then follow the flow and enter the feeder channel 1405.

When all beads exit the first branch channel and are flowed toward the feeder channel, the branch channel pressures are reconfigured to switch the flow of the carrier fluid so that the beads in the second branch channel 1420 are emptied into the main channel introducing spaces between the beads as described above. Then beads from the second branch channel are flowed into the feeder channel using a similar differential pressurizing method as the one described above. Once all beads are moved back into the feeder channel, the pressure applied to the ports is turned off and flow in the main channel is directed away from the bottom of the main channel 1409, toward the top of the main channel 1410, 1418, 1426.

Example 8: Positional Encoding Device—Routing Beads into Main Channel

Following completion of distributing and chemical treatment of the beads, the system is reset for a subsequent positioning of beads. To accomplish this, we first turn off the pressure applied to each port, stopping the flow of carrier fluid. Next, we direct flow toward the bottom of the main channel 1409, and apply pressure to the main channel, generating a flow back towards the bottom of the main channel 1409. We then route the beads in the first branch channel 1412 into main channel 1410. We select flow through the first branch channel 1412 via the two-way selector valve 1433. Beads are carried by the resulting flow of the carrier fluid back towards the bottom of the main channel 1409. As described in EXAMPLE: 2 Positional Encoding Device—Bead Spacer for the first separation step, carrier fluid flowing in the main channel is used to separate and space the beads as they emerged from the branch channel. These beads were flowed toward the bottom of the main channel 1409. When all beads exit the first branch channel 1412 and are flowed toward the bottom of the main channel, the branch channel flow activation is selected so that the beads in the second branch channel 1420 is emptied into the main channel introducing spaces between the beads as described above. Bead spacing is maintained in the flow. Once all beads are moved back into the main channel 1410, the flow is stopped. The flow in the main channel is directed toward the top of the main channel 1410, 1418, 1426 reversing the flow in the main channel.

Example 9: Positional Encoding Device—Optical Detection System

An optical detection system (FIGS. 16A and 16B) was developed to detect units in a capillary. The system comprises a source optical fiber 1607 and receiver optical fiber 1608 (50 μm core, 125 μm cladding, 0.22NA custom multimode fiber, Thorlabs) abutted directly to a fused silica capillary 1612 (360 μm OD, 50 μm ID, Molex) for which the polyimide coating was removed for optical transparency. The optical fibers were positioned in direct opposition to one another and aligned within 10 μm center-to-center using a 3D printed alignment device. The source fiber was coupled to a laser diode 1601 (635 nm, 8 mW, Thorlabs LMP-635-SMA) powered by a compact laser diode driver (Thorlabs CLD1010LP). The receiver fiber was coupled to a photo detector 1604 (Thorlabs, PDA8A). The detector output was coupled to a multifunction data acquisition (DAQ) device (National Instruments, USB-6001, not shown) that digitized the signal using an internal analog to digital converter. The DAQ was connected to a computer 1605 via USB and the signal was displayed using National Instruments DAQExpress software. The capillary was connected to a syringe 1602 at one end and left open at the other end. Particles (monodisperse 40 μm polystyrene beads, CV 1.3%, Thermo Fisher 4240A) were loaded into the capillary by manual actuation of the syringe while the outlet was immersed in a suspension of beads 1603. Further actuation of the syringe allowed beads to flow through the optical path 1613 resulting in a reproducible "W" shape intensity signal 1606, without being bound by theory, likely due to the scattering of light as the leading edge of the bead enters the optical path, but then lensing of the light into the receiver fiber when the bead is centered on the optical path, leading to a momentary increase in transmitted light followed again by a decreased signal from scattering from the trailing edge of the bead.

Example 10: Positional Encoding Device—Bead Detection and Counting

Using the optical detection system of EXAMPLE 9: Positional Encoding Device—Optical Detection System, intensity signal signatures of bead doubles, bead triples, and n-tuplets were detected. FIG. 17A shows the intensity signal signature of a single bead passing through the optical detection system, with a "W" shaped intensity signal. FIG. 17B shows the intensity signature of a bead double as a double "W." Without being bound by theory, this signal likely results from the leading edge of the first bead (a), followed by the centering of the first bead (b), followed by the combined scattering from both the trailing edge of the first bead and the leading edge of the second bead, followed by the centering of the second bead (d), followed by the trailing edge of the second bead (e).

Complex combinations of bead singles, doubles, triples, and n-tuples can be distinguished by analysis of the signal pattern of transmitted light (FIG. 17C). Traversal of a single bead passing through the optical detection system described in EXAMPLE 9 was detected by a characteristic "W" pattern. After a brief restoration of full baseline signal intensity (b), traversal of a second bead through the optical path, closely spaced, but not in direct contact, was detected (c), followed by a third bead (d). A space between beads was identified by a restoration of full baseline signal intensity (e) before a bead double was observed to traverse the optical path (f) followed first by a small space, and then a characteristic signal pattern of a bead triple (g).

A bead triple and n-tuples were characterized by a strong decrease in the signal intensity, without being bound by theory, likely coinciding with the traversal of the trailing edge of one bead and the leading edge of the next bead through the optical path (h), with a momentary increase in transmission intensity as each bead center aligns with optical path (i). Full restoration of baseline transmission intensity occurred after the triple had passed through the optical path (j).

Finally, a second bead double was observed to pass through the optical path (k).

Example 11: Positional Encoding Device—Distinguishing Beads from Bubbles

Bubbles traveling through the optical path of the optical detection system described in EXAMPLE 9: Positional Encoding Device—Optical Detection System were identified and differentiated from beads based on the shape and the intensity of their intensity signal. FIG. 18A shows the signal of a bead passing through the path of the optical detection system. The signal change from the baseline for the bead is about −1 (base line is 3.4 and bead is 2.4). FIG. 18B shows the signal of a bubble passing through the path of the same optical detection system. The signal change from the baseline for the bubble is about −2.5 (baseline is about 3.2 and bubble is about 0.6). Without being bound by theory, this difference likely corresponds to the difference between the indices of refraction of the bead and the bubble. The signal change from baseline is greater in the case of the bubble by about 2.5×. In addition, the signal for the bubble is wider than the signal for the bead. Without being bound by theory, this is likely because the bubble has a larger diameter than the bead. Thus, bead and bubble signals can be distinguished from each other using the optical detection system previously described.

Example 12: Unit Size Selection Via FACS

Beads for use in the microfluidic devices described herein are selected to have a size or diameter with minimal size deviation by sorting the beads via Fluorescent Activated Cell Sorter (e.g. Influx, Becton Dickinson). The dispersion of bead sizes is constrained to a suitable range for use in the devices described herein. Highly spherical polymeric or glass bead solid supports are used with a mean diameter approximately the same as a desired mean bead size (e.g. a bead size of 35 μm). A 100-130 μm nozzle may be used for a greater unit size, but a smaller nozzle size can be used when handling units of smaller dimensions. Beads are suspended in water and 0.10% Tween-20 and placed in the specimen holder of the FACS instrument. Per manufacturer instructions, fluidic pressures and flow rates are adjusted to obtain a consistent and stable flow stream of droplets having a single bead per droplet. Sorting is accomplished by first evaluating the distribution of common FACS parameters for the used beads such as forward-scatter, side-scatter, and/or fluorescence. Without being bound by theory, such parameters correlate to some degree with bead diameter. Any appropriate laser wavelength may be used to establish forward-scatter, side-scatter, and/or fluorescence distributions. Finally, gating, per manufacturer's instructions, is established in the forward-scatter, side-scatter, and/or fluorescence signals to narrow the distribution of these signals in the population. A sub-population of the sorted beads may be reanalyzed using the same analysis settings as the sort procedure to confirm that sorting has narrowed the distribution of beads as measured by FACS parameters to a desired range. Subsequent confirmation of narrowing of the size distribution may be performed by microscopic inspection of the sorted beads and/or using an appropriate particle size analyzer that utilizes a different modality for particle sizing (e.g. Multisizer 4e, Beckman Coulter).

Example 13: Unit Size Selection Via Mechanical Sieving

Selecting units with the appropriate size can also be accomplished via mechanical sieving. Highly spherical polymeric or glass bead solid supports are used with a mean diameter approximately the same as a desired mean bead size (e.g. a bead size of 35 μm). Mechanical sieves made of wire mesh (Precision Micro-Mesh Sieves, Industrial Netting) or precision etched holes (Photo Chemical Etched Screen, Industrial Netting) are selected with the desired bead size, e.g. 31 µm and 38 µm. Polymeric or glass beads are first placed on the 38 µm sieve and agitated over a collection tray. The collected beads are transferred to the 31 µm sieve and agitated over a waste tray. For processing of large numbers of beads, the sieving at 31 µm is repeated multiple times to ensure all beads less than this diameter have been removed. This process results in a population of beads that are less than 38 µm and larger than 31 µm. Subsequent confirmation of narrowing of the size distribution can be confirmed by microscopic inspection of the sorted beads and/or using an appropriate particle size analyzer that utilizes a different modality for particle sizing (e.g. Multisizer 4e, Beckman Coulter).

Example 14A. Bead Manipulation

Figure 19:
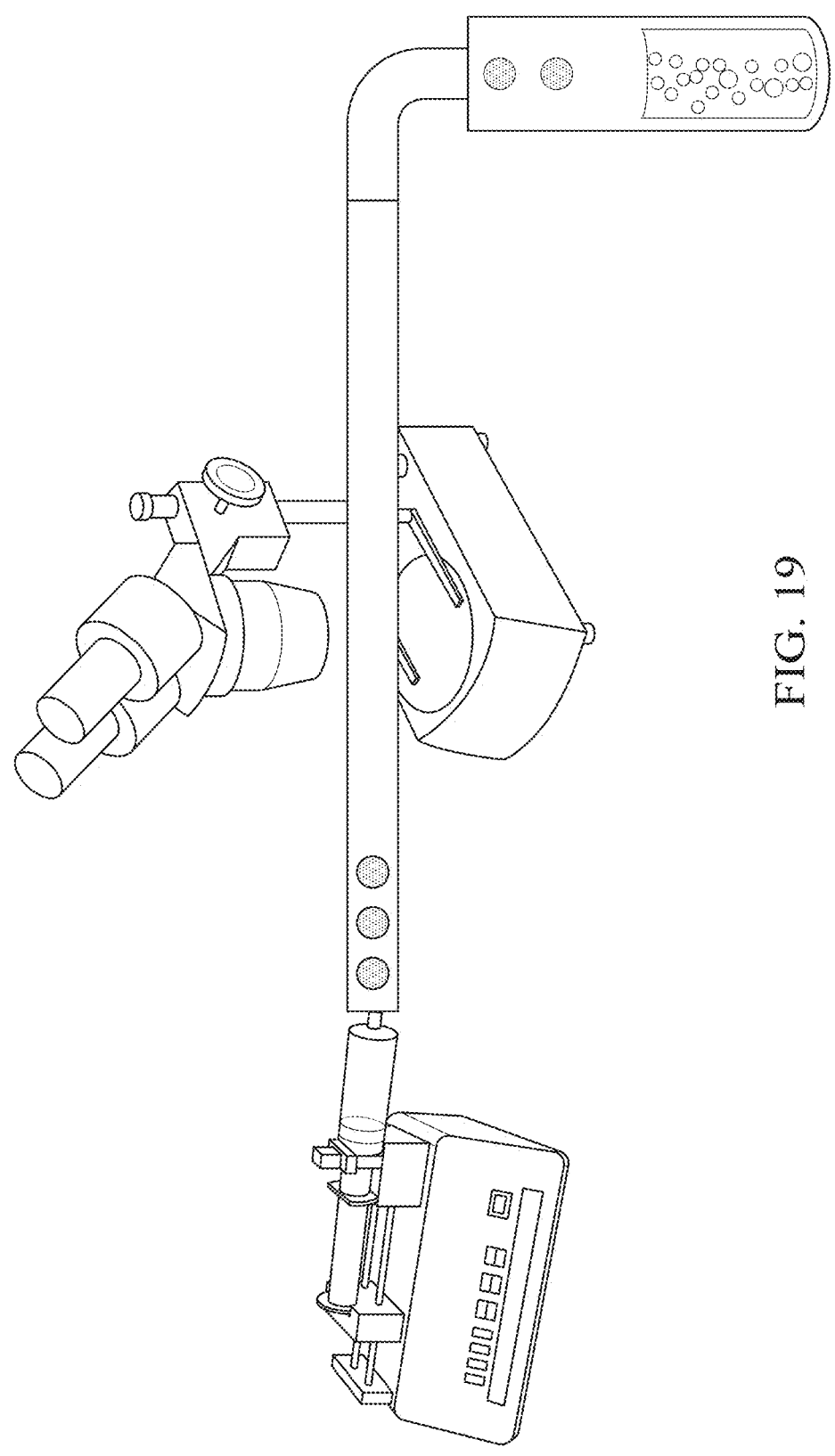
FIG. 19 provides an illustrative example of a set-up for bead manipulation.

In one example, a DNA synthesis device comprises a fused silica capillary with a diameter slightly larger than the microbead. Highly monodisperse cross-linked polymer beads are commercially available. 6-10 µm diameter beads are used with 10-15 µm diameter capillaries. FIG. 19 provides an illustrative example for such a system for packing and moving beads through a capillary. Such an exemplary system may comprise a syringe pump, a glass capillary and a fluid reservoir. A stereo microscope with an attached camera may be used to image the flow through the capillary. The test tube may be used as a reservoir for the fluid containing microbeads.

Prepared solutions of beads may be agitated, for example in a vortex mixer and sonicated in an ultrasonic cleaner.

The system can be used to load a bead containing fluid into a syringe. The syringe may connect directly to the capillary using, for example, a luer lock adapter. The bead containing fluid may be moved through the capillary channel using displacement induced flow. A syringe pump can generate over 100 lbs of displacement force, sufficient to move fluid through the 15 µm diameter, 1 m long capillary. Pressure induced flow with a pressure pump is another option for generating flow through the capillary.

The fluid flowing through the capillary may be imaged with a stereo microscope, for example one with magnification up to 200×, which could be sufficient to see <10 µm diameter beads. The stereo microscope may contain an auxiliary port for a camera attachment for recording the flow field.

The syringe pump may be operated in both infusion and injection modes to move the beads in both directions. A next step may comprise bead packing of the capillary. A flow restrictive orifice, such as a frit, attached to the end of the capillary, may be used to capture the beads, still allowing fluid flow. A frit may be used to modify the characteristics of the flow, as the fluid may need to pass around the packed beads and the frit. This method may be used to decrease the flow rate or equivalently increase the applied pressure differential.

Next, toluene, one of the reagents used for DNA synthesis may be used to flow beads or units through the device or capillary. Without being bound by theory, toluene has a different dynamic viscosity from water and may induce additional bead swelling. Processes for handling toluene or a similar reagent and demonstrating bead flow may be used.

Example 14B. Bead Manipulation and Loading into a Capillary

In an example of a configuration using opposing forces, a loading capillary was oriented upward (e.g., parallel to gravitational forces) such that the beads or other units naturally rested in the reservoir due to gravity. Flow of fluid into the opening of the capillary carried the beads or other units upward into the capillary, while gravity countered the tendency for beads to form aggregates at the opening into the capillary. In more detail, a loading capillary was oriented vertically (or nearly vertical, where variations of the example had the loading capillary oriented between 10 and 90 degrees relative to the direction of gravitational force) and positioned with a first end of the capillary in a reservoir (e.g., conical sample tube) containing a set of beads therein. The capillary passed though the cap of the conical tube, and a gas was introduced through a second port in the cap of the conical tube in order to apply positive pressure within the conical tube. This example promoted flowing of beads into the capillary without jamming, clogging, aggregating and/or keystoning at and/or about the loading channel entry (e.g., at pressures from 50 mbar to 5000 mbar). Pressures (e.g., opposing pressures for loading) can be about, at least, or at least about 1 mbar, 2 mbar, 3 mbar, 4 mbar, 5 mbar, 6 mbar, 7 mbar, 8 mbar, 9 mbar, 10 mbar, 20 mbar, 30 mbar, 40 mbar, 50 mbar, 60 mbar, 70 mbar, 80 mbar, 90 mbar, 100 mbar, 200 mbar, 300 mbar, 400 mbar, 500 mbar, 600 mbar, 700 mbar, 800 mbar, 900 mbar, 1000 mbar, 2000 mbar, 3000 mbar, 4000 mbar, 5000 mbar, 6000 mbar, 7000 mbar, 8000 mbar, 9000 mbar, 10000 mbar, or greater. Stresses (e.g., shear stresses, compressive stresses, tensile stresses, etc.) exerted on the beads can be about, at least, or at least about 1 $dyn/cm^2$, 2 $dyn/cm^2$, 3 $dyn/cm^2$, 4 $dyn/cm^2$, 5 $dyn/cm^2$, 6 $dyn/cm^2$, 7 $dyn/cm^2$, 8 $dyn/cm^2$, 9 $dyn/cm^2$, 10 $dyn/cm^2$, 20 $dyn/cm^2$, 30 $dyn/cm^2$, 40 $dyn/cm^2$, 50 $dyn/cm^2$, 60 $dyn/cm^2$, 70 $dyn/cm^2$, 80 $dyn/cm^2$, 90 $dyn/cm^2$, 100 $dyn/cm^2$, 200 $dyn/cm^2$, 300 $dyn/cm^2$, 400 $dyn/cm^2$, 500 $dyn/cm^2$, 600 $dyn/cm^2$, 700 $dyn/cm^2$, 800 $dyn/cm^2$, 900 $dyn/cm^2$, 1000 $dyn/cm^2$, 2000 $dyn/cm^2$, 3000 $dyn/cm^2$, 4000 $dyn/cm^2$, 5000 $dyn/cm^2$, 6000 $dyn/cm^2$, 7000 $dyn/cm^2$, 8000 $dyn/cm^2$, 9000 $dyn/cm^2$, 10000 $dyn/cm^2$, or greater.

In a variation of this example, the capillary had a diameter of 150 µm and a tapered opening into the reservoir having a narrow edge, where the diameter of the tapered opening was 185 µm. In more detail, the beads entered into a 50 µm inner diameter capillary, with a −500 µm length of 150 µm inner diameter channel immediately before the main capillary. The tapered opening flared out from the end of the 150 µm section, growing to approximately 185 um along a length of approximately 1 mm. Tapered loading channel orifices may be utilized to promote desired flow of beads or other units into a loading channel, e.g. a capillary one unit at a time.

Example 15. Mechanism for Mixing Reagents with Beads

Devices and systems described herein may be used for oligonucleotide synthesis processes comprising a mechanism for sequentially combining solvents with beads. The beads may be initially flowed in an aqueous solution and pack the capillary channel. Next, a particular reagent that will flush away the residual solution and coat the beads may be introduced. This flow and flush cycle is repeated until a target base is synthesized.

Figure 20:
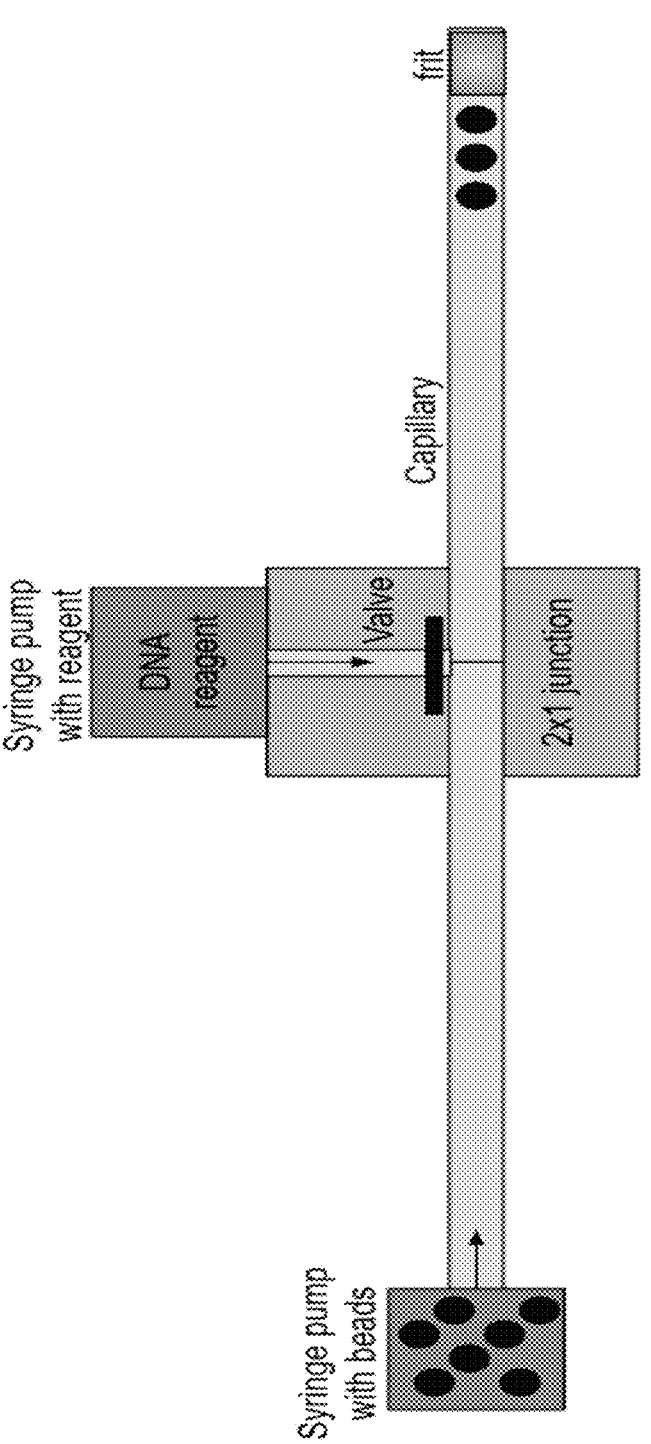
FIG. 20 provides an illustrative example for a bead mixing mechanism with reagents.

Introduction of a new reagent can be accomplished by removing the reservoir that introduces the beads into the capillary and replacing it with the reagent reservoir. This method may be slow and inefficient, since replacing the reservoirs would involve replacing air-tight fittings and handling fragile capillaries. In a high-throughput oligonucleotide synthesis process the reagent reservoirs may be permanently attached to the device and reagent switching may be automated. FIG. 20 shows an exemplary embodiment of a system for a reagent mixing mechanism. A device containing a 2×1 branch point is shown. The output is a main capillary channel. One of the inputs comes from syringe filled with beads, the main bead flow channel. The second input contains one of the reagents. The reagent is injected via a second syringe pump. A valve at the input branch point in combination with the syringe pump controls reagent flow. The valve at the branch point may be used to control the dispensing volume of the reagent.

Exemplary microfluidic devices may combine two capillary channels into one. A device may comprise two input channels that are configured to accept two capillary tubes. The output channel may be configured attach to the output capillary. Internally, the device may be configured to combine the flow from two channels into one. Exemplary valves at the branch point may be selected from pressure-actuated (Quake-valve) or mechanically actuated valves. Exemplary mechanisms, such as the 2-fluid mixing mechanism can be scaled to the number of discrete chemistry steps needed for the desired modifications, such as steps of an oligonucleotide synthesis reaction.

Example 16. A Device or Mechanism for Reagent Mixing with Beads

The oligonucleotide synthesis on beads or other types of units mat comprise packing a capillary by a number of beads. Next, the beads or other types of units may be subjected to steps of a DNA synthesis reaction, for example by flowing and flushing a sequence of reagents, until a desired sequence is synthesized. Reagent volume and reaction times may be optimized, as are conditions to reduce DNA fragmentation during synthesis, for example fragmentation due to shear via fluid flow or collisions with other mobile units, using any suitable method known in the art. After synthesizing a target sequence, the target sequence, e.g. a DNA sequence, may be sequenced to assess the quality of the synthesized oligonucleotide.

Example 17. Spacing and Re-Stacking Demonstrated with >5000 Beads

An integrated example system, as shown in FIGS. 37(*a*) through (*f*), combined various elements from EXAMPLE 2: Positional Encoding Device—Bead Spacer, EXAMPLE 9: Positional Encoding Device—Optical Detection System, and EXAMPLE 10: Positional Encoding Device—Bead Detection and Counting. Embodiments of this example system were used to space and re-stack a population of greater than 5000 beads for more than 500 cycles without any permanent bead jams.

In more detail, a column of beads was initially stacked against a bead stop, which was formed by inserting a 50 μm inner diameter capillary into a machined 50 μm union wherein the channel in the machined part was offset from the capillary center by ~25 μm. Fluid traversed the union, but the polystyrene beads, which have a diameter of 40 μm, could not traverse the union. By applying pressure behind the bead stop, the beads were then driven towards a spacer, where the spacer (e.g., a simplified version of the spacer shown in FIG. 22D) included a small gap in the capillary (~15 μm wide gap), with a high-flow side channel (75 μm inner diameter) coupled to the union, all aligned in a 3D printed structure. As shown in FIGS. 37 (*a*) through (*f*), a separate pressure source was used to drive the side channel (e.g., the side channel with a 75 μm inner diameter and length of 20 cm), but, in variations the side channel could also be connected to the primary channel with a tee junction before the bead stop as a bypass, with the reduced fluidic resistance of the 75 μm channel ensuring higher flow. In this example, the beads exited the spacer separated by ~10 bead widths [see FIG. 37(*b*), left, and snapshot of video in FIG. 37(*c*)].

After the spacer (see FIG. 37(*b*), left), the spaced beads traveled through a 50 μm inner diameter capillary that passes between a pair of optical fibers aligned to the capillary in a 3D printed structure (see FIG. 37(*d*)), as in EXAMPLE 9: Positional Encoding Device—Optical Detection System. A computer data acquisition system then recorded a time-varying signal (see FIG. 37(*e*)), which allowed for individual bead counting as in EXAMPLE 10: Positional Encoding Device—Bead Detection and Counting.

After the detector, the beads entered a second spacer (see FIG. 37(*b*), right), which is a reversed version of the first spacer (see FIG. 37(*b*), left). The configuration of the second spacer produced a decrease in the distance between the beads after they passed through the detector. In variations where the system pressures are set symmetrically, the beads are completely re-stacked (e.g., by returning the spaced beads to a non-spaced arrangement). In the example, the second bypass pressure was slightly offset from the first bypass pressure, which produced residual spacing [see FIG. 37(*f*)], which was eliminated when the beads arrive at the final bead stop. While 3D-printed structures are described in relation to Example 17 and FIGS. 37(*a*)-(*f*), variations of the example can be implemented without 3D-printed structures.

Example 18. Steering—Single Branch, Combined with Spacer

Figure 38:
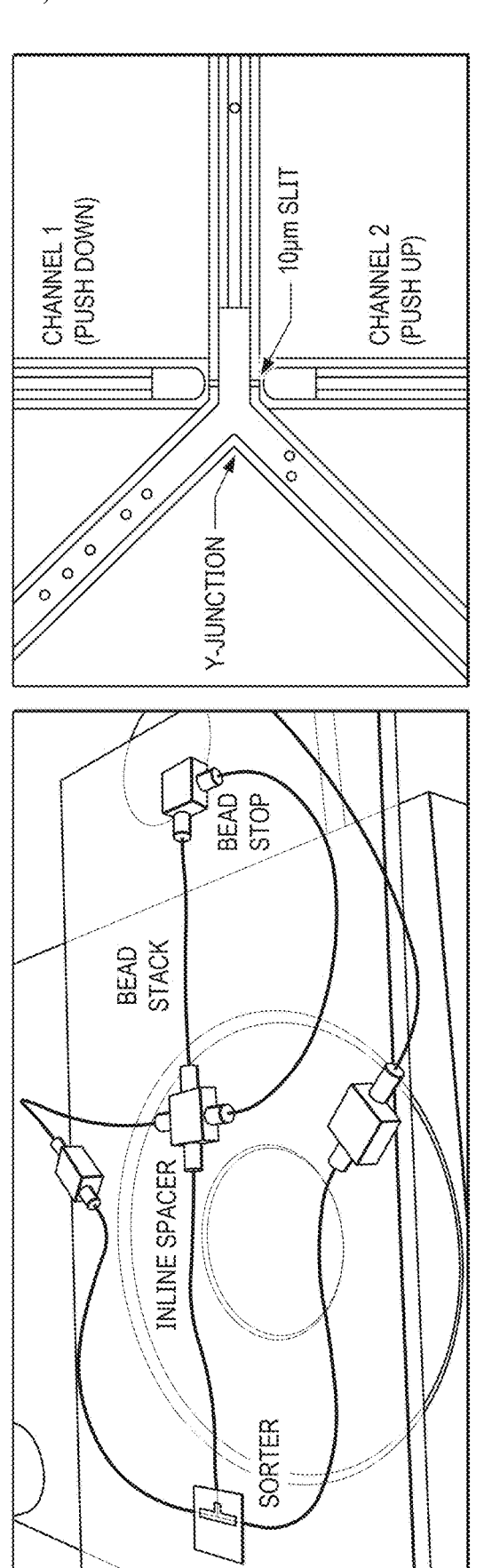
FIG. 38 depicts images of an example device portion for steering beads using an in-line spacer element coupled to a Y-channel. Additional, fluidic connections at the Y-channel junction deliver a volume of fluid into the Y-junction, causing beads to be deflected and move into the opposing leg of the bifurcation.

As shown in FIG. 38, an integrated system comprises a spacer (an inline spacer, similar to that shown in FIG. 22D) and a cross-flow steering junction. In this example, beads were configured to exit the spacer inside a 50 μm inner diameter capillary, with separation of 5-10 bead widths between exiting beads. The beads subsequently entered a 3D-printed Y-junction ~300 μm upstream of the branch point (see FIG. 38, right). A pair of perpendicular side channels were connected via 10 μm slits to the main channel (see FIG. 38, right), immediately prior to the Y-junction. By applying pressure to channel 1 and/or channel 2, the beads were controlled to enter a desired portion of the Y-junction.

Example 19. Positional Encoding Device—Solid-Phase Synthesis

A device with one of the branch channel configurations described in Example 4 is used to perform solid-phase peptide synthesis on beads distributed into branch channels.

Insoluble porous or non-porous resin beads are functionalized to have reactive chemical groups such as amino, hydroxyl, chloromethyl, aminomethyl, or benzhydrylamino groups for future chemical reactions. In addition, beads with additional, alternative, or secondary functionalization (e.g., beads having specific pre-attached amino acids or other useful initializing moieties or compounds) may be used.

Functionalized beads and amino acids with a temporary protecting group (e.g., tert-butyloxycarbonyl (Boc) or fluorenylmethyloxycarbonyl (Fmoc) on the N-terminus are routed into branch channels or reaction chambers.

De-Protecting

Temporary protecting groups attached to amino acids are removed by flowing into the branch channel or reaction chamber a solution such as an acid (e.g., trifluoroacetic acid (TFA)) or a base (e.g., 20-50% piperidine in DMF). The de-protecting solution is removed by washing the beads in the branch channel or reaction chamber, for example with a wash solution (e.g., DCM).

Coupling

After deprotection, a coupling reaction is performed by flowing a desired amino acid into the branch channel or reaction chamber. An amino acid is added to functionalized beads by flowing an activated amino acid solution into the branch channel or reaction chamber that contains the functionalized bead via the reagent delivery channel. The amino acid solution may be activated for example by a solution of a carbodiimide such as dicyclohexylcarbodiimide (DCC) or diisopropylcarbodiimide (DIC), or a similar compound known in the art, in a sufficiently high concentration. In order to avoid racemization of the activated amino acids, a racemization suppressing reagent such as 1-hydroxybenzotriazole (HOBt), 1-hydroxy-7-aza-benzotriazole (HOAt), or ethyl cyanohydroxyiminoacetate (Oxyma) may be added to the branch channel or reaction chamber via the reagent delivery channel. After the new amino acid has coupled to the amino acid bound to the beads, any unbound amino acids and chemical by-products are washed out, for example by flowing DMF and methylene chloride acetic anhydride-triethylamine-DCM solution and/or DMF and methylene chloride solution into the branch channel or reaction chamber.

Capping

Next, any remaining reactive groups are removed with an optional capping procedure. Capping is performed by flowing an acetylating reagent (e.g., a mixture of acetic anhydride and 1-methylimidazole or 4-Dimethylaminopyridine (DMAP)) into the branch channel or reaction chamber. The capping solution is washed out by flowing wash buffer into the branch channel or reaction chamber.

After another washing step the beads are ready for another round of peptide synthesis in the same branch channels or reaction chamber. Alternatively, the beads may be flowed out of the branch channels or reaction chamber into the main channel and re-distributed as described in Example 3. The synthesized peptides may be cleaved from the beads using a reagent such as anhydrous hydrogen fluoride, hydrogen bromide (HBr) or trifluoromethane sulfonic acid. Single or multiple cycles of peptide synthesis may be performed with the device as described herein.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

All publications, patents, and patent applications mentioned in this specification are herein incorporated by reference to the same extent as if each individual publication, patent, or patent application was specifically and individually indicated to be incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of synthesizing oligomers associated with mobile units, the method comprising:
   (a) routing k mobile units through a first channel of a microfluidic device in a first order;
   (b) distributing at least a subset of the k mobile units into at least z branch channels; and
   (c) routing the at least a subset of the k mobile units from the at least z branch channels into the first channel in a second order;
   wherein at least a subset of the k mobile units are functionalized with a group suitable to synthesize an oligomer; wherein at least a subset of the k mobile units are mappable to a path comprising a specific one of the z branch channels; wherein at least a subset of the k mobile units are subjected to reaction conditions comprising conditions for a step of a synthesis reaction inside the z branch channels;
   and wherein steps a-c are repeated for n cycles, wherein n is at least 2 and z is at least 2.

2. The method of claim 1, wherein the synthesis reaction comprises a nucleic acid synthesis reaction or a peptide synthesis reaction.

3. The method of claim 2, wherein the nucleic acid synthesis reaction is a template independent nucleic acid synthesis reaction.

4. The method of claim 1, wherein the reaction conditions comprise an enzyme.

5. The method of claim 4, wherein the enzyme is selected from a terminal deoxynucleotidyl transferase, a thermostable DNA polymerase, a DNA polymerase theta, a Poly (A) polymerase, and a DNA polymerase encoded by a variant of the 9°N DNA Polymerase gene from *Thermococcus* species 9°N-7.

6. The method of claim 5, wherein the variant of the 9°N DNA Polymerase gene comprises the 9°N (D141A/E143A/A485L) DNA Polymerase gene or the 9°N (E143D) DNA Polymerase gene.

7. The method of claim 4, wherein the enzyme is conjugated to a nucleotide or a nucleotide analog.

8. The method of claim 1, wherein the reaction conditions comprise a nucleotide or a nucleotide analog.

9. The method of claim 1, wherein at least a subset of the k mobile units are functionalized with an initiator nucleic acid or a nascent oligonucleotide.

10. The method of claim 1, wherein the synthesis reaction inside the z branch channels comprises performing a coupling reaction by catalyzing formation of a covalent bond between a terminal nucleotide of initiator nucleic acids or nascent oligonucleotides associated with at least a subset of the k mobile units and a new nucleotide or nucleotide analog in the presence of a transferase enzyme.

11. The method of claim 10, wherein the new nucleotide or nucleotide analog comprises a blocking moiety.

12. The method of claim 11, further comprising performing a deblocking reaction thereby removing the blocking moiety from the newly incorporated nucleotide or nucleotide analog.

13. The method of claim 10, further comprising one or more steps selected from the group consisting of a washing step, a modification step, a cleaving step, and a capping step.

14. The method of claim 13, wherein two or more of the steps selected from the group consisting of the coupling reaction, the deblocking reaction, the washing step, the modification step, the cleaving step, and the capping step are performed in different cycles.

15. The method of claim 1, wherein the oligomers are oligonucleotides and wherein the method further comprises assembling the oligonucleotides into genes.

16. The method of claim 1, wherein the reaction conditions comprise one or more of reagents selected from the group consisting of an amino acid, a dipeptide, a polypeptide, and a carbodiimide.

17. The method of claim 16, further comprising performing a coupling reaction by catalyzing the formation of a covalent bond between the terminal end of nascent peptides associated with at least a subset of the k mobile units and a new amino acid, dipeptide or polypeptide.

18. The method of claim 17, further comprising performing one or more step selected from the group consisting of a capping step, a washing step, and a deprotecting step.

19. The method of claim 18, wherein two or more of the steps selected from the group consisting of the coupling reaction, capping step, washing step and the deprotecting step are performed in different cycles.

20. The method of claim 1, wherein the same z branch channels are used in at least two of the n cycles.

21. The method of claim 1, wherein k is at least 2.

22. The method of claim 1, wherein (a) the mobile units are selected from the group consisting of beads, droplets, cells, bubbles, slugs, immiscible volumes, glass beads, polymer beads, cross-linked beads, cross-linked polymer beads, divinylbenzene cross-linked polymer beads, and divinylbenzene cross-linked polystyrene beads; and/or (b) the first order is different in at least two of the n cycles; and/or (c) the second order is different in at least two of the n cycles.

* * * * *